US007094409B2

(12) United States Patent
Bachmann et al.

(10) Patent No.: US 7,094,409 B2
(45) **Date of Patent: *Aug. 22, 2006**

(54) ANTIGEN ARRAYS FOR TREATMENT OF ALLERGIC EOSINOPHILIC DISEASES

(75) Inventors: Martin Bachmann, Seuzach (CH); Gary Jennings, Zurich (CH); Ivo Sonderegger, Zurich (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 134 days.

This patent is subject to a terminal disclaimer.

(21) Appl. No.: 10/289,454

(22) Filed: Nov. 7, 2002

(65) Prior Publication Data

US 2003/0157479 A1 Aug. 21, 2003

Related U.S. Application Data

(63) Continuation-in-part of application No. 10/050,902, filed on Jan. 18, 2002.

(60) Provisional application No. 60/396,636, filed on Jul. 19, 2002, provisional application No. 60/331,045, filed on Nov. 7, 2001, provisional application No. 60/326,998, filed on Oct. 5, 2001, provisional application No. 60/288,549, filed on May 4, 2001, provisional application No. 60/262,379, filed on Jan. 19, 2001.

(51) Int. Cl.
*A61K 39/385* (2006.01)
*C12N 7/00* (2006.01)
*C07K 17/00* (2006.01)

(52) U.S. Cl. ............................ 424/196.11; 424/192.1; 424/193.1; 424/184.1; 424/185.1; 424/85.2; 424/194.1; 435/235.1; 435/320.1; 530/350; 530/403

(58) Field of Classification Search ................ 424/400, 424/192.1, 193.1, 184.1, 185.1, 85.2, 810, 424/196.11, 194.1; 435/235.1, 320.1; 530/350, 530/403

See application file for complete search history.

(56) References Cited

U.S. PATENT DOCUMENTS

| | | | | |
|---|---|---|---|---|
| 4,722,840 | A | 2/1988 | Valenzuela et al. | |
| 4,918,166 | A | 4/1990 | Kingsman et al. | |
| 4,959,314 | A | 9/1990 | Mark et al. | |
| 5,071,651 | A | 12/1991 | Sabara et al. | |
| 5,143,726 | A | 9/1992 | Thornton et al. | |
| 5,334,394 | A | 8/1994 | Kossovsky et al. | |
| 5,374,426 | A | 12/1994 | Sabara et al. | |
| 5,565,548 | A | 10/1996 | Neurath et al. | |
| 5,580,589 | A | 12/1996 | Felgner et al. | |
| 5,580,859 | A | 12/1996 | Felgner et al. | |
| 5,698,424 | A * | 12/1997 | Mastico et al. | 435/477 |
| 5,739,026 | A | 4/1998 | Garoff et al. | |
| 5,766,602 | A | 6/1998 | Xiong et al. | |
| 5,770,380 | A | 6/1998 | Hamilton et al. | |
| 5,789,245 | A | 8/1998 | Dubensky, Jr. et al. | |
| 5,792,462 | A | 8/1998 | Johnston et al. | |
| 5,814,482 | A | 9/1998 | Dubensky, Jr. et al. | |
| 5,935,821 | A | 8/1999 | Chatterjee et al. | |
| 6,231,864 | B1 | 5/2001 | Birkett | |
| 6,380,364 | B1 | 4/2002 | Mueller et al. | |
| 6,719,978 | B1 * | 4/2004 | Schiller et al. | 424/199.1 |
| 2002/0064533 | A1 | 5/2002 | Murray | |
| 2002/0081295 | A1 | 6/2002 | Schiller et al. | |
| 2003/0175290 | A1 | 9/2003 | Renner et al. | |
| 2003/0175711 | A1 | 9/2003 | Renner et al. | |
| 2004/0028650 | A1 * | 2/2004 | Van Snick et al. | 424/85.2 |
| 2004/0059094 | A1 | 3/2004 | Bachmann et al. | |
| 2004/0076611 | A1 | 4/2004 | Bachmann et al. | |
| 2004/0076645 | A1 | 4/2004 | Bachmann et al. | |
| 2004/0136962 | A1 | 7/2004 | Renner et al. | |

FOREIGN PATENT DOCUMENTS

| | | | |
|---|---|---|---|
| EP | 0 201 416 | B1 | 11/1986 |
| EP | 0 421 635 | B1 | 4/1991 |
| EP | 0 259 149 | B1 | 12/1993 |
| EP | 0 385 610 | B1 | 3/1994 |
| EP | 0 465 081 | B1 | 4/1994 |
| EP | 0 283 505 | B1 | 7/1994 |
| EP | 0 425 082 | A1 | 4/1995 |
| EP | 0 677 111 | B1 | 10/1995 |
| WO | WO 92/11291 | A1 | 7/1992 |
| WO | WO 92/13081 | A1 | 8/1992 |

(Continued)

OTHER PUBLICATIONS

Leong et al. Annals of Allergy, Asthma, and Immunology. Aug. 2001. 87(2): 96-110.*

(Continued)

*Primary Examiner*—Mary E. Mosher
(74) *Attorney, Agent, or Firm*—Sterne, Kessler, Goldstein & Fox P.L.L.C.

(57) ABSTRACT

The present invention is related to the fields of molecular biology, virology, immunology and medicine. The invention provides a composition comprising an ordered and repetitive antigen or antigenic determinant array, and in particular an array comprising a protein or peptide of IL-5, IL-13 or eotaxin. More specifically, the invention provides a composition comprising a virus-like particle and at least one protein, or peptide of IL-5, IL-13 and/or eotaxin bound thereto. The invention also provides a process for producing the conjugates and the ordered and repetitive arrays, respectively. The compositions of the invention are useful in the production of vaccines for the treatment of allergic diseases with an eosinophilic component and as a pharmaccine to prevent or cure allergic diseases with an eosinophilic component and to efficiently induce immune responses, in particular antibody responses. Furthermore, the compositions of the invention are particularly useful to efficiently induce self-specific immune responses within the indicated context.

79 Claims, 12 Drawing Sheets

FOREIGN PATENT DOCUMENTS

| | | | |
|---|---|---|---|
| WO | WO 94/06472 | A1 | 3/1994 |
| WO | WO 94/15585 | A1 | 7/1994 |
| WO | WO 96/05293 | A1 | 2/1996 |
| WO | WO 96/30523 | A2 | 10/1996 |
| WO | WO 97/31948 | A1 | 9/1997 |
| WO | WO 97/45448 | A1 | 12/1997 |
| WO | WO 98/15631 | A1 | 4/1998 |
| WO | WO 98/40100 | | 9/1998 |
| WO | WO 99/07839 | A2 | 2/1999 |
| WO | WO 99/28478 | | 6/1999 |
| WO | WO 99/40934 | A1 | 8/1999 |
| WO | WO 99/57289 | | 11/1999 |
| WO | WO 99/67293 | A1 | 12/1999 |
| WO | WO 00/23955 | A1 | 4/2000 |
| WO | WO 00/32227 | A2 | 6/2000 |
| WO | WO 00/50461 | | 8/2000 |
| WO | WO 00/59928 | A1 | 10/2000 |
| WO | WO 00/65058 | A1 | 11/2000 |
| WO | WO 01/62284 | A2 | 8/2001 |
| WO | WO 01/77158 | A1 | 10/2001 |
| WO | WO 01/85208 | A2 | 11/2001 |
| WO | WO 01/98333 | A2 | 12/2001 |
| WO | WO 01/98333 | A3 | 12/2001 |
| WO | WO 02/14478 | A2 | 2/2002 |
| WO | WO 02/056905 | A2 | 7/2002 |
| WO | WO 02/056907 | A2 | 7/2002 |

OTHER PUBLICATIONS

Apostopoulos et al. European Journal of Immunology. 2000. 30:1733-1739.*
Brombacher. BioEssays 22:646-656, 2000.*
Vallance et al. Parasite Immunology. 2000. 22:487-492.*
Mishra et al. Blood. Aug. 15, 2000. 96(4):1538-1544.*
Yang et al. Blood. Nov. 15, 1998. 92(10):3912-3923.*
Kato et al. Hepatology. 2003. 37(2):304-312.*
Chackerian et al, Proceedings of the National Academy of Sciences US 96:2373-2378, 1999.*
NCBI Entrez, GenBank Report, Accession No. P03153, from Seeger, C., et al. (Jan. 1990).
NCBI Entrez, GenBank Report, Accession No. X59397, from Jordan, C.T., et al. (Nov. 1991).
NCBI Entrez, GenBank Report, Accession No. 711678A, from Shipolini, R.A., et al. (Jul. 1992).
NCBI Entrez, GenBank Report, Accession No. M27603, from Orndorff, P.E., and Falkow, S. (Apr. 1993).
NCBI Entrez, GenBank Report, Accession No. M20706, from Nassal M. (Apr. 1993).
NCBI Entrez, GenBank Report, Accession No. AAA37490, from Rouvier E. (Jul. 1993).
NCBI Entrez, GenBank Report, Accession No. M90520, from Kew, M.C., et al. (Aug. 1993).
NCBI Entrez, GenBank Report, Accession No. X00981, from Klemm, P. (Sep. 1993).
NCBI Entrez, GenBank Report, Accession No. VCBPQB, from Maita, T., and Konigsberg, W. (Dec. 1993).
NCBI Entrez, GenBank Report, Accession No. AAA16663, from Kozlovska, T.M., et al. (Mar. 1994).
NCBI Entrez, GenBank Report, Accession No. X02514, from Yanisch-Perron, C., et al. (May 1994).
NCBI Entrez, GenBank Report, Accession No. X85256, from Lai, M.E., et al. (Apr. 1995).
NCBI Entrez, GenBank Report, Accession No. X85259, from Lai, M.E., et al., (Apr. 1995).
NCBI Entrez, GenBank Report, Accession No. X85260, from Lai, M.E., et al. (Apr. 1995).
NCBI Entrez, GenBank Report, Accession No. X85272, from Lai, M.E., et al. (Apr. 1995).
NCBI Entrez, GenBank Report, Accession No. X85275, from Lai, M.E., et al. (Apr. 1995).
NCBI Entrez, GenBank Report, Accession No. X85284, from Lai, M.E., et al. (Apr. 1995).
NCBI Entrez, GenBank Report, Accession No. X85285, from Lai, M.E., et al. (Apr. 1995).
NCBI Entrez, GenBank Report, Accession No. X85286, from Lai, M.E., et al. (Apr. 1995).
NCBI Entrez, GenBank Report, Accession No. X85287, from Lai, M.E., et al. (Apr. 1995).
NCBI Entrez, GenBank Report, Accession No. X85291, from Lai, M.E., et al. (Apr. 1995).
NCBI Entrez, GenBank Report, Accession No. X85293, from Lai, M.E., et al. (Apr. 1995).
NCBI Entrez, GenBank Report, Accession No. X85295, from Lai, M.E., et al. (Apr. 1995).
NCBI Entrez, GenBank Report, Accession No. X85296, from Lai, M.E., et al. (Apr. 1995).
NCBI Entrez, GenBank Report, Accession No. X85297, from Lai, M.E., et al. (Apr. 1995).
NCBI Entrez, GenBank Report, Accession No. X85298, from Lai, M.E., et al. (Apr. 1995).
NCBI Entrez, GenBank Report, Accession No. X85299, from Lai, M.E., et al. (Apr. 1995).
NCBI Entrez, GenBank Report, Accession No. X85301, from Lai, M.E., et al. (Apr. 1995).
NCBI Entrez, GenBank Report, Accession No. X85302, from Lai, M.E., et al. (Apr. 1995).
NCBI Entrez, GenBank Report, Accession No. X85303, from Lai, M.E., et al. (Apr. 1995).
NCBI Entrez, GenBank Report, Accession No. X85305, from Lai, M.E., et al. (Apr. 1995).
NCBI Entrez, GenBank Report, Accession No. X85307, from Lai, M.E., et al. (Apr. 1995).
NCBI Entrez, GenBank Report, Accession No. X85311, from Lai, M.E., et al. (Apr. 1995).
NCBI Entrez, GenBank Report, Accession No. X85314, from Lai, M.E., et al. (Apr. 1995).
NCBI Entrez, GenBank Report, Accession No. X85315, from Lai, M.E., et al. (Apr. 1995).
NCBI Entrez, GenBank Report, Accession No. X85316, from Lai, M.E., et al. (Apr. 1995).
NCBI Entrez, GenBank Report, Accession No. X85317, from Lai, M.E., et al. (Apr. 1995).
NCBI Entrez, GenBank Report, Accession No. X85319, from Lai, M.E., et al. (Apr. 1995).
NCBI Entrez, GenBank Report, Accession No. X80925, from Karayiannis, P. (Dec. 1995).
NCBI Entrez, GenBank Report, Accession No. AAC50341, from Yao, Z., et al. (Jan. 1996).
NCBI Entrez, GenBank Report, Accession No. X72702, from Preisler-Adams, S., et al. (Feb. 1996).
NCBI Entrez, GenBank Report, Accession No. VCBPR7, from Weber, K., et al. (Apr. 1996).
NCBI Entrez, GenBank Report, Accession No. 1604193A, from Gomez, F., et al. (Oct. 1996).
NCBI Entrez, GenBank Report, Accession No. B56338, from Hoffman, D.R. (May 1997).
NCBI Entrez, GenBank Report, Accession No. U95551, from Rao, B.S., et al. (Jun. 1997).
NCBI Entrez, GenBank Report, Accession No. S14764, from Vandermeers, A., et al. (Oct. 1997).
NCBI Entrez, GenBank Report, Accession No. P03611, from Weber, K., et al. (Nov. 1997).
NCBI Entrez, GenBank Report, Accession No. AAC14699, from Beekwilder, M.J., et al. (Apr. 1998).
NCBI Entrez, GenBank Report, Accession No. AAC14704, from Beekwilder, M.J., et al. (Apr. 1998).
NCBI Entrez, GenBank Report, Accession No. AF043593, from Gunther, S., et al. (May 1998).
NCBI Entrez, GenBank Report, Accession No. 1POC, from Scott, D.L., et al. (Sep. 1998).
NCBI Entrez, GenBank Report, Accession No. CAA30374, from Inokuchi, Y., et al. (Feb. 1999).

NCBI Entrez, GenBank Report, Accession No. X02496, from Bichko, V., et al. (Apr. 1999).
NCBI Entrez, GenBank Report, Accession No. MFIV62, from Cox, N.J., et al. (Jul. 1999).
NCBI Entrez, GenBank Report, Accession No. VCBPFR, from Wittmann-Liebold, B., et al. (Jul. 1999).
NCBI Entrez, GenBank Report, Accession No. A59055, from Hoffman, D.R., and Schmidt, J.O. (Aug. 1999).
NCBI Entrez, GenBank Report, Accession No. B59055, from Hoffman, D.R., and Schmidt, J.O. (Aug. 1999).
NCBI Entrez, GenBank Report, Accession No. AF051814, from Boyd, E.F., and Hartl, D.L. (Sep. 1999).
NCBI Entrez, GenBank Report, Accession No. AF051815, from Boyd, E.F., and Hartl, D.L. (Sep. 1999).
NCBI Entrez, GenBank Report, Accession No. AF110999, from Chang, S.F., et al. (Oct. 1999).
NCBI Entrez, GenBank Report, Accession No. AB033559, from Okamoto, H., et al. (Oct. 1999).
NCBI Entrez, GenBank Report, Accession No. AB010289, from Koseki, T., et al. (Dec. 1999).
NCBI Entrez, GenBank Report, Accession No. AJ132364, from Graupner, S., et al. (Apr. 2000).
NCBI Entrez, GenBank Report, Accession No. AF237482, from Johnson, J.R., et al. (May 2000).
NCBI Entrez, GenBank Report, Accession No. M32138, from Tong, S.P., et al. (Jul. 2000).
NCBI Entrez, GenBank Report, Accession No. AF229646, from Skerker, J.M., and Shapiro, L. (Aug. 2000).
NCBI Entrez, GenBank Report, Accession No. M95589, from Shi, H., et al. (Jan. 2001).
NCBI Entrez, GenBank Report, Accession No. VCBPM2, from Min Jou, W., et al. (Jan. 2001).
NCBI Entrez, GenBank Report, Accession No. AF323080, from Steppan, C.M., et al. (Jan. 2001).
NCBI Entrez, GenBank Report, Accession No. AF323081, from Steppan, C.M., et al. (Jan. 2001).
NCBI Entrez, GenBank Report, Accession No. U14003, from Plunket, G., III, et al. (Jan. 2001).
NCBI Entrez, GenBank Report, Accession No. AF121239, from Hannoun, C., et al. (Feb. 2001).
NCBI Entrez, GenBank Report, Accession No. AF121240, from Hannoun, C., et al. (Feb. 2001).
NCBI Entrez, GenBank Report, Accession No. AF121242, from Hannoun, C., et al. (Feb. 2001).
NCBI Entrez, GenBank Report, Accession No. X59795, from Lai, M.E., et al. (Mar. 2001).
NCBI Entrez, GenBank Report, Accession No. X65257, from Lai, M.E., et al. (Mar. 2001).
NCBI Entrez, GenBank Report, Accession No. X65258, from Lai, M.E., et al. (Mar. 2001).
NCBI Entrez, GenBank Report, Accession No. AF151735, from Gerner, P., et al. (Apr. 2001).
NCBI Entrez, GenBank Report, Accession No. AJ000636, from Gousset, N., et al. (Nov. 2001).
NCBI Entrez, GenBank Report, Accession No. AAB59424, from Kenten, J.H., et al. (Feb. 2002).
NCBI Entrez, GenBank Report, Accession No. AAC06250, from Beekwilder, M.J., et al. (Mar. 2002).
NCBI Entrez, GenBank Report, Accession No. L09137, from Yanisch-Perron, C., et al. (May 2002).
NCBI Entrez, GenBank Report, Accession No. O09006, from Hromas, R., et al. (Jun. 2002).
NCBI Entrez, GenBank Report, Accession No. P40224, from Nagasawa, T., et al. (Jun. 2002).
NCBI Entrez, GenBank Report, Accession No. P34884, from Bernhagen, J., et al. (Jun. 2002).
NCBI Entrez, GenBank Report, Accession No. P06821, from Winter, G., et al. (Jun. 2002).
NCBI Entrez, GenBank Report, Accession No. P30904, from Sakai, M., et al. (Jun. 2002).
NCBI Entrez, GenBank Report, Accession No. NP_040754, from Inokuchi, Y., et al. (Jun. 2003).
NCBI Entrez, GenBank Report, Accession No. NP_061354, from Ishikawa, S., et al. (Sep. 2003).
NCBI Entrez, GenBank Report, Accession No. NP_031804, from Lenda, D.M., et al. (Sep. 2003).
NCBI Entrez, GenBank Report, Accession No. NP_006410, from Luther, S.A., et al. (Sep. 2003).
NCBI Entrez, GenBank Report, Accession No. NP_000748, from Yao, G.Q., et al. (Sep. 2003).
NCBI Entrez, GenBank Report, Accession No. P03069, from Hinnebusch, A.G., et al. (Sep. 2003).
NCBI Entrez, GenBank Report, Accession No. O00585, from Hromas, R., et al. (Sep. 2003).
NCBI Entrez, GenBank Report, Accession No. P14174, from Weiser, W.Y., et al. (Sep. 2003).
NCBI Entrez, GenBank Report, Accession No. P48061, from Spotila, L.D., et al. (Sep. 2003).
NCBI Entrez, GenBank Report, Accession No. P80003, from Vandermeers, A., et al. (Sep. 2003).
Swiss-Prot/TrEMBL, TN11_Mouse, Primary Accession No. O35235, entered in Swiss-Prot in Oct. 2001.
Swiss-Prot/TrEMBL, TN11_Human, Primary Accession No. O14788, entered in Swiss-Prot in Oct. 2001.
Co-pending U.S. Appl. No. 10/622,064, inventors Bachmann et al,, filed Jul. 18, 2003 (Not Published).
Co-pending U.S. Appl. No. 10/617,876, inventors Bachmann et al., filed Jul. 14, 2003 (Not Published).
Co-pending U.S. Appl. No. 10/622,087, inventors Bachmann et al., filed Jul. 18, 2003 (Not Published).
Co-pending U.S. Appl. No. 10/622,124, inventors Bachmann et al., filed Jul. 18, 2003 (Not Published).
Co-pending U.S. Appl. No. 09/449,631, inventors Renner et al., filed Nov. 30, 1999 (Not Published).
Jegerlehner, A., et al., "A molecular assembly system that renders antigens of choice highly repetitive for induction of protective B cell responses," *Vaccine 20*:3104-3112, Elsevier Science, Ltd. (Aug. 2002).
*The Biology of Animal Viruses*, 2nd ed., Fenner, F., et al., eds., Academic Press, New York, NY, pp. 117-119 (1974).
NCBI Entrez, PubMed Abstract, PMID: 2205968, Diallo, A., et al., "Morbillivirus group: genome organization and proteins," *Vet. Microbiol. 23*:155-163 (1990).
International Search Report for International Application No. PCT/EP02/12455 mailed on Aug. 22, 2003, European Patent Office, Netherlands.
Borisova, G.P., et al., "Recombinant core particles of hepatitis B virus exposing foreign antigenic determinants on their surface," *FEBS Lett. 259*:121-124, Elsevier Science Publishers (1989).
Guo, R-F., et al., "Eotaxin Expression in Sephadex-Induced Lung Injury in Rats," *Am. J. Pathol. 155*:2001-2008, American Society for Investigative Pathology (1999).
Hertz, M., et al., "Active Vaccination Against IL-5 Bypasses Immunological Tolerance and Ameliorates Experimental Asthma," *J. Immunol. 167*:3792-3799, American Association of Immunologists (Oct. 2001).
Koletzki, D., et al., "Mosaic hepatitis B virus core particles allow insertion of extended foreign protein segments," *J. Gen. Virol. 78*:2049-2053, Society For General Microbiology (1997).
Abraham, J.M., et al., "An invertible element of DNA controls phase variation of type 1 fimbriae of *Escherichia coli*," *Proc. Natl. Acad. Sci. USA 82*:5724-5727, National Academy Press (1985).
Abraham, S.N., et al., "Glycerol-Induced Unraveling of the Tight Helical Conformation of *Escherichia coli* Type 1 Fimbriae," *J. Bacteriol. 174*:5145-5148, American Society for Microbiology (1992).
Aguzzi, A., "Prion diseases, blood and the immune system: concerns and reality," *Haematologica 85*:3-10, Il Pensiero Scientifico Editore (Jan. 2000).
Ansel, K.M., et al., "In Vivo-activated CD4 T Cells Upregulate CXC Cheomkine Receptor 5 and Reprogram Their Response to Lymphoid Chemokines," *J. Exp. Med. 190*:1123-1134, The Rockefeller University Press (1999).

Ansel, K.M., et al., "A chemokine-driven positive feedback loop organizes lymphoid follicles," *Nature 406*:309-314, Nature Publishing Group (Jul. 2000).
Antonysamy, M.A., et al., "Evidence for a Role of IL-17 in Organ Allograft Rejection: IL-17 Promotes the Functional Differentiation of Dendritic Cell Progenitors," *J. Immunol. 162*:577-584, The American Association of Immunologists (1999).
Arenberg, D.A., et al., "The murine CC chemokine, 6C-kine, inhibits tumor growth and angiogenesis in a human lung cancer SCID mouse model," *Cancer Immunol. Immunother. 49*:587-592, Springer-Verlag (Jan. 2001).
Arnon, R., et al., "A mimotope peptide-based vaccine against *Schistosoma mansoni*: synthesis and characterization," *Immunology 101*:555-562, Blackwell Science, Ltd. (Dec. 2000).
Bachmann, M.F., et al., "TRANCE, a Tumor Necrosis Factor Family Member Critical for CD40 Ligand-independent T Helper Cell Activation," *J. Exp. Med. 189*:1025-1031, The Rockefeller University Press (1999).
Banerjee, R.R., and Lazar, M.A., "Dimerization of Resistin and Resistin-like Molecules Is Determined by a Single Cysteine," *J. Biol. Chem. 276*:25970-25973, The American Society for Biochemistry and Molecular Biology, Inc. (Jul. 2001).
Bard, F. et al., "Peripherally administered antibodies against amyloid β-peptide enter the central nervous system and reduce pathology in a mouse model of Alzheimer disease," *Nat. Med. 6*:916-919, Nature Publishing Company (Aug. 2000).
Bass, S., and Yang, M., "Expressing cloned genes in *Escherichia coli*," in *Protein Function: A Practical Approach*, 2nd ed., Creighton, T.E., ed., IRL Press, Oxford, Great Britain, pp. 29-55 (1997).
Bernhagen, J., et al., "Purification, Bioactivity, and Secondary Structure Analysis of Mouse and Human Macrophage Migration Inhibitory Factor (MIF)," *Biochemistry 33*:14144-14155, American Chemical Society (1994).
Biaselle, C.J., and Millar, D.B., "Studies on Triton X-100 detergent micelles," *Biophys. Chem. 3*:355-361, North-Holland Publushing Company (1975).
Bleul, C.C., et al., "The lymphocyte chemoattractant SDF-1 is a ligand for LESTR/fusin and blocks HIV-1 entry," *Nature 382*:829-833, Nature Publishing Group (1996).
Blomfield, I.C., et al., "Type 1 Fimbriation and *fimE* Mutants of *Escherichia coli* K-12," *J. Bacteriol. 173*:5298-5307, American Society for Microbiology (1991).
Blomfield, I.C., et al., "Integration host factor stimulates both FimB- and FimE-mediated site-specific DNA inversion that controls phase variation of type 1 fimbriae expression in *Escherichia coli," Mol. Microbiol. 23*:705-717, Blackwell Science, Ltd. (1997).
Boder, E.T., and Wittrup, K.D., "Yeast Surface Display for Directed Evolution of Protein Expression, Affinity, and Stability," *Methods Enzymol. 328*:430-444, Academic Press (Oct. 2000).
Bonci, A., et al., "Relatedness and Phylogeny Within the Family of Periplasmic Chaperones Involved in the Assembly of Pili or Capsule-Like Structures of Gram-Negative Bacteria," *J. Mol. Evol. 44*:299-309, Springer-Verlag.
Brandner, S., et al., "A crucial role B cells in neuroinvasive scrapie," *Transfus. Clin. Biol. 6*:17-23, Elsevier, Paris (1999).
Brinton, Jr., C.C., "The structure, function, synthesis and genetic control of bacterial pili and a molecular model for DNA and RNA transport in gram negative bacteria," *Trans. N.Y. Acad. Sci. 27*:1003-1054, New York Academy of Sciences (1965).
Brown, K.L., et al., "Scrapie replication in lymphoid tissues depends on prion protein-expressing follicular dendritic cells," *Nat. Med. 11*:1308-1312, Nature Publishing Company (1999).
Burger, J.A., et al., "Blood-derived nurse-like cells protect chronic lymphocytic leukemia B cells from spontaneous through stromal cell-derived factor-1," *Blood 96*:2655-2663. The American Society of Hematology (Oct. 2000).
Burghoff, R.L., et al., "Utilization of the Mouse Large Intestine To Select an *Escherichia coli* F-18 DNA Sequence That Enhances Colonizing Ability and Stimulates Synthesis of Type 1 Fimbriae," *Infect. Immun. 6*:1293-1300, American Society for Microbiology (1993).
Chabaud, M., et al., "Enhancing Effect of IL-17 on IL-1-Induced IL-6 and Leukemia Inhibitory Factor Production by Rheumatoid Arthritis Synoviocytes and Its Regulation by Th2 Cytokines," *J. Immunol. 161*: 409-414, The American Association of Immunologists (1998).
Chabaud, M., et al., "Human Interleukin-17. A T Cell-Derived Proinflammatory Cytokine Produced by the Rheumatoid Synovium," *Arthritis Rheum. 42*:963-970, Wiley-Liss, Inc. (1999).
Chabaud, M., et al., "Contribution of Interleukin 17 to synovium matrix destruction in rheumatoid arthritis," *Cytokine 12*:1092-1099, Cell Press (Jul. 2000).
Cohen, C., and Parry D.A.D, "α-Helical coiled coils-a widespread motif in proteins," *Trends Biochem. Sci. 11*:245-248, Elsevier Science Publishers B.V. (1986).
Corti, M., et al., "GM1-ganglioside-Triton X-100 mixed micelles: changes of micellar properties studied by laser-light scattering and enzymatic methods," *Chem. Phys. Lipids 28*:197-214, Elsevier/North-Holland Scientific Publishers, Ltd. (1981).
Coutelier, J. -P., et al., "IgG2a Restriction of murine antibodies elicited by viral infections," *J. Exp. Med. 165*:64-69, The Rockefeller University Press (1987).
Daugherty, P.S., et al., "Development of an optimized expression system for the screening of antibody libraries displayed on the *Escherichia coli* surface," *Protein Eng. 12*:613-621, Oxford University Press (1999).
Dealwis, C., et al., "Crystal structure of chemically synthesized [N33A] stromal cell-derived factor 1α, a potent ligand for the HIV-1 "fusin" coreceptor," *Proc. Natl. Acad. Sci. USA 95*:6941-6946, National Academy Science (Jun. 2001).
Dodson, K.W., et al., "Outer-membrane PapC molecular usher discriminately recognizes periplasmic chaperone-pilus subunit complexes," *Proc. Natl. Acad. Sci. USA 90*:3670-3674, National Academy Press (1993).
Dudler, J., et al., "Effect of interleukin 17 on proteoglycan degradation in murine knee joints," *Ann. Rheum. Dis. 59*:529-532, Bmj Publishing Group (Jul. 2000).
Eckhardt, S.G., et al., "Hepatitis B Virus Core Antigen Has Two Nuclear Localization Sequences in the Arginine-Rich Carboxyl Terminus," *J. Virol. 65*:575-582, American Society for Microbiology (1991).
Eisenstein, B.I., "Phase Variation of Type 1 Fimbriae in *Escherichia coli* Is Under Transcriptional Control," *Science 214*:337-339, American Association for the Advancement of Science (1981).
Elisseeva, E.L., et al., "NMR Studies of Active N-terminal Peptides of Stromal Cell-derived Factor-1," *J. Biol. Chem. 275*:26799-26805, The American Society for Biochemistry and Molecular Biology, Inc. (Sep. 2000).
Ettinger, R., et al., "A Critical Role for Lymphotoxin-β Receptor in the Development of Diabetes in Nonobese Diabetic Mice," *J. Exp. Med. 193*:1333-1339, The Rockefeller University Press (Jun. 2001).
Folkman, J., and Klagsbrun, M., "Angiogenic Factors," *Science 235*:442-447, American Association for the Advancement of Science (1987).
Folkman, J., "Angiogenesis in cancer, vascular, rheumatoid and other disease," *Nat. Med. 1*:27-31, Nature Publishing Company (1995).
Fossiez, F., et al., "T Cell Interleukin-17 Induces Stromal Cells to Produce Proinflammatory and Hematopoietic Cytokines," *J. Exp. Med. 183*:2593-2603, The Rockefeller University Press (1996).
Fossiez F., et al., "Interleukin-17," *Intern. Rev. Immunol. 16*:541-551, Harwood Academic Publishers (1998).
Fujiwara, K., et al., "Novel preparation method of immunogen for hydrophobic hapten, enzyme immunoassay for daunomycin and adriamycin," *J. Immunol. Methods 45*:195-203, Elsevier/North-Holland Biomedical Press (1981).
Gally, D.L., et al., "Environmental Regulation of the *fim* Switch Controlling Type 1 Fimbrial Phase Variation in *Escherichia coli* K-12: Effects of Temperature and Media," *J. Bacteriol. 175*:6186-6193, American Society for Microbiology (1993).
Gally, D.L., et al., "Interaction of FimB and FimE with the *fim* switch that controls the phase variation of type 1 fimbriate in *Escherichia coli* K-12," *Mol. Microbiol. 21*:725-738, Blackwell Science, Ltd. (1996).

Gherardi, E. et al., "A single-step procedure for cloning and selection of antibody-secreting hybridomas," *J. Immunol. Methods 126*: 61-68, Elsevier (1990).
Gunn, M.D., et al., "A B-cell-homing chemokine made in lymphoid follicles activates Burkitt's lymphoma receptor-1," *Nature 391*:799-803, Nature Publishing Group (1998).
Hanes, J., et al., "Picomolar affinity antibodies from a fully synthetic naive library selected and evolved by ribosome display," *Nat. Biotechnol. 18*:1287-1292, Nature Publishing Company (Dec. 2000).
Hanson, M.S., et al., "Purification of the *Escherichia coli* Type 1 Pilin and Minor Pilus Proteins and Partial Characterization of the Adhesin Protein," *J. Bacteriol. 170*:3350-3358, American Society for Microbiology (1988).
Hanson, M.S., and Brinton, Jr., C.C., "Identification and characterization of *E. coli* type-1 pilus tip adhesion protein," *Nature 332*:265-268, Nature Publishing Group (1988).
Harrison, J.L., et al., "Screening of Phage Antibody Libraries," *Methods Enzymol. 267*:83-109, Macmillan Publishers, Ltd. (1996).
Haslam, D.B., et al., "the amino-terminal domain of the P-pilus adhesin determines receptor specificity," *Mol. Microbiol. 14*:399-409, Blackwell Scientific Publications (1994).
Hedrick, J.A., and Zlotnik, A., "Identification and Characterization of a Novel β Chemokine Containing Six Conserved Cysteines," *J. Immunol. 159*: 1589-1593, The American Association of Immunologists (1997).
Heveker, N., et al., Dissociation of the signalling and antiviral properties of SDF-1-derived small peptides, *Curr. Biol. 8*:369-376, Current Biology, Ltd. (1998).
Hirel, P. -H., et al., "Extent of N-terminal methionine excision from *Escherichia coli* proteins is governed by the side-chain length of the penultimate amino acid," *Proc. Acad. Sci. USA 86*:8247-8251, National Academy Press (1989).
Holmes, W.D., et al., "Solution Studies of Recombinant Human Stromal-Cell-Derived Factor-1," *Prot. Expr. Purif. 21*:367-377, Academic Press (Apr. 2001).
Holmgren, A., et al., "Conserved immunoglobulin-like features in a family of periplasmic pilus chaperones in bacteria," *EMBO J. 11*:1617-1622, Oxford University Press (1992).
Holmgren, A., and Brändén, C.-I., "Crystal structure of chaperone protein PapD reveals an immunoglobulin fold," *Nature 342*:248-251, Nature Publishing Group (1989).
Hultgren, S.J., et al., "The PapG Adhesin of uropathogenic *Escherichia coli* contains separate regions for receptor binding and for the incorporation into the pilus," *Proc. Nat. Acad. Sci. USA 86*:4357-4361, National Academy Press (1989).
Hultgren, S.J., et al., "PapD and superfamily of periplasmic immunoglobulin-like pilus chaperones," *Adv. Prot. Chem. 44*:99-123, Academic Press, Inc. (1993).
Hultgren, S.J., et al., "Pilus and Nonpilus Bacterial Adhesins: Assembly and Function in Cell Recognition," Cell 73:887-901, Cell Press (1993).
Hultgren, S.J., et al., "Bacterial Adhesins and Their Assembly," in *Escherichia coli and Salmonella*, Neidhardt, F.C., et al., eds., ASM Press, Washington, D.C. pp. 2730-2756 (1996).
Hung, D.L., et al., "Molecular basis of two subfamilies of immunoglobulin-like chaperones" *EMBO J. 15*:3792-3805, Oxford University Press (1996).
Hung, D.L. and Hultgren, S.J., "Pilus Biogenesis via the Chaperone/Usher Pathway: An Integration of Structure and Function," *J. Struct. Biol. 124*:201-220, Academic Press (1998).
Ikeda, T., et al., "Determination of Three Isoforms of the Receptor Activator of Nuclear Factor-kB Ligand and Their Differential Expression in Bone and Thymus," *Endocrinology 142*:1419-1426, The Endocrine Society (Apr. 2001).
Jacob-Dubuisson, F., et al., "PapD chaperone function in pilus biogenesis depends on oxidant and chaperone-like activities of DsbA," *Proc. Natl. Acad. Sci. USA 91*:11552-11556, National Academy Press (1994).
Jacob-Dubuisson, F., et al., "Initiation of assembly and association of the structural elements of a bacterial pilus depend on two specialized tip proteins," *EMBO J. 12*:837-847, Oxford University Press (1993).
Jacob-Dubuisson, F., et al., "Chaperone-assisted Self-assembly of Pili Independent of Cellular Energy," *J. Biol. Chem. 269*:12447-12455, The American Society for Biochemistry and Molecular Biology, Inc. (1994).
Jones, C.H., et al., "FimC is a periplasmic PapD-like chaperone that directs assembly of type 1 pili in bacteria," *Proc. Natl. Acad. Sci. USA 90*:8397-8401, National Academy Press (1993).
Jones, C.H., et al., "FimH adhesin of type 1 pili is assembled into a fibrillar tip structure in the Enterobacteriaceae," *Proc. Natl. Acad. Sci. USA 92*:2081-2085, National Academy Press (1995).
Josien, R., et al., "TRANCE, a Tumor Necrosis Factor Family Member, Enhances the Longevity and Adjuvant Properties of Dendritic Cells In Vivo," *J. Exp. Med. 191*:495-501, The Rockefeller University Press (Feb. 2000).
Jovanovic, D.V., et al., "IL-17 Stimulates the Production and Expression of Proinflammatory Cytokines, IL-β and TNF-α, by Human Macrophages," *J. Immunol. 160*:3513-3521, The American Association of Immunologists (1998).
Kim, K.J., et al., "Inhibition of vascular endothelial growth factor-induced angiogenesis suppresses tumour growth in vivo," *Nature 362*:841-844, Nature Publishing Group (1993).
Kim, K.-H., et al., "A Cysteine-rich Adipose Tissue-specific Secretory Factor Inhibits Adipocyte Differentiation," *J. Biol. Chem. 276*:11252-11256, The American Society for Biochemistry and Molecular Biology, Inc. (Apr. 2001).
Klemm, P., "The *fimA* gene encoding the type-1 fimbrial subunit of *Escherichia coli*. Nucleotide sequence and primary structure of the protein," *Euro. J. Biochem. 143*:395-399, Blackwell Science, Ltd. (1984).
Klemm, P., and Christiansen, G., "Three *fim* genes required for the regulation of length and mediation of adhesion of *Escherichia coli* type 1 fimbriae," Mol. Gen. Genet. 208:439-445, Springer-Verlag (1987).
Klemm, P., et al., "The major subunit of *Escherichia coli* type 1 fimbriate is not required for D-mannose-specific adhesion," *Mol. Microbiol. 4*:553-559, Blackwell Scientific Publications (1990).
Klemm, P., and Christiansen, G., "The *fimD* gene required for cell surface localization of *Escherichia coli* type 1 fimbriae," *Mol. Gen. Genet. 220*:334-338, Springer-Verlag (1990).
Klemm, P., "FimC, a chaperone-like periplasmic protein of *Escherichia coli* involved in biogenesis of type 1 fimbriae," *Res. Microbiol. 143*:831-838, Institut Pasteur/Elsevier (1992).
Klemm, P., and Krogfelt, K.A., "Type 1 Fimbriae of *Escherichia coli*,"in *Fimbriae*, Klemm, P., ed., CRC Press, Inc., Boca Raton, FL., pp. 9-26 (1994).
Koschel, M., et al., "Extensive Mutagenesis of the Hepatitis B Virus Core Gene and Mapping of Mutations That Allow Capsid Formation," *J. Virol 73*:2153-2160, American Society for Microbiology (1999).
Koths, K., et al., "Structure-Function Studies on Human Macrophage Colony-Stimulating Factor (M-CSF) ," *Mol. Reprod. Dev. 46*:31-38, Wiley-Liss, Inc. (1997).
Kuehn, M.J., et al., "Structural Basis of Pilus Subunit Recognition by the PapD Chaperone," *Science 262*:1234-1241, American Association for the Advancement of Science (1993).
Kunimoto, D.Y, et al., "High-level production of murine interleukin-5 (IL-5) utilizing recombinant baculovirus expression. Purification of the rIL-5 and its use in assessing the biologic role of IL-5 glycosylation," *Cytokine 3*:224-230, W.B. Saunders Company (1991).
Landschulz, W.H., et al., "The Leucine Zipper: A Hypothetical Structure Common to a New Class of DNA Binding Proteins," *Science 240*:1759-1764, American Association for the Advancement of Science (1988).
Leech, M., et al., "Involvement of macrophage migration inhibitory factor in the evolution of rat adjuvant arthritis," *Arthritis Rheum. 41*:910-917, Arthritis Foundation (1998).
Leech, M., et al. "Regulation of macrophage migration inhibitory factor by endogenous glucocorticoid in rat adjuvant-induced arthritis," *Arthritis Rheum. 43*:827-833, Arthritis Foundation (Apr. 2000).
Lin, E.Y., et al., "Colony-stimulating Factor 1 Promotes Progression of Mammary Tumors to Malignancy," *J. Exp. Med. 193*:727-739, The Rockefeller University Press (Mar. 2001).

Lindberg, F., et al., "PapD, a Periplasmic Transport Protein in P-Pilus Biogenesis," *J. Bacteriol. 171*:6052-6058, American Society for Microbiology (1989).
Lo-Man, R., et al., "A recombinant virus-like particle system derived from parvovirus as an efficient antigen carrier to elicit a polarized Th1 immune response without adjuvant," *Eur. J. Immunol. 28*:1401-1407, Wiley-VCH Verlag GmbH (1998).
López, O., et al., "Direct formation of mixed micelles in the solubilization of phospholipid liposomes by Triton X-100," *FEBS Lett. 426*:314-318, Elsevier (1998).
Lowe, M.A., et al., "Immunoelectron Microscopic Analysis of Elongation of Type 1 Fimbriae in *Escherichia coli*," *J. Bacteriol. 169*:157-163, Amerian Society for Microbiology (1987).
Lu, D., et al., "Identification of the Residues in the Extracellular Region of KDR Important for Interaction with Vascular Endothelial Growth Factor and Neutralizing Anti-KDR Antibodies," *J. Biol. Chem. 275*:14321-14330, The American Society for Biochemistry and Molecular Biology, Inc. (May 2000).
Lum, L., et al., "Evidence for a Role of a Tumor Necrosis Factor-α(TNF-α) -converting Enzyme-like Protease in Shedding of TRANCE, a TNF Family Member Involved in Osteoclastogenesis and Dendritic Cell Survival," *J. Biol. Chem. 274*:13613-13618, The American Society for Biochemistry and Molecular Biology, Inc. (1999).
Luther, S.A., et al., "BLC Expression in Pancreatic Islets Causes B Cell Recruitment and Lymphotoxin-Dependent Lymphoid Neogenesis," *Immunity 12*:471-481, Cell Press (May 2000).
Mackay, J.L., and Browning, J.L., "Turning off follicular dendritic cells," *Nature 395*:26-27, Macmillan Magazines, Ltd. (1998).
Martiny-Baron, G., and Marmé, D., "VEGF-mediated tumour angiogenesis: a new target for cancer therapy," *Curr. Opin. Biotechnol. 6*:675-680, Current Biology, Ltd. (1995).
Matsumoto, M., et al., "Role of Lymphotoxin and the Type 1 TNF Receptor in the Formation of Germinal Centers," *Science 271*:1289-1291, American Association for the Advancement of Science (1996).
Matthews, W., et al., "A receptor tyrosine kinase cDNA isolated from a population of enriched primitive hematopoietic cells and exhibiting close genetic linkage to *c-kit," Proc. Natl. Acad. Sci. USA 88*:9026-9030, National Academy Press (1991).
Matusevicius, D., et al., "Interleukin-17 mRNA expression in blood and CSF mononuclear cells is augmented in multiple sclerosis," *Mult. Scler. 5*:101-104, Stockton Press (1999).
McClain, M.S., et al., "Roles of *fimB* and *fimE* in Site-Specific DNA Inversion Associated with Phase Variation of Type 1 Fimbriae in *Escherichia coli," J. Bacteriol. 173*:5308-5314, American Society for Microbiology (1991).
McPherson, P.S., "Regulatory Role of SH3 Domain-mediated Protein-Protein Interactions in Synaptic Vesicle Endocytosis," *Cell Signal 11*:229-238, Elsevier Science, Inc. (1999).
Mikulowska, A., et al., "Macrophage Migration Inhibitory Factor Is Involved in the Pathogenesis of Collagen Type II-Induced Arthritis in Mice," *J. Immunol. 158*:5514-5517, The American Association of Immunologists (1997).
Millauer, B., et al., "Glioblastoma growth inhibited *in vivo* by a dominant-negative Flk-1 mutant," *Nature 367*:576-579, Nature Publishing Group (1994).
Min, H., et al., "Osteoprotegerin Reverses Osteoporosis by Inhibiting Endosteal Osteoclasts and Prevents Vascular Calcification by Blocking a Process Resembling Osteoclastogenesis," *J. Exp. Med. 192*:463-474, The Rockefeller University Press (Aug. 2000).
Montrasio, F. et al., "Impaired Prion Replication in Spleens of Mice Lacking Functional Follicular Dendritic Cells," *Science 288*:1257-1259, American Association for the Advancement of Science (May 2000).
Morein, B., et al., "Iscom, a novel structure for antigenic presentation of membrane proteins from enveloped viruses," *Nature 308*:457-460, Nature Publishing Group (1984).
Moriya, C., et al., "Large quantity production with extreme convenience of human SDF-1α and SDF-1β by a Sendai virus vector," *FEBS Lett. 425*:105-111, Amsterdam Elsevier Science B.V. (1998).
Müller, A., et al., "Involvement of chemokine receptors in breast cancer metastasis," *Nature 410*:50-56, Nature Publishing Group (Mar. 2001).
Murphy, Jr., K.P., et al., "Expression of Human Interleukin-17 in *Pichia pastoris*: Purification and Characterization," *Protein Expr. Purif. 12*:208-214, Academic Press (1998).
Nagira, M., et al., "Molecular Cloning of a Novel Human CC Chemokine Secondary Lymphoid-Tissue Chemokine That Is a Potent Chemoattractant for Lymphocytes and Mapped to Chromosome 9p13," *J. Biol. Chem. 272*:19518-19524, The American Society for Biochemistry and Molecular Biology, Inc. (1997).
Nanki, T., et al., "Stromal Cell-Derived Factor-1-CXC Chemokine Receptor 4 Interactions Play a Central Role in CD4* T Cell Accumulation in Rheumatoid Arthritis Synovium," *J. Immunol. 165*:6590-6598, The American Association of Immunologists (Dec. 2000).
Naureckiene, S., and Uhlin., B.E., "In vitro analysis of mRNA processing by Rnase E in the pap operon of *Esherichia coli*," *Mol. Microbiol. 21*:55-68, Blackwell Science, Ltd. (1996).
Newman, J.V., et al., "Stimulation of *Escherichia coli* F-18Col$^-$ Type-1 fimbriae synthesis by *leuX*," *FEMS Microbiol. Lett. 122*:281-287, Elsevier (1994).
Nilsson, P., et al., "Mutations Affecting mRNA Processing and Fimbrial Biogenesis in the *Escherichia coli pap* Operon," *J. Bacteriol. 178*:683-690, American Society for Microbiology (1996).
Oberlin, E., et al., "The CXC chemokine SDF-1 is the ligand for LESTR/fusin and prevents infection by T-cell—line-adapted HIV-1," *Nature 382*:833-835, Nature Publishing Group (1996).
Ohnishi, Y., et al., "Crystal Structure of Recombinant Native SDF-1α with Additional Mutagenesis Studies: An Attempt at a More Comprehensive Interpretation of Accumulated Structure-Activity Relationship Data," *J. Interferon Cytokine Res. 20*:691-700, Mary Ann Liebert, Inc. (Aug. 2000).
Olszewska, W., et al., "Protection against Measles Virus-Induced Encephalitis by Anti-mimotope Antibodies: The Role of Antibody Affinity," *Virology 272*:98-105, Academic Press (Jun. 2000).
Orndorff, P.E., and Falkow, S., "Identification and Characterization of a Gene Product That Regulates Type 1 Piliation in *Escherichia coli," J. Bacteriol. 160*:61-66, American Society for Microbiology (1984).
Orndorff, P.E., and Falkow, S., "Nucleotide Sequence of *pilA*, the Gene Encoding the Structural Component of Type 1 Pili in *Escherichia coli," J. Bacteriol. 162*:454-457, American Society for Microbiology (1985).
O'Shea, E.K., et al., "Evidence That the Leucine Zipper Is a Coiled Coil," *Science 243*:538-542, American Association for the Advancement of Science (1989).
Piossek, C., et al., "Vascular Endothelial Growth Factor (VEGF) Receptor II-derived Peptides Inhibit VEGF," *J. Biol. Chem. 274*:5612-5619, The American Society for Biochemistry and Molecular Biology, Inc. (1999).
Presta, L.G., et al., "Humanization of an Anti-Vascular Endothelial Growth Factor Monoclonal Antibody for the Therapy of Solid Tumors and Other Disorders," *Cancer Res. 57*:4593-4599, The American Association for Cancer Research (1997).
Risau, W., "Mechanisms of angiogenesis," *Nature 386*:671-674, Nature Publishing Group (1997).
O'Shea, E.K., et al., "Mechanism of Specificity in the Fos-Jun Oncoprotein Heterodimer," *Cell 68*:699-708, Cell Press (1992).
Pandit, J., et al., "Three-dimensional Structure of Dimeric Human Recombinant Macrophage Colony-Stimulating Factor," *Science 258*:1358-1362, American Association for the Advancement of Science (1992).
Pierson-Mullany, L.K., et al. "Characterization of polyclonal allergen-specific IgE responses by affinity distributions," *Mol. Immunol. 37*:613-620, Elsevier Science, Ltd. (Aug. 2000).
Ritter, A., et al., "The Pai-associated *lueX* specific $tRNA_5^{Leu}$ affects type 1 fimbriation in pathogenic *Escherichia coli* by control of FimB recombinase expression," *Mol. Microbiol. 25*:871-882, Blackwell Science, Ltd. (1997).
Roesch, P.L., and Blomfield, I.C., "Leucine alters the interaction of the leucine-responsive regulatory protein (Lrp) with the *fim* switch to stimulate site-specific recombination in *Escherichia coli*," *Mol. Microbiol.* 27:751-761, Blackwell Science, Ltd. (1998).

Roher, A.E., et al., "Isolation and Chemical Characterization of Alzheimer's Disease Paired Helical Filament Cytoskeletons: Differentiation from Amyloid Plaque Core Protein," *J. Cell Biol.* 107:2703-2716, The Rockefeller University Press (1988).

Roher, A.E., et al., "Morphological and Biochemical Analyses of Amyloid Plaque Core Proteins Purified from Alzheimer Disease Brain Tissue," *J. Neurochem.* 61:1916-1926, Raven Press, Ltd. (1993).

Romagnani, S., "The Th1/Th2 paradigm," *Immunol. Today* 18:263-266, Elsevier Science, Ltd. (1997).

Rusconi, S., et al., "In vitro inhibition of HIV-1 by Met-SDF-1β alone or in combination with antiretroviral drugs," *Antivir. Ther.* 5:199-204, International Medical Press (Sep. 2000).

Russell, P.W., and Orndorff, P.E., "Lesions in Two *Escherichia coli* Type 1 Pilus Genes Alter Pilus Number and Length without Affecting Receptor Binding," *J. Bacteriol.* 174:5923-5935, American Society for Microbiology (1992).

Santos, L., et al., "Role of macrophage migration inhibitory factor (MIF) in murine antigen-induced arthritis: interaction with glucocorticoids," *Clin. Exp. Immunol.* 123:309-314, Blackwell Science (Feb. 2001).

Saulino, E.T., et al., "Ramifications of kinetic partitioning on usher-mediated pilus biogenesis," *EMBO J.* 17:2177-2185, Oxford University Press (1998).

Schenk, D., et al., "Immunization with amyloid-β attenuates Alzheimer-disease-like pathology in the PDAPP mouse," *Nature* 400:173-177, Nature Publishing Group (1999).

Selkoe, D.J., "Translating cell biology into therapeutic advances in Alzheimer's disease," *Nature* 399:A23-A31, Nature Publishing Group (1999).

Slonim, L.N., et al., "Interactive surface in the PapD chaperone cleft is conserved in pilus chaperone superfamily and essential in subunit recognition and assembly," *EMBO J.* 11:4747-4756, Oxford University Press (1992).

Smyth, C.J., et al., "Fimbrial adhesins: similarities and variations in structure and biogenesis," *FEMS Immun. Med. Microbiol.* 16:127-139, Elsevier (1996).

Soto, H., et al., "The CC chemokine 6Ckine binds the CXC chemokine receptor CXCR3," *Proc. Natl. Acad. Sci. USA* 95:8205-8210, National Academy Press (1998).

Soto, G.E., et al., "Periplasmic chaperone recognition motif of subunits mediates quaternary interactions in the pilus," *EMBO J.* 17:6155-6167, Oxford University Press (1998).

Soto, G.E., and Hultgren, S.J., "Bacterial Adhesins: Common Themes and Variations in Architecture and Assembly," *J. Bacteriol.* 181:1059-1071, American Society for Microbiology (1999).

Steppan, C.M., et al., "The hormone resistin links obesity to diabetes," *Nature* 409:307-312, Nature Publishing Group (Jan. 2001).

Striker, R.T., et al., "Stable Fiber-forming and Nonfiber-forming Chaperone-Subunit Complexes in Pilus Biogenesis," *J. Biol. Chem.* 269:12233-12239, The American Society for Biochemistry and Molecular Biology, Inc. (1994).

Sturchler-Pierrat, C., et al., "Two amyloid precursor protein transgenic mouse models with Alzheimer disease-like pathology," *Proc. Natl. Acad. Sci. USA* 94:13287-13292, National Academy Press (1997).

Sun, H.-W., et al., "Crystal structure at the 2.6-Å resolution of human macrophage migration inhibitory factor," *Proc. Natl. Acad. Sci. USA* 93:5191-5196, National Academy Press (1996).

Tang, J.-L., et al., "Interleukin-17 antagonism inhibits acute but not chronic vascular rejection," *Transplantation* 72:348-350, Lippincott Williams & Wilkens (Jul. 2001).

Tanimori, H., et al., "Enzyme immunoassay of neocarzinostatin using β-galactosidase as label," *J. Pharm. Dyn.* 4:812-819, Pharmaceutical Society of Japan (1981).

Tewari, R., et al., "Neutrophil Activation by Nascent FimH Subunits of Type I Fimbriae Purified from the Periplasm of *Escherichia coli*," *J. Biol. Chem.* 268:3009-3015, The American Society for Biochemistry and Molecular Biology, Inc. (1993).

Teunissen, M.B.M., et al., "Interleukin-17 and Interferon-γ Synergize in the Enhancement of Proinflammatory Cytokine Production by Human Keratinocytes," *J. Invest. Dermatol.* 111:645-649, The Society for Investigate Dermatology, Inc. (1998).

Thanassi, D.G., et al., "The PapC usher forms an oligomeric channel: Implications for pilus biogenesis across the outer membrane," *Proc. Natl. Acad. Sci. USA* 95:3146-3151, National Academy Press (1998).

De Togni, P., et al., "Abnormal Development of Peripheral Lymphoid Organs in Mice Deficient in Lymphotoxin," *Science* 264:703-707, American Association for the Advancement of Science (1994).

Topchieva, I., and Karezin, K., "Self-Assembled Supramolecular Micellar Structures Based on Non-ionic Surfactants and Cyclodextrins," *J. Colloid Interface Sci.* 213:29-35, Academic Press (1999).

Vicari, A.P., et al., "Antitumor Effects of the Mouse Chemokine 6Ckine/SLC Through Angiostatic and Immunological Mechanisms," *J. Immunol.* 165:1992-2000, The American Association of Immunologists (Aug. 2000).

Visintin, M. et al., "Selection of antibodies for intracellular function using a two-hybrid *in vivo* system," *Proc. Natl. Acad. Sci. USA* 96:11723-11728, National Academy Press (1999).

Walse, B., et al., "Transferred nuclear Overhauser effect spectroscopy study of a peptide from the PapG pilus subunit bound by the *Escherichia coli* PapD chaperone," *FEBS Lett.* 412:115-120, Elsevier Science B.V. (1997).

Wei, Y.Q., et al., "Immunotherapy of tumors with xenogeneic endothelial cells as a vaccine," *Nat. Med.* 6:1160-1166, Nature Publishing Company (Oct. 2000).

Wong, C.K., et al., "Elevation of proinflammatory cytosine (IL-18, IL-17, IL-12) and Th2 cytokine (IL-4) concentrations in patients with systemic lupus erythematosus," *Lupus* 9:589-593, Macmillan Publishers Ltd. (2000).

Wu, Q., et al. "Reversal of Spontaneous Autoimmune Insulitis in Nonobese Diabetic Mice by Solube Lymphotoxin Receptor," *J. Exp. Med.* 193:1327-1332, The Rockefeller University Press (Jun. 2001).

Wuttke, M., et al., "Structural Characterization of Human Recombinant and Bone-derived Bone Sialoprotein," *J. Biol. Chem.* 276:36839-36848, The American Society for Biochemistry and Molecular Biology, Inc. (2001).

Wynne, S.A., et al., "The Crystal Structure of the Human Hepatitis B Virus Capsid," *Mol. Cell* 3:771-780, Cell Press (1999).

Yao, Z., et al., "Human IL-17: A Novel Cytokine Derived from T Cells," *J. Immunol.* 155:5483-5486, The American Association of Immunologists (1995).

Yao, Z., et al., "Molecular characterization of the human interleukin (IL)-17 receptor," *Cytokine* 9:794-800, Academic Press, Ltd. (1997).

Yone, K., et al., "Epitopic Regions for Antibodies against Tumor Necrosis Factor α," *J. Biol. Chem.* 270:19509-19515, The American Society for Biochemistry and Molecular Biology, Inc. (1995).

Ziolkowska, M., et al., "High Levels of IL-17 in Rheumatoid Arthritis Patients: IL-15 Triggers In Vitro IL-17 Production Via Cyclosporin A-Sensitive Mechanism," *J. Immunol.* 164:2832-2838, The American Association of Immunologists (Mar. 2000).

Zuercher, A.W., et al., "Oral anti-IgE immunization with epitode-displaying phage," *Eur. J. Immunol.* 30:128-135, Wiley-Vch Verlag GmbH (Jan. 2000).

Fehr, T., et al., "T cell-independent type I antibody response against B cell epitopes expressed repetitively on recombinant virus particles," *Proc. Acad. Sci. USA* 95:9477-9481, National Academy Press (1998).

Frenkel, D., et al., "Generation of auto-antibodies towards Alzheimer's disease vaccination," *Vaccine* 19:2615-2619, Elsevier Science, Ltd. (Mar. 2001).

International Search Report for International Application No. PCT/IB02/00166 mailed on Oct. 29, 2002.

International Search Report for International Application No. PCT/IB02/00168 mailed on Nov. 4, 2002.

Kratz, P.A., et al., "Native display of complete foreign protein domains on the surface of hepatitis B virus capsids," *Proc. Natl. Acad. Sci. USA* 96:1915-1920, National Academy of Science.

Nieland, J.D., et al., "Chimeric Papillomavirus Virus-like Particles Induce a Murine Self-Antigen-Specific Protective and Therapeutic Antitumor Immune Response," *J. Cell. Biochem. 73*:145-152, Wiley-Liss, Inc. (1999).
Slepushkin, V.A., et al., "Protection of mice against influenza A virus challenge by vaccination with baculovirus-expressed M2 protein," *Vaccine 13*:1399-1402, Elsevier Science Ltd. (1995).
Vasiljeva, I., et al., "Mosaic Qβ coats as a new presentation model," *FEBS Lett. 431*:7-11, Federation of European Biochemical Societies (1998).
Brown, K.D., et al., "A family of small inducible proteins secreted by leukocytes are members of a new superfamily that includes leukocyte and fibroblast-derived inflammatory agents, growth factors, and indicators of various activation processes," *J. Immunol. 142*:679-687. The American Association of Immunologists (1989).
Bachmann, M.F., and Zinkernagel R.M., "The influence of virus structure on antibody responses and virus serotype formation," *Immunol. Today 17*:553-558, Elsevier Science Ltd. (1996).
Bachmann, M.F., and Zinkernagel, R.M., "Neutralizing Antiviral B Cell Responses," *Annu. Rev. Immunol. 15*:235-270, Annual Reviews, Inc. (1997).
Beasley, R., et al., "Cellular Events in the Bronchi in Mild Asthma and after Bronchial Provocation," *Am. Rev. Respir. Dis. 139*:806-817, American Lung Association (1989).
Boeke. J.D., and Sandmeyer, S.B., "Yeast transposable elements," in *The Molecular and Cellular Biology of the Yeast Saccharomyces: Genome Dynamics, Protein Synthesis and Energetics*, Cold Spring Harbor Laboratory Press, pp. 193-261 (1991).
Bousquet, J., et al., "Eosinophilic inflammation in asthma," *N. Engl. J. Med. 323*:1033-1039, Massachusetts Medical Society (1990).
Broide, D.H., et al., "Evidence of ongoing mast cell and eosinophil degranulation in symptomatic asthma airways," *J. Allergy Clin. Immunol. 88*:637-648, Mosby-Year Book (1991).
Brombacher. F., "The role of interleukin-13 in infectious diseases and allergy." *Bioessays 22*:646-656, John Wiley & Sons, Inc. (Jul. 2000).
Brown, K.D., et al., "A family of small inducible proteins secreted by leukocytes are members of a new superfamily that includes leukocyte and fibroblast-derived inflammatory agents, growth factors, and indicators of various activation processes," *J. Immunol. 142*:679-687, The American Association of Immunologists (1989).
Brown, P.M., et al., "A Single-Step Purification of Biologically Active Recombinant Human Interleukin-5 from a Baculovirus Expression System," *Protein Expr. Purif. 6*:63-71, Academic Press, Inc. (1995).
Bullitt, E., and Makowski, L., "Bacterial Adhesion Pili Are Heterologous Assemblies of Similar Subunits," *Biophys. J. 74*:623-632, Biophysical Society (1998).
Bullitt, E., et al., "Development of pilus organelle subassemblies in vitro depends on chaperone uncapping of a beta zipper," *Proc. Natl. Acad. Sci. USA 93*:12890-12895, National Academy Press (1996).
Cannon-Carlson S., et al., "Expression, Purification, and Characterization of Recombinant Human Interleukin-13 from NS-O Cells," *Protein Expr. Purif. 12*:239-248, Academic Press (1998).
Chackerian, B., et al., "Induction of autoantibodies to mouse CCR5 with recombinant papilloma particles," *Proc. Natl. Acad. Sci. USA 96*:2373-2378, National Academy Press (1999).
Clark, H.F, et al., "Comparative Characterization of a C-Type Virus-Producing Cell Line (VSW) and a Virus-Free Cell Line (VH2) From Vipera russelli, " *J. Natl. Cancer Inst. 51*:645-657, Oxford University Press (1973).
Clark-Lewis, I., et al., "Chemical Synthesis, Purification, and Characterization of Two Inflammatory Proteins, Neutrophil Activating Peptide 1 (Interleukin-8) and Neutrophil Activating Peptide 2," *Biochemistry 30*:3128-3135, American Chemical Society (1991).
Coffman, R.L., et al., "Antibody to Interleukin-5 Inhibits Helminth-Induced Eosinophilia in Mice," *Science 245*:308-310, American Association for the Advancement of Science (1989).
Crump, M.P., et al., "Solution Structure of Eotaxin, a Chemokine That Selectively Recruits Eosinophils in Allergic Inflammation," *J. Biol. Chem. 273*:22471-22479. The American Society for Biochemistry and Molecular Biology, Inc. (1998).
Davis, N.L., et al., "In Vitro Synthesis of Infectious Venezuelan Equine Encephalitis Virus RNA from a cDNA Clone: Analysis of a Viable Deletion Mutant," *Virology 171*:189-204, Academic Press (1989).
De Monchy, J.G.R., et al., "Bronchoalveolar Eosinophilia during Allergen-induced Late Asthmatic Reactions," *Am. Rev. Respir. Dis. 131*:373-376, American Lung Association (1985).
Dickason, R.R., et al., "Engineering of a functional interleukin-5 monomer: a paradigm for redesigning helical bundle cytokines with therapeutic potential in allergy and asthma," *J. Mol. Med. 74*:535-546, Springer-Verlag (1996).
Dickason, R.R., et al., "Delineation of IL-5 Domains Predicted to Engage the IL-5 Receptor Complex," *J. Immunol. 156*:1030-1037, The American Association of Immunologists (1996).
Drazen, J. M., et al., "Sorting Out the Cytokines of Asthma," *J. Exp. Med. 183*:1-5, The Rockefeller University Press (1996).
Egan, R.W., et al., "Effect of Sch 55700, a Humanized Monoclonal Antibody to Human Interleukin-5, on Eosinophilic Responses and Bronchial Hyperreactivity," *Arzneim.-Forsch/Drug Res. 49*:779-790, Editio Cantor (1999).
Eisenmesser, E.Z., et al., "Expression, Purification, Refolding, and Characterization of Recombinant Human Interleukin-13: Uitilization of Intracellular Processing," *Protein Expr. Purif. 20*:186-195, Academic Press (Nov. 2000).
Eisenmesser, E.Z., et al., "Solution Structure of Interleukin-13 and Insights into Receptor Engagement," *J. Mol. Biol. 310*:231-241, Academic Press (Jun. 2001).
Eshdat, Y., et al., "Dissociation and Reassembly of *Escherichia coli* Type 1 Pili," *J. Bacteriol. 148*:308-314, American Society for Microbiology (1981).
Fehr, T., et al., "Role of Repetitive Antigen Patterns for Induction of Antibodies Against Antibodies," *J. Exp. Med. 185*:1785-1792, The Rockefeller University Press (1997).
Fitzgerald, K.A., et al., *The Cytokines Fact Book*, 2nd ed., Academic Press, San Diego, CA, pp. 64-68, 105-110, 213-220 (Sep. 2001).
Forssmann, U., et al., "Eotaxin-2, a Novel CC Chemokine that Is Selective for the Chemokine Receptor CCR3, and Acts Like Eotaxin on Human Eosinophil and Basophil Leukocytes," *J. Exp. Med. 185*:2171-2176, The Rockefeller University Press (1997).
Foster, P.S., et al., "Interleukin-5 and eosinophils as therapeutic targets for asthma," *Trends Mol. Med. 8*:162-167, Elsevier Science, Ltd. (Apr. 2002).
Foster, P.S., et al., "Interleukins-4, -5, and -13: emerging therapeutic targets in allergic disease," *Pharmacol. Ther. 94*:253-264 Elsevier Science, Inc. (Jun. 2002).
Geyson, H.M., et al., "Use of peptide synthesis to probe viral antigens for eptiopes to a resolution of a single amino acid," *Proc. Natl. Acad. Sci. USA 81*:3998-4002, National Academy Press (1984).
Golmohammadi, R., et al., "The crystal structure of bacteriophage Qβ at 3.5Å resolution," *Structure 4*:543-554, Current Biology, Ltd. (1996).
Graber, P., et al., "Identification of Key Charged Residues of Human Interleukin-5 in Receptor Binding and Cellular Activation," *J. Biol. Chem. 270*:15762-15769, The American Society for Biochemistry and Molecular Biology, Inc. (1995).
Grünig, G., et al., "Requirement for IL-13 Independently of IL-4 in Experimental Asthma," *Science 282*:2261-2263. American Association for the Advancement of Science (1998).
Harriman, G.R., "Measurment of Mouse and Human Interleukin 5," in *Current Protocols in Immunology*. Coligan, J.E., et al., eds., John Wiley & Sons, Inc., New York, NY, pp. 6.5.1-6.5.5 (1991).
Hart, L.A., et al., "Activation and Localization of Transcription Factor, Nuclear Factor-kβ, in Asthma," *Am. J. Respir. Crit. Care Med. 158*:1585-1592, American Thoracic Society (1998).
Hermanson, G.T., *Bioconjugate Techniques*, Academic Press, Inc., San Diego, CA, pp. 154-160 (1996).
Ho. S.N., et al., "Site-directed mutagenesis by overlap extension using the polymerase chain reaction," *Gene 77*:51-59, Elsevier (1989).
Humbles, A.A., et al., "Kinetics of Eotaxin Generation and Its Relationship to Eosinophil Accumulation in Allergic Airways Disease: Analysis in a Guinea Pig Model In Vivo," *J. Exp. Med. 186*:601-612, The Rockefeller University Press (1997).
Ingley E., et al., "Production and purification of recombinant human interleukin-5 from yeast and baculovirus expression systems," *Eur. J. Biochem. 196*:623-629, Blackwell Science, Ltd. (1991).
Jiang, X., et al., "Norwalk Virus Genome Cloning and Characterization," *Science 250*:1580-1583, American Association for the Advancement of Science (1990).
Kang, C.Y., et al., "Development of HIV/AIDS Vaccine Using Chimeric gag-env Virus-Like Particles," *Biol. Chem. 380*:353-364. Walter de Gruyter (1999).
Kapp, U., et al., "Interleukin 13 Is Secreted by and Stimulates the Growth of Hodgkin and Reed-Sternberg Cells," *J. Exp. Med. 189*:1939-1945, The Rockefeller University Press (1999).
Kastelein, R.A., et al., "Effect of the sequence upstream from the ribosome-binding site on the yield of protein from the cloned gene for phage MS2 coat protein," *Gene 23*:245-254, Elsevier (1983).
Kay, A.B., "Asthma and inflammation," *J. Allergy Clin. Immunol. 87*:893-910, Mosby-Year Book, Inc. (1991).
Klovins, J., et al., "Nucleotide sequence of a ssRNA phage from *Acinetobacter*. kinship to coliphages," *J. Gen. Virol. 83*:1523-1533, Society for General Microbiology (Jun. 2002).
Kodama, S., et al., "Characterization of recombinant murine interleukin 5 expressed in Chinese hamster ovary cells," *Glycobiology 2*:419-427, Oxford University Press (1992).
Kodama, S., et al., "Carbohydrate Structures of Human Interleukin 5 Expressed in Chinese Hamster Ovary Cells," *J. Biochem.* (*Tokyo*) 110:693-701, Japanese Biochemical Society (1991).
Kopf, M., et al., "IL-5-Deficient Mice Have a Developmental Defect in CD5+ B-1 Cells and Lack Eosinophilia but have Normal Antibody and Cytotoxic T Cell Responses," *Immunity 4*:15-24, Cell Press (1996).
Kozlovska, T.M., et al., "Recombinant RNA phage Qβ capsid particles synthesized and self-assembled in Escherichia coli," *Gene 13*:133-137, Elsevier Science Publishers B.V. (1993).
Kozlovska, T.M., et al., "RNA Phage Qβ Coat Protein as a Carrier for Foreign Epitopes," *Intervirology 39*:9-15, Karger (1996).
Kozlovskaya, T.M., et al., "Formation of capsid-like structures as a result of the expression of a cloned envelope protein gene from RNA-containing bacteriophage fr," *Dokl. Akad. Nauk. SSSR 287*: 452-455, Erivan Akademiia Nauk Armianskoi Ssr (1986).
Kozlovskaya, T.M., et al., "Formation of capsid-like structures as a result of the expression of a cloned envelope protein gene from RNA-containing bacteriophage fr," STNEasy, Accession No. 1986:219892, CAplus English abstract (1986) (Document AT37).
Kunimoto, D.Y., et al., "High-level production of murine interleukin-5 (IL-5) utilizing recombinant baculovirus expression. Purification of the rIL-5 and its use in assessing the biologic role of IL-5 glycosylation," *Cytokine 3*:224-230, W.B. Saunders Company (1991).
Kuperman. D.A., et al., "Direct effects of interleukin-13 on epithelial cells cause airway hyperreactivity and mucus overproduction in asthma," *Nat. Med. 8*:885-889, Nature Publishing Company (Aug. 2002).
Leake, C.J., et al., "Cytopathic Effect and Plaque Formation by Abroviruses in a Continuous Cell Line (XTC-2) from the Toad Xenopus laevis," *J. gen. Virol. 35*:335-339, Cambridge University Press (1977).
Lee, K.H., et al., "Two-Dimensional Electrophoresis of Proteins as a Tool in the Metabolic Engineering of Cell Cycle Regulation," *Biotech. Bioeng. 50*:336-340, John Wiley & Sons, Inc. (1996).
Liljeström, P., and Garoff, H., "A new generation of animal cell expression vectors based on the semliki forest virus replicon," *Bio/technology 9*:1356-1361. Nature Publishing Company (1991).
Liljeström, P., "Alphavirus expression systems," *Curr. Opin. Biotechnol. 5*:495-500, Current Biology, Ltd. (1994).
Lim, F., et al., "The RNA-binding Site of Bacteriophage Qβ Coat Protein," *J. Biol. Chem. 271*:31839-31845, The American Society for Biochemistry and Molecular Biology, Inc. (1996).
Lundstrom, K., "Alphaviruses as expression vectors," *Curr. Opin. Biotechnol. 8*:578-582, Current Biology, Ltd. (1997).
Matsui, S.M., et al., "The Isolation and Characterization of a Norwalk Virus-Specific cDNA," *J. Clin. Invest. 87*:1456-1461, The American Society for Clinical Investigation, Inc. (1991).
Mayer, K.L., and Stone, M.J., "NMR Solution Structure and Receptor Peptide Binding of the CC Chemokine Eotaxin-2," *Biochemistry 39*:8382-8395, American Chemical Society (Jul. 2000).
Milburn, M.V., et al., "A novel dimer configuration revealed by the crystal structure at 2.4 Å resolution of human interleukin-5," *Nature 363*:172-176, Nature Publishing Company (1993).
Mitchell, D.L., et al., "Purification and characterization of recombinant murine interleukin-5 glycoprotein, from a Baculovirus expression system," *Biochem. Soc. Trans. 21*:332S, Portland Press (1993).
Nakajima, H., et al., "CD4+ T Lymphocytes and Interleukin-5 Mediate Antigen-induced Eosinophil Infiltration into the Mouse Trachea," *Am. Rev. Respir. Dis. 146*:374-377, American Lung Association (1992).
Neirynck, S., et al., "A universal influenza A vaccine based on the extracellular domain of the M2 protein," *Nat. Med. 5*:1157-1163, Nature Publishing Company (1999).
Ni, C.-Z., et al., "Crystal structure of the coat protein from the GA bacteriophage: Model of the unassembled dimer," *Protein Sci. 5*:2485-2493, Cambridge University Press (1996).
Noso, N., et al., "Delayed production of biologically active O-glycosylated forms of human eotaxin by tumor-necrosis-factor-α-stimulated dermal fibroblasts," *Eur. J. Biochem. 253*:114-122, Blackwell Science Ltd. on behalf of the Federation of European Biochemical Societies (1998).
Ohashi, Y., et al., "Airway Hyperresponsiveness, Increased Intracellular Spaces of Bronchial Epithelium, and Increased Infiltration of Eosinophils and Lymphocytes in Bronchial Mucosa in Asthma," *Am. Rev. Respir. Dis. 145*:1469-1476, American Lung Association (1992).
Pierrot, C., et al., "Expression of Rat Interleukin-5 and Generation of Neutralizing Antiserum: a Comparative Study of Rat IL-5 Produced in Escherichia coli and Insect Cells," *Biochem. Biophys. Res. Commun. 253*:756-760, Academic Press (1998).
Priano, C., et al., "A Complete Plasmid-based Complementaion System for RNA Coliphage Qβ: Three Proteins of Bacteriophages Qβ (Group III) and SP (Group IV) can be Interchanged," *J. Mol. Biol. 249*:283-297, Academic Press, Ltd. (1995).
Proudfoot, A.E.I., et al., "The Carboxy-Terminal Region of Human Interleukin-5 Is Essential for Maintenance of Tertiary Structure but Not for Dimerization," *J. Protein Chem. 15*:491-499, Plenum Publishing Corporation (1996).
Proudfoot, A.E.I., et al., "Preparation and characterization of human interleukin-5 expressed in recombinant Escherichia coli," *Biochem. J. 270*:357-361, Portland Press, Ltd. (1990).
Pumpens, P., and Grens, E., "HBV Core Particles as a Carrier for B Cell/T Cell Epitopes," *Intervirology 44*:98-114, S. Karger AG (Aug. 2001).
Pushko, P., et al., "Analysis of RNA phage *fr* coat protein assembly by insertion, deletion and substitution mutagenesis," *Prot. Eng. 6*:883-891, Oxford University Press (1993).
Renner, W.A., et al., "Recombinant Cyclin E Expression Activates Proliferation and Obviates Surface Attachment of Chinese Hamster Ovary (CHO) Cells in Protein-Free Medium," *Biotech. Bioeng. 47*:476-482. John Wiley & Sons, Inc. (1995).
Robinson, D.S., et al., "Predominant $T_{H2}$-Like Bronchoalveolar T-Lymphocyte Population in Atopic Asthman," *N. Engl. J. Med. 326*:298-304, Massachusetts Medical Society (1992).
Robinson, D., et al., "Activation of CD4+ T cells, increased $T_{H2}$-type cytokine mRNA expression, and eosinophil recruitment in bronchoalveolar lavage after allergen inhalation challenge in patients with atopic asthma," *J. Allergy Clin. Immunol. 92*:313-324, Mosby-Year Book, Inc. (1993).
Robinson, D.S., et al., "Relationships among numbers of bronchoalveolar lavage cells expressing messenger ribonucleic acid for cytokines, asthma symptoms, and airway methacholine responsiveness in atopic asthma," *J. Allergy Clin. Immunol. 92*:397-403, Mosby-Year Book, Inc. (1993).
Roth, J.-F., "The yeast Ty virus-like particles," *Yeast 16*:785-795, John Wiley & Sons, Ltd. (Jun. 2000).

Rothenberg, M.E., et al., "Targeted Disruption of the Chemokine Eotaxin Partially Reduces Antigen-induced Tissue Eosinophilia," *J. Exp. Med. 185*:785-790, The Rockefeller University Press (1997).
Rueda, P., et al., "Minor Displacements in the Insertion Site Provoke Major Differences in the Induction of Antibody Responses by Chimeric Parvovirus-like Particles," *Virology 263*:89-99, Academic Press (1999).
Schlesinger, S., "Alphaviruses—vectors for the expression of heterologous genes," *Trends Biotechnol. 11*:18-22, Elsevier Science Publishers, Ltd. (1993).
Smiley, B.K., and Minion, F.C., "Enhanced readthrough of opal (UGA) stop codons and production of *Mycoplasma pneumoniae* P1 epitopes in *Escherichia coli*," Gene 134:33-40, Elsevier Science Publishers B.V. (1993).
Stoll, E., et al., "Revised Amino Acid Sequence of Qβ Coat Protein between Positions 1 and 60," *J. Biol. Chem. 252*:990-993, American Society for Biochemistry and Molecular Biology (1977).
Stollar, V., "Togaviruses in Cultured Arthropod Cells," in *The Togaviruses. Biology, Structure, Replication*, Schlesinger, R.W., ed., Academic Press, Inc. New York, N.Y., pp. 583-621 (1980).
Strauss, J., and Strauss, E.G., "The Alphviruses: Gene Expression, Replication, and Evolution," *Microbiol. Rev. 58*:491-562, American Society for Microbiology (1994).
Takahashi, T., et al., "Structural comparison of murine T-cell (B151K12)-derived T-cell-replacing factor (IL-5)with rIL-5: Dimer formation is essential for the expression of biological activity," *Mol. Immunol. 27*:911-920, Pergamon Press (1990).
Taylor, K.M., et al., "Position-Dependent Processing of Peptides Presented on the Surface of Cowpea Mosaic Virus," *Biol. Chem. 380*:387-392, Walter de Gruyter (1999).
Teixeira, M.M., et al., "Chemokine-induced Eosinophil Recruitment. Evidence of a Role for Endogenous Eotaxin in an In Vivo Allergy Model in Mouse Skin," *J. Clin. Invest. 100*:1657-1666, The American Society for Clinical Investigation, Inc. (1997).
Tominaga, A., et al., "Role of carbohydrate moiety of IL-5: Effect of Tunicamycin on the Glycosylation of IL-5 and the Biologic Activity of Deglycosylated IL-5," *J. Immunol. 144*:1345-1352, The American Association of Immunologists (1990).
Trifilieff, A., et al., "IL-5 deficiency abolishes aspects of airways remodelling in a murine model of lung inflammation," *Clin. Exp. Allergy 31*:934-942, Blackwell Science, Ltd. (Jun. 2001.)
Twomey, T., et al., "Structure and immunogenicity of experimental foot-and-mouth disease and poliomyelitis vaccines," *Vaccine 13*:1603-1610, Elsevier Science. Ltd. (1995).
Ulrich, R., et al., "Core particles of hepatitis B virus as carrier for foreign epitopes," *Adv. Virus Res. 50*:141-182, Academic Press (1998).
Walker, C., et al., "Activated T cells and eosinophilia in bronchoalveolar lavages from subjects with asthma correlated with disease severity," *J. Allergy Clin. Immunol. 88*:935-942, Mosby-Year Book (1991).
Walker, C., et al., "Allergic and Nonallergic Asthmatics Have Distinct Patterns of T-Cell Activation and Cytokine Production in Peripheral Blood and Bronchoalveolar Lavage," *Am. Rev. Respir. Dis. 146*:109-115, American Lung Association (1992).
Walter, D., et al., "Critical Role for IL-13 in the Development of Allergen-Induced Airway Hyperreactivity," *J. Immunol. 167*:4668-4675, The American Association of Immunologists (Oct. 2001).
Wardlaw, A.J., et al., "Eosinophils and Mast Cells in Bronchoalveolar Lavage in Subjects with Mild Asthma, Relationship to Bronchial Hyperreactivity," *Am. Rev. Respir. Dis. 137*:62-69, American Lung Association (1988).
Warnes, A., et al., "Expression of the measles virus nucleoprotein gene in Escherichia coli and assembly of nucleocapsid-like structures," *Gene 160*:173-178, Elsevier Science B.V. (1995).
Watson, E., et al., "Structure determination of the intact major sialylated oligosaccharide chains of recombinant human erythropoietin expressed in Chinese hamster ovary cells," *Glycobiology 4*:227-237, Oxford University Press (1994).
Wills-Karp, M., et al., "Interleukin-13: Central Mediator of Allergic Asthma," *Science 282*:2258-2261, American Association for the Advancement of Science (1998).
Witherell, G.W., and Uhlenbeck, O.C., "Specific RNA Binding by Qβ Coat Protein," *Biochemistry 28*:71-76, American Chemical Society (1989).
Xiong, C., et al., "Sindbis Virus: An Efficient, Broad Host Range Vector for Gene Expression in Animal Cells," *Science 243*:1188-1191, American Association for the Advancement of Science (1989).
Yuan, T-T., et al., "Subtype-Independent Immature Secretion and Subtype-Dependent Replication Deficiency of a Highly Frequent, Naturally Occurring Mutation of Human Hepatitis B Virus Core Antigen," *J. Virol. 73*:10122-10128, American Society for Microbiology (1999).
Zang, M., et al., "Production of Recombinant Proteins in Chinese Hamster Ovary Cells Using A Protein-Free Cell Culture Medium," *Bio/Technology 13*:389-392, Nature Publishing Company (1995).
Zhou, S., and Standring, D.N., "Cys Residues of the Hepatitis B Virus Capsid Protein Are Not Essential for the Assembly of Viral Core Particles but Can Influence Their Stability," *J. Virol 66*:5393-5398, American Society for Microbiology (1992).
Zia-Amirhosseini, P., et al., "Pharmacokinetics and Pharmacodynamics of SB-240563, a Humanized Monoclonal Antibody Directed to Human Interleukin-5, in Monkeys," *J. Pharmacol. Exp. Ther. 291*:1060-1067, The American Society for Pharmacology and Experimental Therapeutics (1999).
Zimmermann, N., et al., "Murine Eotaxin-2: A Constitutive Eosinophil Chemokine Induced by Allergen Challenge and IL-4 Overexpression," *J. Immunol. 165*:5839-5846, The American Association of Immunologists (Nov. 2000).
Dialog File 351, Accession No. 4796523, Derwent WPI English language abstract for EP 0 201 416 (Document AL1).
Invitrogen Catalog No. K750-01, "Sindbis Expression System," Version E, Invitrogen Corporation (1998).
Baba, T.W., et al., "Pathogenicity of Live, Attenuated SIV After Mucosal Infection of Neonatal Macaques," *Science 267*:1820-1825, American Association for the Advancement of Science (1995).
Bachmann, M.F., et al., "Dendritic cells process exogenous viral proteins and virus-like particles for Class I presentation to $CD8^+$ cytotoxic T lymphocytes," *Eur. J. Immunol. 26*:2595-2600, VCH Verlagsgesellschaft mbH (1996).
Boorsma, M., et al., "A temperature-regulated replicon-based DNA expression system," *Nat. Biotechnol. 18*:429-432, Nature America, Inc. (Apr. 2000).
Borisova, G., et al., "Hybrid Hepatitis B Virus Nucleocapsid Bearing an Immunodominant Region from Hepatitis B Virus Surface Antigen," *J. Virol. 67*:3696-3701, American Society for Microbiology (1993).
Cesareni, G., "Peptide display on filamentous phage capsids: A new powerful tool to study protein-ligand interaction," *FEBS Lett. 307*:66-70, Elsevier Science Publishers B.V. (1992).
Connor, R.I., et al., "Immunological and Virological Analyses of Persons Infected by Human Immunodeficiency Virus Type 1 while Participating in Trials of Recombinant gpl20 Subunit Vaccines," *J. Virol. 72*:1552-1576, American Society for Microbiology (1998).
Crameri, R. and Suter, M., "Display of biologically active proteins on the surface of filamentous phages: a cDNA cloning system for selection of functional gene products linked to the genetic information responsible for their production," *Gene 137*:69-75, Elsevier Science Publishers B.V. (1993).
Daniel, M.D., et al., "Protective Effects of a Live Attenuated SIV Vaccine with a Deletion in the *nef* Gene," *Science 258*:1938-1941, American Association for the Advancement of Science (1992).
de la Cruz, V.F., et al., "Immunogenicity and Epitope Mapping of Foreign Sequences via Genetically Engineered Filamentous Phage," *J. Biol. Chem. 263*:4318-4322, The American Society for Biochemistry and Molecular Biology, Inc. (1988)
Donnelly, J.J., et al., "DNA Vaccines," *Annu. Rev. Immunol. 15*:617-648, Annual Reviews, Inc. (1997).
Ebina, S., et al., "Chemical Modification of Bovine Pancreatic Trypsin Inhibitor for Single Site Coupling of Immunogenic Peptides for NMR Conformational Analysis," *J. Biol. Chem. 264*:7882-7888, The American Society for Biochemistry and Molecular Biology, Inc. (1989).

Esposito, G., et al., "Conformational study of a short *Pertussis* toxin T Cell epitope incorporated in a multiple antigen peptide template by CD and two-dimensional NMR: Analysis of the structural effects on the activity of synthetic immunogens," *Eur. J. Biochem. 217*:171-187, Blackwell Science Ltd. on behalf of the Federation of European Biochemical Societies (1993).
Förster, E., et al., "Natural and recombinant enzymatically active or inactive bee venom phospholipase $A_2$ has the same potency to release histamine from basophils in patients with Hymenoptera allergy," *J. Allergy Clin. Immunol. 95*:1229-1235, Mosby-Year Book, Inc. (1995).
Frolov, I., et al., "Alphavirus-based expression vectors: Strategies and applications," *Proc. Natl. Acad. Sci. USA 93*:11371-11377, National Academy Press (1996).
Gilbert, S.C., et al., "A protein particle vaccine containing multiple malaria epitopes," *Nat. Biotechnol. 15*:1280-1284, Nature America Publishing (1997).
Greenstone, H.L., et al., "Chimeric paillomavirus virus-like particles elicit antitumor immunity against the E7 oncoprotein in an HPV16 tumor model," *Proc. Natl. Acad. Sci. USA 95*:1800-1805, National Academy Press (1998).
Hahn, C.S., et al., "Infectious Sindbis virus transient expression vectors for studying antigen processing and presentation," *Proc. Natl. Acad. Sci. USA 89*:2679-2683, National Academy Press (1992).
Harding, C.V., and Song, R., "Phagocytic Processing of Exogenous Particulate Antigens by Macrophages for Presentation by MHC Molecules," *J. Immunol. 153*:4925-4933, The American Association of Immunologists (1994).
Hilleman, M.R., "Six decades of vaccine development —a personal history," *Nat. Med. Vaccine Suppl. 4*:507-514 (May 1998).
Hui, E. K-W. et al., "Hepatitis B viral core proteins with an N-terminal extension can assemble into core-like particles but cannot be enveloped," *J. Gen. Virol. 80*:2647-2659, Society for General Microbiology (1999).
Iannolo, G., et al., "Construction, Exploitation and Evolution of a New Peptide Library Displayed at High Density by Fusion to the Major Coat Protein of Filamentous Phage," *Biol. Chem. 378*:517-521, Walter de Gruyter & Co. (1997).
Iannolo, G., et al., "Modifying Filamentous Phage Capsid: Limits in the Size of the Major Capsid Protein," *J. Mol. Biol. 248*:835-844, Academic Press, Ltd. (1995).
Ikram, H., and Prince, A.M., "A method for coupling the Hepatitis B surface antigen to aldehyde-fixed erythrocytes for use in passive hemagglutination," *J. Virol. Methods 2*:269-275, Elsevier/North-Holland Biomedical Press (1981).
Kovacsovics-Bankowski, M., et al., "Efficient major histocompatibility complex class I presentation of exogenous antigen upon phagocytosis by macrophages," *Proc. Natl. Acad. Sci. USA 90*:4942-4946, National Academy Press (1993).
Lo, K. K-W., et al., "Surface-modified mutants of cytochrome P450cam: enzymatic properties and electrochemistry," *FEBS Lett. 451*:342-346, Elsevier Science B.V. on behalf of the Federation of European Biochemical Societies (1999).
Minenkova, O.O., et al., "Design of specific immunogens using filamentous phage as the carrier," *Gene 128*:85-88, Elsevier Science Publishers B.V. (1993).
Neurath, A.R., et al., "Hepatitis B Virus surface antigen (HBsAg) as carrier for synthetic peptides having an attached hydrophobic tail," *Mol. Immunol. 26*:53-62, Pergamon Press (1989).
Perham, R.N., et al., "Engineering a peptide epitope display system on filamentous bacteriophage," *FEMS Microbiol. Rev. 17*:25-31, Elsevier Science Publishers on behalf of the Federation of European Microbiological Societies (1995).
Petrenko, V.A., et al., "A library of organic landscapes on filamentous phage," *Protein Engin. 9*:797-801, Oxford University Press (1996).
Pumpens, P. and Grens, E., "Hepatitis B core particles as a universal display model: a structure-function basis for development," *FEBS Lett. 442*:1-6, Elsevier Science B.V. on behalf of the Federation of European Biochemical Societies (1999).
Quash, G., et al., "The preparation of latex particles with covalently bound polyamines IgG and measles agglutinins and their use in visual agglutination tests," *J. Immunol. Methods 22*:165-174, Elsevier/North-Holland Biomedical Press (1978).
Raychaudhuri, S., and Rock, K.L., "Fully mobilizing host defense: Building better vaccines," *Nat. Biotechnol. 16*:1025-1031, Nature America, Inc. (1998).
Redfield, R.R., et al., "Disseminated vaccinia in a military recruit with Human Immunodeficiency Virus (HIV) disease," *N. Eng. J. Med. 316*:673-676, Massachusetts Medical Society (1987).
Rudolf, M.P., et al., Molecular Basis for Nonanaphylactogenicity of a Monoclonal Anti-IgE Antibody, *J. Immunol. 165*:813-819, The American Association of Immunologists (2000).
Sedlik, C., et al., "Recombinant parvovirus-like particles as an antigen carrier: A novel nonreplicative exogenous antigen to elicit protective antiviral cytotoxic T cells," *Proc. Natl. Acad. Sci. USA 94*:7503-7508, National Academy Press (1997).
Shen, L., et al., "Recombinant Virus Vaccine-Induced SIV-Specific $CD8^+$ Cytotoxic T Lymphocytes," *Science 252*:440-443, American Association for the Advancement of Science (1991).
Tanimori, h., et al., "Enzyme Immunoassay of Neocarzinostatin Using β-Galactosidase as Label," *J. Pharm. Dyn. 4*:812-819, Pharmaceutical Society of Japan (1981).
Townsend, A., and Bodmer, H., "Antigen recognition by class I-restricted T lymphocytes," *Ann. Rev. Immunol. 7*:601-624, Annual Reviews, Inc. (1989).
Van Cott, T.C., et al., "Antibodies with Specificity to Native gp120 and Neutralization Activity against Primary Human Immunodeficiency Virus Type 1 Isolates Elicited by Immunization with Oligomeric gp160," *J. Virol. 71*:4319-4330, American Society for Microbiology (1997).
Watkins, S.J., et al., "The 'adenobody' approach to viral targeting: specific and enhanced adenoviral gene delivery," *Gene Ther. 4*:1004-1012, Stockton Press (1997).
Willis, A.E., et al., "Immunological properties of foreign peptides in multiple display on a filamentous bacteriophage," *Gene 128*:79-83, Elsevier Science Publishers B.V. (1993)
Dialog File 351, Accession No. 7431992, Derwent WPI English language abstract for WO 94/06472 (Document AM6).
International Preliminary Examination Report for International Application No. PCT/IB99/01925, European Patent Office, Munich (Aug., 2000) (not for publication).
International Search Report for International Application No. PCT/IB99/01925, European Patent Office, Netherlands (Jun., 2000) (not for publication).
Adams. S.E., et al., "The expression of hybrid HIV: Ty virus-like particles in yeast," *Nature 329*:68-70, Nature Publishing Group (1987).
Adhin, M.R., et al., "Nucleotide Sequence from the ssRNA Bacteriophage JP34 Resolves the Discrepancy between Serological and Biophysical Classification," *Virology 170*:238-242, Academic Press, Inc. (1989).
Azzawi. M., et al., "Identification of Activated T Lymphocytes and Eosinophils in Bronchial Biopsies in Stable Atopic Asthma," *Am. Rev. Respir. Dis. 142*:1407-1413, American Lung Association (1990).
Cho, Y.S., et al., "α-Lipoic acid inhibits airway inflammation and hyperresponsiveness in a mouse model of asthma," *J. Allergy Clin. Immunol. 114*:429-435, American Academy of Allergy, Asthma, and Immunology (2004).
Egan, R.W., et al., Abstract of "Inhibition of pulmonary eosinophilia and hyperreactivity by antibodies to interleukin-5," *Int. Arch. Allergy Immunol. 107*:321-322, S. Karger (1995).
Egan, R.W., et al., Abstract of "Pulmonary biology of anti-interleukin 5 antibodies," *Mem. Inst. Oswaldo Cruz 92* (*Suppl. 2*):69-73, Instituto Oswaldo Cruz (1997).
Eum, S-Y., et al., "Inhibition of allergic airways inflammation and airway hyperresponsiveness in mice by dexamethasone: Role of eosinophils, IL-5, eotaxin, and IL-13," *J. Allergy Clin. Immunol. 111*:1049-1061, Mosby-Year Book (2003).
Flood-Page, P., et al., "Anti-IL-5 treatment reduces deposition of ECM proteins in the bronchial subepithelial basement membrane of mild atopic asthmatics," *J. Clin. Invest. 112*:1029-1036, American Society for Clinical Investigation (2003).

Fujitani, Y., et al., "Pronounced Eosinophilic Lung Inflammation and Th2 Cytokine Realease in Human Lipocalin-Type Prostaglandin D Synthase Transgenic Mice," *J. Immunol. 168*:443-449, American Association of Immunologists (Jan. 2002).

Heiser, A., et al., "Autologous dendritic cells transfected with prostate-specific antigen RNA stimulate CTL resposes against metastatic prostate tumors," *J. Clin. Invest. 109*:409-417, American Society for Clinical Investigation (Feb. 2002).

Hodge, J.W., et al., "Vaccine Therapy of Established Tumors in the Absence of Autoimmunity," *Clin. Cancer Res. 9*:1837-1849, American Association for Cancer Research (2003).

Iwata, A., et al., "A Broad-Spectrum Caspase Inhibitor Attenuates Allergic Airway Inflammation in Murine Asthma Model," *J. Immunol. 170*:3386-3391, American Association of Immunologists (2003).

Kips, J.C., et al., "Effect of SCH55700, a Humanized Anti-Human Interleukin-5 Antibody, in Severe Persistent Asthma: A Pilot Study," *Am. J. Respir. Crit. Care Med. 167*:1655-1659, American Thoracic Society (2003).

Mattes, J., et al., "Intrinsic Defect in T Cell Production Production of Interleukin (IL)-13 in the Absence of Both IL-5 and Eotaxin Precludes the Development of Eosinophilia and Airways Hyperreactivity in Experimental Asthma," *J. Exp. Med. 195*:1433-1444, Rockefeller University Press (Jun. 2002).

McKay, A., et al., "A Novel Anti-Inflammatory Role of Simvastatin in a Murine Model of Allergic Asthma," *J. Immunol. 172*:2903-2908, American Association of Immunologists (2004).

Pasek, M., et al., "Hepatitis B virus genes and their expression in *E. coli*," *Nature 282*:575-579, Macmillan Journal Ltd (1979).

Pastva, A., et al., "Aerobic Exercise Attenuates Airway Inflammatory Responses in a Mouse Model of Atopic Asthma," *J. Immunol. 172*:4520-4526, American Association of Immunologists (2004).

Rådinger, M., et al., "Eotaxin-2 regulates newly produced and $CD34^+$ airway eosinophils after allergen exposure," *J. Allergy Clin. Immunol. 113*:1109-1116, American Academy of Allergy, Asthma, and Immunology (2004).

Rothenberg, M.E., et al., "Targeted Disruption of the Chemokine Eotaxin Partially reduces Antigen-induced Tissue Eosinophilia," *J. Exp. Med. 185*:785-790, Rockefeller University Press (1997).

Singer, M., et al., "A MARCKS-related peptide blocks mucus hypersecretion in a mouse model of asthma," *Nat. Med. 10*:193-196, Nature Pub. Co. (2004).

Tomkinson, A., et al., "A Murine IL-4 Receptor Antagonist That Inhibits IL-4- and IL-13-Induced Responses Prevents Antigen-Induced Airway Eosinophilia and Airway Hyperresponsiveness," *J. Immunol. 166*:5792-5800, American Association of Immunologists (2001).

Webb, D.C., et al., "Distinct spatial requirement for eosinophil-induced airways hyperreactivity," *Immunol. Cell Biol. 79*:165-169, Blackwell Scientific Publications (2001).

Wills-Karp, M., et al., "Interleukin-13: Central Mediator of Allergic Asthma," *Science 282*:2258-2261, American Association for the Advancement of Science (1998).

Zhu, Z., et al., "Acidic Mammalian Chitinase in Asthmatic Th2 Inflammation and IL-13 Pathway Activation," *Science 304*:1678-1682, American Association for the Advancement of Science (2004).

Office Action mailed Jun. 6, 2001, for U.S. Appl. No. 09/449,631, Renner et al., filed Nov. 30, 1999.

Office Action mailed Feb. 27, 2002, for U.S. Appl. No. 09/449,631, Renner et al., filed Nov. 30, 1999.

Office Action mailed Aug. 30, 2002, for U.S. Appl. No. 09/848,616, Sebbel et al., filed May 4, 2001.

Office Action mailed Nov. 14, 2002, for U.S. Appl. No. 09/449,631, Renner et al., filed Nov. 30, 1999.

Office Action mailed Feb. 7, 2003, for U.S. Appl. No. 09/848,616, Sebbel et al., filed May 4, 2001.

Office Action mailed Oct. 31, 2003, for U.S. Appl. No. 09/848,616, Sebbel et al., filed May 4, 2001.

Office Action mailed Mar. 1, 2004, for U.S. Appl. No. 10/050,902, Renner et al., filed Jan. 18, 2002.

International Search Report for International Patent Application No. PCT/IB02/00166, mailed Jan. 31, 2003, European Patent Office, Netherlands.

International Search Report for International Patent Application No. PCT/IB01/00741, mailed Mar. 5, 2002, European Patent Office, Netherlands.

Klion, A.D., et al., "Safety and efficacy of the monoclonal anti-interleukin-5 antibody SCH55700 in the treatment of patients with hypereosinophilic syndrome," *Blood 103*:2939-2941, American Society of Hematology (2004).

* cited by examiner

SEQUENCE LISTING

```
<160> NUMBER OF SEQ ID NOS: 386

<210> SEQ ID NO 1
<211> LENGTH: 212
<212> TYPE: PRT
<213> ORGANISM: Haemophilus influenzae

<400> SEQUENCE: 1

Met Lys Lys Thr Leu Leu Gly Ser Leu Ile Leu Leu Ala Phe Ala Gly
1               5                   10                  15

Asn Val Gln Ala Ala Ala Asn Ala Asp Thr Ser Gly Thr Val Thr Phe
            20                  25                  30

Phe Gly Lys Val Val Glu Asn Thr Cys Gln Val Asn Gln Asp Ser Glu
        35                  40                  45

Tyr Glu Cys Asn Leu Asn Asp Val Gly Lys Asn His Leu Ser Gln Gln
    50                  55                  60

Gly Tyr Thr Ala Met Gln Thr Pro Phe Thr Ile Thr Leu Glu Asn Cys
65                  70                  75                  80
```

-continued

```
Asn Val Thr Thr Thr Asn Asn Lys Pro Lys Ala Thr Lys Val Gly Val
                85                  90                  95

Tyr Phe Tyr Ser Trp Glu Ile Ala Asp Lys Asp Asn Lys Tyr Thr Leu
            100                 105                 110

Lys Asn Ile Lys Glu Asn Thr Gly Thr Asn Asp Ser Ala Asn Lys Val
        115                 120                 125

Asn Ile Gln Leu Leu Glu Asp Asn Gly Thr Ala Glu Ile Lys Val Val
    130                 135                 140

Gly Lys Thr Thr Thr Asp Phe Thr Ser Glu Asn His Asn Gly Ala Gly
145                 150                 155                 160

Ala Asp Pro Val Ala Thr Asn Lys His Ile Ser Ser Leu Thr Pro Leu
                165                 170                 175

Asn Asn Gln Asn Ser Ile Asn Leu His Tyr Ile Ala Gln Tyr Tyr Ala
            180                 185                 190

Thr Gly Val Ala Glu Ala Gly Lys Val Pro Ser Ser Val Asn Ser Gln
        195                 200                 205

Ile Ala Tyr Glu
    210


<210> SEQ ID NO 2
<211> LENGTH: 139
<212> TYPE: PRT
<213> ORGANISM: Pseudomonas stutzeri

<400> SEQUENCE: 2

Met Lys Ala Gln Met Gln Lys Gly Phe Thr Leu Ile Glu Leu Met Ile
1               5                   10                  15

Val Val Ala Ile Ile Gly Ile Leu Ala Ala Ile Ala Leu Pro Ala Tyr
            20                  25                  30

Gln Asp Tyr Thr Val Arg Ser Asn Ala Ala Ala Ala Leu Ala Glu Ile
        35                  40                  45

Thr Pro Gly Lys Ile Gly Phe Glu Gln Ala Ile Asn Glu Gly Lys Thr
    50                  55                  60

Pro Ser Leu Thr Ser Thr Asp Glu Gly Tyr Ile Gly Ile Thr Asp Ser
65                  70                  75                  80

Thr Ser Tyr Cys Asp Val Asp Leu Asp Thr Ala Ala Asp Gly His Ile
                85                  90                  95

Glu Cys Thr Ala Lys Gly Gly Asn Ala Gly Lys Phe Asp Gly Lys Thr
            100                 105                 110

Ile Thr Leu Asn Arg Thr Ala Asp Gly Glu Trp Ser Cys Ala Ser Thr
        115                 120                 125

Leu Asp Ala Lys Tyr Lys Pro Gly Lys Cys Ser
    130                 135


<210> SEQ ID NO 3
<211> LENGTH: 59
<212> TYPE: PRT
<213> ORGANISM: Caulobacter crescentus

<400> SEQUENCE: 3

Met Thr Lys Phe Val Thr Arg Phe Leu Lys Asp Glu Ser Gly Ala Thr
      1               5                    10                  15

Ala Ile Glu Tyr Gly Leu Ile Val Ala Leu Ile Ala Val Val Ile Val
            20                  25                  30

Thr Ala Val Thr Thr Leu Gly Thr Asn Leu Arg Thr Ala Phe Thr Lys
        35                  40                  45
```

-continued

```
Ala Gly Ala Ala Val Ser Thr Ala Ala Gly Thr
    50                  55


<210> SEQ ID NO 4
<211> LENGTH: 173
<212> TYPE: PRT
<213> ORGANISM: Escherichia coli

<400> SEQUENCE: 4

Met Ala Val Val Ser Phe Gly Val Asn Ala Ala Pro Thr Ile Pro Gln
1               5                   10                  15

Gly Gln Gly Lys Val Thr Phe Asn Gly Thr Val Val Asp Ala Pro Cys
            20                  25                  30

Ser Ile Ser Gln Lys Ser Ala Asp Gln Ser Ile Asp Phe Gly Gln Leu
        35                  40                  45

Ser Lys Ser Phe Leu Glu Ala Gly Gly Val Ser Lys Pro Met Asp Leu
    50                  55                  60

Asp Ile Glu Leu Val Asn Cys Asp Ile Thr Ala Phe Lys Gly Gly Asn
65                  70                  75                  80

Gly Ala Gln Lys Gly Thr Val Lys Leu Ala Phe Thr Gly Pro Ile Val
                85                  90                  95

Asn Gly His Ser Asp Glu Leu Asp Thr Asn Gly Gly Thr Gly Thr Ala
            100                 105                 110

Ile Val Val Gln Gly Ala Gly Lys Asn Val Val Phe Asp Gly Ser Glu
        115                 120                 125

Gly Asp Ala Asn Thr Leu Lys Asp Gly Glu Asn Val Leu His Tyr Thr
    130                 135                 140

Ala Val Val Lys Lys Ser Ser Ala Val Gly Ala Ala Val Thr Glu Gly
145                 150                 155                 160

Ala Phe Ser Ala Val Ala Asn Phe Asn Leu Thr Tyr Gln
                165                 170


<210> SEQ ID NO 5
<211> LENGTH: 173
<212> TYPE: PRT
<213> ORGANISM: Escherichia coli

<400> SEQUENCE: 5

Met Ala Val Val Ser Phe Gly Val Asn Ala Ala Pro Thr Ile Pro Gln
1               5                   10                  15

Gly Gln Gly Lys Val Thr Phe Asn Gly Thr Val Val Asp Ala Pro Cys
            20                  25                  30

Ser Ile Ser Gln Lys Ser Ala Asp Gln Ser Ile Asp Phe Gly Gln Leu
        35                  40                  45

Ser Lys Ser Phe Leu Glu Ala Gly Gly Val Ser Lys Pro Met Asp Leu
    50                  55                  60

Asp Ile Glu Leu Val Asn Cys Asp Ile Thr Ala Phe Lys Gly Gly Asn
65                  70                  75                  80

Gly Ala Gln Lys Gly Thr Val Lys Leu Ala Phe Thr Gly Pro Ile Val
                85                  90                  95

Asn Gly His Ser Asp Glu Leu Asp Thr Asn Gly Gly Thr Gly Thr Ala
            100                 105                 110

Ile Val Val Gln Gly Ala Gly Lys Asn Val Val Phe Asp Gly Ser Glu
        115                 120                 125

Gly Asp Ala Asn Thr Leu Lys Asp Gly Glu Asn Val Leu His Tyr Thr
    130                 135                 140
```

-continued

```
Ala Val Val Lys Lys Ser Ser Ala Val Gly Ala Ala Val Thr Glu Gly
145                 150                 155                 160

Ala Phe Ser Ala Val Ala Asn Phe Asn Leu Thr Tyr Gln
                165                 170


<210> SEQ ID NO 6
<211> LENGTH: 181
<212> TYPE: PRT
<213> ORGANISM: Escherichia coli

<400> SEQUENCE: 6

Met Lys Ile Lys Thr Leu Ala Ile Val Val Leu Ser Ala Leu Ser Leu
1               5                   10                  15

Ser Ser Thr Ala Ala Leu Ala Ala Ala Thr Thr Val Asn Gly Gly Thr
            20                  25                  30

Val His Phe Lys Gly Glu Val Val Asn Ala Ala Cys Ala Val Asp Ala
        35                  40                  45

Gly Ser Val Asp Gln Thr Val Gln Leu Gly Gln Val Arg Thr Ala Ser
    50                  55                  60

Leu Ala Gln Glu Gly Ala Thr Ser Ser Ala Val Gly Phe Asn Ile Gln
65                  70                  75                  80

Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
        115                 120                 125

Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Gly Ala Ala Thr Pro Gly Ala Ala Asn Ala Asp Ala Thr Phe
                165                 170                 175

Lys Val Gln Tyr Gln
            180


<210> SEQ ID NO 7
<211> LENGTH: 172
<212> TYPE: PRT
<213> ORGANISM: Escherichia coli

<400> SEQUENCE: 7

Met Ala Val Val Ser Phe Gly Val Asn Ala Ala Pro Thr Thr Pro Gln
1               5                   10                  15

Gly Gln Gly Arg Val Thr Phe Asn Gly Thr Val Val Asp Ala Pro Cys
            20                  25                  30

Ser Ile Ser Gln Lys Ser Ala Asp Gln Ser Ile Asp Phe Gly Gln Leu
        35                  40                  45

Ser Lys Ser Phe Leu Ala Asn Asp Gly Gln Ser Lys Pro Met Asn Leu
    50                  55                  60

Asp Ile Glu Leu Val Asn Cys Asp Ile Thr Ala Phe Lys Asn Gly Asn
65                  70                  75                  80

Ala Lys Thr Gly Ser Val Lys Leu Ala Phe Thr Gly Pro Thr Val Ser
                85                  90                  95

Gly His Pro Ser Glu Leu Ala Thr Asn Gly Gly Pro Gly Thr Ala Ile
            100                 105                 110
```

-continued

```
Met Ile Gln Ala Ala Gly Lys Asn Val Pro Phe Asp Gly Thr Glu Gly
        115                 120                 125

Asp Pro Asn Leu Leu Lys Asp Gly Asp Asn Val Leu His Tyr Thr Thr
    130                 135                 140

Val Gly Lys Lys Ser Ser Asp Gly Asn Ala Gln Ile Thr Glu Gly Ala
145                 150                 155                 160

Phe Ser Gly Val Ala Thr Phe Asn Leu Ser Tyr Gln
                165                 170


<210> SEQ ID NO 8
<211> LENGTH: 182
<212> TYPE: PRT
<213> ORGANISM: Escherichia coli

<400> SEQUENCE: 8

Met Lys Ile Lys Thr Leu Ala Ile Val Val Leu Ser Ala Leu Ser Leu
1               5                   10                  15

Ser Ser Thr Thr Ala Leu Ala Ala Ala Thr Thr Val Asn Gly Gly Thr
            20                  25                  30

Val His Phe Lys Gly Glu Val Val Asn Ala Ala Cys Ala Val Asp Ala
        35                  40                  45

Gly Ser Val Asp Gln Thr Val Gln Leu Gly Gln Val Arg Thr Ala Ser
    50                  55                  60

Leu Ala Gln Glu Gly Ala Thr Ser Ser Ala Val Gly Phe Asn Ile Gln
65                  70                  75                  80

Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
        115                 120                 125

Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Thr Gly Ala Ala Thr Pro Gly Ala Ala Asn Ala Asp Ala Thr
                165                 170                 175

Phe Lys Val Gln Tyr Gln
            180


<210> SEQ ID NO 9
<211> LENGTH: 853
<212> TYPE: DNA
<213> ORGANISM: Escherichia coli

<400> SEQUENCE: 9

acgtttctgt ggctcgacgc atcttcctca ttcttctctc caaaaaccac ctcatgcaat      60

ataaacatct ataaataaag ataacaaata gaatattaag ccaacaaata aactgaaaaa     120

gtttgtccgc gatgctttac ctctatgagt caaaatggcc ccaatgtttc atcttttggg     180

ggaaactgtg cagtgttggc agtcaaactc gttgacaaac aaagtgtaca gaacgactgc     240

ccatgtcgat ttagaaatag ttttttgaaa ggaaagcagc atgaaaatta aaactctggc     300

aatcgttgtt ctgtcggctc tgtccctcag ttctacgacg gctctggccg ctgccacgac     360

ggttaatggt gggaccgttc actttaaagg ggaagttgtt aacgccgctt gcgcagttga     420

tgcaggctct gttgatcaaa ccgttcagtt aggacaggtt cgtaccgcat cgctggcaca     480
```

-continued

```
ggaaggagca accagttctg ctgtcggttt taacattcag ctgaatgatt gcgataccaa    540

tgttgcatct aaagccgctg ttgccttttt aggtacggcg attgatgcgg gtcataccaa    600

cgttctggct ctgcagagtt cagctgcggg tagcgcaaca aacgttggtg tgcagatcct    660

ggacagaacg ggtgctgcgc tgacgctgga tggtgcgaca tttagttcag aaacaaccct    720

gaataacgga accaatacca ttccgttcca ggcgcgttat tttgcaaccg ggccgcaac    780

cccgggtgct gctaatgcgg atgcgacctt caaggttcag tatcaataac ctacctaggt    840

tcagggacgt tca                                                       853
```

```
<210> SEQ ID NO 10
<211> LENGTH: 132
<212> TYPE: PRT
<213> ORGANISM: Bacteriophage Q-beta

<400> SEQUENCE: 10

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130


<210> SEQ ID NO 11
<211> LENGTH: 329
<212> TYPE: PRT
<213> ORGANISM: Bacteriophage Q-beta CP

<400> SEQUENCE: 11

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110
```

-continued

```
Leu Ala Ala Leu Leu Ala Ser Pro Leu Leu Ile Asp Ala Ile Asp Gln
        115                 120                 125

Leu Asn Pro Ala Tyr Trp Thr Leu Leu Ile Ala Gly Gly Gly Ser Gly
    130                 135                 140

Ser Lys Pro Asp Pro Val Ile Pro Asp Pro Pro Ile Asp Pro Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
        195                 200                 205

Gly Asn Thr Lys Trp Arg Asp Trp Asp Ser Arg Leu Ser Tyr Thr Thr
    210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
        275                 280                 285

Ala Asp Gly Val Ile Val Gly Phe Trp Arg Asp Pro Ser Ser Gly Gly
    290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
                325


<210> SEQ ID NO 12
<211> LENGTH: 129
<212> TYPE: PRT
<213> ORGANISM: Bacteriophage R17

<400> SEQUENCE: 12

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Met Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr


<210> SEQ ID NO 13
<211> LENGTH: 130
```

-continued

<212> TYPE: PRT
<213> ORGANISM: Bacteriophage fr

<400> SEQUENCE: 13

```
Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Asn Asn Arg Lys Tyr Thr Val Lys Val Glu
    50                  55                  60

Val Pro Lys Val Ala Thr Gln Val Gln Gly Gly Val Glu Leu Pro Val
65                  70                  75                  80

Ala Ala Trp Arg Ser Tyr Met Asn Met Glu Leu Thr Ile Pro Val Phe
                85                  90                  95

Ala Thr Asn Asp Asp Cys Ala Leu Ile Val Lys Ala Leu Gln Gly Thr
            100                 105                 110

Phe Lys Thr Gly Asn Pro Ile Ala Thr Ala Ile Ala Ala Asn Ser Gly
        115                 120                 125

Ile Tyr
    130
```

<210> SEQ ID NO 14
<211> LENGTH: 130
<212> TYPE: PRT
<213> ORGANISM: Bacteriophage GA

<400> SEQUENCE: 14

```
Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
            20                  25                  30

Leu Ser Asn Asn Ser Arg Ser Gln Ala Tyr Arg Val Thr Ala Ser Tyr
        35                  40                  45

Arg Ala Ser Gly Ala Asp Lys Arg Lys Tyr Ala Ile Lys Leu Glu Val
    50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130
```

<210> SEQ ID NO 15
<211> LENGTH: 132
<212> TYPE: PRT
<213> ORGANISM: Bacteriophage SP

<400> SEQUENCE: 15

```
Met Ala Lys Leu Asn Gln Val Thr Leu Ser Lys Ile Gly Lys Asn Gly
1               5                   10                  15

Asp Gln Thr Leu Thr Leu Thr Pro Arg Gly Val Asn Pro Thr Asn Gly
```

-continued

```
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Phe Lys
    50                  55                  60

Val Gln Ile Lys Leu Gln Asn Pro Thr Ala Cys Thr Arg Asp Ala Cys
65                  70                  75                  80

Asp Pro Ser Val Thr Arg Ser Ala Phe Ala Asp Val Thr Leu Ser Phe
                85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
    130


<210> SEQ ID NO 16
<211> LENGTH: 329
<212> TYPE: PRT
<213> ORGANISM: Bacteriophage SP CP

<400> SEQUENCE: 16

Ala Lys Leu Asn Gln Val Thr Leu Ser Lys Ile Gly Lys Asn Gly Asp
1               5                   10                  15

Gln Thr Leu Thr Leu Thr Pro Arg Gly Val Asn Pro Thr Asn Gly Val
            20                  25                  30

Ala Ser Leu Ser Glu Ala Gly Ala Val Pro Ala Leu Glu Lys Arg Val
        35                  40                  45

Thr Val Ser Val Ala Gln Pro Ser Arg Asn Arg Lys Asn Phe Lys Val
    50                  55                  60

Gln Ile Lys Leu Gln Asn Pro Thr Ala Cys Thr Arg Asp Ala Cys Asp
65                  70                  75                  80

Pro Ser Val Thr Arg Ser Ala Phe Ala Asp Val Thr Leu Ser Phe Thr
                85                  90                  95

Ser Tyr Ser Thr Asp Glu Glu Arg Ala Leu Ile Arg Thr Glu Leu Ala
            100                 105                 110

Ala Leu Leu Ala Asp Pro Leu Ile Val Asp Ala Ile Asp Asn Leu Asn
        115                 120                 125

Pro Ala Tyr Trp Ala Ala Leu Leu Val Ala Ser Ser Gly Gly Gly Asp
    130                 135                 140
Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
                165                 170                 175

Ser Ile Tyr Glu Val Gly Lys Glu Gly Ser Pro Asp Ile Tyr Glu Arg
            180                 185                 190

Gly Asp Glu Val Ser Val Thr Phe Asp Tyr Ala Leu Glu Asp Phe Leu
        195                 200                 205

Gly Asn Thr Asn Trp Arg Asn Trp Asp Gln Arg Leu Ser Asp Tyr Asp
    210                 215                 220

Ile Ala Asn Arg Arg Arg Cys Arg Gly Asn Gly Tyr Ile Asp Leu Asp
225                 230                 235                 240

Ala Thr Ala Met Gln Ser Asp Asp Phe Val Leu Ser Gly Arg Tyr Gly
                245                 250                 255

Val Arg Lys Val Lys Phe Pro Gly Ala Phe Gly Ser Ile Lys Tyr Leu
```

-continued

```
            260                 265                 270

Leu Asn Ile Gln Gly Asp Ala Trp Leu Asp Leu Ser Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Gln Phe Asn Ser Ala Asn Cys Pro
305                 310                 315                 320

Val Gln Thr Val Ile Ile Ile Pro Ser
                325


<210> SEQ ID NO 17
<211> LENGTH: 130
<212> TYPE: PRT
<213> ORGANISM: Bacteriophage MS2

<400> SEQUENCE: 17

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130


<210> SEQ ID NO 18
<211> LENGTH: 133
<212> TYPE: PRT
<213> ORGANISM: Bacteriophage M11

<400> SEQUENCE: 18

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
            100                 105                 110

Leu Gln Ala Leu Leu Ala Asp Pro Met Leu Val Asn Ala Ile Asp Asn
```

-continued

```
        115                 120                 125

Leu Asn Pro Ala Tyr
    130


<210> SEQ ID NO 19
<211> LENGTH: 133
<212> TYPE: PRT
<213> ORGANISM: Bacteriophage MX1

<400> SEQUENCE: 19

Met Ala Lys Leu Gln Ala Ile Thr Leu Ser Gly Ile Gly Lys Asn Gly
1               5                   10                  15

Asp Val Thr Leu Asn Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ala Asp Val Thr Phe Ser
                85                  90                  95

Phe Thr Gln Tyr Ser Thr Asp Glu Glu Arg Ala Leu Val Arg Thr Glu
            100                 105                 110

Leu Lys Ala Leu Leu Ala Asp Pro Met Leu Ile Asp Ala Ile Asp Asn
        115                 120                 125

Leu Asn Pro Ala Tyr
    130


<210> SEQ ID NO 20
<211> LENGTH: 330
<212> TYPE: PRT
<213> ORGANISM: Bacteriophage NL95

<400> SEQUENCE: 20

Met Ala Lys Leu Asn Lys Val Thr Leu Thr Gly Ile Gly Lys Ala Gly
1               5                   10                  15

Asn Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Tyr Lys
    50                  55                  60

Val Gln Ile Lys Leu Gln Asn Pro Thr Ala Cys Thr Lys Asp Ala Cys
65                  70                  75                  80

Asp Pro Ser Val Thr Arg Ser Gly Ser Arg Asp Val Thr Leu Ser Phe
                85                  90                  95

Thr Ser Tyr Ser Thr Glu Arg Glu Arg Ala Leu Ile Arg Thr Glu Leu
            100                 105                 110

Ala Ala Leu Leu Lys Asp Asp Leu Ile Val Asp Ala Ile Asp Asn Leu
        115                 120                 125

Asn Pro Ala Tyr Trp Ala Ala Leu Leu Ala Ala Ser Pro Gly Gly Gly
    130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
```

-continued 165 170 175

Glu Leu Ile Thr Glu Ala Lys Asp Gly Ala Cys Ala Leu Tyr Ala Cys
180 185 190

Gly Ser Glu Ala Leu Val Glu Phe Glu Tyr Ala Leu Glu Asp Phe Leu
195 200 205

Gly Asn Glu Phe Trp Arg Asn Trp Asp Gly Arg Leu Ser Lys Tyr Asp
210 215 220

Ile Glu Thr His Arg Arg Cys Arg Gly Asn Gly Tyr Val Asp Leu Asp
225 230 235 240

Ala Ser Val Met Gln Ser Asp Glu Tyr Val Leu Ser Gly Ala Tyr Asp
245 250 255

Val Val Lys Met Gln Pro Pro Gly Thr Phe Asp Ser Pro Arg Tyr Tyr
260 265 270

Leu His Leu Met Asp Gly Ile Tyr Val Asp Leu Ala Glu Val Thr Ala
275 280 285

Tyr Arg Ser Tyr Gly Met Val Ile Gly Phe Trp Thr Asp Ser Lys Ser
290 295 300

Pro Gln Leu Pro Thr Asp Phe Thr Arg Phe Asn Arg His Asn Cys Pro
305 310 315 320

Val Gln Thr Val Ile Val Ile Pro Ser Leu
325 330

<210> SEQ ID NO 21
<211> LENGTH: 129
<212> TYPE: PRT
<213> ORGANISM: Bacteriophage f2

SEQUENCE: 21

Ala Ser Asn Phe Thr Gln Phe Val Leu Val Asn Asp Gly Gly Thr Gly
1 5 10 15

Asn Val Thr Val Ala Pro Ser Asn Phe Ala Asn Gly Val Ala Glu Trp
20 25 30

Ile Ser Ser Asn Ser Arg Ser Gln Ala Tyr Lys Val Thr Cys Ser Val
35 40 45

Arg Gln Ser Ser Ala Gln Asn Arg Lys Tyr Thr Ile Lys Val Glu Val
50 55 60

Pro Lys Val Ala Thr Gln Thr Val Gly Gly Val Glu Leu Pro Val Ala
65 70 75 80

Ala Trp Arg Ser Tyr Leu Asn Leu Glu Leu Thr Ile Pro Ile Phe Ala
85 90 95

Thr Asn Ser Asp Cys Glu Leu Ile Val Lys Ala Met Gln Gly Leu Leu
100 105 110

Lys Asp Gly Asn Pro Ile Pro Ser Ala Ile Ala Ala Asn Ser Gly Ile
115 120 125

Tyr

<210> SEQ ID NO 22
<211> LENGTH: 128
<212> TYPE: PRT
<213> ORGANISM: Bacteriophage PP7

<400> SEQUENCE: 22

Met Ser Lys Thr Ile Val Leu Ser Val Gly Glu Ala Thr Arg Thr Leu
1 5 10 15

Thr Glu Ile Gln Ser Thr Ala Asp Arg Gln Ile Phe Glu Glu Lys Val
20 25 30

-continued

```
Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125


<210> SEQ ID NO 23
<211> LENGTH: 132
<212> TYPE: PRT
<213> ORGANISM: Bacteriophage Q-beta-240

<400> SEQUENCE: 23

Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130


<210> SEQ ID NO 24
<211> LENGTH: 132
<212> TYPE: PRT
<213> ORGANISM: Bacteriophage Q-beta-243

<400> SEQUENCE: 24

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95
```

```
Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130


<210> SEQ ID NO 25
<211> LENGTH: 132
<212> TYPE: PRT
<213> ORGANISM: Bacteriophage Q-beta-250

<400> SEQUENCE: 25

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130


<210> SEQ ID NO 26
<211> LENGTH: 132
<212> TYPE: PRT
<213> ORGANISM: Bacteriophage Q-beta-251

<400> SEQUENCE: 26

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130
```

<210> SEQ ID NO 27
<211> LENGTH: 132
<212> TYPE: PRT
<213> ORGANISM: Bacteriophage Q-beta-259

<400> SEQUENCE: 27

```
Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130
```

<210> SEQ ID NO 28
<211> LENGTH: 185
<212> TYPE: PRT
<213> ORGANISM: Hepatitis B virus

<400> SEQUENCE: 28

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185
```

-continued

<210> SEQ ID NO 29
<211> LENGTH: 183
<212> TYPE: PRT
<213> ORGANISM: Hepatitis B virus

<400> SEQUENCE: 29

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Gly Ser Gln Cys
            180
```

<210> SEQ ID NO 30
<211> LENGTH: 183
<212> TYPE: PRT
<213> ORGANISM: Hepatitis B virus

<400> SEQUENCE: 30

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Thr Asn Ala Pro Ile Leu Ser Thr Leu Pro
    130                 135                 140
```

-continued

```
Glu Thr Cys Val Ile Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Gly Ser Gln Cys
            180


<210> SEQ ID NO 31
<211> LENGTH: 212
<212> TYPE: PRT
<213> ORGANISM: Hepatitis B virus

<400> SEQUENCE: 31

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 32
<211> LENGTH: 212
<212> TYPE: PRT
<213> ORGANISM: Hepatitis B virus

<400> SEQUENCE: 32

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Asn Ala Ser
    50                  55                  60
```

-continued

```
Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 33
<211> LENGTH: 183
<212> TYPE: PRT
<213> ORGANISM: Hepatitis B virus

<400> SEQUENCE: 33

Met Asp Ile Asp Pro Tyr Lys Glu Phe Gly Ala Thr Val Glu Leu Leu
1               5                   10                  15

Ser Phe Leu Pro Thr Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 34
<211> LENGTH: 212
<212> TYPE: PRT
```

-continued

<213> ORGANISM: Hepatitis B virus

<400> SEQUENCE: 34

Met Gln Leu Phe His Leu Cys Leu Ile Ile Ser Cys Ser Cys Pro Thr
1 5 10 15

Val Gln Ala Ser Lys Leu Cys Leu Gly Trp Leu Trp Gly Met Asp Ile
20 25 30

Asp Pro Tyr Lys Glu Phe Gly Ala Thr Val Glu Leu Leu Ser Phe Leu
35 40 45

Pro Ser Asp Phe Phe Pro Ser Val Arg Asp Leu Leu Asp Thr Ala Ser
50 55 60

Ala Leu Tyr Arg Glu Ala Leu Glu Ser Pro Glu His Cys Ser Pro His
65 70 75 80

His Thr Ala Leu Arg Gln Ala Ile Leu Cys Trp Gly Asp Leu Met Thr
85 90 95

Leu Ala Thr Trp Val Gly Gly Asn Leu Glu Asp Pro Val Ser Arg Asp
100 105 110

Leu Val Val Ser Tyr Val Asn Thr Asn Val Gly Leu Lys Phe Arg Gln
115 120 125

Leu Leu Trp Phe His Ile Ser Cys Leu Thr Phe Gly Arg Glu Thr Val
130 135 140

Ile Glu Tyr Leu Val Ser Phe Gly Val Trp Ile Arg Thr Pro Pro Ala
145 150 155 160

Tyr Arg Pro Pro Asn Ala Pro Ile Leu Ser Thr Leu Pro Glu Thr Thr
165 170 175

Val Val Arg Arg Arg Gly Arg Ser Pro Arg Arg Arg Thr Pro Ser Pro
180 185 190

Arg Arg Arg Arg Ser Gln Ser Pro Arg Arg Arg Arg Ser Gln Ser Arg
195 200 205

Glu Ser Gln Cys
210

<210> SEQ ID NO 35
<211> LENGTH: 212
<212> TYPE: PRT
<213> ORGANISM: Hepatitis B virus

<400> SEQUENCE: 35

Met Gln Leu Phe His Leu Cys Leu Ile Ile Ser Cys Ser Cys Pro Thr
1 5 10 15

Val Gln Ala Ser Lys Leu Cys Leu Gly Trp Leu Trp Asp Met Asp Ile
20 25 30

Asp Pro Tyr Lys Glu Phe Gly Ala Thr Val Glu Leu Leu Ser Phe Leu
35 40 45

Pro Ser Asp Phe Phe Pro Ser Val Arg Asp Leu Leu Asp Thr Ala Ser
50 55 60

Ala Leu Tyr Arg Glu Ala Leu Glu Ser Pro Glu His Cys Ser Pro His
65 70 75 80

His Thr Ala Leu Arg Gln Ala Ile Leu Cys Trp Gly Asp Leu Met Thr
85 90 95

Leu Ala Thr Trp Val Gly Gly Asn Leu Glu Asp Pro Val Ser Arg Asp
100 105 110

Leu Val Val Ser Tyr Val Asn Thr Asn Val Gly Leu Lys Phe Arg Gln
115 120 125

Leu Leu Trp Phe His Ile Ser Cys Leu Thr Phe Gly Arg Glu Thr Val

-continued

```
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 36
<211> LENGTH: 212
<212> TYPE: PRT
<213> ORGANISM: Hepatitis B virus

<400> SEQUENCE: 36

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro Gln
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 37
<211> LENGTH: 212
<212> TYPE: PRT
<213> ORGANISM: Hepatitis B virus

<400> SEQUENCE: 37

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
```

-continued

```
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Lys Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Gly Ser Gln Cys
    210


<210> SEQ ID NO 38
<211> LENGTH: 183
<212> TYPE: PRT
<213> ORGANISM: Hepatitis B virus

<400> SEQUENCE: 38

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Phe Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Asp Thr Val Ile Glu Tyr Leu Val Ser Phe Gly Val Trp Ile Arg Thr
        115                 120                 125

Pro Pro Ala Tyr Arg Pro Ser Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175
```

-continued

```
Gln Ser Arg Glu Ser Gln Cys
            180


<210> SEQ ID NO 39
<211> LENGTH: 183
<212> TYPE: PRT
<213> ORGANISM: Hepatitis B virus

<400> SEQUENCE: 39

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 40
<211> LENGTH: 212
<212> TYPE: PRT
<213> ORGANISM: Hepatitis B virus

<400> SEQUENCE: 40

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg His Ala Ile Leu Cys Trp Gly Asp Leu Arg Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125
```

-continued

```
Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 41
<211> LENGTH: 212
<212> TYPE: PRT
<213> ORGANISM: Hepatitis B virus

<400> SEQUENCE: 41

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Asp Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Phe Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Ala Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Gln Ala
145                 150                 155                 160

Tyr Arg Pro Pro Asn Ala Pro Ile Leu Ser Thr Leu Pro Glu Thr Cys
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 42
<211> LENGTH: 183
<212> TYPE: PRT
<213> ORGANISM: Hepatitis B virus

<400> SEQUENCE: 42

Met Asp Ile Asp Pro Tyr Lys Glu Phe Gly Ala Thr Val Glu Leu Leu
1               5                   10                  15
```

-continued

```
Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 43
<211> LENGTH: 212
<212> TYPE: PRT
<213> ORGANISM: Hepatitis B virus

<400> SEQUENCE: 43

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Ser
                85                  90                  95

Leu Ala Thr Trp Val Gly Val Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205
```

```
Glu Ser Gln Cys
    210


<210> SEQ ID NO 44
<211> LENGTH: 183
<212> TYPE: PRT
<213> ORGANISM: Hepatitis B virus

<400> SEQUENCE: 44

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 45
<211> LENGTH: 183
<212> TYPE: PRT
<213> ORGANISM: Hepatitis B virus

<400> SEQUENCE: 45

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125
```

-continued

```
Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 46
<211> LENGTH: 183
<212> TYPE: PRT
<213> ORGANISM: Hepatitis B virus

<400> SEQUENCE: 46

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Ala Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Thr Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 47
<211> LENGTH: 212
<212> TYPE: PRT
<213> ORGANISM: Hepatitis B virus

<400> SEQUENCE: 47

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Asp Ala Leu Glu Ser Pro Glu His Cys Ser Pro His
65                  70                  75                  80
```

```
His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 48
<211> LENGTH: 212
<212> TYPE: PRT
<213> ORGANISM: Hepatitis B virus

<400> SEQUENCE: 48

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

-continued

<210> SEQ ID NO 49
<211> LENGTH: 212
<212> TYPE: PRT
<213> ORGANISM: Hepatitis B virus

<400> SEQUENCE: 49

```
Met Gln Leu Phe His Leu Cys Leu Ile Ile Ser Cys Thr Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ala Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 50
<211> LENGTH: 212
<212> TYPE: PRT
<213> ORGANISM: Hepatitis B virus

<400> SEQUENCE: 50

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Phe Glu Cys Ser Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
```

-continued

```
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 51
<211> LENGTH: 212
<212> TYPE: PRT
<213> ORGANISM: Hepatitis B virus
<220> FEATURE:
<221> NAME/KEY: MISC_FEATURE
<222> LOCATION: (28)..(28)
<223> OTHER INFORMATION: Xaa can represent any amino acid

<400> SEQUENCE: 51

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Xaa Asp Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Ile Thr
                85                  90                  95

Leu Ser Thr Trp Val Gly Gly Asn Leu Glu Asp Pro Thr Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Thr Gln Ser Arg
        195                 200                 205

Glu Ser Gln Cys
    210


<210> SEQ ID NO 52
<211> LENGTH: 212
<212> TYPE: PRT
<213> ORGANISM: Hepatitis B virus
```

-continued

```
<400> SEQUENCE: 52

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Asn Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 53
<211> LENGTH: 212
<212> TYPE: PRT
<213> ORGANISM: Hepatitis B virus

<400> SEQUENCE: 53

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Cys Cys Leu Thr Phe Gly Arg Glu Thr Val
    130                 135                 140
```

-continued

```
Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 54
<211> LENGTH: 212
<212> TYPE: PRT
<213> ORGANISM: Hepatitis B virus

<400> SEQUENCE: 54

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Pro Gln Cys
    210


<210> SEQ ID NO 55
<211> LENGTH: 212
<212> TYPE: PRT
<213> ORGANISM: Hepatitis B virus

<400> SEQUENCE: 55

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30
```

-continued

```
Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Ser Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 56
<211> LENGTH: 212
<212> TYPE: PRT
<213> ORGANISM: Hepatitis B virus

<400> SEQUENCE: 56

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Leu Thr Leu Pro Glu Thr Thr
                165                 170                 175

Val Val Arg Arg Arg Gly Arg Ser Pro Arg Arg Arg Thr Pro Ser Pro
```

-continued

```
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 57
<211> LENGTH: 212
<212> TYPE: PRT
<213> ORGANISM: Hepatitis B virus

<400> SEQUENCE: 57

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Lys Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 58
<211> LENGTH: 212
<212> TYPE: PRT
<213> ORGANISM: Hepatitis B virus

<400> SEQUENCE: 58

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ala
    50                  55                  60

Ala Leu Tyr Arg Asp Ala Leu Glu Ser Pro Glu His Cys Ser Pro His
```

-continued

```
65                  70                  75                  80

His Thr Ala Leu Arg Gln Ala Ile Leu Cys Trp Gly Glu Leu Met Thr
                85                  90                  95

Leu Ala Thr Trp Val Gly Thr Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 59
<211> LENGTH: 183
<212> TYPE: PRT
<213> ORGANISM: Hepatitis B virus

<400> SEQUENCE: 59

```
Met Asp Ile Asp Pro Tyr Lys Glu Phe Gly Ala Ser Met Glu Leu Leu
1               5                   10                  15

Ser Phe Leu Pro Ser Asp Phe Tyr Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Thr Pro His His Thr Ala Leu Arg Gln Ala Ile Leu Cys Trp Gly Glu
    50                  55                  60

Leu Met Thr Leu Ala Thr Trp Val Gly Gly Asn Leu Gln Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Val Ser Cys Leu Thr Phe Gly Arg
            100                 105                 110

Glu Thr Val Val Glu Tyr Leu Val Ser Phe Gly Val Trp Ile Arg Thr
        115                 120                 125

Pro Gln Ala Tyr Arg Pro Pro Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 60
<211> LENGTH: 183
<212> TYPE: PRT
<213> ORGANISM: Hepatitis B virus -continued

<400> SEQUENCE: 60

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg His Val Phe Leu Cys Trp Gly Asp
    50                  55                  60

Leu Met Thr Leu Ala Thr Trp Val Gly Gly Asn Leu Glu Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 61
<211> LENGTH: 212
<212> TYPE: PRT
<213> ORGANISM: Hepatitis B virus

<400> SEQUENCE: 61

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Thr Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175
```

-continued

```
Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 62
<211> LENGTH: 212
<212> TYPE: PRT
<213> ORGANISM: Hepatitis B virus

<400> SEQUENCE: 62

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Ile Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 63
<211> LENGTH: 183
<212> TYPE: PRT
<213> ORGANISM: Hepatitis B virus

<400> SEQUENCE: 63

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Asp
    50                  55                  60
```

-continued

```
Leu Met Thr Leu Ala Thr Trp Val Gly Val Asn Leu Glu Asp Pro Val
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Ala Arg Arg Arg Ser Gln Ser Pro Arg Arg Arg Arg Ser
                165                 170                 175

Gln Ser Arg Glu Ser Gln Cys
            180


<210> SEQ ID NO 64
<211> LENGTH: 212
<212> TYPE: PRT
<213> ORGANISM: Hepatitis B virus

<400> SEQUENCE: 64

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Asn
                85                  90                  95

Leu Ala Thr Trp Val Gly Gly Asn Leu Glu Asp Pro Val Ser Arg Asp
            100                 105                 110

Leu Val Val Gly Tyr Val Asn Thr Thr Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 65
<211> LENGTH: 183
<212> TYPE: PRT
<213> ORGANISM: Hepatitis B virus
```

<400> SEQUENCE: 65

Met Asp Ile Asp Pro Tyr Lys Glu Phe Gly Ala Thr Val Glu Leu Leu
1 5 10 15

Ser Phe Leu Pro Ser Asp Phe Phe Pro Ser Val Arg Asp Leu Leu Asp
20 25 30

Thr Ala Ser Ala Leu Tyr Arg Asp Ala Leu Glu Ser Pro Glu His Cys
35 40 45

Ser Pro His His Thr Ala Leu Arg Gln Ala Ile Leu Cys Trp Gly Asp
50 55 60

Leu Met Thr Leu Ala Thr Trp Val Gly Val Asn Leu Glu Asp Pro Ala
65 70 75 80

Ser Arg Asp Leu Val Val Ser Tyr Val Asn Thr Asn Met Gly Leu Lys
85 90 95

Phe Arg Gln Leu Leu Trp Phe His Ile Ser Cys Leu Thr Phe Gly Arg
100 105 110

Glu Thr Val Ile Glu Tyr Leu Val Ser Phe Gly Val Trp Ile Arg Thr
115 120 125

Pro Pro Ala Tyr Arg Pro Pro Asn Ala Pro Ile Leu Ser Thr Leu Pro
130 135 140

Glu Thr Thr Val Val Arg Arg Arg Gly Arg Thr Pro Arg Arg Arg Thr
145 150 155 160

Pro Ser Pro Arg Arg Arg Arg Ser Gln Ser Pro Arg Arg Arg Arg Ser
165 170 175

Gln Ser Arg Glu Ser Gln Cys
180

<210> SEQ ID NO 66
<211> LENGTH: 212
<212> TYPE: PRT
<213> ORGANISM: Hepatitis B virus

<400> SEQUENCE: 66

Met Gln Leu Phe His Leu Cys Leu Ile Ile Ser Cys Ser Cys Pro Thr
1 5 10 15

Val Gln Ala Ser Lys Leu Cys Leu Gly Trp Leu Trp Gly Met Asp Ile
20 25 30

Asp Pro Tyr Lys Glu Phe Gly Ala Thr Val Glu Leu Leu Ser Phe Leu
35 40 45

Pro Ser Asp Phe Phe Pro Ser Val Arg Ala Leu Leu Asp Thr Ala Ser
50 55 60

Ala Leu Tyr Arg Glu Ala Leu Glu Ser Pro Glu His Cys Ser Pro His
65 70 75 80

His Thr Ala Leu Arg Gln Ala Ile Leu Cys Trp Gly Glu Leu Met Thr
85 90 95

Leu Ala Thr Trp Val Gly Val Asn Leu Glu Asp Pro Ala Ser Arg Asp
100 105 110

Leu Val Val Ser Tyr Val Asn Thr Asn Met Gly Leu Lys Phe Arg Gln
115 120 125

Ile Leu Trp Phe His Ile Ser Cys Leu Thr Phe Gly Arg Glu Thr Val
130 135 140

Ile Glu Tyr Leu Val Ser Phe Gly Val Trp Ile Arg Thr Pro Pro Ala
145 150 155 160

Tyr Arg Pro Pro Asn Ala Pro Ile Leu Ser Thr Leu Pro Glu Thr Thr
165 170 175

-continued

```
Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 67
<211> LENGTH: 212
<212> TYPE: PRT
<213> ORGANISM: Hepatitis B virus

<400> SEQUENCE: 67

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Thr Arg Asp
            100                 105                 110

Leu Val Val Ser Tyr Val Asn Thr Asn Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 68
<211> LENGTH: 212
<212> TYPE: PRT
<213> ORGANISM: Hepatitis B virus

<400> SEQUENCE: 68

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60
```

-continued

```
Ala Leu Tyr Arg Glu Ala Leu Glu Ser Pro Glu His Cys Ser Pro His
65                  70                  75                  80

His Thr Ala Leu Arg Gln Arg Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Thr Arg Ser Gln Ser Arg
        195                 200                 205

Glu Ser Gln Cys
    210


<210> SEQ ID NO 69
<211> LENGTH: 212
<212> TYPE: PRT
<213> ORGANISM: Hepatitis B virus

<400> SEQUENCE: 69

Met Gln Leu Phe His Leu Cys Leu Val Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ala
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Asn Asn Leu Glu Asp Pro Ala Ser Arg Asp
            100                 105                 110

Leu Val Val Asn Tyr Val Asn Thr Asn Met Gly Leu Lys Ile Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
```

-continued

210

<210> SEQ ID NO 70
<211> LENGTH: 212
<212> TYPE: PRT
<213> ORGANISM: Hepatitis B virus

<400> SEQUENCE: 70

Met Gln Leu Phe His Leu Cys Leu Ile Ile Ser Cys Ser Cys Pro Thr
1 5 10 15

Val Gln Ala Ser Lys Leu Cys Leu Gly Trp Leu Trp Gly Met Asp Ile
20 25 30

Asp Pro Tyr Lys Glu Phe Gly Ala Thr Val Glu Leu Leu Ser Phe Leu
35 40 45

Pro Ser Ala Phe Phe Pro Ser Val Arg Asp Leu Leu Asp Thr Ala Ser
50 55 60

Ala Leu Tyr Arg Glu Ala Leu Glu Ser Pro Glu His Cys Ser Pro His
65 70 75 80

His Thr Ala Leu Arg Gln Ala Ile Leu Cys Trp Gly Asp Leu Met Thr
85 90 95

Leu Ala Thr Trp Val Gly Val Asn Leu Glu Asp Pro Ala Ser Arg Asp
100 105 110

Leu Val Val Ser Tyr Val Asn Thr Asn Met Gly Leu Lys Phe Arg Gln
115 120 125

Leu Leu Trp Phe His Ile Ser Cys Leu Thr Phe Gly Arg Glu Thr Val
130 135 140

Ile Glu Tyr Leu Val Ser Phe Gly Val Trp Ile Arg Thr Pro Pro Ala
145 150 155 160

Tyr Arg Pro Pro Asn Ala Pro Ile Leu Ser Thr Leu Pro Glu Thr Thr
165 170 175

Val Val Arg Arg Arg Gly Arg Ser Pro Arg Arg Arg Thr Pro Ser Pro
180 185 190

Arg Arg Arg Arg Ser Gln Ser Pro Arg Arg Arg Arg Ser Gln Ser Arg
195 200 205

Glu Ser Gln Cys
210

<210> SEQ ID NO 71
<211> LENGTH: 183
<212> TYPE: PRT
<213> ORGANISM: Hepatitis B virus

<400> SEQUENCE: 71

Met Asp Ile Asp Pro Tyr Lys Glu Phe Gly Ala Thr Val Glu Leu Leu
1 5 10 15

Ser Phe Leu Pro Ser Asp Phe Phe Pro Ser Val Arg Asp Leu Leu Asp
20 25 30

Thr Ala Ala Ala Leu Tyr Arg Glu Ala Leu Glu Ser Pro Glu His Cys
35 40 45

Ser Pro His His Thr Ala Leu Arg Gln Ala Ile Leu Cys Trp Gly Glu
50 55 60

Leu Met Thr Leu Ala Thr Trp Val Gly Asn Asn Leu Glu Asp Pro Ala
65 70 75 80

Ser Arg Asp Leu Val Val Asn Tyr Val Asn Thr Asn Met Gly Leu Lys
85 90 95

Ile Arg Gln Leu Leu Trp Phe His Ile Ser Cys Leu Thr Phe Gly Arg

-continued

```
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 72
<211> LENGTH: 183
<212> TYPE: PRT
<213> ORGANISM: Hepatitis B virus

<400> SEQUENCE: 72

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Gly Ser Gln Cys
            180


<210> SEQ ID NO 73
<211> LENGTH: 188
<212> TYPE: PRT
<213> ORGANISM: Hepatitis B virus

<400> SEQUENCE: 73

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
```

-continued

```
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Arg Ser Gln Ser Pro
                165                 170                 175

Arg Arg Arg Arg Ser Gln Ser Pro Ser Thr Asn Cys
            180                 185


<210> SEQ ID NO 74
<211> LENGTH: 217
<212> TYPE: PRT
<213> ORGANISM: Hepatitis B virus

<400> SEQUENCE: 74

Met Tyr Leu Phe His Leu Cys Leu Val Phe Ala Cys Val Pro Cys Pro
1               5                   10                  15

Thr Val Gln Ala Ser Lys Leu Cys Leu Gly Trp Leu Trp Asp Met Asp
            20                  25                  30

Ile Asp Pro Tyr Lys Glu Phe Gly Ser Ser Tyr Gln Leu Leu Asn Phe
        35                  40                  45

Leu Pro Leu Asp Phe Phe Pro Asp Leu Asn Ala Leu Val Asp Thr Ala
    50                  55                  60

Ala Ala Leu Tyr Glu Glu Glu Leu Thr Gly Arg Glu His Cys Ser Pro
65                  70                  75                  80

His His Thr Ala Ile Arg Gln Ala Leu Val Cys Trp Glu Glu Leu Thr
                85                  90                  95

Arg Leu Ile Thr Trp Met Ser Glu Asn Thr Thr Glu Glu Val Arg Arg
            100                 105                 110

Ile Ile Val Asp His Val Asn Asn Thr Trp Gly Leu Lys Val Arg Gln
        115                 120                 125

Thr Leu Trp Phe His Leu Ser Cys Leu Thr Phe Gly Gln His Thr Val
    130                 135                 140

Gln Glu Phe Leu Val Ser Phe Gly Val Trp Ile Arg Thr Pro Ala Pro
145                 150                 155                 160

Tyr Arg Pro Pro Asn Ala Pro Ile Leu Ser Thr Leu Pro Glu His Thr
                165                 170                 175

Val Ile Arg Arg Arg Gly Gly Ser Arg Ala Ala Arg Ser Pro Arg Arg
            180                 185                 190

Arg Thr Pro Ser Pro Arg Arg Arg Arg Ser Gln Ser Pro Arg Arg Arg
        195                 200                 205

Arg Ser Gln Ser Pro Ala Ser Asn Cys
    210                 215


<210> SEQ ID NO 75
<211> LENGTH: 262
```

<212> TYPE: PRT
<213> ORGANISM: Hepatitis B virus

<400> SEQUENCE: 75

```
Met Asp Val Asn Ala Ser Arg Ala Leu Ala Asn Val Tyr Asp Leu Pro
1               5                   10                  15

Asp Asp Phe Phe Pro Lys Ile Glu Asp Leu Val Arg Asp Ala Lys Asp
            20                  25                  30

Ala Leu Glu Pro Tyr Trp Lys Ser Asp Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ala Ile Arg Ala Val Ile Pro Pro
65                  70                  75                  80

Thr Thr Ala Pro Val Pro Ser Gly Tyr Leu Ile Gln His Asp Glu Ala
                85                  90                  95

Glu Glu Ile Pro Leu Gly Asp Leu Phe Lys Glu Gln Glu Glu Arg Ile
            100                 105                 110

Val Ser Phe Gln Pro Asp Tyr Pro Ile Thr Ala Arg Ile His Ala His
        115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Thr
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Val Ala Gln Gly Gly Arg Lys Thr Ser Thr Ala Thr Arg Lys
        195                 200                 205

Pro Arg Gly Leu Glu Pro Arg Arg Arg Lys Val Lys Thr Thr Val Val
    210                 215                 220

Tyr Gly Arg Arg Arg Ser Lys Ser Arg Glu Arg Arg Ala Ser Ser Pro
225                 230                 235                 240

Gln Arg Ala Gly Ser Pro Leu Pro Arg Ser Ser Ser Ser His His Arg
                245                 250                 255

Ser Pro Ser Pro Arg Lys
            260
```

<210> SEQ ID NO 76
<211> LENGTH: 305
<212> TYPE: PRT
<213> ORGANISM: Hepatitis B virus

<400> SEQUENCE: 76

```
Met Trp Asp Leu Arg Leu His Pro Ser Pro Phe Gly Ala Ala Cys Gln
1               5                   10                  15

Gly Ile Phe Thr Ser Ser Leu Leu Leu Phe Leu Val Thr Val Pro Leu
            20                  25                  30

Val Cys Thr Ile Val Tyr Asp Ser Cys Leu Cys Met Asp Ile Asn Ala
        35                  40                  45

Ser Arg Ala Leu Ala Asn Val Tyr Asp Leu Pro Asp Asp Phe Phe Pro
    50                  55                  60

Lys Ile Asp Asp Leu Val Arg Asp Ala Lys Asp Ala Leu Glu Pro Tyr
65                  70                  75                  80
```

-continued

```
Trp Arg Asn Asp Ser Ile Lys Lys His Val Leu Ile Ala Thr His Phe
                85                  90                  95

Val Asp Leu Ile Glu Asp Phe Trp Gln Thr Thr Gln Gly Met His Glu
            100                 105                 110

Ile Ala Glu Ala Leu Arg Ala Ile Ile Pro Ala Thr Thr Ala Pro Val
        115                 120                 125

Pro Gln Gly Phe Leu Val Gln His Glu Glu Ala Glu Glu Ile Pro Leu
    130                 135                 140

Gly Glu Leu Phe Arg Tyr Gln Glu Glu Arg Leu Thr Asn Phe Gln Pro
145                 150                 155                 160

Asp Tyr Pro Val Thr Ala Arg Ile His Ala His Leu Lys Ala Tyr Ala
                165                 170                 175

Lys Ile Asn Glu Glu Ser Leu Asp Arg Ala Arg Arg Leu Leu Trp Trp
            180                 185                 190

His Tyr Asn Cys Leu Leu Trp Gly Glu Pro Asn Val Thr Asn Tyr Ile
        195                 200                 205

Ser Arg Leu Arg Thr Trp Leu Ser Thr Pro Glu Lys Tyr Arg Gly Lys
    210                 215                 220

Asp Ala Pro Thr Ile Glu Ala Ile Thr Arg Pro Ile Gln Val Ala Gln
225                 230                 235                 240

Gly Gly Arg Asn Lys Thr Gln Gly Val Arg Lys Ser Arg Gly Leu Glu
                245                 250                 255

Pro Arg Arg Arg Arg Val Lys Thr Thr Ile Val Tyr Gly Arg Arg Arg
            260                 265                 270

Ser Lys Ser Arg Glu Arg Arg Ala Pro Thr Pro Gln Arg Ala Gly Ser
        275                 280                 285
Pro Leu Pro Arg Thr Ser Arg Asp His His Arg Ser Pro Ser Pro Arg
    290                 295                 300

Glu
305


<210> SEQ ID NO 77
<211> LENGTH: 185
<212> TYPE: PRT
<213> ORGANISM: Hepatitis B virus

<400> SEQUENCE: 77

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140
```

-continued

```
Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185


<210> SEQ ID NO 78
<211> LENGTH: 152
<212> TYPE: PRT
<213> ORGANISM: Hepatitis B virus

<400> SEQUENCE: 78

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Gly Gly
65                  70                  75                  80

Lys Gly Gly Ser Arg Asp Leu Val Val Ser Tyr Val Asn Thr Asn Val
                85                  90                  95

Gly Leu Lys Phe Arg Gln Leu Leu Trp Phe His Ile Ser Cys Leu Thr
            100                 105                 110

Phe Gly Arg Glu Thr Val Leu Glu Tyr Leu Val Ser Phe Gly Val Trp
        115                 120                 125

Ile Arg Thr Pro Pro Ala Tyr Arg Pro Pro Asn Ala Pro Ile Leu Ser
    130                 135                 140

Thr Leu Pro Glu Thr Thr Val Val
145                 150


<210> SEQ ID NO 79
<211> LENGTH: 3635
<212> TYPE: DNA
<213> ORGANISM: Artificial Sequence
<220> FEATURE:
<223> OTHER INFORMATION: Plasmid pAP283-58

<400> SEQUENCE: 79

cgagctcgcc cctggcttat cgaaattaat acgactcact atagggagac cggaattcga      60

gctcgcccgg ggatcctcta gaattttctg cgcacccatc ccgggtggcg cccaaagtga     120

ggaaaatcac atggcaaata agccaatgca accgatcaca tctacagcaa ataaaattgt     180

gtggtcggat ccaactcgtt tatcaactac attttcagca agtctgttac gccaacgtgt     240

taaagttggt atagccgaac tgaataatgt ttcaggtcaa tatgtatctg tttataagcg     300

tcctgcacct aaaccggaag gttgtgcaga tgcctgtgtc attatgccga atgaaaacca     360

atccattcgc acagtgattt cagggtcagc cgaaaacttg gctaccttaa aagcagaatg     420

ggaaactcac aaacgtaacg ttgacacact cttcgcgagc ggcaacgccg gtttgggttt     480

ccttgaccct actgcggcta tcgtatcgtc tgatactact gcttaagctt gtattctata     540

gtgtcaccta aatcgtatgt gtatgataca taaggttatg tattaattgt agccgcgttc     600

taacgacaat atgtacaagc ctaattgtgt agcatctggc ttactgaagc agaccctatc     660
```

-continued

```
atctctctcg taaactgccg tcagagtcgg tttggttgga cgaaccttct gagtttctgg    720
taacgccgtt ccgcaccccg gaaatggtca ccgaaccaat cagcagggtc atcgctagcc    780
agatcctcta cgccggacgc atcgtggccg gcatcaccgg cgccacaggt gcggttgctg    840
gcgcctatat cgccgacatc accgatgggg aagatcgggc tcgccacttc gggctcatga    900
gcgcttgttt cggcgtgggt atggtggcag gccccgtggc cgggggactg ttgggcgcca    960
tctccttgca tgcaccattc cttgcggcgg cggtgctcaa cggcctcaac ctactactgg   1020
gctgcttcct aatgcaggag tcgcataagg gagagcgtcg atatggtgca ctctcagtac   1080
aatctgctct gatgccgcat agttaagcca actccgctat cgctacgtga ctgggtcatg   1140
gctgcgcccc gacacccgcc aacacccgct gacgcgccct gacgggcttg tctgctcccg   1200
gcatccgctt acagacaagc tgtgaccgtc tccgggagct gcatgtgtca gaggttttca   1260
ccgtcatcac cgaaacgcgc gaggcagctt gaagacgaaa gggcctcgtg atacgcctat   1320
ttttataggt taatgtcatg ataataatgg tttcttagac gtcaggtggc acttttcggg   1380
gaaatgtgcg cggaacccct atttgtttat ttttctaaat acattcaaat atgtatccgc   1440
tcatgagaca ataaccctga taaatgcttc aataatattg aaaaaggaag agtatgagta   1500
ttcaacattt ccgtgtcgcc cttattccct tttttgcggc attttgcctt cctgtttttg   1560
ctcacccaga aacgctggtg aaagtaaaag atgctgaaga tcagttgggt gcacgagtgg   1620
gttacatcga actggatctc aacagcggta agatccttga gagttttcgc cccgaagaac   1680
gttttccaat gatgagcact tttaaagttc tgctatgtgg cgcggtatta tcccgtattg   1740
acgccgggca agagcaactc ggtcgccgca tacactattc tcagaatgac ttggttgagt   1800
actcaccagt cacagaaaag catcttacgg atggcatgac agtaagagaa ttatgcagtg   1860
ctgccataac catgagtgat aacactgcgg ccaacttact tctgacaacg atcggaggac   1920
cgaaggagct aaccgctttt ttgcacaaca tgggggatca tgtaactcgc cttgatcgtt   1980
gggaaccgga gctgaatgaa gccataccaa acgacgagcg tgacaccacg atgcctgtag   2040
caatggcaac aacgttgcgc aaactattaa ctggcgaact acttactcta gcttcccggc   2100
aacaattaat agactggatg gaggcggata aagttgcagg accacttctg cgctcggccc   2160
ttccggctgg ctggtttatt gctgataaat ctggagccgg tgagcgtggg tctcgcggta   2220
tcattgcagc actggggcca gatggtaagc cctcccgtat cgtagttatc tacacgacgg   2280
ggagtcaggc aactatggat gaacgaaata gacagatcgc tgagataggt gcctcactga   2340
ttaagcattg gtaactgtca gaccaagttt actcatatat actttagatt gatttaaaac   2400
ttcattttta atttaaaagg atctaggtga agatcctttt tgataatctc atgaccaaaa   2460
tcccttaacg tgagttttcg ttccactgag cgtcagaccc cgtagaaaag atcaaaggat   2520
cttcttgaga tccttttttt ctgcgcgtaa tctgctgctt gcaaacaaaa aaaccaccgc   2580
taccagcggt ggtttgtttg ccggatcaag agctaccaac tctttttccg aaggtaactg   2640
gcttcagcag agcgcagata ccaaatactg tccttctagt gtagccgtag ttaggccacc   2700
acttcaagaa ctctgtagca ccgcctacat acctcgctct gctaatcctg ttaccagtgg   2760
ctgctgccag tggcgataag tcgtgtctta ccgggttgga ctcaagacga tagttaccgg   2820
ataaggcgca gcggtcgggc tgaacggggg gttcgtgcac acagcccagc ttggagcgaa   2880
cgacctacac cgaactgaga tacctacagc gcgagcattg agaaagcgcc acgcttcccg   2940
aagggagaaa ggcggacagg tatccggtaa gcggcagggt cggaacagga gagcgcacga   3000
gggagcttcc agggggaaac gcctggtatc tttatagtcc tgtcgggttt cgccacctct   3060
```

-continued

```
gacttgagcg tcgatttttg tgatgctcgt caggggggcg gagcctatgg aaaaacgcca   3120

gcaacgcggc ctttttacgg ttcctggcct tttgctggcc ttttgctcac atgttctttc   3180

ctgcgttatc ccctgattct gtggataacc gtattaccgc ctttgagtga gctgataccg   3240

ctcgccgcag ccgaacgacc gagcgcagcg agtcagtgag cgaggaagcg gaagagcgcc   3300

caatacgcaa accgcctctc cccgcgcgtt ggccgattca ttaatgcagc tgtggtgtca   3360

tggtcggtga tcgccagggt gccgacgcgc atctcgactg catggtgcac caatgcttct   3420

ggcgtcaggc agccatcgga agctgtggta tggccgtgca ggtcgtaaat cactgcataa   3480

ttcgtgtcgc tcaaggcgca ctcccgttct ggataatgtt ttttgcgccg acatcataac   3540

ggttctggca aatattctga aatgagctgt tgacaattaa tcatcgaact agttaactag   3600

tacgcaagtt cacgtaaaaa gggtatcgcg gaatt                              3635
```

```
<210> SEQ ID NO 80
<211> LENGTH: 131
<212> TYPE: PRT
<213> ORGANISM: Artificial Sequence
<220> FEATURE:
<223> OTHER INFORMATION: Ap205 coat protein

<400> SEQUENCE: 80

Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130


<210> SEQ ID NO 81
<211> LENGTH: 131
<212> TYPE: PRT
<213> ORGANISM: Artificial Sequence
<220> FEATURE:
<223> OTHER INFORMATION: AP205 coat protein

<400> SEQUENCE: 81

Met Ala Asn Lys Thr Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60
```

-continued

```
Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130


<210> SEQ ID NO 82
<211> LENGTH: 3613
<212> TYPE: DNA
<213> ORGANISM: Artificial Sequence
<220> FEATURE:
<223> OTHER INFORMATION: Plasmid pAP281-32

<400> SEQUENCE: 82

cgagctcgcc cctggcttat cgaaattaat acgactcact atagggagac cggaattcga     60

gctcgcccgg ggatcctcta gattaaccca acgcgtagga gtcaggccat ggcaaataag    120

acaatgcaac cgatcacatc tacagcaaat aaaattgtgt ggtcggatcc aactcgttta    180

tcaactacat tttcagcaag tctgttacgc caacgtgtta aagttggtat agccgaactg    240

aataatgttt caggtcaata tgtatctgtt tataagcgtc ctgcacctaa accggaaggt    300

tgtgcagatg cctgtgtcat tatgccgaat gaaaaccaat ccattcgcac agtgatttca    360

gggtcagccg aaaacttggc taccttaaaa gcagaatggg aaactcacaa acgtaacgtt    420

gacacactct tcgcgagcgg caacgccggt ttgggtttcc ttgaccctac tgcggctatc    480

gtatcgtctg atactactgc ttaagcttgt attctatagt gtcacctaaa tcgtatgtgt    540

atgatacata aggttatgta ttaattgtag ccgcgttcta acgacaatat gtacaagcct    600

aattgtgtag catctggctt actgaagcag accctatcat ctctctcgta aactgccgtc    660

agagtcggtt tggttggacg aaccttctga gtttctggta acgccgttcc gcaccccgga    720

aatggtcacc gaaccaatca gcagggtcat cgctagccag atcctctacg ccggacgcat    780

cgtggccggc atcaccggcg ccacaggtgc ggttgctggc gcctatatcg ccgacatcac    840

cgatggggaa gatcgggctc gccacttcgg gctcatgagc gcttgtttcg gcgtgggtat    900

ggtggcaggc cccgtggccg ggggactgtt gggcgccatc tccttgcatg caccattcct    960

tgcggcggcg gtgctcaacg gcctcaacct actactgggc tgcttcctaa tgcaggagtc   1020

gcataaggga gagcgtcgat atggtgcact ctcagtacaa tctgctctga tgccgcatag   1080

ttaagccaac tccgctatcg ctacgtgact gggtcatggc tgcgccccga cacccgccaa   1140

cacccgctga cgcgccctga cgggcttgtc tgctcccggc atccgcttac agacaagctg   1200

tgaccgtctc cgggagctgc atgtgtcaga ggttttcacc gtcatcaccg aaacgcgcga   1260

ggcagcttga agacgaaagg gcctcgtgat acgcctattt ttataggtta atgtcatgat   1320

aataatggtt tcttagacgt caggtggcac ttttcgggga aatgtgcgcg gaacccctat   1380

ttgtttattt ttctaaatac attcaaatat gtatccgctc atgagacaat aaccctgata   1440

aatgcttcaa taatattgaa aaaggaagag tatgagtatt caacatttcc gtgtcgccct   1500

tattcccttt tttgcggcat tttgccttcc tgtttttgct cacccagaaa cgctggtgaa   1560

agtaaaagat gctgaagatc agttgggtgc acgagtgggt tacatcgaac tggatctcaa   1620
```

-continued

```
cagcggtaag atccttgaga gttttcgccc cgaagaacgt tttccaatga tgagcacttt   1680
taaagttctg ctatgtggcg cggtattatc ccgtattgac gccgggcaag agcaactcgg   1740
tcgccgcata cactattctc agaatgactt ggttgagtac tcaccagtca cagaaaagca   1800
tcttacggat ggcatgacag taagagaatt atgcagtgct gccataacca tgagtgataa   1860
cactgcggcc aacttacttc tgacaacgat cggaggaccg aaggagctaa ccgctttttt   1920
gcacaacatg ggggatcatg taactcgcct tgatcgttgg gaaccggagc tgaatgaagc   1980
cataccaaac gacgagcgtg acaccacgat gcctgtagca atggcaacaa cgttgcgcaa   2040
actattaact ggcgaactac ttactctagc ttcccggcaa caattaatag actggatgga   2100
ggcggataaa gttgcaggac cacttctgcg ctcggccctt ccggctggct ggtttattgc   2160
tgataaatct ggagccggtg agcgtgggtc tcgcggtatc attgcagcac tggggccaga   2220
tggtaagccc tcccgtatcg tagttatcta cacgacgggg agtcaggcaa ctatggatga   2280
acgaaataga cagatcgctg agataggtgc ctcactgatt aagcattggt aactgtcaga   2340
ccaagtttac tcatatatac tttagattga tttaaaactt catttttaat ttaaaaggat   2400
ctaggtgaag atcctttttg ataatctcat gaccaaaatc ccttaacgtg agttttcgtt   2460
ccactgagcg tcagaccccg tagaaaagat caaaggatct tcttgagatc cttttttct    2520
gcgcgtaatc tgctgcttgc aaacaaaaaa accaccgcta ccagcggtgg tttgtttgcc   2580
ggatcaagag ctaccaactc tttttccgaa ggtaactggc ttcagcagag cgcagatacc   2640
aaatactgtc cttctagtgt agccgtagtt aggccaccac ttcaagaact ctgtagcacc   2700
gcctacatac ctcgctctgc taatcctgtt accagtggct gctgccagtg gcgataagtc   2760
gtgtcttacc gggttggact caagacgata gttaccggat aaggcgcagc ggtcgggctg   2820
aacggggggt tcgtgcacac agcccagctt ggagcgaacg acctacaccg aactgagata   2880
cctacagcgc gagcattgag aaagcgccac gcttcccgaa gggagaaagg cggacaggta   2940
tccggtaagc ggcagggtcg gaacaggaga gcgcacgagg gagcttccag ggggaaacgc   3000
ctggtatctt tatagtcctg tcgggtttcg ccacctctga cttgagcgtc gatttttgtg   3060
atgctcgtca ggggggcgga gcctatggaa aaacgccagc aacgcggcct ttttacggtt   3120
cctggccttt tgctggcctt ttgctcacat gttctttcct gcgttatccc ctgattctgt   3180
ggataaccgt attaccgcct ttgagtgagc tgataccgct cgccgcagcc gaacgaccga   3240
gcgcagcgag tcagtgagcg aggaagcgga agagcgccca atacgcaaac cgcctctccc   3300
cgcgcgttgg ccgattcatt aatgcagctg tggtgtcatg gtcggtgatc gccagggtgc   3360
cgacgcgcat ctcgactgca tggtgcacca atgcttctgg cgtcaggcag ccatcggaag   3420
ctgtggtatg gccgtgcagg tcgtaaatca ctgcataatt cgtgtcgctc aaggcgcact   3480
cccgttctgg ataatgtttt ttgcgccgac atcataacgg ttctggcaaa tattctgaaa   3540
tgagctgttg acaattaatc atcgaactag ttaactagta cgcaagttca cgtaaaaagg   3600
gtatcgcgga att                                                      3613
```

<210> SEQ ID NO 83

<400> SEQUENCE: 83

000 3

<210> SEQ ID NO 84

-continued

<400> SEQUENCE: 84

000 3

<210> SEQ ID NO 85

<400> SEQUENCE: 85

000 3

<210> SEQ ID NO 86

<400> SEQUENCE: 86

000 3

<210> SEQ ID NO 87

<400> SEQUENCE: 87

000 3

<210> SEQ ID NO 88

<400> SEQUENCE: 88

000 3

<210> SEQ ID NO 89

<400> SEQUENCE: 89

000 3

<210> SEQ ID NO 90

<400> SEQUENCE: 90

000 3

<210> SEQ ID NO 91

<400> SEQUENCE: 91

000 3

<210> SEQ ID NO 92

<400> SEQUENCE: 92

000 3

<210> SEQ ID NO 93

<400> SEQUENCE: 93

000 3

<210> SEQ ID NO 94

<400> SEQUENCE: 94

000 3

<210> SEQ ID NO 95

<400> SEQUENCE: 95

-continued 000 3

<210> SEQ ID NO 96

<400> SEQUENCE: 96

000 3

<210> SEQ ID NO 97

<400> SEQUENCE: 97

000 3

<210> SEQ ID NO 98

<400> SEQUENCE: 98

000 3

<210> SEQ ID NO 99

<400> SEQUENCE: 99

000 3

<210> SEQ ID NO 100

<400> SEQUENCE: 100

000 3

<210> SEQ ID NO 101

<400> SEQUENCE: 101

000 3

<210> SEQ ID NO 102

<400> SEQUENCE: 102

000 3

<210> SEQ ID NO 103

<400> SEQUENCE: 103

000 3

<210> SEQ ID NO 104

<400> SEQUENCE: 104

000 3

<210> SEQ ID NO 105

<400> SEQUENCE: 105

000 3

<210> SEQ ID NO 106

<400> SEQUENCE: 106

000 3

-continued

<210> SEQ ID NO 107

<400> SEQUENCE: 107

000 3

<210> SEQ ID NO 108

<400> SEQUENCE: 108

000 3

<210> SEQ ID NO 109

<400> SEQUENCE: 109

000 3

<210> SEQ ID NO 110

<400> SEQUENCE: 110

000 3

<210> SEQ ID NO 111

<400> SEQUENCE: 111

000 3

<210> SEQ ID NO 112

<400> SEQUENCE: 112

000 3

<210> SEQ ID NO 113

<400> SEQUENCE: 113

000 3

<210> SEQ ID NO 114

<400> SEQUENCE: 114

000 3

<210> SEQ ID NO 115

<400> SEQUENCE: 115

000 3

<210> SEQ ID NO 116

<400> SEQUENCE: 116

000 3

<210> SEQ ID NO 117

<400> SEQUENCE: 117

000 3

<210> SEQ ID NO 118

-continued

<400> SEQUENCE: 118

000 3

<210> SEQ ID NO 119

<400> SEQUENCE: 119

000 3

<210> SEQ ID NO 120

<400> SEQUENCE: 120

000 3

<210> SEQ ID NO 121

<400> SEQUENCE: 121

000 3

<210> SEQ ID NO 122

<400> SEQUENCE: 122

000 3

<210> SEQ ID NO 123

<400> SEQUENCE: 123

000 3

<210> SEQ ID NO 124

<400> SEQUENCE: 124

000 3

<210> SEQ ID NO 125

<400> SEQUENCE: 125

000 3

<210> SEQ ID NO 126

<400> SEQUENCE: 126

000 3

<210> SEQ ID NO 127

<400> SEQUENCE: 127

000 3

<210> SEQ ID NO 128

<400> SEQUENCE: 128

000 3

<210> SEQ ID NO 129

<400> SEQUENCE: 129

000 3

<210> SEQ ID NO 130
<400> SEQUENCE: 130

000 3

<210> SEQ ID NO 131
<400> SEQUENCE: 131

000 3

<210> SEQ ID NO 132
<400> SEQUENCE: 132

000 3

<210> SEQ ID NO 133
<400> SEQUENCE: 133

000 3

<210> SEQ ID NO 134
<400> SEQUENCE: 134

000 3

<210> SEQ ID NO 135
<400> SEQUENCE: 135

000 3

<210> SEQ ID NO 136
<400> SEQUENCE: 136

000 3

<210> SEQ ID NO 137
<400> SEQUENCE: 137

000 3

<210> SEQ ID NO 138
<400> SEQUENCE: 138

000 3

<210> SEQ ID NO 139
<400> SEQUENCE: 139

000 3

<210> SEQ ID NO 140
<400> SEQUENCE: 140

000 3

-continued

<210> SEQ ID NO 141
<400> SEQUENCE: 141
000 3

<210> SEQ ID NO 142
<400> SEQUENCE: 142
000 3

<210> SEQ ID NO 143
<400> SEQUENCE: 143
000 3

<210> SEQ ID NO 144
<400> SEQUENCE: 144
000 3

<210> SEQ ID NO 145
<400> SEQUENCE: 145
000 3

<210> SEQ ID NO 146
<400> SEQUENCE: 146
000 3

<210> SEQ ID NO 147
<400> SEQUENCE: 147
000 3

<210> SEQ ID NO 148
<400> SEQUENCE: 148
000 3

<210> SEQ ID NO 149
<400> SEQUENCE: 149
000 3

<210> SEQ ID NO 150
<400> SEQUENCE: 150
000 3

<210> SEQ ID NO 151
<400> SEQUENCE: 151
000 3

-continued

<210> SEQ ID NO 152

<400> SEQUENCE: 152

000 3

<210> SEQ ID NO 153

<400> SEQUENCE: 153

000 3

<210> SEQ ID NO 154

<400> SEQUENCE: 154

000 3

<210> SEQ ID NO 155

<400> SEQUENCE: 155

000 3

<210> SEQ ID NO 156

<400> SEQUENCE: 156

000 3

<210> SEQ ID NO 157

<400> SEQUENCE: 157

000 3

<210> SEQ ID NO 158

<400> SEQUENCE: 158

000 3

<210> SEQ ID NO 159

<400> SEQUENCE: 159

000 3

<210> SEQ ID NO 160

<400> SEQUENCE: 160

000 3

<210> SEQ ID NO 161

<400> SEQUENCE: 161

000 3

<210> SEQ ID NO 162

<400> SEQUENCE: 162

000 3

<210> SEQ ID NO 163

-continued

<400> SEQUENCE: 163

000 3

<210> SEQ ID NO 164

<400> SEQUENCE: 164

000 3

<210> SEQ ID NO 165

<400> SEQUENCE: 165

000 3

<210> SEQ ID NO 166

<400> SEQUENCE: 166

000 3

<210> SEQ ID NO 167

<400> SEQUENCE: 167

000 3

<210> SEQ ID NO 168

<400> SEQUENCE: 168

000 3

<210> SEQ ID NO 169

<400> SEQUENCE: 169

000 3

<210> SEQ ID NO 170

<400> SEQUENCE: 170

000 3

<210> SEQ ID NO 171

<400> SEQUENCE: 171

000 3

<210> SEQ ID NO 172

<400> SEQUENCE: 172

000 3

<210> SEQ ID NO 173

<400> SEQUENCE: 173

000 3

<210> SEQ ID NO 174

<400> SEQUENCE: 174

-continued 000 3

<210> SEQ ID NO 175

<400> SEQUENCE: 175

000 3

<210> SEQ ID NO 176

<400> SEQUENCE: 176

000 3

<210> SEQ ID NO 177

<400> SEQUENCE: 177

000 3

<210> SEQ ID NO 178

<400> SEQUENCE: 178

000 3

<210> SEQ ID NO 179

<400> SEQUENCE: 179

000 3

<210> SEQ ID NO 180

<400> SEQUENCE: 180

000 3

<210> SEQ ID NO 181

<400> SEQUENCE: 181

000 3

<210> SEQ ID NO 182

<400> SEQUENCE: 182

000 3

<210> SEQ ID NO 183

<400> SEQUENCE: 183

000 3

<210> SEQ ID NO 184

<400> SEQUENCE: 184

000 3

<210> SEQ ID NO 185

<400> SEQUENCE: 185

000 3

-continued

<210> SEQ ID NO 186

<400> SEQUENCE: 186

000 3

<210> SEQ ID NO 187

<400> SEQUENCE: 187

000 3

<210> SEQ ID NO 188

<400> SEQUENCE: 188

000 3

<210> SEQ ID NO 189

<400> SEQUENCE: 189

000 3

<210> SEQ ID NO 190

<400> SEQUENCE: 190

000 3

<210> SEQ ID NO 191

<400> SEQUENCE: 191

000 3

<210> SEQ ID NO 192

<400> SEQUENCE: 192

000 3

<210> SEQ ID NO 193

<400> SEQUENCE: 193

000 3

<210> SEQ ID NO 194

<400> SEQUENCE: 194

000 3

<210> SEQ ID NO 195

<400> SEQUENCE: 195

000 3

<210> SEQ ID NO 196

<400> SEQUENCE: 196

000 3

<210> SEQ ID NO 197

-continued

<400> SEQUENCE: 197

000 3

<210> SEQ ID NO 198

<400> SEQUENCE: 198

000 3

<210> SEQ ID NO 199

<400> SEQUENCE: 199

000 3

<210> SEQ ID NO 200

<400> SEQUENCE: 200

000 3

<210> SEQ ID NO 201

<400> SEQUENCE: 201

000 3

<210> SEQ ID NO 202

<400> SEQUENCE: 202

000 3

<210> SEQ ID NO 203

<400> SEQUENCE: 203

000 3

<210> SEQ ID NO 204

<400> SEQUENCE: 204

000 3

<210> SEQ ID NO 205

<400> SEQUENCE: 205

000 3

<210> SEQ ID NO 206

<400> SEQUENCE: 206

000 3

<210> SEQ ID NO 207

<400> SEQUENCE: 207

000 3

<210> SEQ ID NO 208

<400> SEQUENCE: 208

-continued 000 3

<210> SEQ ID NO 209

<400> SEQUENCE: 209

000 3

<210> SEQ ID NO 210

<400> SEQUENCE: 210

000 3

<210> SEQ ID NO 211

<400> SEQUENCE: 211

000 3

<210> SEQ ID NO 212

<400> SEQUENCE: 212

000 3

<210> SEQ ID NO 213

<400> SEQUENCE: 213

000 3

<210> SEQ ID NO 214

<400> SEQUENCE: 214

000 3

<210> SEQ ID NO 215

<400> SEQUENCE: 215

000 3

<210> SEQ ID NO 216

<400> SEQUENCE: 216

000 3

<210> SEQ ID NO 217

<400> SEQUENCE: 217

000 3

<210> SEQ ID NO 218

<400> SEQUENCE: 218

000 3

<210> SEQ ID NO 219

<400> SEQUENCE: 219

000 3

-continued

<210> SEQ ID NO 220

<400> SEQUENCE: 220

000 3

<210> SEQ ID NO 221

<400> SEQUENCE: 221

000 3

<210> SEQ ID NO 222

<400> SEQUENCE: 222

000 3

<210> SEQ ID NO 223

<400> SEQUENCE: 223

000 3

<210> SEQ ID NO 224

<400> SEQUENCE: 224

000 3

<210> SEQ ID NO 225

<400> SEQUENCE: 225

000 3

<210> SEQ ID NO 226

<400> SEQUENCE: 226

000 3

<210> SEQ ID NO 227

<400> SEQUENCE: 227

000 3

<210> SEQ ID NO 228

<400> SEQUENCE: 228

000 3

<210> SEQ ID NO 229

<400> SEQUENCE: 229

000 3

<210> SEQ ID NO 230
<211> LENGTH: 132
<212> TYPE: PRT
<213> ORGANISM: precursor human IL-13

<400> SEQUENCE: 230

-continued

```
Met Ala Leu Leu Leu Thr Thr Val Ile Ala Leu Thr Cys Leu Gly Gly
1               5                   10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Arg Phe Asn
    130


<210> SEQ ID NO 231
<211> LENGTH: 112
<212> TYPE: PRT
<213> ORGANISM: processed human IL-13

<400> SEQUENCE: 231

Gly Pro Val Pro Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110



<210> SEQ ID NO 232
<211> LENGTH: 111
<212> TYPE: PRT
<213> ORGANISM: processed mouse IL-13

<400> SEQUENCE: 232

Gly Pro Val Pro Arg Ser Val Ser Leu Pro Leu Thr Leu Lys Glu Leu
1               5                   10                  15

Ile Glu Glu Leu Ser Asn Ile Thr Gln Asp Gln Thr Pro Leu Cys Asn
            20                  25                  30

Gly Ser Met Val Trp Ser Val Asp Leu Ala Ala Gly Gly Phe Cys Val
        35                  40                  45

Ala Leu Asp Ser Leu Thr Asn Ile Ser Asn Cys Asn Ala Ile Tyr Arg
    50                  55                  60

Thr Gln Arg Ile Leu His Gly Leu Cys Asn Arg Lys Ala Pro Thr Thr
```

-continued

```
65                  70                  75                  80

Val Ser Ser Leu Pro Asp Thr Lys Ile Glu Val Ala His Phe Ile Thr
                85                  90                  95

Lys Leu Leu Ser Tyr Thr Lys Gln Leu Phe Arg His Gly Pro Phe
            100                 105                 110


<210> SEQ ID NO 233
<211> LENGTH: 134
<212> TYPE: PRT
<213> ORGANISM: precursor human IL-5

<400> SEQUENCE: 233

Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Lys Cys Gly Glu Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser
    130


<210> SEQ ID NO 234
<211> LENGTH: 115
<212> TYPE: PRT
<213> ORGANISM: processed human IL-5

<400> SEQUENCE: 234

Ile Pro Thr Glu Ile Pro Thr Ser Ala Leu Val Lys Glu Thr Leu Ala
1               5                   10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
65                  70                  75                  80

Gly Gln Lys Lys Lys Cys Gly Glu Glu Arg Arg Arg Val Asn Gln Phe
                85                  90                  95

Leu Asp Tyr Leu Gln Glu Phe Leu Gly Val Met Asn Thr Glu Trp Ile
            100                 105                 110

Ile Glu Ser
        115


<210> SEQ ID NO 235
<211> LENGTH: 113
<212> TYPE: PRT
```

-continued

<213> ORGANISM: processed mouse IL-5

<400> SEQUENCE: 235

```
Met Glu Ile Pro Met Ser Thr Val Val Lys Glu Thr Leu Thr Gln Leu
1               5                   10                  15

Ser Ala His Arg Ala Leu Leu Thr Ser Asn Glu Thr Met Arg Leu Pro
            20                  25                  30

Val Pro Thr His Lys Asn His Gln Leu Cys Ile Gly Glu Ile Phe Gln
        35                  40                  45

Gly Leu Asp Ile Leu Lys Asn Gln Thr Val Arg Gly Gly Thr Val Glu
    50                  55                  60

Met Leu Phe Gln Asn Leu Ser Leu Ile Lys Lys Tyr Ile Asp Arg Gln
65                  70                  75                  80

Lys Glu Lys Cys Gly Glu Glu Arg Arg Arg Thr Arg Gln Phe Leu Asp
                85                  90                  95

Tyr Leu Gln Glu Phe Leu Gly Val Met Ser Thr Glu Trp Ala Met Glu
            100                 105                 110

Gly
```

SEQ ID NO 236

<400> SEQUENCE: 236

000 3

<210> SEQ ID NO 237

<400> SEQUENCE: 237

000 3

<210> SEQ ID NO 238

<400> SEQUENCE: 238

000 3

<210> SEQ ID NO 239

<400> SEQUENCE: 239

000 3

<210> SEQ ID NO 240

<400> SEQUENCE: 240

000 3

<210> SEQ ID NO 241

<400> SEQUENCE: 241

000 3

<210> SEQ ID NO 242
<211> LENGTH: 97
<212> TYPE: PRT
<213> ORGANISM: Human Eotaxin-1

<400> SEQUENCE: 242

```
Met Lys Val Ser Ala Ala Leu Leu Trp Leu Leu Leu Ile Ala Ala Ala
1               5                   10                  15
```

-continued

```
Phe Ser Pro Gln Gly Leu Ala Gly Pro Ala Ser Val Pro Thr Thr Cys
            20                  25                  30

Cys Phe Asn Leu Ala Asn Arg Lys Ile Pro Leu Gln Arg Leu Glu Ser
        35                  40                  45

Tyr Arg Arg Ile Thr Ser Gly Lys Cys Pro Gln Lys Ala Val Ile Phe
    50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Asp Gln Lys Ser Pro Thr Pro Lys
                85                  90                  95

Pro


<210> SEQ ID NO 243
<211> LENGTH: 119
<212> TYPE: PRT
<213> ORGANISM: Human Eotaxin-2

<400> SEQUENCE: 243

Met Ala Gly Leu Met Thr Ile Val Thr Ser Leu Leu Phe Leu Gly Val
1               5                   10                  15

Cys Ala His His Ile Ile Pro Thr Gly Ser Val Val Ile Pro Ser Pro
            20                  25                  30

Cys Cys Met Phe Phe Val Ser Lys Arg Ile Pro Glu Asn Arg Val Val
        35                  40                  45

Ser Tyr Gln Leu Ser Ser Arg Ser Thr Cys Leu Lys Ala Gly Val Ile
    50                  55                  60

Phe Thr Thr Lys Lys Gly Gln Gln Phe Cys Gly Asp Pro Lys Gln Glu
65                  70                  75                  80

Trp Val Gln Arg Tyr Met Lys Asn Leu Asp Ala Lys Gln Lys Lys Ala
                85                  90                  95

Ser Pro Arg Ala Arg Ala Val Ala Val Lys Gly Pro Val Gln Arg Tyr
            100                 105                 110

Pro Gly Asn Gln Thr Thr Cys
        115


<210> SEQ ID NO 244
<211> LENGTH: 94
<212> TYPE: PRT
<213> ORGANISM: Human Eotaxin-3

<400> SEQUENCE: 244

Met Met Gly Leu Ser Leu Ala Ser Ala Val Leu Leu Ala Ser Leu Leu
1               5                   10                  15

Ser Leu His Leu Gly Thr Ala Thr Arg Gly Ser Asp Ile Ser Lys Thr
            20                  25                  30

Cys Cys Phe Gln Tyr Ser His Lys Pro Leu Pro Trp Thr Trp Val Arg
        35                  40                  45

Ser Tyr Glu Phe Thr Ser Asn Ser Cys Ser Gln Arg Ala Val Ile Phe
    50                  55                  60

Thr Thr Lys Arg Gly Lys Lys Val Cys Thr His Pro Arg Lys Lys Trp
65                  70                  75                  80

Val Gln Lys Tyr Ile Ser Leu Leu Lys Thr Pro Lys Gln Leu
                85                  90


<210> SEQ ID NO 245
<211> LENGTH: 97
```

-continued

<212> TYPE: PRT
<213> ORGANISM: Mouse Eotaxin-1

<400> SEQUENCE: 245

```
Met Gln Ser Ser Thr Ala Leu Leu Phe Leu Leu Leu Thr Val Thr Ser
1               5                   10                  15

Phe Thr Ser Gln Val Leu Ala His Pro Gly Ser Ile Pro Thr Ser Cys
            20                  25                  30

Cys Phe Ile Met Thr Ser Lys Lys Ile Pro Asn Thr Leu Leu Lys Ser
        35                  40                  45

Tyr Lys Arg Ile Thr Asn Asn Arg Cys Thr Leu Lys Ala Ile Val Phe
    50                  55                  60

Lys Thr Arg Leu Gly Lys Glu Ile Cys Ala Asp Pro Lys Lys Lys Trp
65                  70                  75                  80

Val Gln Asp Ala Thr Lys His Leu Asp Gln Lys Leu Gln Thr Pro Lys
                85                  90                  95

Pro
```

<210> SEQ ID NO 246
<211> LENGTH: 119
<212> TYPE: PRT
<213> ORGANISM: Mouse Eotaxin-2

<400> SEQUENCE: 246

```
Met Ala Gly Ser Ala Thr Ile Val Ala Gly Leu Leu Leu Leu Val Ala
1               5                   10                  15

Cys Ala Cys Cys Ile Phe Pro Ile Asp Ser Val Thr Ile Pro Ser Ser
            20                  25                  30

Cys Cys Thr Ser Phe Ile Ser Lys Lys Ile Pro Glu Asn Arg Val Val
        35                  40                  45

Ser Tyr Gln Leu Ala Asn Gly Ser Ile Cys Pro Lys Ala Gly Val Ile
    50                  55                  60

Phe Ile Thr Lys Lys Gly His Lys Ile Cys Thr Asp Pro Lys Leu Leu
65                  70                  75                  80

Trp Val Gln Arg His Ile Gln Lys Leu Asp Ala Lys Lys Asn Gln Pro
                85                  90                  95

Ser Lys Gly Ala Lys Ala Val Arg Thr Lys Phe Ala Val Gln Arg Arg
            100                 105                 110

Arg Gly Asn Ser Thr Glu Val
        115
```

<210> SEQ ID NO 247

<400> SEQUENCE: 247

```
000                                                                    3
```

<210> SEQ ID NO 248

<400> SEQUENCE: 248

```
000                                                                    3
```

<210> SEQ ID NO 249

<400> SEQUENCE: 249

```
000                                                                    3
```

-continued

<210> SEQ ID NO 250

<400> SEQUENCE: 250

000 3

<210> SEQ ID NO 251

<400> SEQUENCE: 251

000 3

<210> SEQ ID NO 252

<400> SEQUENCE: 252

000 3

<210> SEQ ID NO 253

<400> SEQUENCE: 253

000 3

<210> SEQ ID NO 254

<400> SEQUENCE: 254

000 3

<210> SEQ ID NO 255

<400> SEQUENCE: 255

000 3

<210> SEQ ID NO 256

<400> SEQUENCE: 256

000 3

<210> SEQ ID NO 257

<400> SEQUENCE: 257

000 3

<210> SEQ ID NO 258

<400> SEQUENCE: 258

000 3

<210> SEQ ID NO 259

<400> SEQUENCE: 259

000 3

<210> SEQ ID NO 260

<400> SEQUENCE: 260

000 3

<210> SEQ ID NO 261

-continued

<400> SEQUENCE: 261

000 3

<210> SEQ ID NO 262

<400> SEQUENCE: 262

000 3

<210> SEQ ID NO 263

<400> SEQUENCE: 263

000 3

<210> SEQ ID NO 264

<400> SEQUENCE: 264

000 3

<210> SEQ ID NO 265

<400> SEQUENCE: 265

000 3

<210> SEQ ID NO 266

<400> SEQUENCE: 266

000 3

<210> SEQ ID NO 267

<400> SEQUENCE: 267

000 3

<210> SEQ ID NO 268

<400> SEQUENCE: 268

000 3

<210> SEQ ID NO 269

<400> SEQUENCE: 269

000 3

<210> SEQ ID NO 270

<400> SEQUENCE: 270

000 3

<210> SEQ ID NO 271

<400> SEQUENCE: 271

000 3

<210> SEQ ID NO 272

<400> SEQUENCE: 272

-continued 000 3

<210> SEQ ID NO 273

<400> SEQUENCE: 273

000 3

<210> SEQ ID NO 274

<400> SEQUENCE: 274

000 3

<210> SEQ ID NO 275

<400> SEQUENCE: 275

000 3

<210> SEQ ID NO 276

<400> SEQUENCE: 276

000 3

<210> SEQ ID NO 277

<400> SEQUENCE: 277

000 3

<210> SEQ ID NO 278

<400> SEQUENCE: 278

000 3

<210> SEQ ID NO 279

<400> SEQUENCE: 279

000 3

<210> SEQ ID NO 280

<400> SEQUENCE: 280

000 3

<210> SEQ ID NO 281

<400> SEQUENCE: 281

000 3

<210> SEQ ID NO 282

<400> SEQUENCE: 282

000 3

<210> SEQ ID NO 283

<400> SEQUENCE: 283

000 3

-continued

<210> SEQ ID NO 284

<400> SEQUENCE: 284

000 3

<210> SEQ ID NO 285

<400> SEQUENCE: 285

000 3

<210> SEQ ID NO 286

<400> SEQUENCE: 286

000 3

<210> SEQ ID NO 287

<400> SEQUENCE: 287

000 3

<210> SEQ ID NO 288

<400> SEQUENCE: 288

000 3

<210> SEQ ID NO 289

<400> SEQUENCE: 289

000 3

<210> SEQ ID NO 290

<400> SEQUENCE: 290

000 3

<210> SEQ ID NO 291

<400> SEQUENCE: 291

000 3

<210> SEQ ID NO 292

<400> SEQUENCE: 292

000 3

<210> SEQ ID NO 293

<400> SEQUENCE: 293

000 3

<210> SEQ ID NO 294

<400> SEQUENCE: 294

000 3

<210> SEQ ID NO 295

-continued

<400> SEQUENCE: 295

000 3

<210> SEQ ID NO 296

<400> SEQUENCE: 296

000 3

<210> SEQ ID NO 297

<400> SEQUENCE: 297

000 3

<210> SEQ ID NO 298

<400> SEQUENCE: 298

000 3

<210> SEQ ID NO 299

<400> SEQUENCE: 299

000 3

<210> SEQ ID NO 300

<400> SEQUENCE: 300

000 3

<210> SEQ ID NO 301

<400> SEQUENCE: 301

000 3

<210> SEQ ID NO 302

<400> SEQUENCE: 302

000 3

<210> SEQ ID NO 303

<400> SEQUENCE: 303

000 3

<210> SEQ ID NO 304

<400> SEQUENCE: 304

000 3

<210> SEQ ID NO 305

<400> SEQUENCE: 305

000 3

<210> SEQ ID NO 306

<400> SEQUENCE: 306

-continued 000 3

<210> SEQ ID NO 307

<400> SEQUENCE: 307

000 3

<210> SEQ ID NO 308

<400> SEQUENCE: 308

000 3

<210> SEQ ID NO 309

<400> SEQUENCE: 309

000 3

<210> SEQ ID NO 310

<400> SEQUENCE: 310

000 3

<210> SEQ ID NO 311

<400> SEQUENCE: 311

000 3

<210> SEQ ID NO 312

<400> SEQUENCE: 312

000 3

<210> SEQ ID NO 313

<400> SEQUENCE: 313

000 3

<210> SEQ ID NO 314

<400> SEQUENCE: 314

000 3

<210> SEQ ID NO 315

<400> SEQUENCE: 315

000 3

<210> SEQ ID NO 316

<400> SEQUENCE: 316

000 3

<210> SEQ ID NO 317

<400> SEQUENCE: 317

000 3

-continued

<210> SEQ ID NO 318

<400> SEQUENCE: 318

000 3

<210> SEQ ID NO 319

<400> SEQUENCE: 319

000 3

<210> SEQ ID NO 320

<400> SEQUENCE: 320

000 3

<210> SEQ ID NO 321

<400> SEQUENCE: 321

000 3

<210> SEQ ID NO 322

<400> SEQUENCE: 322

000 3

<210> SEQ ID NO 323

<400> SEQUENCE: 323

000 3

<210> SEQ ID NO 324

<400> SEQUENCE: 324

000 3

<210> SEQ ID NO 325

<400> SEQUENCE: 325

000 3

<210> SEQ ID NO 326

<400> SEQUENCE: 326

000 3

<210> SEQ ID NO 327

<400> SEQUENCE: 327

000 3

<210> SEQ ID NO 328
<211> LENGTH: 132
<212> TYPE: PRT
<213> ORGANISM: Mouse C-IL-13-F

<400> SEQUENCE: 328

-continued

```
Ala Asp Pro Gly Cys Gly Gly Gly Gly Gly Leu Ala Gly Pro Val Pro
1               5                   10                  15

Arg Ser Val Ser Leu Pro Leu Thr Leu Lys Glu Leu Ile Glu Glu Leu
            20                  25                  30

Ser Asn Ile Thr Gln Asp Gln Thr Pro Leu Cys Asn Gly Ser Met Val
        35                  40                  45

Trp Ser Val Asp Leu Ala Ala Gly Gly Phe Cys Val Ala Leu Asp Ser
    50                  55                  60

Leu Thr Asn Ile Ser Asn Cys Asn Ala Ile Tyr Arg Thr Gln Arg Ile
65                  70                  75                  80

Leu His Gly Leu Cys Asn Arg Lys Ala Pro Thr Thr Val Ser Ser Leu
                85                  90                  95

Pro Asp Thr Lys Ile Glu Val Ala His Phe Ile Thr Lys Leu Leu Ser
            100                 105                 110

Tyr Thr Lys Gln Leu Phe Arg His Gly Pro Phe Leu Glu Val Leu Ala
        115                 120                 125

Ile Glu Gly Arg
    130


<210> SEQ ID NO 329
<211> LENGTH: 119
<212> TYPE: PRT
<213> ORGANISM: Mouse C-IL-13-S

<400> SEQUENCE: 329

Leu Ala Cys Gly Gly Gly Gly Gly Gly Pro Val Pro Arg Ser Val Ser
1               5                   10                  15

Leu Pro Leu Thr Leu Lys Glu Leu Ile Glu Glu Leu Ser Asn Ile Thr
            20                  25                  30

Gln Asp Gln Thr Pro Leu Cys Asn Gly Ser Met Val Trp Ser Val Asp
        35                  40                  45

Leu Ala Ala Gly Gly Phe Cys Val Ala Leu Asp Ser Leu Thr Asn Ile
    50                  55                  60

Ser Asn Cys Asn Ala Ile Tyr Arg Thr Gln Arg Ile Leu His Gly Leu
65                  70                  75                  80

Cys Asn Arg Lys Ala Pro Thr Thr Val Ser Ser Leu Pro Asp Thr Lys
                85                  90                  95

Ile Glu Val Ala His Phe Ile Thr Lys Leu Leu Ser Tyr Thr Lys Gln
            100                 105                 110

Leu Phe Arg His Gly Pro Phe
        115


<210> SEQ ID NO 330
<211> LENGTH: 133
<212> TYPE: PRT
<213> ORGANISM: Human C-IL-13-F

<400> SEQUENCE: 330

Ala Asp Pro Gly Cys Gly Gly Gly Gly Gly Leu Ala Gly Pro Val Pro
1               5                   10                  15

Pro Ser Thr Ala Leu Arg Glu Leu Ile Glu Glu Leu Val Asn Ile Thr
            20                  25                  30

Gln Asn Gln Lys Ala Pro Leu Cys Asn Gly Ser Met Val Trp Ser Ile
        35                  40                  45

Asn Leu Thr Ala Gly Met Tyr Cys Ala Ala Leu Glu Ser Leu Ile Asn
    50                  55                  60
```

-continued

```
Val Ser Gly Cys Ser Ala Ile Glu Lys Thr Gln Arg Met Leu Ser Gly
65                  70                  75                  80

Phe Cys Pro His Lys Val Ser Ala Gly Gln Phe Ser Ser Leu His Val
                85                  90                  95

Arg Asp Thr Lys Ile Glu Val Ala Gln Phe Val Lys Asp Leu Leu Leu
            100                 105                 110

His Leu Lys Lys Leu Phe Arg Glu Gly Arg Phe Asn Leu Glu Val Leu
        115                 120                 125

Ala Ile Glu Gly Arg
    130


<210> SEQ ID NO 331
<211> LENGTH: 120
<212> TYPE: PRT
<213> ORGANISM: Human C-IL-13-S

<400> SEQUENCE: 331

Leu Ala Cys Gly Gly Gly Gly Gly Gly Pro Val Pro Pro Ser Thr Ala
1               5                   10                  15

Leu Arg Glu Leu Ile Glu Glu Leu Val Asn Ile Thr Gln Asn Gln Lys
            20                  25                  30

Ala Pro Leu Cys Asn Gly Ser Met Val Trp Ser Ile Asn Leu Thr Ala
        35                  40                  45

Gly Met Tyr Cys Ala Ala Leu Glu Ser Leu Ile Asn Val Ser Gly Cys
    50                  55                  60

Ser Ala Ile Glu Lys Thr Gln Arg Met Leu Ser Gly Phe Cys Pro His
65                  70                  75                  80

Lys Val Ser Ala Gly Gln Phe Ser Ser Leu His Val Arg Asp Thr Lys
                85                  90                  95

Ile Glu Val Ala Gln Phe Val Lys Asp Leu Leu Leu His Leu Lys Lys
            100                 105                 110

Leu Phe Arg Glu Gly Arg Phe Asn
        115                 120


<210> SEQ ID NO 332
<211> LENGTH: 136
<212> TYPE: PRT
<213> ORGANISM: Mouse C-IL-5-E

<400> SEQUENCE: 332

Ala Leu Val Gly Cys Gly Gly Pro Lys Pro Ser Thr Pro Pro Gly Ser
1               5                   10                  15

Ser Gly Gly Ala Pro Ala Ser Met Glu Ile Pro Met Ser Thr Val Val
            20                  25                  30

Lys Glu Thr Leu Thr Gln Leu Ser Ala His Arg Ala Leu Leu Thr Ser
        35                  40                  45

Asn Glu Thr Met Arg Leu Pro Val Pro Thr His Lys Asn His Gln Leu
    50                  55                  60

Cys Ile Gly Glu Ile Phe Gln Gly Leu Asp Ile Leu Lys Asn Gln Thr
65                  70                  75                  80

Val Arg Gly Gly Thr Val Glu Met Leu Phe Gln Asn Leu Ser Leu Ile
                85                  90                  95

Lys Lys Tyr Ile Asp Arg Gln Lys Glu Lys Cys Gly Glu Glu Arg Arg
            100                 105                 110

Arg Thr Arg Gln Phe Leu Asp Tyr Leu Gln Glu Phe Leu Gly Val Met
        115                 120                 125
```

-continued

```
Ser Thr Glu Trp Ala Met Glu Gly
    130                 135


<210> SEQ ID NO 333
<211> LENGTH: 134
<212> TYPE: PRT
<213> ORGANISM: Mouse C-IL-5-F

<400> SEQUENCE: 333

Ala Asp Pro Gly Cys Gly Gly Gly Gly Gly Leu Ala Met Glu Ile Pro
1               5                   10                  15

Met Ser Thr Val Val Lys Glu Thr Leu Thr Gln Leu Ser Ala His Arg
            20                  25                  30

Ala Leu Leu Thr Ser Asn Glu Thr Met Arg Leu Pro Val Pro Thr His
        35                  40                  45

Lys Asn His Gln Leu Cys Ile Gly Glu Ile Phe Gln Gly Leu Asp Ile
    50                  55                  60

Leu Lys Asn Gln Thr Val Arg Gly Gly Thr Val Glu Met Leu Phe Gln
65                  70                  75                  80

Asn Leu Ser Leu Ile Lys Lys Tyr Ile Asp Arg Gln Lys Glu Lys Cys
                85                  90                  95

Gly Glu Glu Arg Arg Arg Thr Arg Gln Phe Leu Asp Tyr Leu Gln Glu
            100                 105                 110

Phe Leu Gly Val Met Ser Thr Glu Trp Ala Met Glu Gly Leu Glu Val
        115                 120                 125

Leu Ala Ile Glu Gly Arg
    130


<210> SEQ ID NO 334
<211> LENGTH: 121
<212> TYPE: PRT
<213> ORGANISM: Mouse C-IL-5-S

<400> SEQUENCE: 334

Leu Ala Cys Gly Gly Gly Gly Gly Met Glu Ile Pro Met Ser Thr Val
1               5                   10                  15

Val Lys Glu Thr Leu Thr Gln Leu Ser Ala His Arg Ala Leu Leu Thr
            20                  25                  30

Ser Asn Glu Thr Met Arg Leu Pro Val Pro Thr His Lys Asn His Gln
        35                  40                  45

Leu Cys Ile Gly Glu Ile Phe Gln Gly Leu Asp Ile Leu Lys Asn Gln
    50                  55                  60

Thr Val Arg Gly Gly Thr Val Glu Met Leu Phe Gln Asn Leu Ser Leu
65                  70                  75                  80

Ile Lys Lys Tyr Ile Asp Arg Gln Lys Glu Lys Cys Gly Glu Glu Arg
                85                  90                  95

Arg Arg Thr Arg Gln Phe Leu Asp Tyr Leu Gln Glu Phe Leu Gly Val
            100                 105                 110

Met Ser Thr Glu Trp Ala Met Glu Gly
        115                 120


<210> SEQ ID NO 335
<211> LENGTH: 138
<212> TYPE: PRT
<213> ORGANISM: Human C-IL-5-E

<400> SEQUENCE: 335

Ala Leu Val Gly Cys Gly Gly Pro Lys Pro Ser Thr Pro Pro Gly Ser
```

-continued 1 5 10 15

Ser Gly Gly Ala Pro Ala Ser Ile Pro Thr Glu Ile Pro Thr Ser Ala
20 25 30

Leu Val Lys Glu Thr Leu Ala Leu Leu Ser Thr His Arg Thr Leu Leu
35 40 45

Ile Ala Asn Glu Thr Leu Arg Ile Pro Val Pro Val His Lys Asn His
50 55 60

Gln Leu Cys Thr Glu Glu Ile Phe Gln Gly Ile Gly Thr Leu Glu Ser
65 70 75 80

Gln Thr Val Gln Gly Gly Thr Val Glu Arg Leu Phe Lys Asn Leu Ser
85 90 95

Leu Ile Lys Lys Tyr Ile Asp Gly Gln Lys Lys Lys Cys Gly Glu Glu
100 105 110

Arg Arg Arg Val Asn Gln Phe Leu Asp Tyr Leu Gln Glu Phe Leu Gly
115 120 125

Val Met Asn Thr Glu Trp Ile Ile Glu Ser
130 135

<210> SEQ ID NO 336
<211> LENGTH: 136
<212> TYPE: PRT
<213> ORGANISM: Human C-IL-5-F

<400> SEQUENCE: 336

Ala Asp Pro Gly Cys Gly Gly Gly Gly Gly Leu Ala Ile Pro Thr Glu
1 5 10 15

Ile Pro Thr Ser Ala Leu Val Lys Glu Thr Leu Ala Leu Leu Ser Thr
20 25 30

His Arg Thr Leu Leu Ile Ala Asn Glu Thr Leu Arg Ile Pro Val Pro
35 40 45

Val His Lys Asn His Gln Leu Cys Thr Glu Glu Ile Phe Gln Gly Ile
50 55 60

Gly Thr Leu Glu Ser Gln Thr Val Gln Gly Gly Thr Val Glu Arg Leu
65 70 75 80

Phe Lys Asn Leu Ser Leu Ile Lys Lys Tyr Ile Asp Gly Gln Lys Lys
85 90 95

Lys Cys Gly Glu Glu Arg Arg Arg Val Asn Gln Phe Leu Asp Tyr Leu
100 105 110

Gln Glu Phe Leu Gly Val Met Asn Thr Glu Trp Ile Ile Glu Ser Leu
115 120 125

Glu Val Leu Ala Ile Glu Gly Arg
130 135

<210> SEQ ID NO 337
<211> LENGTH: 123
<212> TYPE: PRT
<213> ORGANISM: Human C-IL-5-S

<400> SEQUENCE: 337

Leu Ala Cys Gly Gly Gly Gly Gly Ile Pro Thr Glu Ile Pro Thr Ser
1 5 10 15

Ala Leu Val Lys Glu Thr Leu Ala Leu Leu Ser Thr His Arg Thr Leu
20 25 30

Leu Ile Ala Asn Glu Thr Leu Arg Ile Pro Val Pro Val His Lys Asn
35 40 45

His Gln Leu Cys Thr Glu Glu Ile Phe Gln Gly Ile Gly Thr Leu Glu

-continued

```
    50                  55                  60

Ser Gln Thr Val Gln Gly Gly Thr Val Glu Arg Leu Phe Lys Asn Leu
65                  70                  75                  80

Ser Leu Ile Lys Lys Tyr Ile Asp Gly Gln Lys Lys Lys Cys Gly Glu
                85                  90                  95

Glu Arg Arg Arg Val Asn Gln Phe Leu Asp Tyr Leu Gln Glu Phe Leu
            100                 105                 110

Gly Val Met Asn Thr Glu Trp Ile Ile Glu Ser
        115                 120
```

<210> SEQ ID NO 338
<211> LENGTH: 27
<212> TYPE: DNA
<213> ORGANISM: Artificial Sequence
<220> FEATURE:
<223> OTHER INFORMATION: primer NheIL13-F

<400> SEQUENCE: 338
ctagctagcc gggccggtgc caagatc 27

<210> SEQ ID NO 339
<211> LENGTH: 26
<212> TYPE: DNA
<213> ORGANISM: Artificial Sequence
<220> FEATURE:
<223> OTHER INFORMATION: primer NheIL13-R

<400> SEQUENCE: 339
tttctcgagg aaggggccgt ggcgaa 26

<210> SEQ ID NO 340
<211> LENGTH: 55
<212> TYPE: DNA
<213> ORGANISM: Artificial Sequence
<220> FEATURE:
<223> OTHER INFORMATION: primer Spelinker3-F1

<400> SEQUENCE: 340
ccccgccggg ttcttctggc ggtgctccgg ctagcatgga gattcccatg agcac 55

<210> SEQ ID NO 341
<211> LENGTH: 52
<212> TYPE: DNA
<213> ORGANISM: Artificial Sequence
<220> FEATURE:
<223> OTHER INFORMATION: primer SpeNlinker3-F2

<400> SEQUENCE: 341
ttttactagt tggttgcggc ggcccgaaac cgagcacccc gccgggttct tc 52

<210> SEQ ID NO 342
<211> LENGTH: 49
<212> TYPE: DNA
<213> ORGANISM: Artificial Sequence
<220> FEATURE:
<223> OTHER INFORMATION: primer IL5StopXho-R

<400> SEQUENCE: 342
ttttgcggcc gcgtttaaac tcgagttatt agccttccat tgcccactc 49

<210> SEQ ID NO 343
<211> LENGTH: 35
<212> TYPE: DNA
<213> ORGANISM: Artificial Sequence -continued
<220> FEATURE:
<223> OTHER INFORMATION: Shine Delagarno sequence of vector pQb185

<400> SEQUENCE: 343
tctagattaa cccaacgcgt aggagtcagg ccatg 35

<210> SEQ ID NO 344
<211> LENGTH: 9
<212> TYPE: PRT
<213> ORGANISM: Artificial Sequence
<220> FEATURE:
<223> OTHER INFORMATION: Amino acid linker
<220> FEATURE:
<221> NAME/KEY: MISC_FEATURE
<222> LOCATION: (1)..(1)
<223> OTHER INFORMATION: Glycine can be repeated from zero to five times
<220> FEATURE:
<221> NAME/KEY: MISC_FEATURE
<222> LOCATION: (3)..(3)
<223> OTHER INFORMATION: Glycine can be repeated from zero to ten times
<220> FEATURE:
<221> NAME/KEY: MISC_FEATURE
<222> LOCATION: (4)..(4)
<223> OTHER INFORMATION: Serine can be repeated from zero to two times
<220> FEATURE:
<221> NAME/KEY: MISC_FEATURE
<222> LOCATION: (5)..(9)
<223> OTHER INFORMATION: These amino acids can be repeated from zero to
three times as a group

<400> SEQUENCE: 344

Gly Cys Gly Ser Gly Gly Gly Gly Ser
1 5

<210> SEQ ID NO 345
<211> LENGTH: 10
<212> TYPE: PRT
<213> ORGANISM: Artificial Sequence
<220> FEATURE:
<223> OTHER INFORMATION: Amino Acid Linker
<220> FEATURE:
<221> NAME/KEY: MISC_FEATURE
<222> LOCATION: (1)..(1)
<223> OTHER INFORMATION: Glycine can be repeated from zero to ten times
<220> FEATURE:
<221> NAME/KEY: MISC_FEATURE
<222> LOCATION: (2)..(2)
<223> OTHER INFORMATION: Serine can be repeated from zero to two times
<220> FEATURE:
<221> NAME/KEY: MISC_FEATURE
<222> LOCATION: (3)..(7)
<223> OTHER INFORMATION: These amino acids can be repeated from zero to
three times as a group
<220> FEATURE:
<221> NAME/KEY: MISC_FEATURE
<222> LOCATION: (8)..(8)
<223> OTHER INFORMATION: Glycine can be repeated from zero to eight
times
<220> FEATURE:
<221> NAME/KEY: MISC_FEATURE
<222> LOCATION: (10)..(10)
<223> OTHER INFORMATION: Glycine can be repeated from zero to five times

<400> SEQUENCE: 345

Gly Ser Gly Gly Gly Gly Ser Gly Cys Gly
1 5 10

<210> SEQ ID NO 346
<211> LENGTH: 5
<212> TYPE: PRT
<213> ORGANISM: Glycine serine linkers

<400> SEQUENCE: 346

-continued

Gly Gly Gly Gly Ser
1 5

<210> SEQ ID NO 347
<211> LENGTH: 10
<212> TYPE: PRT
<213> ORGANISM: N-terminal gamma 1

<400> SEQUENCE: 347

Cys Gly Asp Lys Thr His Thr Ser Pro Pro
1 5 10

<210> SEQ ID NO 348
<211> LENGTH: 10
<212> TYPE: PRT
<213> ORGANISM: C-terminal gamma 1

<400> SEQUENCE: 348

Asp Lys Thr His Thr Ser Pro Pro Cys Gly
1 5 10

<210> SEQ ID NO 349
<211> LENGTH: 17
<212> TYPE: PRT
<213> ORGANISM: N-terminal gamma 3

<400> SEQUENCE: 349

Cys Gly Gly Pro Lys Pro Ser Thr Pro Pro Gly Ser Ser Gly Gly Ala
1 5 10 15

Pro

<210> SEQ ID NO 350
<211> LENGTH: 18
<212> TYPE: PRT
<213> ORGANISM: C-terminal gamma 3

<400> SEQUENCE: 350

Pro Lys Pro Ser Thr Pro Pro Gly Ser Ser Gly Gly Ala Pro Gly Gly
1 5 10 15

Cys Gly

<210> SEQ ID NO 351
<211> LENGTH: 6
<212> TYPE: PRT
<213> ORGANISM: N-terminal glycine linker

<400> SEQUENCE: 351

Gly Cys Gly Gly Gly Gly
1 5

<210> SEQ ID NO 352
<211> LENGTH: 6
<212> TYPE: PRT
<213> ORGANISM: C-terminal glycine linker

<400> SEQUENCE: 352

Gly Gly Gly Gly Cys Gly
1 5

<210> SEQ ID NO 353
<211> LENGTH: 6
<212> TYPE: PRT
<213> ORGANISM: C-terminal glycine-lysine linker -continued

<400> SEQUENCE: 353

Gly Gly Lys Lys Gly Cys
1 5

<210> SEQ ID NO 354
<211> LENGTH: 6
<212> TYPE: PRT
<213> ORGANISM: N-terminal glycine-lysine linker

<400> SEQUENCE: 354

Cys Gly Lys Lys Gly Gly
1 5

<210> SEQ ID NO 355
<211> LENGTH: 4
<212> TYPE: PRT
<213> ORGANISM: C-terminal linker

<400> SEQUENCE: 355

Gly Gly Cys Gly
1

<210> SEQ ID NO 356
<211> LENGTH: 37
<212> TYPE: DNA
<213> ORGANISM: Artificial Sequence
<220> FEATURE:
<223> OTHER INFORMATION: oligonucleotide primer

<400> SEQUENCE: 356
ggtaacatcg gtcgagatgg aaaacaaact ctggtcc 37

<210> SEQ ID NO 357
<211> LENGTH: 37
<212> TYPE: DNA
<213> ORGANISM: Artificial Sequence
<220> FEATURE:
<223> OTHER INFORMATION: oligonucleotide primer

<400> SEQUENCE: 357
ggaccagagt ttgttttcca tctcgaccga tgttacc 37

<210> SEQ ID NO 358
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 358
agctcgcccg gggatcctct ag 22

<210> SEQ ID NO 359
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 359
cgatgcattt catccttagt tatcaatacg ctgggttcag 40

<210> SEQ ID NO 360
<211> LENGTH: 36

-continued

<212> TYPE: DNA
<213> ORGANISM: Artificial Sequence
<220> FEATURE:
<223> OTHER INFORMATION: oligonucleotide primer

<400> SEQUENCE: 360
ggcaaaatta gagactgtta ctttaggtaa gatcgg 36

<210> SEQ ID NO 361
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 361
ccgatcttac ctaaagtaac agtctctaat tttgcc 36

<210> SEQ ID NO 362
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 362
ggccatggca cgactcgaga ctgttacttt agg 33

<210> SEQ ID NO 363
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 363
gatttaggtg acactatag 19

<210> SEQ ID NO 364
<211> LENGTH: 37
<212> TYPE: DNA
<213> ORGANISM: Artificial Sequence
<220> FEATURE:
<223> OTHER INFORMATION: oligonucloetide primer

<400> SEQUENCE: 364
gatggacgtc aaactctggt cctcaatccg cgtgggg 37

<210> SEQ ID NO 365
<211> LENGTH: 37
<212> TYPE: DNA
<213> ORGANISM: Artificial Sequence
<220> FEATURE:
<223> OTHER INFORMATION: oligonucleotide primer

<400> SEQUENCE: 365
ccccacgcgg attgaggacc agagtttgac gtccatc 37

<210> SEQ ID NO 366
<211> LENGTH: 31
<212> TYPE: DNA
<213> ORGANISM: Artificial Sequence
<220> FEATURE:
<223> OTHER INFORMATION: EcoRIHBcAg(s)

<400> SEQUENCE: 366

-continued ccggaattca tggacattga cccttataaa g 31

<210> SEQ ID NO 367
<211> LENGTH: 51
<212> TYPE: DNA
<213> ORGANISM: Artificial Sequence
<220> FEATURE:
<223> OTHER INFORMATION: Lys-HBcAg(as)

<400> SEQUENCE: 367
cctagagcca cctttgccac catcttctaa attagtaccc acccaggtag c 51

<210> SEQ ID NO 368
<211> LENGTH: 48
<212> TYPE: DNA
<213> ORGANISM: Artificial Sequence
<220> FEATURE:
<223> OTHER INFORMATION: Lys-HBcAg(s)

<400> SEQUENCE: 368
gaagatggtg gcaaaggtgg ctctagggac ctagtagtca gttatgtc 48

<210> SEQ ID NO 369
<211> LENGTH: 38
<212> TYPE: DNA
<213> ORGANISM: Artificial Sequence
<220> FEATURE:
<223> OTHER INFORMATION: HbcAg(1-149)Hind(as)

<400> SEQUENCE: 369
cgcgtcccaa gcttctaaac aacagtagtc tccggaag 38

<210> SEQ ID NO 370
<211> LENGTH: 37
<212> TYPE: DNA
<213> ORGANISM: Artificial Sequence
<220> FEATURE:
<223> OTHER INFORMATION: 48as primer

<400> SEQUENCE: 370
gtgcagtatg gtgaggtgag gaatgctcag gagactc 37

<210> SEQ ID NO 371
<211> LENGTH: 37
<212> TYPE: DNA
<213> ORGANISM: Artificial Sequence
<220> FEATURE:
<223> OTHER INFORMATION: 48s primer

<400> SEQUENCE: 371
gsgtctcctg agcattcctc acctcaccat actgcac 37

<210> SEQ ID NO 372
<211> LENGTH: 33
<212> TYPE: DNA
<213> ORGANISM: Artificial Sequence
<220> FEATURE:
<223> OTHER INFORMATION: 107as primer

<400> SEQUENCE: 372
cttccaaaag tgagggaaga aatgtgaaac cac 33

<210> SEQ ID NO 373
<211> LENGTH: 33
<212> TYPE: DNA
<213> ORGANISM: Artificial Sequence -continued
<220> FEATURE:
<223> OTHER INFORMATION: 107s primer

<400> SEQUENCE: 373
gtggtttcac atttcttccc tcacttttgg aag 33

<210> SEQ ID NO 374
<211> LENGTH: 38
<212> TYPE: DNA
<213> ORGANISM: Artificial Sequence
<220> FEATURE:
<223> OTHER INFORMATION: HBcAgwtHindIIII

<400> SEQUENCE: 374
cgcgtcccaa gcttctaaca ttgagattcc cgagattg 38

<210> SEQ ID NO 375
<211> LENGTH: 51
<212> TYPE: DNA
<213> ORGANISM: Artificial Sequence
<220> FEATURE:
<223> OTHER INFORMATION: CepsilonH3 foreward

<400> SEQUENCE: 375
gttaacttga cctggtctcg tgcttctggt gcatccaggg atctagtagt c 51

<210> SEQ ID NO 376
<211> LENGTH: 17
<212> TYPE: PRT
<213> ORGANISM: Artificial Sequence
<220> FEATURE:
<223> OTHER INFORMATION: CepsilonH3 foreward

<400> SEQUENCE: 376

Val Asn Leu Thr Trp Ser Arg Ala Ser Gly Ala Ser Arg Asp Leu Val
1 5 10 15

Val

<210> SEQ ID NO 377
<211> LENGTH: 51
<212> TYPE: DNA
<213> ORGANISM: Artificial Sequence
<220> FEATURE:
<223> OTHER INFORMATION: CepsilonH3 reversed

<400> SEQUENCE: 377
accagaagca cgagaccagg tcaagttaac atcttccaaa ttattaccca c 51

<210> SEQ ID NO 378
<211> LENGTH: 7
<212> TYPE: PRT
<213> ORGANISM: Artificial Sequence
<220> FEATURE:
<223> OTHER INFORMATION: CepsilonH3 reversed

<400> SEQUENCE: 378

Asp Glu Leu Asn Asn Gly Val
1 5

<210> SEQ ID NO 379
<211> LENGTH: 26
<212> TYPE: DNA
<213> ORGANISM: Artificial Sequence
<220> FEATURE:
<223> OTHER INFORMATION: GST-BamHI ss -continued

<400> SEQUENCE: 379
cgccggatcc tatactaggt tattgg 26

<210> SEQ ID NO 380
<211> LENGTH: 33
<212> TYPE: DNA
<213> ORGANISM: Artificial Sequence
<220> FEATURE:
<223> OTHER INFORMATION: C1-BsmBI/XhoI as

<400> SEQUENCE: 380
gggcgcgtct cctcgagacc gcaaccacca cca 33

<210> SEQ ID NO 381
<211> LENGTH: 74
<212> TYPE: DNA
<213> ORGANISM: Artificial Sequence
<220> FEATURE:
<223> OTHER INFORMATION: MCS of pET22b(+)

<400> SEQUENCE: 381
gtttaacttt aagaaggaga tatacatatg gatccggcta gcgctcgagg gtttaaacgg 60
cggccgcatg cacc 74

<210> SEQ ID NO 382
<211> LENGTH: 33
<212> TYPE: DNA
<213> ORGANISM: mEotaxin-F

<400> SEQUENCE: 382
ggaattccat atgcacccag gctccatccc aac 33

<210> SEQ ID NO 383
<211> LENGTH: 31
<212> TYPE: DNA
<213> ORGANISM: Nhe-mEotaxin-F

<400> SEQUENCE: 383
cctagctagc gcacccaggc tccatcccaa c 31

<210> SEQ ID NO 384
<211> LENGTH: 30
<212> TYPE: DNA
<213> ORGANISM: mEotaxin-Xho-R

<400> SEQUENCE: 384
cccgctcgag tggttttgga gtttggagtt 30

<210> SEQ ID NO 385
<211> LENGTH: 84
<212> TYPE: PRT
<213> ORGANISM: Mouse eotaxin-C1

<400> SEQUENCE: 385

```
Met His Pro Gly Ser Ile Pro Thr Ser Cys Cys Phe Ile Met Thr Ser
1               5                   10                  15

Lys Lys Ile Pro Asn Thr Leu Leu Lys Ser Tyr Lys Arg Ile Thr Asn
            20                  25                  30

Asn Arg Cys Thr Leu Lys Ala Ile Val Phe Lys Thr Arg Leu Gly Lys
        35                  40                  45

Glu Ile Cys Ala Asp Pro Lys Lys Lys Trp Val Gln Asp Ala Thr Lys
    50                  55                  60
```

-continued

```
His Leu Asp Gln Lys Leu Gln Thr Pro Lys Pro Leu Arg Gly Gly Gly
65                  70                  75                  80

Gly Gly Cys Gly


<210> SEQ ID NO 386
<211> LENGTH: 103
<212> TYPE: PRT
<213> ORGANISM: Mouse His-eotaxin-C1

<400> SEQUENCE: 386

Met Asp Pro His His His His His His Gly Ser Gly Asp Asp Asp Asp
1               5                   10                  15

Lys Ala Leu Ala His Pro Gly Ser Ile Pro Thr Ser Cys Cys Phe Ile
            20                  25                  30

Met Thr Ser Lys Lys Ile Pro Asn Thr Leu Leu Lys Ser Tyr Lys Arg
        35                  40                  45

Ile Thr Asn Asn Arg Cys Thr Leu Lys Ala Ile Val Phe Lys Thr Arg
    50                  55                  60

Leu Gly Lys Glu Ile Cys Ala Asp Pro Lys Lys Lys Trp Val Gln Asp
65                  70                  75                  80

Ala Thr Lys His Leu Asp Gln Lys Leu Gln Thr Pro Lys Pro Leu Arg
                85                  90                  95

Gly Gly Gly Gly Gly Cys Gly
            100
```

ANTIGEN ARRAYS FOR TREATMENT OF ALLERGIC EOSINOPHILIC DISEASES

CROSS REFERENCE TO RELATED APPLICATIONS

The present application claims the benefit of the filing date of U.S. Provisional Appl. No. 60/396,636, filed Jul. 19, 2002. The present application also is a continuation-in-part of, and claims priority to, U.S. patent application Ser. No. 10/050,902, filed Jan. 18, 2002, which claims the benefit of U.S. patent applications 60/262,379, filed Jan. 19, 2001, 60/288,549, filed May 4, 2001, 60/331,045, filed Nov. 7, 2001, and 60/326,998, filed Oct. 5, 2001. The disclosures of all of the above-referenced applications are incorporated by reference herein in their entireties.

BACKGROUND OF THE INVENTION

1. Field of the Invention

The present invention is related to the fields of molecular biology, virology, immunology and medicine. The invention provides a composition comprising an ordered and repetitive antigen or antigenic determinant array, and in particular an array comprising a protein or peptide of IL-5, IL-13 or eotaxin. More specifically, the invention provides a composition comprising a virus-like particle and at least one protein, or peptide of IL-5, IL-13 and/or eotaxin bound thereto. The invention also provides a process for producing the conjugates and the ordered and repetitive arrays, respectively. The compositions of the invention are useful in the production of vaccines for the treatment of allergic diseases with an eosinophilic component and as a pharmaccine to prevent or cure allergic diseases with an eosinophilic component and to efficiently induce immune responses, in particular antibody responses. Furthermore, the compositions of the invention are particularly useful to efficiently induce self-specific immune responses within the indicated context.

2. Related Art

A number of allergic diseases including asthma, nasal rhinitis, nasal polyps, eosinophilic syndromes and atopic dermatitis have prominent inflammatory components characterized by pronounced eosinophilic infiltration.

The most medically important group of these diseases, atopic asthma is recognized as a chronic inflammatory disease of the airways that is clinically characterized by episodic airflow obstruction, inflammation of the airways, and enhanced bronchial reactivity to nonspecific allergens. The degree of obstruction of the airways and hyperreactivity often correlates with the level of airway inflammation. These clinical features are indicative of asthma severity (Kay, A. B., *J Allergy Clin Immunol,* 1991, 87:893; De Monchy, J. G. et al., *Am Rev Respir Dis,* 1985, 131:373; Beasley, R. et al., *Am Rev Respir Dis,* 1989, 139:806; Azzawi, M. et al., *Am Rev Respir Dis,* 1990, 142:1407; Ohashi, Y. et al., *Am Rev Respir Dis,* 1992, 145:1469; Nakajima, H. et al., *Am Rev Respir Dis,* 1992, 146:374; Broide, D. H. et al., *J Allergy Clin Immunol,* 1991, 88:637; Warlaw, A. J. et al., *Am Rev Respir Dis,* 1988, 137:62). Cellular infiltration correlates with disease progression and indicates inflammation of the airways that is a major contributing factor to pathogenesis and pathobiology. The inflammatory infiltrate in asthma is complex; however, it is now widely recognized that $CD4^+$ Th lymphocytes with a Th2 profile (Th2 cells) of cytokine expression play a pivotal role in the clinical expression and pathogenesis of this disorder (Robinson, D. S. et al., *J Allergy Clin Immunol,* 1993, 92:397; Walker, C. et al., *J Allergy Clin Immunol,* 1991, 88:935). Th2 cells regulate disease progression and airways hyperresponsiveness (AHR) by orchestrating allergic inflammation of the airways through the release of a range of cytokines such as IL-4, -5, -9, -10, -13 (Robinson, D. S. et al., *N Eng J Med,* 1992, 326:298; Robinson, D. S. et al., *J Allergy Clin Immunol,* 1993, 92:313; Walker, C. et al., *Am Rev Respir Dis,* 1992, 146:109; Drazen, J. M. et al., *J Exp Med,* 1996, 183:1). Like Th2 cells, the levels of eosinophils and their inflammatory products in the lung correlate with disease severity, and accumulation of this leukocyte in the airways is a central feature of bronchial dysfunction during the late-phase asthmatic response (Bousquet, J. et al., *N Eng J Med,* 1990, 323:1033). Although Th2 cells orchestrate many facets of the allergic response, their role in regulating eosinophilia through the secretion of IL-5 is thought to be a major proinflammatory pathway in asthma.

Interleukin-5 (IL-5) is a proinflammatory cytokine expressed at high levels in asthmatics. Moreover, IL-5 is a cytokine primarily involved in the pathogenesis of atopic diseases. It specifically controls the production, activation and localization of eosinophils, the major cause of tissue damage in atopic diseases. Furthermore, IL-5 is an inducible T-cell derived cytokine with remarkable specificity for the eosinophil lineage. IL-5 is controlled at the level of transcription and regulation of the gene represents a promising target for therapy of eosinophil-dependent allergic disorders such as asthma, eczema and rhinitis.

There is a large body of evidence that eosinophils are a key component of the allergic response in asthma. IL-5 is uniquely involved in the production of eosinophils, and with a variety of other cytokines such as IL-13, chemokines such as Eotaxin and other factors controls their activation, localization and survival. Thus, IL-5 has become an important drug target for new anti-asthmatics (Foster, P. S. et al., *Pharmacol Ther,* 2002, 94(3):253; Foster, P. S. et al., *Trends Mol Med,* 2002, 8(4): 162).

There is 71% homology between human and murine proteins (Cytokine hand book). IL-5 exhibits no significant amino acid sequence homology with other cytokines, except for short stretches in the murine interleukin-3, murine GM-CSF, and murine interferon-γ proteins. The predicted molecular mass of both the human and mouse protein sequences are 13.1 kDa. Biologically active IL-5 is a disulfide-linked homodimer that is covalently linked by highly conserved cysteine residues (44-86' and 86-44') that orient the monomers in a head to tail configuration (Takahashi T. et al Mol. Immunol. 27:911–920 1990). Although wild-type monomeric IL-5 is biologically inactive a functional IL-5 monomer has been engineered by insertional mutagenesis (Dickason R R, et al J. Mol. Med 74: 535–46 1996) Analysis of the crystal structure of human IL-5 demonstrated a novel two-domain configuration with each domain requiring the participation of two chains, with a high degree of similarity to the cytokine fold found in GM-CSF, interleukin-3, and interleukin-4 (Milburn M. V et al Nature 363: 172–176). The C-terminal region of IL-5 appears to be important for binding to the IL-5 receptor and for biological activity (Proudfoot et al J. Protein Chem. 15(5):491–9.1996). Binding of IL-5 to its receptor is thought occur in regions overlapping helices A and D where helix A is principally involved in binding the α-subunit of the receptor (Graber P. et al J. Biol Chem 270: 15762–15769 1995). Native human IL-5 has 2 potential glycosylation sites and mouse IL-5three. Human IL-5 is both N-glycosylated and O-glycosylated at Thr 3. Recombinant IL-5 expressed in eukaryotic systems exhibits a broad range of molecular masses from 45–60 kDa due to differential glycosylation. Deglycosylated IL-5 and IL-5 expressed in prokarytocic cells retain full biologic activity (Tominaga A. et al J. Immunol 144: 1345–1352, 1990).

The routes to drug discovery are typically based on screens for inhibitors of IL-5 production, ligand antagonists, control of receptor expression and receptor activation. In particular, inhibition of the action of IL-5 might provide a way of treatment against asthma and other diseases associated with eosinophils. Immunotherapy represents another and very attractive approach to controlling IL-5 levels and disease conditions associated with eosinophilia such as asthma.

Currently, the commonest treatment for prevention of the symptoms of asthma is the use of inhaled corticosteroids. Generally the use of these agents is fairly safe and cheap. However they function by inducing a general immunosuppressive effect and there are adverse side effects associated with their long term use including high blood pressure, osteoporosis and development of cataracts. Corticosteroids must be taken everyday and hence patient compliance is another issue in the successful use of these medicines. Furthermore there are asthmatic patients refractory to the use of corticosteroids necessitating the use of alternative therapies. Selective targeting of eosinophils using immunotherapeutic agents directed against IL-5 may overcome the adverse effects of using general immunosuppressive agents with pleiotropic actions.

Possible future treatment of diseases such as asthma may include passive immunization and, thus, the use of monoclonal antibodies specific for IL-5. Clinical trials with humanized monoclonal antibodies against IL-5 aimed at reducing eosinophilia in asthmatic patients are ongoing. In particular, clinical trials using SCH55700 (eslizumab, Schering Plough) which is a humanized monoclonal antibody with activity against IL-5 from various species [Egan, R. W. et al., *Arzneimittel-Forschung,* 1999, 49:779] and SB240563 (mepolizumab, Glaxo Smith Kline) which is a humanized antibody with specificity for human and primate interleukin-5 [Hart, T. K. et al., *Am J Respir Crit Care Med,* 1998, 157:A744; Zia-Amirhosseini, P. et al., *J Pharmacol Exp Ther,* 1999, 291:1060] have been reported. Both monoclonal antibodies demonstrated acceptable safety profiles in phase 1 trials and led to reduction of eosinophil numbers but no reduction in airway hypereactivity was, observed. The deleterious action that eosinophils exert on the airways of asthmatics is thought to be a chronic phenomena involving tissue re-modeling. Studies designed to test efficacy of anti IL-5 therapy in this context need to be assessed and are in development.

The treatment with mAbs, however, entails several disadvantages. Monoclonal antibodies are expensive therapeutic agents which must be taken monthly or bimonthly. The issue of patient non-compliance resulting form repeated medical visits for administration of the injected drug is an important problem. Furthermore, allotype variation between the patient and therapeutic antibody may lead to the monoclonal antibody therapy eventually becoming ineffective. The high dose of mAb and the possibility of immune complex formation may also reduce the efficacy of passive immunisation. An active vaccination strategy limits these complications.

Another approach to provide therapeutic agents for chronic asthma or other disease states with demonstrated eosinophilia or other conditions associated with IL-5 has been described in WO 97/45448. Therein, the use of "modified and variant forms of IL5 molecules capable of antagonising the activity of IL5" in ameliorating, abating or otherwise reducing the aberrant effects caused by native or mutant forms of IL5 has been proposed. The antagonizing effect is reported to be the result of the variant forms of IL5 binding to the low affinity a chain of IL5R but not to the high affinity receptors. By this way of action the variants compete with IL5 for binding to its receptors without exerting the physiological effects of IL5.

Eotaxin is a chemokine specific for Chemokine receptor 3, present on eosinophils, basophils and Th2 cells. However, Eotaxin has high specificity for eosinophils (Zimmerman et al., *J. Immunol.* 165: 5839–46 (2000)). Eosinophil migration is reduced by 70% in eotaxin-1 knock-out mice, which however can still develop eosinophilia (Rothenberg et al., *J. Exp. Med.* 185: 785–90 (1997)). IL-5 seems to be responsible for the migration of eosinophils from bone-marrow to blood, and eotaxin for the local migration in the tissue (Humbles et al., *J. Exp. Med.* 186: 601–12 (1997). Thus targeting eotaxin in addition to IL-5 may enhance immunotherapies directed towards lowering eosinophilia.

The human genome contains 3 eotaxin genes, eotaxin1–3 which share 30% homology. To date 2 genes are known in the mouse: eotaxin 1 and eotaxin 2 (Zimmerman et al., *J. Immunol.* 165: 5839–46 (2000)). They share 38% homology. Murine eotaxin-2 shares 59% homology with human eotaxin-2. In the mouse, eotaxin-1 seems to be ubiquitously expressed in the gastro-intestinal tract, while eotaxin-2 seems to be predominantly expressed in the jejunum (Zimmerman et al., *J. Immunol.* 165: 5839–46 (2000)). Eotaxin-1 is present in broncho-alveolar fluid (Teixeira et al., *J. Clin. Invest.* 100: 1657–66 (1997)). The sequence of human eotaxin-1 is shown in SEQ ID No.: 242 (aa 1–23 corresponds to the signal peptide), the sequence of human eotaxin-2 is shown in SEQ ID No.: 243 (aa 1–26 corresponds to the signal peptide), the sequence of human eotaxin-3 is shown in SEQ ID No.: 244 (aa 1–23 corresponds to the signal peptide), the sequence of mouse eotaxin-1 is shown in SEQ ID No.: 245 (aa 1–23 corresponds to the signal peptide), and the sequence of mouse eotaxin-2 is shown in SEQ ID No.: 246 (aa 1–23 corresponds to the signal peptide).

The monomer of eotaxin has a mass of 8.3 kDa and is in equilibrium with dimeric eotaxin over a wide range of conditions. The estimated Kd is 1.3 mM at 37° C. however the monomer is the predominant form (Crump et al., *J. Biol. Chem.* 273: 22471–9 (1998). The structure of Eotaxin has been elucidated by NMR spectroscopy. The binding site to its receptor CCR3, is at the N-terminus and the region preceding the first cysteine is crucial (Crump et al., *J. Biol. Chem.* 273: 22471–9 1998). Peptides derived from chemokine receptors bound to Eotaxin confirmed this finding. Eotaxin has four cysteines forming two disulfidebridges and can be chemically synthesized (Clark-Lewis et al., *Biochemistry* 30:3128–3135 1991). Eotaxin 1 is variably O-glcosylated on Thr 71(Noso, N. et al Eur J. Biochem. 253: 114–122). Expression of Eotaxin 1 in *E. coli* cytosol has also been described (Crump et al., *J. Biol. Chem.* 273: 22471–9 (1998)). Expression in *E. coli* as inclusion bodies with subsequent refolding (Mayer et al., *Biochemistry* 39: 8382–95 (2000)), and Insect cell expression (Forssmann et al., *J. Exp. Med.* 185: 2171–6 (1997)) have been reported for Eotaxin-2.

Interleukin 13 (IL-13) is secreted as a biologically active monomeric Th2 cytokine. The mature form of IL-13 comprises 112 amino acids in humans and 111 amino acids in mice. The calculated molecular mass of the protein is approximately 12.4 kDa. IL-13 can be N-linked glycosylated (Fitzgerald K. A. et al The Cytokines Fact Book 2$^{nd}$ edition Academic Press) IL-13 is produced by Th2 cells, mast cells, basophils and natural killer cells (Brombacher F, 2000 Bioessays July; 22(7):646–56). The functional IL-13 receptor is a heterodimer composed of the Interleukin 4 receptor α chain (IL-4R α chain) and one of the two IL-13 receptor α binding proteins (Brombacher F, 2000 Bioessays July; 22(7):646–56).

IL 13 plays a significant role in the pathology of asthma. It has been shown that IL 13 is involved in the central features of this disease. It has direct effects on allergen-induced airway hyperresponsiveness (AHR) and mucus production and has an involvement in eosinophilia (Kupenman D. A. 2002 Nature Medicine epub ahead of print). Selective neutralization of IL-13 in mice significantly attenuated the asthma phenotype. Furthermore, administration of IL-13 conferred an asthma-like phenotype to nonsensitized T-cell deficient or naive mice, respectively (Grünig G. et al., 1998 Science, 282(5397): 2261–3, Wills-Karp, M. et al, 1998 Science 282(5397): 2258–61). Mice with a targeted deletion of IL-13 failed to develop allergen-induced AHR and showed a marked decrease in mucus production (Walter, D. M. et al, 2001 J Immunol 167(8): 4668–75). Since IL-13 also influences eosinophilia in the murine asthma model (Grünig G. et al., 1998 Science, 282(5397): 2261–3), it possible IL-13 is involved in many more allergic diseases associated with eosinophilia and neutralizing its activity may offers a promising treatment for patients.

Additionally, upregulation of IL-13 and IL-13 receptor has been found in many tumor types (e.g. in all Hodgkin lymphoma disease cell lines examined to date). Thus immunization against IL-13 may provide a way of curing tumor patients overexpressing IL-13.

One way to improve the efficiency of vaccination is to increase the degree of repetitiveness of the antigen applied. Unlike isolated proteins, viruses induce prompt and efficient immune responses in the absence of any adjuvants both with and without T-cell help (Bachmann and Zinkernagel, *Ann. Rev. Immunol:* 15:235–270 (1991)). Although viruses often consist of few proteins, they are able to trigger much stronger immune responses than their isolated components. For B-cell responses, it is known that one crucial factor for the immunogenicity of viruses is the repetitiveness and order of surface epitopes. Many viruses exhibit a quasi-crystalline surface that displays a regular array of epitopes which efficiently crosslinks epitope-specific immunoglobulins on B cells (Bachmann and Zinkernagel, *Immunol. Today* 17:553–558 (1996)). This crosslinking of surface immunoglobulins on B cells is a strong activation signal that directly induces cell-cycle progression and the production of IgM antibodies. Further, such triggered B cells are able to activate T helper cells, which in turn induce a switch from IgM to IgG antibody production in B cells and the generation of long-lived B cell memory—the goal of any vaccination (Bachmann and Zinkernagel, *Ann. Rev. Immunol.* 15:235–270 (1997)). Viral structure is even linked to the generation of anti-antibodies in autoimmune disease and as a part of the natural response to pathogens (see Fehr, T., et al., *J Exp. Med.* 185:1785–1792 (1997)). Thus, antibodies presented by a highly organized viral surface are able to induce strong anti-antibody responses.

As indicated, however, the immune system usually fails to produce antibodies against self-derived structures. For soluble antigens present at low concentrations, this is due to tolerance at the Th cell level. Under these conditions, coupling the self-antigen to a carrier that can deliver T help may break tolerance. For soluble proteins present at high concentrations or membrane proteins at low concentration, B and Th cells may be tolerant. However, B cell tolerance may be reversible (anergy) and can be broken by administration of the antigen in a highly organized fashion coupled to a foreign carrier (Bachmann and Zinkernagel, *Ann. Rev. Immunol.* 15:235–270 (1997)).

BRIEF SUMMARY OF THE INVENTION

We have now found that a protein or peptide of IL-5, IL-13 or eotaxin bound to a core particle having a structure with an inherent repetitive organization, and hereby in particular to virus-like-particles (VLP's) and subunits of VLP's, respectively, leading to highly ordered and repetitive conjugates represent potent immunogens for the induction of antibodies specific for IL-5, IL-13 or eotaxin. Furthermore these auto-reactive antibodies inhibit eosinophilia in a mouse model of asthma. Therefore, the present invention provides a therapeutic mean for the treatment of allergic eosinophilic disease, which is based on an ordered and repetitive protein or peptide of IL-5, IL-13 or eotaxin-core particle array, and in particular a VLP-protein or peptide of IL-5, IL-13 or eotaxin-conjugate and -array, respectively. This therapeutic is able to induce high titers of anti-IL-5, IL-13 or eotaxin antibodies in a vaccinated animal and inhibit eosinophilia in a mouse model of asthma.

The present invention, thus, provides for a composition comprising: (a) a core particle with at least one first attachment site; and (b) at least one antigen or antigenic determinant with at least one second attachment site, wherein said antigen or antigenic determinant is a protein or peptide of IL-5, IL-13 or eotaxin and wherein said second attachment site being selected from the group consisting of (i) an attachment site not naturally occurring with said antigen or antigenic determinant; and (ii) an attachment site naturally occurring with said antigen or antigenic determinant, wherein said second attachment site is capable of association to said first attachment site; and wherein said antigen or antigenic determinant and said core particle interact through said association to form an ordered and repetitive antigen array. Preferred embodiments of core particles suitable for use in the present invention are a virus, a virus-like particle, a bacteriophage, a bacterial pilus or flagella or any other core particle having an inherent repetitive structure capable of forming an ordered and repetitive antigen array in accordance with the present invention.

More specifically, the invention provides a composition comprising an ordered and repetitive antigen or antigenic determinant array, and hereby in particular protein or peptide of IL-5, IL-13 or eotaxin-VLP conjugates. More specifically, the invention provides a composition comprising a virus-like particle and at least one protein or peptide of IL-5, IL-13 or eotaxin bound thereto. The invention also provides a process for producing the conjugates and the ordered and repetitive arrays, respectively. The compositions of the invention are useful in the production of vaccines for the treatment of allergic diseases with an eosinophilic component and as a pharmaccine to prevent or cure allergic diseases with an eosinophilic component and to efficiently induce immune responses, in particular antibody responses. Furthermore, the compositions of the invention are particularly useful to efficiently induce self-specific immune responses within the indicated context.

In the present invention, a protein or peptide of IL-5, IL-13 or eotaxin is bound to a core particle and VLP, respectively, typically in an oriented manner, yielding an ordered and repetitive protein or peptide of IL-5, IL-13 or eotaxin antigen array. Furthermore, the highly repetitive and organized structure of the core particles and VLPs, respectively, mediates the display of the protein or peptide of IL-5, IL-13 or eotaxin in a highly ordered and repetitive fashion leading to a highly organized and repetitive antigen array. Furthermore, binding of the protein or peptide of IL-5, IL-13 or eotaxin to the core particle and VLP, respectively, provides T helper cell epitopes, since the core particle and VLP is foreign to the host immunized with the core particle-protein or peptide of IL-5, IL-13 or eotaxin array and VLP-protein or peptide of IL-5, IL-13 or eotaxin array, respectively. Those arrays differ from prior art conjugates in their highly organized structure, dimensions, and in the repetitiveness of the antigen on the surface of the array.

In one aspect of the invention, the protein or peptide of IL-5, IL-13 or eotaxin is expressed in a suitable expression host compatible with proper folding of the IL-5, IL-13 or eotaxin protein or IL-5, IL-13 or eotaxin peptide, or synthesized, while the core particle and the VLP, repespectively, is expressed and purified from an expression host suitable for the folding and assembly of the core particle and the VLP, repespectively. The protein or peptide of IL-5, IL-13 or eotaxin may be chemically synthesized. The protein or peptide of IL-5, IL-13 or eotaxin array is then assembled by binding the protein or peptide of IL-5, IL-13 or eotaxin to the core particle and the VLP, respectively.

In another aspect, the present invention provides for a composition comprising (a) a virus-like particle, and (b) at least one antigen or antigenic determinant, wherein said antigen or said antigenic determinant is a protein or peptide of IL-5, IL-13 or eotaxin.

In still a further aspect, the present invention provides for a vaccine composition comprising a composition comprising: (a) a core particle with at least one first attachment site; and (b) at least one antigen or antigenic determinant with at least one second attachment site, wherein said antigen or antigenic determinant is a protein or peptide of IL-5, IL-13 or eotaxin, and wherein said second attachment site being selected from the group consisting of (i) an attachment site not naturally occurring with said antigen or antigenic determinant; and (ii) an attachment site naturally occurring with said antigen or antigenic determinant, wherein said second attachment site is capable of association to said first attachment site; and wherein said antigen or antigenic determinant and said core particle interact through said association to form an ordered and repetitive antigen array.

In a further aspect, the present invention provides for a vaccine composition comprising a composition, wherein said composition comprising (a) a virus-like particle; and (b) at least one antigen or antigenic determinant, wherein said antigen or said antigenic determinant is a protein or peptide of IL-5, IL-13 or eotaxin; and wherein said at least one antigen or antigenic determinant is bound to said virus-like particle.

In still a further aspect, the present invention provides for a process for producing a composition the invention comprising (a) providing a virus-like particle; and (b) providing at least one antigen or protein or peptide of IL-5, IL-13 or eotaxin; (c) combining said virus-like particle and said at least one antigen or antigenic determinant so that said at least one antigen or antigenic determinant is bound to said virus-like particle.

In still a further aspect, the present invention provides a process for producing a composition the invention comprising: (a) providing a core particle with at least one first attachment site; (b) providing at least one antigen or antigenic determinant with at least one second attachment site, wherein said antigen or antigenic determinant is a protein or peptide of IL-5, IL-13 or eotaxin, and wherein said second attachment site being selected from the group consisting of (i) an attachment site not naturally occurring with said antigen or antigenic determinant; and (ii) an attachment site naturally occurring with said antigen or antigenic determinant; and wherein said second attachment site is capable of association to said first attachment site; and (c) combining said core particle and said at least one antigen or antigenic determinant, wherein said antigen or antigenic determinant and said core particle interact through said association to form an ordered and repetitive antigen array.

In another aspect, the present invention provides for a method of immunization comprising administering the composition of the invention to an animal or human.

In a further aspect, the present invention provides for a use of the compositions of the invention for the manufacture of a medicament for treatment of allergic diseases with an eosinophilic component.

In a still further aspect, the present invention provides for a use of the compositions of the invention for the preparation of a medicament for the therapeutic or prophylactic treatment of allergic diseases with an eosinophilic component, preferably of asthma. Furthermore, in a still further aspect, the present invention provides for a use of the compositions of the invention, either in isolation or in combination with other agents, for the manufacture of a composition, vaccine, drug or medicament for therapy or prophylaxis of allergic diseases with an eosinophilic component, in particular asthma.

Therefore, the invention provides, in particular, vaccine compositions which are suitable for preventing and/or attenuating allergic diseases with an eosinophilic component or conditions related thereto. The invention further provides and immunization and vaccination methods, respectively, for preventing and/or attenuating allergic diseases with an eosinophilic component or conditions related thereto, in animals, and in particular in cows, sheep and cattles as well as in humans. The inventive compositions may be used prophylactically or therapeutically.

In specific embodiments, the invention provides methods for preventing and/or attenuating allergic diseases with an eosinophilic component or conditions related thereto which are caused or exacerbated by "self" gene products, i.e. "self antigens" as used herein. In related embodiments, the invention provides methods for inducing immunological responses in animals and individuals, respectively, which lead to the production of antibodies that prevent and/or attenuate allergic diseases with an eosinophilic component or conditions related thereto, which are caused or exacerbated by "self" gene products.

As would be understood by one of ordinary skill in the art, when compositions of the invention are administered to an animal or a human, they may be in a composition which contains salts, buffers, adjuvants, or other substances which are desirable for improving the efficacy of the composition. Examples of materials suitable for use in preparing pharmaceutical compositions are provided in numerous sources including *Remington's Pharmaceutical Sciences* (Osol, A, ed., Mack Publishing Co. (1990)).

Compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The compositions of the present invention may be administered by various methods known in the art, but will normally be administered by injection, infusion, inhalation, oral administration, or other suitable physical methods. The compositions may alternatively be administered intramuscularly, intravenously, or subcutaneously. Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Other embodiments of the present invention will be apparent to one of ordinary skill in light of what is known in the art, the following drawings and description of the invention, and the claims.

DETAILED DESCRIPTION OF THE INVENTION

Figure 1:
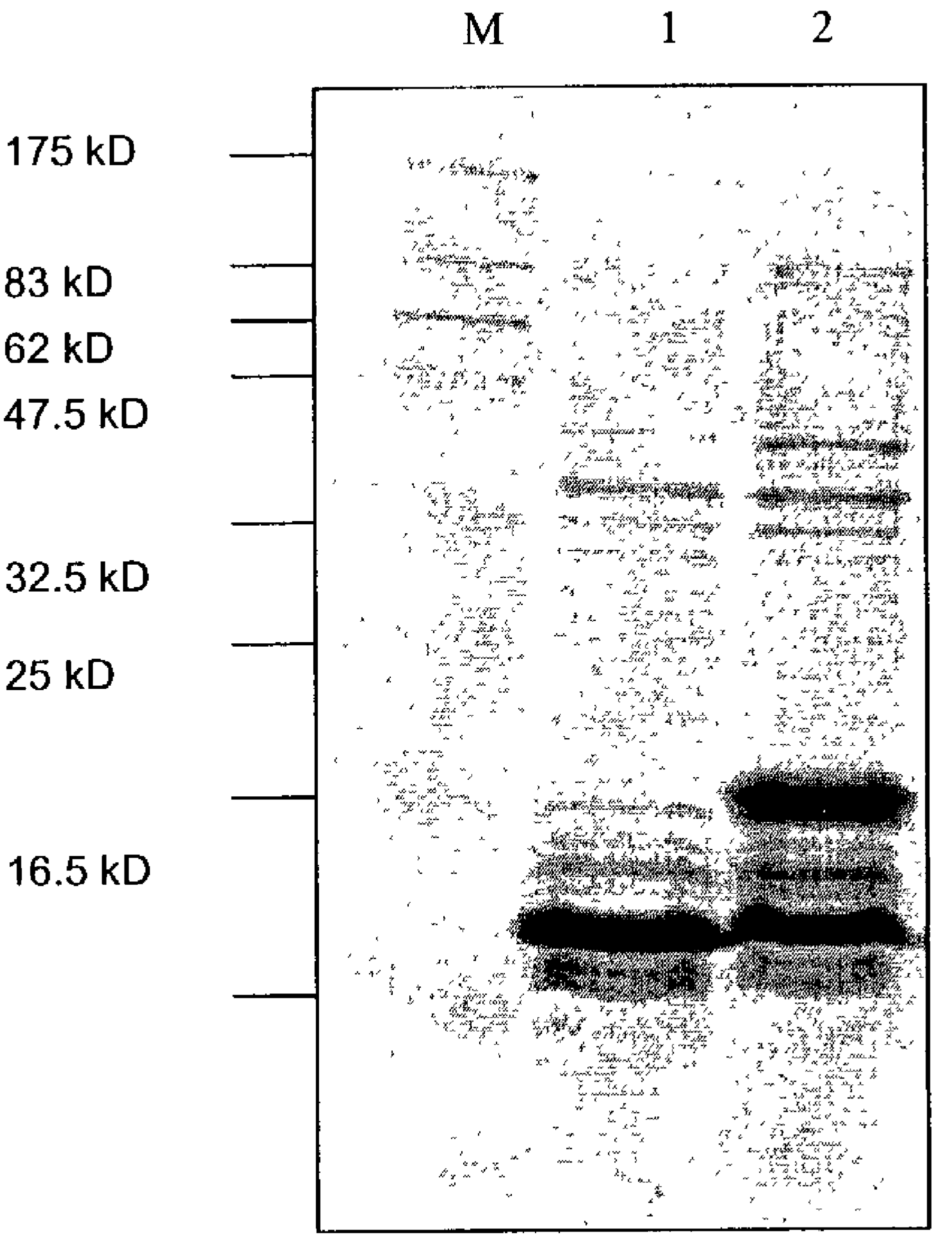
FIG. 1. Expression of mouse His-C-IL5. Extracts from the insoluble cellular fraction obtained after culturing pMODC6-IL5/BL21-DE3, either with or without IPTG, were prepared as described above. Equivalent amounts of extract were loaded onto a 16% SDS-polyacrylamide gel, electrophoresed and stained with Coomassie Blue. Lane M, Size Marker (NEB, Broad range, pre-stained marker), Lane 1, Extract from uninduced culture, Lane 2, extract from culture induced for 4 h with IPTG.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are hereinafter described.

1. Definitions

Allergic diseases with an eosinophilic component: The term allergic diseases with an eosinophilic component as used within refers to disease states or conditions where there is an increase in the number of eosinophils in the circulating blood or body tissues and fluids. Diseases where eosinophils are elevated and have either a direct or indirect effect on the disease state include; asthma, hay fever, nasal rhinitis, nasal polyps, idiopathic eosinophilic syndromes, atopic dermatitis, skin diseases and rashes, lung diseases such as Löefflers syndrome, chronic eosinophilic pneumoniae, Churg-Strauss syndrome and hyper-eosinophilic syndromes of unknown causes. Those skilled in the art can recognize allergic diseases with an eosinophilic component.

Amino acid linker: An "amino acid linker", or also just termed "linker" within this specification, as used herein, either associates the antigen or antigenic determinant with the second attachment site, or more preferably, already comprises or contains the second attachment site, typically—but not necessarily—as one amino acid residue, preferably as a cysteine residue. The term "amino acid linker" as used herein, however, does not intend to imply that such an amino acid linker consists exclusively of amino acid residues, even if an amino acid linker consisting of amino acid residues is a preferred embodiment of the present invention. The amino acid residues of the amino acid linker are, preferably, composed of naturally occuring amino acids or unnatural amino acids known in the art, all-L or all-D or mixtures thereof. However, an amino acid linker comprising a molecule with a sulfhydryl group or cysteine residue is also encompassed within the invention. Such a molecule comprise preferably a C1–C6 alkyl-, cycloalkyl (C5,C6), aryl or heteroaryl moiety. However, in addition to an amino acid linker, a linker comprising preferably a C1–C6 alkyl-, cycloalkyl-(C5,C6), aryl- or heteroaryl-moiety and devoid of any amino acid(s) shall also be encompassed within the scope of the invention. Association between the antigen or antigenic determinant or optionally the second attachment site and the amino acid linker is preferably by way of at least one covalent bond, more preferably by way of at least one peptide bond.

Animal: As used herein, the term "animal" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

Antibody: As used herein, the term "antibody" refers to molecules which are capable of binding an epitope or antigenic determinant. The term is meant to include whole antibodies and antigen-binding fragments thereof, including single-chain antibodies. Most preferably the antibodies are human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies can be from any animal origin including birds and mammals. Preferably, the antibodies are human, murine, rabbit, goat, guinea pig, camel, horse or chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598 by Kucherlapati et al.

Antigen: As used herein, the term "antigen" refers to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

Antigenic determinant: As used herein, the term "antigenic determinant" is meant to refer to that portion of an antigen that is specifically recognized by either B- or T-lymphocytes. B-lymphocytes responding to antigenic determinants produce antibodies, whereas T-lymphocytes respond to antigenic determinants by proliferation and establishment of effector functions critical for the mediation of cellular and/or humoral immunity.

Association: As used herein, the term "association" as it applies to the first and second attachment sites, refers to the binding of the first and second attachment sites that is preferably by way of at least one non-peptide bond. The nature of the association may be covalent, ionic, hydrophobic, polar or any combination thereof, preferably the nature of the association is covalent.

Attachment Site, First: As used herein, the phrase "first attachment site" refers to an element of non-natural or natural origin, to which the second attachment site located on the antigen or antigenic determinant may associate. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. The first attachment site is located, typically and preferably on the surface, of the core particle such as, preferably the virus-like particle. Multiple first attachment sites are present on the surface of the core and virus-like particle, respectively, typically in a repetitive configuration.

Attachment Site, Second: As used herein, the phrase "second attachment site" refers to an element associated with the antigen or antigenic determinant to which the first attachment site located on the surface of the core particle and virus-like particle, respectively, may associate. The second attachment site of the antigen or antigenic determinant may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. At least one second attachment site is present on the antigen or antigenic determinant. The term "antigen or antigenic determinant with at least one second attachment site" refers, therefore, to an antigen or antigenic construct comprising at least the antigen or antigenic determinant and the second attachment site. However, in particular for a second attachment site, which is of non-natural origin, i.e. not naturally occurring within the antigen or antigenic determinant, these antigen or antigenic constructs comprise an "amino acid linker".

Bound: As used herein, the term "bound" refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term "bound" is broader than and includes terms such as "coupled," "fused" and "attached".

Coat protein(s): As used herein, the term "coat protein(s)" refers to the protein(s) of a bacteriophage or a RNA-phage capable of being incorporated within the capsid assembly of the bacteriophage or the RNA-phage. However, when referring to the specific gene product of the coat protein gene of RNA-phages the term "CP" is used. For example, the specific gene product of the coat protein gene of RNA-phage Qβ is referred to as "Qβ CP", whereas the "coat proteins" of bacteriophage Qβ comprise the "Qβ CP" as well as the A1 protein. The capsid of Bacteriophage Qβ is composed mainly of the Qβ CP, with a minor content of the A1 protein. Likewise, the VLP Qβ coat protein contains mainly Qβ CP, with a minor content of A1 protein.

Core particle: As used herein, the term "core particle" refers to a rigid structure with an inherent repetitive organization. A core particle as used herein may be the product of a synthetic process or the product of a biological process.

Coupled: The term "coupled", as used herein, refers to attachment by covalent bonds or by strong non-covalent interactions, typically and preferably to attachment by covalent bonds. Any method normally used by those skilled in the art for the coupling of biologically active materials can be used in the present invention.

Effective Amount: As used herein, the term "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

Eotaxin protein: The term "eotaxin protein" as used herein refers to a protein encoded by an eotaxin gene. Different variants of the eotaxin protein may be caused by nucleotide point mutations and polymorphisms, respectively, as well as insertions, deletions and/or substitutions of one or more nucleotides, and shall be explicitly encompassed within the scope of the present invention. Further variablity can be caused by post-translational modifications, such as differentially glycosylated forms of eotaxin as well as proteolytically cleaved forms of eotaxin. The, term "eotaxin protein", as used herein, shall also encompass eotaxin protein variants, including but not limiting to the above indicated preferred examples.

Eotaxin peptide: As used herein, the term "eotaxin peptide" is broadly defined as any peptide which represents a fraction of an eotaxin protein and containing at least two, preferably at least three, more prefereably at least four, more prefereably at least five, more prefereably at least six consecutive amino acids of the original eotaxin protein which represents part of a eotaxin protein, most preferably representative of a folded part of eotaxin containing a B cell epitope, and again more preferably of the part of eotaxin containing a neutralizing epitope.

The term "eotaxin peptide" shall further preferably encompass any fraction of said eotaxin peptide, wherein said fraction may be, preferably, derived by deletion of one or more amino acids at the N and/or C terminus of eotaxin protein. The eotaxin peptide can be obtained by recombinant expression in eucaryotic or procaryotic expression systems as eotaxin peptide alone or as a fusion with other amino acids or proteins, e.g. to facilitate folding, expression or solubility of the eotaxin peptide or to facilitate purification of the eotaxin peptide. To enable coupling of eotaxin peptides and subunit proteins of VLP's or capsids, at least one second attachment site may be preferably added to the eotaxin peptide. Alternatively eotaxin peptides may be synthesized using methods known to the art. The term eotaxin peptide as used herein shall also prefereably encompass a peptide which simulates the three dimensional surface structure of eotaxin. Such eotaxin peptide is not necessarily derived from a continuous amino acid sequence of eotaxin, but may be formed by discontinuous amino acid residues from eotaxin. Such peptides may even contain amino acids which are not present in the corresponding eotaxin protein.

Epitope: As used herein, the term "epitope" refers to continuous or discontinuous portions of a polypeptide having antigenic or immunogenic activity in an animal, preferably a mammal, and most preferably in a human. An epitope is recognized by an antibody or a T cell through its T cell receptor in the context of an MHC molecule. An "immunogenic epitope," as used herein, is defined as a portion of a polypeptide that elicits an antibody response or induces a T-cell response in an animal, as determined by any method known in the art. (See, for example, Geysen et al., *Proc. Natl. Acad. Sci. USA* 81:3998–4002 (1983)). The term "antigenic epitope," as used herein, is defined as a portion of a protein to which an antibody can immunospecifically bind its antigen as determined by any method well known in the art. Immunospecific binding excludes non-specific binding but does not necessarily exclude cross-reactivity with other antigens. Antigenic epitopes need not necessarily be immunogenic. Antigenic epitopes can also be T-cell epitopes, in which case they can be bound immunospecifically by a T-cell receptor within the context of an MHC molecule.

An epitope can comprise 3 amino acids in a spatial conformation which is unique to the epitope. Generally, an epitope consists of at least about 5 such amino acids, and more usually, consists of at least about 8–10 such amino acids. If the epitope is an organic molecule, it may be as small as Nitrophenyl.

Fusion: As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

Immune response: As used herein, the term "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant. Preferably, antigen presenting cell may be activated.

A substance which "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g. using a $^{51}$Cr release assay, in samples obtained with and without the use of the substance during immunization. The amount of the substance at which the CTL lytic activity is enhanced as compared to the CTL lytic activity without the substance is said to be an amount sufficient to enhance the immune response of the animal to the antigen. In a preferred embodiment, the immune response in enhanced by a factor of at least about 2, more preferably by a factor of about 3 or more. The amount or type of cytokines secreted may also be altered. Alternatively, the amount of antibodies induced or their subclasses may be altered.

Immunization: As used herein, the terms "immunize" or "immunization" or related terms refer to conferring the ability to mount a substantial immune response (comprising antibodies and/or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

Natural origin: As used herein, the term "natural origin" means that the whole or parts thereof are not synthetic and exist or are produced in nature.

Non-natural: As used herein, the term generally means not from nature, more specifically, the term means from the hand of man.

Non-natural origin: As used herein, the term "non-natural origin" generally means synthetic or not from nature; more specifically, the term means from the hand of man.

Ordered and repetitive antigen or antigenic determinant array: As used herein, the term "ordered and repetitive antigen or antigenic determinant array" generally refers to a repeating pattern of antigen or antigenic determinant, characterized by a typically and preferably uniform spacial arrangement of the antigens or antigenic determinants with respect to the core particle and virus-like particle, respectively. In one embodiment of the invention, the repeating pattern may be a geometric pattern. Typical and preferred examples of suitable ordered and repetitive antigen or antigenic determinant arrays are those which possess strictly repetitive paracrystalline orders of antigens or antigenic determinants, preferably with spacings of 1 to 30 nanometers, preferably 5 to 15 nanometers.

Pili: As used herein, the term "pili" (singular being "pilus") refers to extracellular structures of bacterial cells composed of protein monomers (e.g., pilin monomers) which are organized into ordered and repetitive patterns. Further, pili are structures which are involved in processes such as the attachment of bacterial cells to host cell surface receptors, inter-cellular genetic exchanges, and cell-cell recognition. Examples of pili include Type-1 pili, P-pili, FIC pili, S-pili, and 987P-pili. Additional examples of pili are set out below.

Pilus-like structure: As used herein, the phrase "pilus-like structure" refers to structures having characteristics similar to that of pili and composed of protein monomers. One example of a "pilus-like structure" is a structure formed by a bacterial cell which expresses modified pilin proteins that do not form ordered and repetitive arrays that are identical to those of natural pili.

Polypeptide: As used herein, the term "polypeptide" refers to a molecule composed of monomers (amino acids) linearly linked by amide bonds (also known as peptide bonds). It indicates a molecular chain of amino acids and does not refer to a specific length of the product. Thus, peptides, dipeptides, tripeptides, oligopeptides and proteins are included within the definition of polypeptide. This term is also intended to refer to post-expression modifications of the polypeptide, for example, glycosolations, acetylations, phosphorylations, and the like. A recombinant or derived polypeptide is not necessarily translated from a designated nucleic acid sequence. It may also be generated in any manner, including chemical synthesis.

IL-5 protein: The term "IL-5 protein" as used herein refers to a protein encoded by an IL-5 gene. Different variants of the IL-5 protein may be caused by nucleotide point mutations and polymorphisms, respectively, as well as insertions, deletions and/or substitutions of one or more nucleotides, and shall be explicitly encompassed within the scope of the present invention. Further variablity can be caused by post-translational modifications, such as differentially glycosylated forms of IL-5 as well as proteolytically cleaved forms of IL-5. The, term "IL-5 protein", as used herein, shall also encompass IL-5 protein variants, including but not limiting to the above indicated preferred examples.

IL-5 peptide: As used herein, the term "IL-5 peptide" is broadly defined as any peptide which represents a fraction of an IL-5 protein and containing at least two, preferably at least three, more prefereably at least four, more prefereably at least five, more prefereably at least six consecutive amino acids of the original IL-5 protein which represents part of a IL-5 protein, most preferably representative of a folded part of IL-5 containing a B cell epitope, and again more preferably of the part of IL-5 containing a neutralizing epitope.

The term "IL-5 peptide" shall further preferably encompass any fraction of said IL5 peptide, wherein said fraction may be, preferably, derived by deletion of one or more amino acids at the N and/or C terminus of IL-5 protein. The IL-5 peptide can be obtained by recombinant expression in eucaryotic or procaryotic expression systems as IL5 peptide alone or as a fusion with other amino acids or proteins, e.g. to facilitate folding, expression or solubility of the IL-5 peptide or to facilitate purification of the IL-5 peptide. To enable coupling of IL-5 peptides and subunit proteins of VLP's or capsids, at least one second attachment site may be preferably added to the IL-5 peptide. Alternatively IL-5 peptides may be synthesized using methods known to the art. The term IL-5 peptide as used herein shall also prefereably encompass a peptide which simulates the three dimensional surface structure of IL5. Such IL5 peptide is not necessarily derived from a continuous amino acid sequence of IL5, but may be formed by discontinuous amino acid residues from IL5. Such peptides may even contain amino acids which are not present in the corresponding IL5 protein.

IL-13 protein: The term "IL-13 protein" as used herein refers to a protein encoded by an IL-13 gene. Different variants of the IL-13 protein may be caused by nucleotide point mutations and polymorphisms, respectively, as well as insertions, deletions and/or substitutions of one or more nucleotides, and shall be explicitly encompassed within the scope of the present invention. Further variablity can be caused by post-translational modifications, such as differentially glycosylated forms of IL-13 as well as proteolytically cleaved forms of IL-13. The, term "IL-13 protein", as used herein, shall also encompass IL-13 protein variants, including but not limiting to the above indicated preferred examples.

IL-13 peptide: As used herein, the term "IL-13 peptide" is broadly defined as any peptide which represents a fraction of an IL-13 protein and containing at least two, preferably at least three, more prefereably at least four, more prefereably at least five, more prefereably at least six consecutive amino acids of the original IL-13 protein which represents part of a IL-13 protein, most preferably representative of a folded part of IL-13 containing a B cell epitope, and again more preferably of the part of IL-13 containing a neutralizing epitope.

The term "IL-13 peptide" shall further preferably encompass any fraction of said IL-13 peptide, wherein said fraction may be, preferably, derived by deletion of one or more amino acids at the N and/or C terminus of IL-13 protein. The IL-13 peptide can be obtained by recombinant expression in eucaryotic or procaryotic expression systems as IL-13 peptide alone or as a fusion with other amino acids or proteins, e.g. to facilitate folding, expression or solubility of the IL-13 peptide or to facilitate purification of the IL-13 peptide. To enable coupling of IL-13 peptides and subunit proteins of VLP's or capsids, at least one second attachment site may be preferably added to the IL-13 peptide. Alternatively IL-13 peptides may be synthesized using methods known to the art. The term IL-13 peptide as used herein shall also prefereably encompass a peptide which simulates the three dimensional surface structure of IL-13. Such IL-13 peptide is not necessarily derived from a continuous amino acid sequence of IL-13, but may be formed by discontinuous amino acid residues from IL-13. Such peptides may even contain amino acids which are not present in the corresponding IL-13 protein.

Residue: As used herein, the term "residue" is meant to mean a specific amino acid in a polypeptide backbone or side chain.

Self antigen: As used herein, the tern "self antigen" refers to proteins encoded by the host's DNA and products generated by proteins or RNA encoded by the host's DNA are defined as self. In addition, proteins that result from a combination of two or several self-molecules or that represent a fraction of a self-molecule and proteins that have a high homology two self-molecules as defined above (>95%, preferably >97%, more preferably >99%) may also be considered self.

Treatment: As used herein, the terms "treatment", "treat", "treated" or "treating" refer to prophylaxis and/or therapy. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., reduce or eliminate the infection or prevent it from becoming worse. When used with respect to allergic diseases with an eosinophilic component, the term "treatment" refers to a prophylactic or therapeutic treatment which inhibits or reduces, inter alia and preferably, allergic inflammatory components associated with allergic eosinophilic diseases.

Vaccine: As used herein, the term "vaccine" refers to a formulation which contains the composition of the present invention and which is in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

Optionally, the vaccine of the present invention additionally includes an adjuvant which can be present in either a minor or major proportion relative to the compound of the present invention. The term "adjuvant" as used herein refers to non-specific stimulators of the immune response or substances that allow generation of a depot in the host which when combined with the vaccine of the present invention provide for an even more enhanced immune response. A variety of adjuvants can be used. Examples include complete and incomplete Freund's adjuvant, aluminum hydroxide and modified muramyldipeptide.

Virus-like particle (VLP): As used herein, the term "virus-like particle" refers to a structure resembling a virus particle. Moreover, a virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage. The terms "viral capsid" or "capsid", as interchangeably used herein, refer to a macromolecular assembly composed of viral protein subunits. Typically and preferably, the viral protein subunits assemble into a viral capsid and capsid, respectively, having a structure with an inherent repetitive organization, wherein said structure is, typically, spherical or tubular. For example, the capsids of RNA-phages or HBcAg's have a spherical form of icosahedral symmetry. The term "capsid-like structure" as used herein, refers to a macromolecular assembly composed of viral protein subunits ressembling the capsid morphology in the above defined sense but deviating from the typical symmetrical assembly while maintaining a sufficient degree of order and repetitiveness.

Virus-like particle of a bacteriophage: As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage.

VLP of RNA phage coat protein: The capsid structure formed from the self-assembly of 180 subunits of RNA phage coat protein and optionally containing host RNA is referred to as a "VLP of RNA phage coat protein". A specific example is the VLP of Qβ coat protein. In this particular case, the VLP of Qβ coat protein may either be assembled exclusively from Qβ CP subunits (generated by expression of a Qβ CP gene containing, for example, a TAA stop codon precluding any expression of the longer A1 protein through suppression, see Kozlovska, T. M. , et al., *Intervirology* 39: 9–15 (1996)), or additionally contain A1 protein subunits in the capsid assembly.

Virus particle: The term "virus particle" as used herein refers to the morphological form of a virus. In some virus types it comprises a genome surrounded by a protein capsid; others have additional structures (e.g., envelopes, tails, etc.).

One, a, or an: When the terms "one," "a," or "an" are used in this disclosure, they mean "at least one" or "one or more," unless otherwise indicated.

As will be clear to those skilled in the art, certain embodiments of the invention involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and can be conveniently found in published laboratory methods manuals (e.g., Sambrook, J. et al., eds., *Molecular Cloning, A Laboratory Manual,* 2nd. edition, Cold Spring Harbor Laboratory Press, Cold Spring Harbor, N.Y. (1989); Ausubel, F. et al., eds., *Current Protocols in Molecular Biology*, John H. Wiley & Sons, Inc. (1997)). Fundamental laboratory techniques for working with tissue culture cell lines (Celis, J., ed., *Cell Biology*, Academic Press, $2^{nd}$ edition, (1998)) and antibody-based technologies (Harlow, E. and Lane, D., *Antibodies: A Laboratory Manual*, Cold Spring Harbor Laboratory, Cold Spring Harbor, N.Y. (1988); Deutscher, M. P. , "Guide to Protein Purification," *Meth. Enzymol.* 128, Academic Press San Diego (1990); Scopes, R. K., *Protein Purification Principles and Practice,* 3rd ed., Springer-Verlag, New York (1994)) are also adequately described in the literature, all of which are incorporated herein by reference.

2. Compositions and Methods for Enhancing an Immune Response

The disclosed invention provides compositions and methods for enhancing an immune response against protein or peptide of IL-5, IL-13 or eotaxin in an animal. Compositions of the invention comprise, or alternatively consist of (a) a core particle with at least one first attachment site; and (b) at least one antigen or antigenic determinant with at least one second attachment site, wherein said antigen or antigenic determinant is a protein or peptide of IL-5, IL-13 or eotaxin, and wherein said second attachment site being selected from the group consisting of (i) an attachment site not naturally occurring with said antigen or antigenic determinant; and (ii) an attachment site naturally occurring with said antigen or antigenic determinant, wherein said second attachment site is capable of association to said first attachment site; and wherein said antigen or antigenic determinant and said core particle interact through said association to form an ordered and repetitive antigen array. More specifically, compositions of the invention comprise, or alternatively consist of, a virus-like particle and at least one antigen or antigenic determinant, wherein the antigen or antigenic determinant is a protein or peptide of IL-5, IL-13 or eotaxin, and wherein the at least one antigen or antigenic determinant is bound to the virus-like particle so as to form an ordered and repetitive antigen-VLP-array. Furthermore, the invention conveniently enables the practitioner to construct such a composition, inter alia, for treatment and/or prophylactic prevention of allergic diseases with an eosinophilic component.

In one embodiment, the core particle comprises a virus, a bacterial pilus, a structure formed from bacterial pilin, a bacteriophage, a virus-like particle, a viral capsid particle or a recombinant form thereof. Any virus known in the art having an ordered and repetitive coat and/or core protein structure may be selected as a core particle of the invention; examples of suitable viruses include sindbis and other alphaviruses, rhabdoviruses (e.g. vesicular stomatitis virus), picornaviruses (e.g., human rhino virus, Aichi virus), togaviruses (e.g., rubella virus), orthomyxoviruses (e.g., Thogoto virus, Batken virus, fowl plague virus), polyomaviruses (e.g., polyomavirus BK, polyomavirus JC, avian polyomavirus BFDV), parvoviruses, rotaviruses, Norwalk virus, foot and mouth disease virus, a retrovirus, Hepatitis B virus, Tobacco mosaic virus, Flock House Virus, and human Papilomavirus, and preferably a RNA phage, bacteriophage Qβ, bacteriophage R17, bacteriophage M11, bacteriophage MX1, bacteriophage NL95, bacteriophage fr, bacteriophage GA, bacteriophage SP, bacteriophage MS2, bacteriophage f2, bacteriophage PP7 (for example, see Table 1 in Bachmann, M. F. and Zinkernagel, R. M. , *Immunol. Today* 17:553–558 (1996)).

In a further embodiment, the invention utilizes genetic engineering of a virus to create a fusion between an ordered and repetitive viral envelope protein and a first attachment site comprising a heterologous protein, peptide, antigenic determinant or a reactive amino acid residue of choice. Other genetic manipulations known to those in the art may be included in the construction of the inventive compositions; for example, it may be desirable to restrict the replication ability of the recombinant virus through genetic mutation. Furthermore, the virus used for the present invention is replication incompetent due to chemical or physical inactivation or, as indicated, due to lack of a replication competent genome. The viral protein selected for fusion to the first attachment site should have an organized and repetitive structure. Such an organized and repetitive structure includes paracrystalline organizations with a spacing of 5–30 nm, preferably 5–15 nm, on the surface of the virus. The creation of this type of fusion protein will result in multiple, ordered and repetitive first attachment sites on the surface of the virus and reflect the normal organization of the native viral protein. As will be understood by those in the art, the first attachment site may be or be a part of any suitable protein, polypeptide, sugar, polynucleotide, peptide (amino acid), natural or synthetic polymer, a secondary metabolite or combination thereof that may serve to specifically attach the antigen or antigenic determinant leading an ordered and repetitive antigen array.

In another embodiment of the invention, the core particle is a recombinant alphavirus, and more specifically, a recombinant Sinbis virus. Alphaviruses are positive stranded RNA viruses that replicate their genomic RNA entirely in the cytoplasm of the infected cell and without a DNA intermediate (Strauss, J. and Strauss, E. , *Microbiol. Rev.* 58:491–562 (1994)). Several members of the alphavirus family, Sindbis (Xiong, C. et al., *Science* 243:1188–1191 (1989); Schlesinger, S. , *Trends Biotechnol.* 11:18–22 (1993)), Semliki Forest Virus (SFV) (Liljeström, P. & Garoff, H. , *Bio/Technology* 9:1356–1361 (1991)) and others (Davis, N. L. et al., *Virology* 171:189–204 (1989)), have received considerable attention for use as virus-based expression vectors for a variety of different proteins (Lundstrom, K., *Curr. Opin. Biotechnol.* 8:578–582 (1997); Liljeström, P., *Curr. Opin. Biotechnol.* 5:495–500 (1994)) and as candidates for vaccine development. Recently, a number of patents have issued directed to the use of alphaviruses for the expression of heterologous proteins and the development of vaccines (see U.S. Pat. Nos. 5,766,602; 5,792,462; 5,739,026; 5,789,245 and 5,814,482). The construction of the alphaviral core particles of the invention may be done by means generally known in the art of recombinant DNA technology, as described by the aforementioned articles, which are incorporated herein by reference.

A variety of different recombinant host cells can be utilized to produce a viral-based core particle for antigen or antigenic determinant attachment. For example, alphaviruses are known to have a wide host range; Sindbis virus infects cultured mammalian, reptilian, and amphibian cells, as well as some insect cells (Clark, H. , *J. Natl. Cancer Inst.* 51:645 (1973); Leake, C. , *J. Gen. Virol.* 35:335 (1977); Stollar, V. in The Togaviruses, R. W. Schlesinger, Ed., Academic Press, (1980), pp. 583–621). Thus, numerous recombinant host cells can be used in the practice of the invention. BHK, COS, Vero, HeLa and CHO cells are particularly suitable for the production of heterologous proteins because they have the potential to glycosylate heterologous proteins in a manner similar to human cells (Watson, E. et al., *Glycobiology* 4:227, (1994)) and can be selected (Zang, M. et al., *Bio/Technology* 13:389 (1995)) or genetically engineered (Renner W. et al., *Biotech. Bioeng.* 4:476 (1995); Lee K. et al. *Biotech. Bioeng.* 50:336 (1996)) to grow in serum-free medium, as well as in suspension.

Introduction of the polynucleotide vectors into host cells can be effected by methods described in standard laboratory manuals (see, e.g., Sambrook, J. et al., eds., Molecular Cloning, A Laboratory Manual, 2nd. edition, Cold Spring Harbor Laboratory Press, Cold Spring Harbor, N.Y. (1989), Chapter 9; Ausubel, F. et al., eds., Current Protocols in Molecular Biology, John H. Wiley & Sons, Inc. (1997), Chapter 16), including methods such as electroporation, DEAE-dextran mediated transfection, transfection, microinjection, cationic lipid-mediated transfection, transduction, scrape loading, ballistic introduction, and infection. Methods for the introduction of exogenous DNA sequences into host cells are discussed in Felgner, P. et al., U.S. Pat. No. 5,580,859.

Packaged RNA sequences can also be used to infect host cells. These packaged RNA sequences can be introduced to host cells by adding them to the culture medium. For example, the preparation of non-infective alphaviral particles is described in a number of sources, including "Sindbis Expression System", Version C (*Invitrogen* Catalog No. K750-1).

When mammalian cells are used as recombinant host cells for the production of viral-based core particles, these cells will generally be grown in tissue culture. Methods for growing cells in culture are well known in the art (see, e.g., Celis, J., ed., Cell Biology, Academic Press, $2^{nd}$ edition, (1998); Sambrook, J. et al., eds., Molecular Cloning, A Laboratory Manual, 2nd. edition, Cold Spring Harbor Laboratory Press, Cold Spring Harbor, N.Y. (1989); Ausubel, F. et al., eds., Current Protocols in Molecular Biology, John H. Wiley & Sons, Inc. (1997); Freshney, R. , Culture of Animal Cells, Alan R. Liss, Inc. (1983)).

Further examples of RNA viruses suitable for use as core particle in the present invention include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picomaviridae, including the genus Enterovirus (poliovirus, Coxsackie virus A and B, enteric cytopathic human orphan (ECHO) viruses, hepatitis A, C, D, E and G viruses, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses and, filoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that may be used as core particles include, but are not limited to: the family Poxviridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A, B, C, D and E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc.). Finally, DNA viruses may include viruses such as chronic infectious neuropathic agents (CHINA virus).

In other embodiments, a bacterial pilin, a subportion of a bacterial pilin, or a fusion protein which contains either a bacterial pilin or subportion thereof is used to prepare compositions and vaccine compositions, respectively, of the invention. Examples of pilin proteins include pilins produced by *Escherichia coli, Haemophilus influenzae, Neisseria meningitidis, Neisseria gonorrhoeae, Caulobacter crescentus, Pseudomonas stutzeri*, and *Pseudomonas aeruginosa*. The amino acid sequences of pilin proteins suitable for use with the present invention include those set out in GenBank reports AJ000636 (SEQ ID NO:1), AJ132364 (SEQ ID NO:2), AF229646 (SEQ ID NO:3), AF051814 (SEQ ID NO:4), AF051815 (SEQ ID NO:5), and X00981 (SEQ ID NO:6), the entire disclosures of which are incorporated herein by reference.

Bacterial pilin proteins are generally processed to remove N-terminal leader sequences prior to export of the proteins into the bacterial periplasm. Further, as one skilled in the art would recognize, bacterial pilin proteins used to prepare compositions and vaccine compositions, respectively, of the invention will generally not have the naturally present leader sequence.

One specific example of a pilin protein suitable for use in the present invention is the P-pilin of *E. coli* (GenBank report AF237482 (SEQ ID NO:7)). An example of a Type-1 *E. coli* pilin suitable for use with the invention is a pilin having the amino acid sequence set out in GenBank report P04128 (SEQ ID NO:8), which is encoded by nucleic acid having the nucleotide sequence set out in GenBank report M27603 (SEQ ID NO:9). The entire disclosures of these GenBank reports are incorporated herein by reference. Again, the mature form of the above referenced protein would generally be used to prepare compositions and vaccine compositions, respectively, of the invention.

Bacterial pilins or pilin subportions suitable for use in the practice of the present invention will generally be able to associate to form ordered and repetitive antigen arrays.

Methods for preparing pili and pilus-like structures in vitro are known in the art. Bullitt et al., *Proc. Natl. Acad. Sci. USA* 93:12890–12895 (1996), for example, describe the in vitro reconstitution of *E. coli* P-pili subunits. Furthermore, Eshdat et al., *J. Bacteriol.* 148:308–314 (1981) describe methods suitable for dissociating Type-1 pili of *E. coli* and the reconstitution of pili. In brief, these methods are as follows: pili are dissociated by incubation at 37° C. in saturated guanidine hydrochloride. Pilin proteins are then purified by chromatography, after which pilin dimers are formed by dialysis against 5 mM tris(hydroxymethyl) aminomethane hydrochloride (pH 8.0). Eshdat et al. also found that pilin dimers reassemble to form pili upon dialysis against the 5 mM tris(hydroxymethyl) aminomethane (pH 8.0) containing 5 mM $MgCl_2$.

Further, using, for example, conventional genetic engineering and protein modification methods, pilin proteins may be modified to contain a first attachment site to which an antigen or antigenic determinant is linked through a second attachment site. Alternatively, antigens or antigenic determinants can be directly linked through a second attachment site to amino acid residues which are naturally resident in these proteins. These modified pilin proteins may then be used in vaccine compositions of the invention.

Bacterial pilin proteins used to prepare compositions and vaccine compositions, respectively, of the invention may be modified in a manner similar to that described herein for HBcAg. For example, cysteine and lysine residues may be either deleted or substituted with other amino acid residues and first attachment sites may be added to these proteins. Further, pilin proteins may either be expressed in modified form or may be chemically modified after expression. Similarly, intact pili may be harvested from bacteria and then modified chemically.

In another embodiment, pili or pilus-like structures are harvested from bacteria (e.g., *E. coli*) and used to form compositions and vaccine compositions of the invention. One example of pili suitable for preparing compositions and vaccine compositions is the Type-1 pilus of *E. coli*, which is formed from pilin monomers having the amino acid sequence set out in SEQ ID NO:8.

A number of methods for harvesting bacterial pili are known in the art. Bullitt and Makowski (*Biophys. J.* 74:623–632 (1998)), for example, describe a pilus purification method for harvesting P-pili from *E. coli*. According to this method, pili are sheared from hyperpiliated *E. coli* containing a P-pilus plasmid and purified by cycles of solubilization and $MgCl_2$ (1.0 M) precipitation.

Once harvested, pili or pilus-like structures may be modified in a variety of ways. For example, a first attachment site can be added to the pili to which antigens or antigen determinants may be attached through a second attachment site. In other words, bacterial pili or pilus-like structures can be harvested and modified to lead to ordered and repetitive antigen arrays.

Antigens or antigenic determinants could be linked to naturally occurring cysteine resides or lysine residues present in Pili or pilus-like structures. In such instances, the high order and repetitiveness of a naturally occurring amino acid residue would guide the coupling of the antigens or antigenic determinants to the pili or pilus-like structures. For example, the pili or pilus-like structures could be linked to the second attachment sites of the antigens or antigenic determinants using a heterobifunctional cross-linking agent.

When structures which are naturally synthesized by organisms (e.g., pili) are used to prepare compositions and vaccine compositions of the invention, it will often be advantageous to genetically engineer these organisms so that they produce structures having desirable characteristics. For example, when Type-1 pili of *E. coli* are used, the *E. coli* from which these pili are harvested may be modified so as to produce structures with specific characteristics. Examples of possible modifications of pilin proteins include the insertion of one or more lysine residues, the deletion or substitution of one or more of the naturally resident lysine residues, and the deletion or substitution of one or more naturally resident cysteine residues (e.g., the cysteine residues at positions 44 and 84 in SEQ ID NO:8).

Further, additional modifications can be made to pilin genes which result in the expression products containing a first attachment site other than a lysine residue (e.g., a FOS or JUN domain). Of course, suitable first attachment sites will generally be limited to those which do not prevent pilin proteins from forming pili or pilus-like structures suitable for use in vaccine compositions of the invention.

Pilin genes which naturally reside in bacterial cells can be modified in vivo (e.g., by homologous recombination) or pilin genes with particular characteristics can be inserted into these cells. For examples, pilin genes could be introduced into bacterial cells as a component of either a replicable cloning vector or a vector which inserts into the bacterial chromosome. The inserted pilin genes may also be linked to expression regulatory control sequences (e.g., a lac operator).

In most instances, the pili or pilus-like structures used in compositions and vaccine compositions, respectively, of the invention will be composed of single type of a pilin subunit. Pili or pilus-like structures composed of identical subunits will generally be used because they are expected to form structures which present highly ordered and repetitive antigen arrays.

However, the compositions of the invention also include compositions and vaccines comprising pili or pilus-like structures formed from heterogenous pilin subunits. The pilin subunits which form these pili or pilus-like structures can be expressed from genes naturally resident in the bacterial cell or may be introduced into the cells. When a naturally resident pilin gene and an introduced gene are both expressed in a cell which forms pili or pilus-like structures, the result will generally be structures formed from a mixture of these pilin proteins. Further, when two or more pilin genes are expressed in a bacterial cell, the relative expression of each pilin gene will typically be the factor which determines the ratio of the different pilin subunits in the pili or pilus-like structures.

When pili or pilus-like structures having a particular composition of mixed pilin subunits is desired, the expression of at least one of the pilin genes can be regulated by a heterologous, inducible promoter. Such promoters, as well as other genetic elements, can be used to regulate the relative amounts of different pilin subunits produced in the bacterial cell and, hence, the composition of the pili or pilus-like structures.

In additional, the antigen or antigenic determinant can be linked to bacterial pili or pilus-like structures by a bond which is not a peptide bond, bacterial cells which produce pili or pilus-like structures used in the compositions of the invention can be genetically engineered to generate pilin proteins which are fused to an antigen or antigenic determinant. Such fusion proteins which form pili or pilus-like structures are suitable for use in vaccine compositions of the invention.

Virus-like particles in the context of the present application refer to structures resembling a virus particle but which are not pathogenic. In general, virus-like particles lack the viral genome and, therefore, are noninfectious. Also, virus-like particles can be produced in large quantities by heterologous expression and can be easily purified.

In a preferred embodiment, the virus-like particle is a recombinant virus-like particle. The skilled artisan can produce VLPs using recombinant DNA technology and virus coding sequences which are readily available to the public. For example, the coding sequence of a virus envelope or core protein can be engineered for expression in a baculovirus expression vector using a commercially available baculovirus vector, under the regulatory control of a virus promoter, with appropriate modifications of the sequence to allow functional linkage of the coding sequence to the regulatory sequence. The coding sequence of a virus envelope or core protein can also be engineered for expression in a bacterial expression vector, for example.

Examples of VLPs include, but are not limited to, the capsid proteins of Hepatitis B virus (Ulrich, et al., *Virus Res.* 50:141–182 (1998)), measles virus (Warnes, et al., *Gene* 160:173–178 (1995)), Sindbis virus, rotavirus (U.S. Pat. No. 5,071,651 and U.S. Pat. No. 5,374,426), foot-and-mouth-disease virus (Twomey, et al., *Vaccine* 13:1603–1610, (1995)), Norwalk virus (Jiang, X., et al., *Science* 250: 1580–1583 (1990); Matsui, S. M. , et al., *J. Clin. Invest.* 87:1456–1461 (1991)), the retroviral GAG protein (WO 96/30523), the retrotransposon Ty protein p1, the surface protein of Hepatitis B virus (WO 92/11291), human papilloma virus (WO 98/15631), RNA phages, Ty, fr-phage, GA-phage and Qβ-phage.

As will be readily apparent to those skilled in the art, the VLP of the invention is not limited to any specific form. The particle can be synthesized chemically or through a biological process, which can be natural or non-natural. By way of example, this type of embodiment includes a virus-like particle or a recombinant form thereof.

In a more specific embodiment, the VLP can comprise, or alternatively essentially consist of, or alternatively consist of recombinant polypeptides, or fragments thereof, being selected from recombinant polypeptides of Rotavirus, recombinant polypeptides of Norwalk virus, recombinant polypeptides of Alphavirus, recombinant polypeptides of Foot and Mouth Disease virus, recombinant polypeptides of measles virus, recombinant polypeptides of Sindbis virus, recombinant polypeptides of Polyoma virus, recombinant polypeptides of Retrovirus, recombinant polypeptides of Hepatitis B virus (e.g., a HBcAg), recombinant polypeptides of Tobacco mosaic virus, recombinant polypeptides of Flock House Virus, recombinant polypeptides of human Papillomavirus, recombinant polypeptides of bacteriophages, recombinant polypeptides of RNA phages, recombinant polypeptides of Ty, recombinant polypeptides of fr-phage, recombinant polypeptides of GA-phage and recombinant polypeptides of Qβ-phage. The virus-like particle can further comprise, or alternatively essentially consist of, or alternatively consist of, one or more fragments of such polypeptides, as well as variants of such polypeptides. Variants of polypeptides can share, for example, at least 80%, 85%, 90%, 95%, 97%, or 99% identity at the amino acid level with their wild-type counterparts.

In a preferred embodiment, the virus-like particle comprises, consists essentially of, or alternatively consists of recombinant proteins, or fragments thereof, of a RNA-phage. Preferably, the RNA-phage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; and 1) bacteriophage PP7.

In another preferred embodiment of the present invention, the virus-like particle comprises, or alternatively consists essentially of, or alternatively consists of recombinant proteins, or fragments thereof, of the RNA-bacteriophage Qβ or of the RNA-bacteriophage fr.

In a further preferred embodiment of the present invention, the recombinant proteins comprise, or alternatively consist essentially of, or alternatively consist of coat proteins of RNA phages.

RNA-phage coat proteins forming capsids or VLP's, or fragments of the bacteriophage coat proteins compatible with self-assembly into a capsid or a VLP, are, therefore, further preferred embodiments of the present invention. Bacteriophage Qβ coat proteins, for example, can be expressed recombinantly in *E. coli*. Further, upon such expression these proteins spontaneously form capsids. Additionally, these capsids form a structure with an inherent repetitive organization.

Specific preferred examples of bacteriophage coat proteins which can be used to prepare compositions of the invention include the coat proteins of RNA bacteriophages such as bacteriophage Qβ (SEQ ID NO:10; PIR Database, Accession No. VCBPQβ referring to Qβ CP and SEQ ID NO: 11; Accession No. AAA16663 referring to Qβ A1 protein), bacteriophage R17 (SEQ ID NO:12; PIR Accession No. VCBPR7), bacteriophage fr (SEQ ID NO:13; PIR Accession No. VCBPFR), bacteriophage GA (SEQ ID NO:14; GenBank Accession No. NP-040754), bacteriophage SP (SEQ ID NO:15; GenBank Accession No. CAA30374 referring to SP CP and SEQ ID NO: 16; Accession No. referring to SP A1 protein), bacteriophage MS2 (SEQ ID NO:17; PIR Accession No. VCBPM2), bacteriophage M11 (SEQ ID NO: 18; GenBank Accession No. AAC06250), bacteriophage MX1 (SEQ ID NO:19; GenBank Accession No. AAC14699), bacteriophage NL95 (SEQ ID NO:20; GenBank Accession No. AAC14704), bacteriophage f2 (SEQ ID NO: 21; GenBank Accession No. P03611), bacteriophage PP7 (SEQ ID NO: 22). Furthermore, the A1 protein of bacteriophage Qβ or C-terminal truncated forms missing as much as 100, 150 or 180 amino acids from its C-terminus may be incorporated in a capsid assembly of Qβ coat proteins. Generally, the percentage of Qβ A1 protein relative to Qβ CP in the capsid assembly will be limited, in order to ensure capsid formation.

Qβ coat protein has also been found to self-assemble into capsids when expressed in *E. coli* (Kozlovska T M. et al., *GENE* 137: 133–137 (1993)). The obtained capsids or virus-like particles showed an icosahedral phage-like capsid structure with a diameter of 25 nm and T=3 quasi symmetry. Further, the crystal structure of phage Qβ has been solved. The capsid contains 180 copies of the coat protein, which are linked in covalent pentamers and hexamers by disulfide bridges (Golmohammadi, R. et al., *Structure* 4: 543–5554 (1996)) leading to a remarkable stability of the capsid of Qβ coat protein. Capsids or VLP's made from recombinant Qβ coat protein may contain, however, subunits not linked via disulfide links to other subunits within the capsid, or incompletely linked. Thus, upon loading recombinant Qβ capsid on non-reducing SDS-PAGE, bands corresponding to monomeric Qβ coat protein as well as bands corresponding to the hexamer or pentamer of Qβ coat protein are visible. Incompletely disulfide-linked subunits could appear as dimer, trimer or even tetramer band in non-reducing SDS-PAGE. Qβ capsid protein also shows unusual resistance to organic solvents and denaturing agents. Surprisingly, we have observed that DMSO and acetonitrile concentrations as high as 30%, and Guanidinium concentrations as high as 1 M do not affect the stability of the capsid. The high stability of the capsid of Qβ coat protein is an advantageous feature, in particular, for its use in immunization and vaccination of mammals and humans in accordance of the present invention.

Upon expression in *E. coli*, the N-terminal methionine of Qβ coat protein is usually removed, as we observed by N-terminal Edman sequencing as described in Stoll, E. et al. J. Biol. Chem. 252:990–993 (1977). VLP composed from Qβ coat proteins where the N-terminal methionine has not been removed, or VLPs comprising a mixture of Qβ coat proteins where the N-terminal methionine is either cleaved or present are also within the scope of the present invention.

Further RNA phage coat proteins have also been shown to self-assemble upon expression in a bacterial host (Kastelein, R A. et al., *Gene* 23: 245–254 (1983), Kozlovskaya, T M. et al., *Dokl. Akad. Nauk SSSR* 287: 452–455 (1986), Adhin, M R. et al., *Virology* 170: 238–242 (1989), Ni, C Z., et al., *Protein Sci.* 5: 2485–2493 (1996), Priano, C. et al., J. Mol. Biol. 249: 283–297 (1995)). The Qβ phage capsid contains, in addition to the coat protein, the so called read-through protein A1 and the maturation protein A2. A1 is generated by suppression at the UGA stop codon and has a length of 329 aa. The capsid of phage Qβ recombinant coat protein used in the invention is devoid of the A2 lysis protein, and contains RNA from the host. The coat protein of RNA phages is an RNA binding protein, and interacts with the stem loop of the ribosomal binding site of the replicase gene acting as a translational repressor during the life cycle of the virus. The sequence and structural elements of the interaction are known (Witherell, G W. & Uhlenbeck, O C. *Biochemistry* 28: 71–76 (1989); Lim F. et al., *J. Biol. Chem.* 271: 31839–31845 (1996)). The stem loop and RNA in general are known to be involved in the virus assembly (Golmohammadi, R. et al., *Structure* 4: 543–5554 (1996)).

In a further preferred embodiment of the present invention, the virus-like particle comprises, or alternatively consists essentially of, or alternatively consists of recombinant proteins, or fragments thereof, of a RNA-phage, wherein the recombinant proteins comprise, consist essentially of or alternatively consist of mutant coat proteins of a RNA phage, preferably of mutant coat proteins of the RNA phages mentioned above. In another preferred embodiment, the mutant coat proteins of the RNA phage have been modified by removal of at least one lysine residue by way of substitution, or by addition of at least one lysine residue by way of substitution; alternatively, the mutant coat proteins of the RNA phage have been modified by deletion of at least one lysine residue, or by addition of at least one lysine residue by way of insertion.

In another preferred embodiment, the virus-like particle comprises, or alternatively consists essentially of, or alternatively consists of recombinant proteins, or fragments thereof, of the RNA-bacteriophage Qβ, wherein the recombinant proteins comprise, or alternatively consist essentially of, or alternatively consist of coat proteins having an amino acid sequence of SEQ ID NO:10, or a mixture of coat proteins having amino acid sequences of SEQ ID NO:10 and of SEQ ID NO: 11 or mutants of SEQ ID NO: 11 and wherein the N-terminal methionine is preferably cleaved.

In a further preferred embodiment of the present invention, the virus-like particle comprises, consists essentially of or alternatively consists of recombinant proteins of Qβ, or fragments thereof, wherein the recombinant proteins comprise, or alternatively consist essentially of, or alternatively consist of mutant Qβ coat proteins. In another preferred embodiment, these mutant coat proteins have been modified by removal of at least one lysine residue by way of substitution, or by addition of at least one lysine residue by way of substitution. Alternatively, these mutant coat proteins have been modified by deletion of at least one lysine residue, or by addition of at least one lysine residue by way of insertion.

Four lysine residues are exposed on the surface of the capsid of Qβ coat protein. Qβ mutants, for which exposed lysine residues are replaced by arginines can also be used for the present invention. The following Qβ coat protein mutants and mutant Qβ VLP's can, thus, be used in the practice of the invention: "Qβ-240" (Lys13-Arg; SEQ ID NO:23), "Qβ-243" (Asn 10-Lys; SEQ ID NO:24), "Qβ-250" (Lys 2-Arg, Lys13-Arg; SEQ ID NO:25), "Qβ-251" (SEQ ID NO:26) and "Qβ-259" (Lys 2-Arg, Lys16-Arg; SEQ ID NO:27). Thus, in further preferred embodiment of the present invention, the virus-like particle comprises, consists essentially of or alternatively consists of recombinant proteins of mutant Qβ coat proteins, which comprise proteins having an amino acid sequence selected from the group of a) the amino acid sequence of SEQ ID NO:23; b) the amino acid sequence of SEQ ID NO:24; c) the amino acid sequence of SEQ ID NO:25; d) the amino acid sequence of SEQ ID NO:26; and e) the amino acid sequence of SEQ ID NO:27. The construction, expression and purification of the above indicated Qβ coat proteins, mutant Qβ coat protein VLP's and capsids, respectively, are disclosed in pending U.S. application Ser. No. 10/050,902 filed by the present assignee on Jan. 18, 2002. In particular is hereby referred to Example 18 of above mentioned application.

In a further preferred embodiment of the present invention, the virus-like particle comprises, or alternatively consists essentially of, or alternatively consists of recombinant proteins of Qβ, or fragments thereof, wherein the recombinant proteins comprise, consist essentially of or alternatively consist of a mixture of either one of the foregoing Qβ mutants and the corresponding A1 protein.

In a further preferred embodiment of the present invention, the virus-like particle comprises, or alternatively essentially consists of, or alternatively consists of recombinant proteins, or fragments thereof, of RNA-phage AP205.

The AP205 genome consists of a maturation protein, a coat protein, a replicase and two open reading frames not present in related phages; a lysis gene and an open reading frame playing a role in the translation of the maturation gene (Klovins, J., et al., *J. Gen. Virol.* 83: 1523–33 (2002)). AP205 coat protein can be expressed from plasmid pAP283-58 (SEQ ID NO: 79), which is a derivative of pQb10 (Kozlovska, T. M. et al., *Gene* 137:133–37 (1993)), and which contains an AP205 ribosomal binding site. Alternatively, AP205 coat protein may be cloned into pQb185, downstream of the ribosomal binding site present in the vector. Both approaches lead to expression of the protein and formation of capsids as described in the co-pending U.S. provisional patent application with the title "Molecular Antigen Arrays" and having filed by the present assignee on Jul. 16, 2002, which is incorporated by reference in its entirety. Vectors pQb10 and pQb185 are vectors derived from pGEM vector, and expression of the cloned genes in these vectors is controlled by the trp promoter (Kozlovska, T. M. et al., *Gene* 137:133–37 (1993)). Plasmid pAP283-58 (SEQ ID NO:79) comprises a putative AP205 ribosomal binding site in the following sequence, which is downstream of the XbaI site, and immediately upstream of the ATG start codon of the AP205 coat protein: tctagaATTTTCTGCG-CACCCATCCCGGGTGGCGCCCAAA GT <u>GAGGAA</u>AATCACatg (bases 77 to 133 of SEQ ID NO: 94). The vector pQb185 comprises a Shine Delagarno sequence downstream from the XbaI site and upstream of the start codon (tctagaTTAACCCAACGCGT<u>AGGAG</u> TCAGGCCatg, SEQ ID NO: 343, Shine Delagarno sequence underlined).

In a further preferred embodiment of the present invention, the virus-like particle comprises, or alternatively essentially consists of, or alternatively consists of recombinant coat proteins, or fragments thereof, of the RNA-phage AP205.

This preferred embodiment of the present invention, thus, comprises AP205 coat proteins that form capsids. Such proteins are recombinantly expressed, or prepared from natural sources. AP205 coat proteins produced in bacteria spontaneously form capsids, as evidenced by Electron Microscopy (EM) and immunodiffusion. The structural properties of the capsid formed by the AP205 coat protein (SEQ ID NO: 80) and those formed by the coat protein of the AP205 RNA phage are nearly indistinguishable when seen in EM. AP205 VLPs are highly immunogenic, and can be linked with antigens and/or antigenic determinants to generate vaccine constructs displaying the antigens and/or antigenic determinants oriented in a repetitive manner. High titers are elicited against the so displayed antigens showing that bound antigens and/or antigenic determinants are accessible for interacting with antibody molecules and are immunogenic.

In a further preferred embodiment of the present invention, the virus-like particle comprises, or alternatively essentially consists of, or alternatively consists of recombinant mutant coat proteins, or fragments thereof, of the RNA-phage AP205.

Assembly-competent mutant forms of AP205 VLPs, including AP205 coat protein with the subsitution of proline at amino acid 5 to threonine (SEQ ID NO: 81), may also be used in the practice of the invention and leads to a further preferred embodiment of the invention. These VLPs, AP205 VLPs derived from natural sources, or AP205 viral particles, may be bound to antigens to produce ordered repetitive arrays of the antigens in accordance with the present invention.

AP205 P5-T mutant coat protein can be expressed from plasmid pAP281-32 (SEQ ID No. 82), which is derived directly from pQb185, and which contains the mutant AP205 coat protein gene instead of the Qβ coat protein gene. Vectors for expression of the AP205 coat protein are transfected into *E. coli* for expression of the AP205 coat protein.

Methods for expression of the coat protein and the mutant coat protein, respectively, leading to self-assembly into VLPs are described in co-pending U.S. provisional patent application with the title “Molecular Antigen Arrays” and having filed by the present assignee on Jul. 16, 2002, which is incorporated by reference in its entirety. Suitable *E. coli* strains include, but are not limited to, *E. coli* K802, JM 109, RR1. Suitable vectors and strains and combinations thereof can be identified by testing expression of the coat protein and mutant coat protein, respectively, by SDS-PAGE and capsid formation and assembly by optionally first purifying the capsids by gel filtration and subsequently testing them in an immunodiffusion assay (Ouchterlony test) or Electron Microscopy (Kozlovska, T. M. et al., *Gene* 137:133–37 (1993)).

AP205 coat proteins expressed from the vectors pAP283-58 and pAP281-32 may be devoid of the initial Methionine amino-acid, due to processing in the cytoplasm of *E. coli*. Cleaved, uncleaved forms of AP205 VLP, or mixtures thereof are further preferred embodiments of the invention.

In a further preferred embodiment of the present invention, the virus-like particle comprises, or alternatively essentially consists of, or alternatively consists of a mixture of recombinant coat proteins, or fragments thereof, of the RNA-phage AP205 and of recombinant mutant coat proteins, or fragments thereof, of the RNA-phage AP205.

In a further preferred embodiment of the present invention, the virus-like particle comprises, or alternatively essentially consists of, or alternatively consists of fragments of recombinant coat proteins or recombinant mutant coat proteins of the RNA-phage AP205.

Recombinant AP205 coat protein fragments capable of assembling into a VLP and a capsid, respectively are also useful in the practice of the invention. These fragments may be generated by deletion, either internally or at the termini of the coat protein and mutant coat protein, respectively. Insertions in the coat protein and mutant coat protein sequence or fusions of antigen sequences to the coat protein and mutant coat protein sequence, and compatible with assembly into a VLP, are further embodiments of the invention and lead to chimeric AP205 coat proteins, and particles, respectively. The outcome of insertions, deletions and fusions to the coat protein sequence and whether it is compatible with assembly into a VLP can be determined by electron microscopy.

The particles formed by the AP205 coat protein, coat protein fragments and chimeric coat proteins described above, can be isolated in pure form by a combination of fractionation steps by precipitation and of purification steps by gel filtration using e.g. Sepharose CL-4B, Sepharose CL-2B, Sepharose CL-6B columns and combinations thereof as described in the co-pending U.S. provisional patent application with the title “Molecular Antigen Arrays” and having filed by the present assignee on Jul. 16, 2002, which is incorporated by reference in its entirety. Other methods of isolating virus-like particles are known in the art, and may be used to isolate the virus-like particles (VLPs) of bacteriophage AP205. For example, the use of ultracentrifugation to isolate VLPs of the yeast retrotransposon Ty is described in U.S. Pat. No. 4,918,166, which is incorporated by reference herein in its entirety.

The crystal structure of several RNA bacteriophages has been determined (Golmohammadi, R. et al., *Structure* 4:543–554 (1996)). Using such information, surface exposed residues can be identified and, thus, RNA-phage coat proteins can be modified such that one or more reactive amino acid residues can be inserted by way of insertion or substitution. As a consequence, those modified forms of bacteriophage coat proteins can also be used for the present invention. Thus, variants of proteins which form capsids or capsid-like structures (e.g., coat proteins of bacteriophage Qβ, bacteriophage R17, bacteriophage fr, bacteriophage GA, bacteriophage SP, and bacteriophage MS2) can also be used to prepare compositions of the present invention.

Although the sequence of the variants proteins discussed above will differ from their wild-type counterparts, these variant proteins will generally retain the ability to form capsids or capsid-like structures. Thus, the invention further includes compositions and vaccine compositions, respectively, which further includes variants of proteins which form capsids or capsid-like structures, as well as methods for preparing such compositions and vaccine compositions, respectively, individual protein subunits used to prepare such compositions, and nucleic acid molecules which encode these protein subunits. Thus, included within the scope of the invention are variant forms of wild-type proteins which form capsids or capsid-like structures and retain the ability to associate and form capsids or capsid-like structures.

As a result, the invention further includes compositions and vaccine compositions, respectively, comprising proteins, which comprise, or alternatively consist essentially of, or alternatively consist of amino acid sequences which are at least 80%, 85%, 90%, 95%, 97%, or 99% identical to wild-type proteins which form ordered arrays and having an inherent repetitive structure, respectively.

Further included within the scope of the invention are nucleic acid molecules which encode proteins used to prepare compositions of the present invention.

In other embodiments, the invention further includes compositions comprising proteins, which comprise, or alternatively consist essentially of, or alternatively consist of amino acid sequences which are at least 80%, 85%, 90%, 95%, 97%, or 99% identical to any of the amino acid sequences shown in SEQ ID NOs:10–27.

Proteins suitable for use in the present invention also include C-terminal truncation mutants of proteins which form capsids or capsid-like structures, or VLP’s. Specific examples of such truncation mutants include proteins having an amino acid sequence shown in any of SEQ ID NOs:10–27 where 1, 2, 5, 7, 9, 10, 12, 14, 15, or 17 amino acids have been removed from the C-terminus. Typically, theses C-terminal truncation mutants will retain the ability to form capsids or capsid-like structures.

Further proteins suitable for use in the present invention also include N-terminal truncation mutants of proteins which form capsids or capsid-like structures. Specific examples of such truncation mutants include proteins having an amino acid sequence shown in any of SEQ ID NOs:10–27 where 1, 2, 5, 7, 9, 10, 12, 14, 15, or 17 amino acids have been removed from the N-terminus. Typically, these N-terminal truncation mutants will retain the ability to form capsids or capsid-like structures.

Additional proteins suitable for use in the present invention include N- and C-terminal truncation mutants which form capsids or capsid-like structures. Suitable truncation mutants include proteins having an amino acid sequence shown in any of SEQ ID NOs:10–27 where 1, 2, 5, 7, 9, 10, 12, 14, 15, or 17 amino acids have been removed from the N-terminus and 1, 2, 5, 7, 9, 10, 12, 14, 15, or 17 amino acids have been removed from the C-terminus. Typically, these N-terminal and C-terminal truncation mutants will retain the ability to form capsids or capsid-like structures.

The invention further includes compositions comprising proteins which comprise, or alternatively consist essentially of, or alternatively consist of, amino acid sequences which are at least 80%, 85%, 90%, 95%, 97%, or 99% identical to the above described truncation mutants.

The invention thus includes compositions and vaccine compositions prepared from proteins which form capsids or VLP's, methods for preparing these compositions from individual protein subunits and VLP's or capsids, methods for preparing these individual protein subunits, nucleic acid molecules which encode these subunits, and methods for vaccinating and/or eliciting immunological responses in individuals using these compositions of the present invention.

As previously stated, the invention includes virus-like particles or recombinant forms thereof. In one further preferred embodiment, the particles used in compositions of the invention are composed of a Hepatitis B core protein (HBcAg) or a fragment of a HBcAg. In a further embodiment, the particles used in compositions of the invention are composed of a Hepatitis B core protein (HBcAg) or a fragment of a HBcAg protein, which has been modified to either eliminate or reduce the number of free cysteine residues. Zhou et al. (*J. Virol.* 66:5393–5398 (1992)) demonstrated that HBcAgs which have been modified to remove the naturally resident cysteine residues retain the ability to associate and form capsids. Thus, VLP's suitable for use in compositions of the invention include those comprising modified HBcAgs, or fragments thereof, in which one or more of the naturally resident cysteine residues have been either deleted or substituted with another amino acid residue (e.g., a serine residue).

The HBcAg is a protein generated by the processing of a Hepatitis B core antigen precursor protein. A number of isotypes of the HBcAg have been identified and their amino acids sequences are readily available to those skilled in the art. In most instances, compositions and vaccine compositions, respectively, of the invention will be prepared using the processed form of a HBcAg (i.e., a HBcAg from which the N-terminal leader sequence of the Hepatitis B core antigen precursor protein have been removed).

Further, when HBcAgs are produced under conditions where processing will not occur, the HBcAgs will generally be expressed in "processed" form. For example, when an *E. coli* expression system directing expression of the protein to the cytoplasm is used to produce HBcAgs of the invention, these proteins will generally be expressed such that the N-terminal leader sequence of the Hepatitis B core antigen precursor protein is not present.

The preparation of Hepatitis B virus-like particles, which can be used for the present invention, is disclosed, for example, in WO 00/32227, and hereby in particular in Examples 17 to 19 and 21 to 24, as well as in WO 01/85208, and hereby in particular in Examples 17 to 19, 21 to 24, 31 and 41, and in pending U.S. application Ser. No. 10/050,902 filed by the present assignee on Jan. 18, 2002. For the latter application, it is in particular referred to Example 23, 24, 31 and 51. All three documents are explicitly incorporated herein by reference.

The present invention also includes HBcAg variants which have been modified to delete or substitute one or more additional cysteine residues. It is known in the art that free cysteine residues can be involved in a number of chemical side reactions. These side reactions include disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. The toxic adducts would thus be distributed between a multiplicity of species, which individually may each be present at low concentration, but reach toxic levels when together.

In view of the above, one advantage to the use of HBcAgs in vaccine compositions which have been modified to remove naturally resident cysteine residues is that sites to which toxic species can bind when antigens or antigenic determinants are attached would be reduced in number or eliminated altogether.

A number of naturally occurring HBcAg variants suitable for use in the practice of the present invention have been identified. Yuan et al., (*J. Virol.* 73:10122–10128 (1999)), for example, describe variants in which the isoleucine residue at position corresponding to position 97 in SEQ ID NO:28 is replaced with either a leucine residue or a phenylalanine residue. The amino acid sequences of a number of HBcAg variants, as well as several Hepatitis B core antigen precursor variants, are disclosed in GenBank reports AAF121240 (SEQ ID NO:29), AF121239 (SEQ ID NO:30), X85297 (SEQ ID NO:31), X02496 (SEQ ID NO:32), X85305 (SEQ ID NO:33), X85303 (SEQ ID NO:34), AF151735 (SEQ ID NO:35), X85259 (SEQ ID NO:36), X85286 (SEQ ID NO:37), X85260 (SEQ ID NO:38), X85317 (SEQ ID NO:39), X85298 (SEQ ID NO:40), AF043593 (SEQ ID NO:41), M20706 (SEQ ID NO:42), X85295 (SEQ ID NO:43), X80925 (SEQ ID NO:44), X85284 (SEQ ID NO:45), X85275 (SEQ ID NO:46), X72702 (SEQ ID NO:47), X85291 (SEQ ID NO:48), X65258 (SEQ ID NO:49), X85302 (SEQ ID NO:50), M32138 (SEQ ID NO:51), X85293 (SEQ ID NO:52), X85315 (SEQ ID NO:53), U95551 (SEQ ID NO:54), X85256 (SEQ ID NO:55), X85316 (SEQ ID NO:56), X85296 (SEQ ID NO:57), AB033559 (SEQ ID NO:58), X59795 (SEQ ID NO:59), X85299 (SEQ ID NO:60), X85307 (SEQ ID NO:61), X65257 (SEQ ID NO:62), X85311 (SEQ ID NO:63), X85301 (SEQ ID NO:64), X85314 (SEQ ID NO:65), X85287 (SEQ ID NO:66), X85272 (SEQ ID NO:67), X85319 (SEQ ID NO:68), AB010289 (SEQ ID NO:69), X85285 (SEQ ID NO:70), AB010289 (SEQ ID NO:71), AF121242 (SEQ ID NO:72), M90520 (SEQ ID NO:73), P03153 (SEQ ID NO:74), AF110999 (SEQ ID NO:75), and M95589 (SEQ ID NO:76), the disclosures of each of which are incorporated herein by reference. These HBcAg variants differ in amino acid sequence at a number of positions, including amino acid residues which corresponds to the amino acid residues located at positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO:77. Further HBcAg variants suitable for use in the compositions of the invention, and which may be further modified according to the disclosure of this specification are described in WO 00/198333, WO 00/177158 and WO 00/214478.

As noted above, generally processed HBcAgs (i.e., those which lack leader sequences) will be used in the compositions and vaccine compositions, respectively, of the invention. The present invention includes vaccine compositions, as well as methods for using these compositions, which employ the above described variant HBcAgs.

Whether the amino acid sequence of a polypeptide has an amino acid sequence that is at least 80%, 85%, 90%, 95%, 97% or 99% identical to one of the above wild-type amino acid sequences, or a subportion thereof, can be determined conventionally using known computer programs such the Bestfit program. When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed.

The HBcAg variants and precursors having the amino acid sequences set out in SEQ ID NOs: 29–72 and 73–77 are relatively similar to each other. Thus, reference to an amino acid residue of a HBcAg variant located at a position which corresponds to a particular position in SEQ ID NO:77, refers to the amino acid residue which is present at that position in the amino acid sequence shown in SEQ ID NO:77. The homology between these HBcAg variants is for the most part high enough among Hepatitis B viruses that infect mammals so that one skilled in the art would have little difficulty reviewing both the amino acid sequence shown in SEQ ID NO:77 and that of a particular HBcAg variant and identifying "corresponding" amino acid residues. Furthermore, the HBcAg amino acid sequence shown in SEQ ID NO:73, which shows the amino acid sequence of a HBcAg derived from a virus which infect woodchucks, has enough homology to the HBcAg having the amino acid sequence shown in SEQ ID NO:77 that it is readily apparent that a three amino acid residue insert is present in SEQ ID NO:64 between amino acid residues 155 and 156 of SEQ ID NO:77.

The invention also includes vaccine compositions which comprise HBcAg variants of Hepatitis B viruses which infect birds, as wells as vaccine compositions which comprise fragments of these HBcAg variants. For these HBcAg variants one, two, three or more of the cysteine residues naturally present in these polypeptides could be either substituted with another amino acid residue or deleted prior to their inclusion in vaccine compositions of the invention.

As discussed above, the elimination of free cysteine residues reduces the number of sites where toxic components can bind to the HBcAg, and also eliminates sites where cross-linking of lysine and cysteine residues of the same or of neighboring HBcAg molecules can occur. Therefore, in another embodiment of the present invention, one or more cysteine residues of the Hepatitis B virus capsid protein have been either deleted or substituted with another amino acid residue.

In other embodiments, compositions and vaccine compositions, respectively, of the invention will contain HBcAgs from which the C-terminal region (e.g., amino acid residues 145–185 or 150–185 of SEQ ID NO:77) has been removed. Thus, additional modified HBcAgs suitable for use in the practice of the present invention include C-terminal truncation mutants. Suitable truncation mutants include HBcAgs where 1, 5, 10, 15, 20, 25, 30, 34, 35, amino acids have been removed from the C-terminus.

HBcAgs suitable for use in the practice of the present invention also include N-terminal truncation mutants. Suitable truncation mutants include modified HBcAgs where 1, 2, 5, 7, 9, 10, 12, 14, 15, or 17 amino acids have been removed from the N-terminus.

Further HBcAgs suitable for use in the practice of the present invention include N- and C-terminal truncation mutants. Suitable truncation mutants include HBcAgs where 1, 2, 5, 7, 9, 10, 12, 14, 15, and 17 amino acids have been removed from the N-terminus and 1, 5, 10, 15, 20, 25, 30, 34, 35 amino acids have been removed from the C-terminus.

The invention further includes compositions and vaccine compositions, respectively, comprising HBcAg polypeptides comprising, or alternatively essentially consisting of, or alternatively consisting of, amino acid sequences which are at least 80%, 85%, 90%, 95%, 97%, or 99% identical to the above described truncation mutants.

In certain embodiments of the invention, a lysine residue is introduced into a HBcAg polypeptide, to mediate the binding of the protein or peptide of IL-5, IL-13 or eotaxin o the VLP of HBcAg. In preferred embodiments, compositions of the invention are prepared using a HBcAg comprising, or alternatively consisting of, amino acids 1–144, or 1–149, 1–185 of SEQ ID NO:77, which is modified so that the amino acids corresponding to positions 79 and 80 are replaced with a peptide having the amino acid sequence of Gly-Gly-Lys-Gly-Gly (SEQ ID NO:78). In further preferred embodiments, the cysteine residues at positions 48 and 107 of SEQ ID NO:77 are mutated to serine. The invention further includes compositions comprising the corresponding polypeptides having amino acid sequences shown in any of SEQ ID NOs:29–74, which also have above noted amino acid alterations. Further included within the scope of the invention are additional HBcAg variants which are capable of associating to form a capsid or VLP and have the above noted amino acid alterations. Thus, the invention further includes compositions and vaccine compositions, respectively, comprising HBcAg polypeptides which comprise, or alternatively consist of, amino acid sequences which are at least 80%, 85%, 90%, 95%, 97% or 99% identical to any of the wild-type amino acid sequences, and forms of these proteins which have been processed, where appropriate, to remove the N-terminal leader sequence and modified with above noted alterations.

Compositions or vaccine compositions of the invention may comprise mixtures of different HBcAgs. Thus, these vaccine compositions may be composed of HBcAgs which differ in amino acid sequence. For example, vaccine compositions could be prepared comprising a "wild-type" HBcAg and a modified HBcAg in which one or more amino acid residues have been altered (e.g., deleted, inserted or substituted). Further, preferred vaccine compositions of the invention are those which present highly ordered and repetitive antigen array, wherein the antigen is a protein or peptide of IL-5, IL-13 or eotaxin In a further preferred embodiment of the present invention, the at least one protein or peptide of IL-5, IL-13 or eotaxin is bound to said core particle and virus-like particle, respectively, by at least one covalent bond. Preferably, the least one protein or peptide of IL-5, IL-13 or eotaxin is bound to the core particle and virus-like particle, respectively, by at least one covalent bond, said covalent bond being a non-peptide bond leading to a core particle—protein or peptide of IL-5, IL-13 or eotaxin ordered and repetitive array and a protein or peptide of IL-5, IL-13 or eotaxin -VLP-array or—conjugate, respectively. This protein or peptide of IL-5, IL-13 or eotaxin—VLP-array and conjugate, respectively, has typically and preferably a repetitive and ordered structure since the at least one, but usually more than one, protein or peptide of IL-5, IL-13 or eotaxin is bound to the VLP in an oriented manner. Preferably, more than 10, 20, 40, 80, 120 protein or peptide of IL-5, IL-13 or eotaxin are bound to the VLP or VLP subunit. The formation of a repetitive and ordered protein or peptide of IL-5, IL-13 or eotaxin array and conjugate, respectively, is ensured by an oriented and directed as well as defined binding and attachment, respectively, of the at least one protein or peptide of IL-5, IL-13 or eotaxin to the VLP as will become apparent in the following. Furthermore, the typical inherent highly repetitive and organized structure of the VLP's advantageously contributes to the display of the protein or peptide of IL-5, IL-13 or eotaxin in a highly ordered and repetitive fashion leading to a highly organized and repetitive protein or peptide of IL-5, IL-13 or eotaxin array and conjugate, respectively.

Therefore, the preferred inventive conjugates and arrays, respectively, differ from prior art conjugates in their highly organized structure, dimensions, and in the repetitiveness of the antigen on the surface of the array. The preferred embodiment of this invention, furthermore, allows expression of both the particle and the antigen in an expression host guaranteeing proper folding of the antigen, i.e. the at least one protein or peptide of IL-5, IL-13 or eotaxin, and proper folding and assembly of the VLP.

The present invention discloses methods of binding of protein or peptide of IL-5, IL-13 or eotaxin to core particles and VLPs, repectively. As indicated, in one aspect of the invention, the protein or peptide of IL-5, IL-13 or eotaxin is bound to the core particle and VLP, respectively, by way of chemical cross-linking, typically and preferably by using a heterobifunctional cross-linker. Several hetero-bifunctional cross-linkers are known to the art. In preferred embodiments, the hetero-bifunctional cross-linker contains a functional group which can react with preferred first attachment sites, i.e. with the side-chain amino group of lysine residues of the core particle and the VLP or at least one VLP subunit, respectively, and a further functional group which can react with a preferred second attachment site, i.e. a cysteine residue naturally present, made available for reaction by reduction, or engineered on the protein or peptide of IL-5, IL-13 or eotaxin, and optionally also made available for reaction by reduction. The first step of the procedure, typically called the derivatization, is the reaction of the core particle or the VLP with the cross-linker. The product of this reaction is an activated core particle or activated VLP, also called activated carrier. In the second step, unreacted cross-linker is removed using usual methods such as gel filtration or dialysis. In the third step, the protein or peptide of IL-5, IL-13 or eotaxin is reacted with the activated carrier, and this step is typically called the coupling step. Unreacted protein or peptide of IL-5, IL-13 or eotaxin may be optionally removed in a fourth step, for example by dialysis. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., U.S.A.) , and having one functional group reactive towards amino groups and one functional group reactive towards cysteine residues. The above mentioned cross-linkers all lead to formation of a thioether linkage. Another class of cross-linkers suitable in the practice of the invention is characterized by the introduction of a disulfide linkage between the protein or peptide of IL-5, IL-13 or eotaxin and the core particle or VLP upon coupling. Preferred cross-linkers belonging to this class include for example SPDP and Sulfo-LC-SPDP (Pierce). The extent of derivatization of the core particle and VLP, respectively, with cross-linker can be influenced by varying experimental conditions such as the concentration of each of the reaction partners, the excess of one reagent over the other, the pH, the temperature and the ionic strength. The degree of coupling, i.e. the amount of protein or peptide of IL-5, IL-13 or eotaxin per subunits of the core particle and VLP, respectively, can be adjusted by varying the experimental conditions described above to match the requirements of the vaccine. Solubility of the protein or peptide of IL-5, IL-13 or eotaxin peptide may impose a limitation on the amount of protein or peptide of IL-5, IL-13 or eotaxin that can be coupled on each subunit, and in those cases where the obtained vaccine would be insoluble, reducing the amount of protein or peptide of IL-5, IL-13 or eotaxin per subunit is beneficial.

A particularly favored method of binding of protein or peptide of IL-5, IL-13 or eotaxin to the core particle and the VLP, respectively, is the linking of a lysine residue on the surface of the core particle and the VLP, respectively, with a cysteine residue on the protein or peptide of IL-5, IL-13 or eotaxin. Thus, in a preferred embodiment of the present invention, the first attachment site is a lysine residue and the second attachment site is a cysteine residue. In some embodiments, engineering of an amino acid linker containing a cysteine residue, as a second attachment site or as a part thereof, to the protein or peptide of IL-5, IL-13 or eotaxin for coupling to the core particle and VLP, respectively, may be required. Alternatively, a cysteine may be introduced either by insertion or mutation within the protein or peptide of IL-5, IL-13 or eotaxin. Alternatively, the cysteine residue or a thiol group may be introduced by chemical coupling.

The selection of the amino acid linker will be dependent on the nature of the antigen and self-antigen, respectively, i.e. on the nature of the protein or peptide of IL-5, IL-13 or eotaxin, on its biochemical properties, such as pI, charge distribution and glycosylation. In general, flexible amino acid linkers are favored. Preferred embodiments of the amino acid linker are selected from the group consisting of: (a) CGG; (b) N-terminal gamma 1-linker; (c) N-terminal gamma 3-linker; (d) Ig hinge regions; (e) N-terminal glycine linkers; (f) $(G)_kC(G)_n$ with n=0–12 and k=0–5; (g) N-terminal glycine-serine linkers; (h) $(G)_kC(G)_m(S)_l(GGGGS)_n$ with n=0–3, k=0–5, m=0–10, l=0–2 (SEQ ID NO: 344); (i) GGC; (k) GGC-NH2; (1) C-terminal gamma 1-linker; (m) C-terminal gamma 3-linker; (n) C-terminal glycine linkers; (o) $(G)_nC(G)_k$ with n=0–12 and k=0–5; (p) C-terminal glycine-serine linkers; (q) $(G)_m(S)_l(GGGGS)_n(G)_oC(G)_k$ with n=0–3, k=0–5, m=0–10, l=0–2, and o=0–8 (SEQ ID NO: 345).

Further preferred examples of amino acid linkers are the hinge region of Immunoglobulins, glycine serine linkers (GGGGS)$_n$(SEQ ID NO: 346), and glycine linkers (G)$_n$ all further containing a cysteine residue as second attachment site and optionally further glycine residues. Typically preferred examples of said amino acid linkers are N-terminal gamma1: CGDKTHTSPP (SEQ ID NO: 347); C-terminal gamma 1: DKTHTSPPCG (SEQ ID NO: 348); N-terminal gamma 3: CGGPKPSTPPGSSGGAP (SEQ ID NO: 349); C-terminal gamma 3: PKPSTPPGSSGGAPGGCG (SEQ ID NO: 350); N-terminal glycine linker: GCGGGG (SEQ ID NO: 351); C-terminal glycine linker: GGGGCG (SEQ ID NO: 352); C-terminal glycine-lysine linker: GGKKGC (SEQ ID NO: 353); N-terminal glycine-lysine linker: CGKKGG (SEQ ID NO: 354).

In a further preferred embodiment of the present invention, and in particular if the antigen is a IL-5, IL-13 or eotaxin peptide, GGCG (SEQ ID NO: 355), GGC or GGC-NH2 ("NH2" stands for amidation) linkers at the C-terminus of the peptide or CGG at its N-terminus are preferred as amino acid linkers. In general, glycine residues will be inserted between bulky amino acids and the cysteine to be used as second attachment site, to avoid potential steric hindrance of the bulkier amino acid in the coupling reaction.

The cysteine residue present on the protein or peptide of IL-5, IL-13 or eotaxin has to be in its reduced state to react with the hetero-bifunctional cross-linker on the activated VLP, that is a free cysteine or a cysteine residue with a free sulfhydryl group has to be available. In the instance where the cysteine residue to function as binding site is in an oxidized form, for example if it is forming a disulfide bridge, reduction of this disulfide bridge with e.g. DTT, TCEP or β-mercaptoethanol is required.

Binding of the protein or peptide of IL-5, IL-13 or eotaxin to the core particle and VLP, respectively, by using a hetero-bifunctional cross-linker according to the preferred methods described above, allows coupling of the protein or peptide of IL-5, IL-13 or eotaxin to the core particle and the VLP, respectively, in an oriented fashion. Other methods of binding the protein or peptide of IL-5, IL-13 or eotaxin to the core particle and the VLP, respectively, include methods wherein the protein or peptide of IL-5, IL-13 or eotaxin is cross-linked to the core particle and the VLP, respectively, using the carbodiimide EDC, and NHS. The protein or peptide of IL-5, IL-13 or eotaxin may also be first thiolated through reaction, for example with SATA, SATP or iminothiolane. The protein or peptide of IL-5, IL-13 or eotaxin, after deprotection if required, may then be coupled to the core particle and the VLP, respectively, as follows. After separation of the excess thiolation reagent, the protein or peptide of IL-5, IL-13 or eotaxin is reacted with the core particle and the VLP, respectively, previously activated with a hetero-bifunctional cross-linker comprising a cysteine reactive moiety, and therefore displaying at least one or several functional groups reactive towards cysteine residues, to which the thiolated protein or peptide of IL-5, IL-13 or eotaxin can react, such as described above. Optionally, low amounts of a reducing agent are included in the reaction mixture. In further methods, the protein or peptide of IL-5, IL-13 or eotaxin is attached to the core particle and the VLP, respectively, using a homo-bifunctional cross-linker such as glutaraldehyde, DSG, BM[PEO]$_4$, BS$^3$, (Pierce Chemical Company, Rockford, Ill., U.S.A.) or other known homo-bifunctional cross-linkers whith functional groups reactive towards amine groups or carboxyl groups of the core particle and the VLP, respectively.

In a further embodiment, the protein or peptide of IL-5, IL-13 or eotaxin is bound to the core particle and the VLP, respectively, through modification of the carbohydrate moieties present on glycosylated protein or peptide of IL-5, IL-13 or eotaxin and subsequent reaction with the core particle and the VLP, respectively. In one embodiment, the glycosylated protein or peptide of IL-5, IL-13 or eotaxin is reacted with sodium periodate in a mild oxidation reaction of the carbohydrate moiety, to yield an activated protein or peptide of IL-5, IL-13 or eotaxin with one or more aldehyde functional groups. The so activated protein or peptide of IL-5, IL-13 or eotaxin is separated from excess sodium periodate, and further reacted with the core particle and the VLP, respectively, wherein lysine residues of the core particle and the VLP, respectively, or of at least one VLP subunit are reacting with the previously formed aldehyde functional group on the protein or peptide of IL-5, IL-13 or eotaxin, for example as described by Hermanson, G. T. in *Bioconjugate Techniques*, Academic Press Inc., San Diego, Calif., U.S.A. Self polymerization of the activated protein or peptide of IL-5, IL-13 or eotaxin may be controlled by adjusting the pH as described in the aforementioned publication. The formed Schiff base is preferably further reduced with sodium cyanoborohydride, which is subsequently removed by gel filtration or dialysis. Alternatively, the core particle and the VLP, respectively, may be reacted with EDC at carboxyl groups of the core particle and the VLP, respectively, or at least one VLP subunit and a dihydrazide, such as adipic acid dihydrazide, to yield a hydrazide moiety available for reaction with the one or more aldehyde functional groups present on the activated protein or peptide of IL-5, IL-13 or eotaxin. The so formed hydrazone may be further reduced with sodium cyanoborohydride. Alternatively, the activated protein or peptide of IL-5, IL-13 or eotaxin with one or more aldehyde functional groups is reacted with cysteamine, resulting in the introduction of a cysteine group in the protein or peptide of IL-5, IL-13 or eotaxin. Additional cross-linking methods and cross-linkers, suitable for protein or peptide of IL-5, IL-13 or eotaxin to a core particle and a VLP, respectively, as well as guidance on performing the coupling reactions and on the use of chemical cross-linkers and chemical cross-linking procedures can be found in Hermanson, G. T. in *Bioconjugate Techniques*, Academic Press Inc., San Diego, Calif., U.S.A.

Other methods of binding the VLP to a protein or peptide of IL-5, IL-13 or eotaxin include methods where the core particle and the VLP, respectively, is biotinylated, and the protein or peptide of IL-5, IL-13 or eotaxin expressed as a streptavidin-fusion protein, or methods wherein both the protein or peptide of IL-5, IL-13 or eotaxin and the core particle and the VLP, respectively, are biotinylated, for example as described in WO 00/23955. In this case, the protein or peptide of IL-5, IL-13 or eotaxin may be first bound to streptavidin or avidin by adjusting the ratio of protein or peptide of IL-5, IL-13 or eotaxin to streptavidin such that free binding sites are still available for binding of the core particle and the VLP, respectively, which is added in the next step. Alternatively, all components may be mixed in a "one pot" reaction. Other ligand-receptor pairs, where a soluble form of the receptor and of the ligand is available, and are capable of being cross-linked to the core particle and the VLP, respectively, or the protein or peptide of IL-5, IL-13 or eotaxin, may be used as binding agents for binding the protein or peptide of IL-5, IL-13 or eotaxin to the core particle and the VLP, respectively. Alternatively, either the ligand or the receptor may be fused to the protein or peptide of IL-5, IL-13 or eotaxin and so mediate binding to the core particle and the VLP, respectively, chemically bound or fused either to the receptor, or the ligand respectively. Fusion may also be effected by insertion or substitution.

As already indicated, in a favored embodiment of the present invention, the VLP is the VLP of a RNA phage, and in a more preferred embodiment, the VLP is the VLP of RNA phage Qβ coat protein.

One or several antigen molecules, i.e. a protein or peptide of IL-5, IL-13 or eotaxin, can be attached to one subunit of the capsid or VLP of RNA phages coat proteins, preferably through the exposed lysine residues of the VLP of RNA phages, if sterically allowable. A specific feature of the VLP of the coat protein of RNA phages and in particular of the Qβ coat protein VLP is thus the possibility to couple several antigens per subunit. This allows for the generation of a dense antigen array.

In a preferred embodiment of the invention, the binding and attachment, respectively, of the at least protein or peptide of IL-5, IL-13 or eotaxin to the core particle and the virus-like particle, respectively, is by way of interaction and association, respectively, between at least one first attachment site of the virus-like particle and at least one second attachment of the antigen or antigenic determinant.

VLPs or capsids of Qβ coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of antigens to the exterior of the particle, rather than to the interior of the particle where the lysine residues interact with RNA. VLPs of other RNA phage coat proteins also have a defined number of lysine residues on their surface and a defined topology of these lysine residues.

In further preferred embodiments of the present invention, the first attachment site is a lysine residue and/or the second attachment comprises sulfhydryl group or a cysteine residue. In a very preferred embodiment of the present invention, the first attachment site is a lysine residue and the second attachment is a cysteine residue.

In very preferred embodiments of the invention, the protein or peptide of IL-5, IL-13 or eotaxin is bound via a cysteine residue, either naturally present on the protein or peptide of IL-5, IL-13 or eotaxin or engineered, to lysine residues of the VLP of RNA phage coat protein, and in particular to the VLP of Qβ coat protein.

Another advantage of the VLPs derived from RNA phages is their high expression yield in bacteria that allows production of large quantities of material at affordable cost.

As indicated, the inventive conjugates and arrays, respectively, differ from prior art conjugates in their highly organized structure, dimensions, and in the repetitiveness of the antigen on the surface of the array. Moreover, the use of the VLPs as carriers allow the formation of robust antigen arrays and conjugates, respectively, with variable antigen density. In particular, the use of VLP's of RNA phages, and hereby in particular the use of the VLP of RNA phage Qβ coat protein allows to achieve very high epitope density. The preparation of compositions of VLPs of RNA phage coat proteins with a high epitope density can be effected by using the teaching of this application.

The second attachment site, as defined herein, may be either naturally or non-naturally present with the antigen or the antigenic determinant. In the case of the absence of a suitable natural occurring second attachment site on the antigen or antigenic determinant, such a, then non-natural second attachment has to be engineered to the antigen.

As described above, four lysine residues are exposed on the surface of the VLP of Qβ coat protein. Typically these residues are derivatized upon reaction with a cross-linker molecule. In the instance where not all of the exposed lysine residues can be coupled to an antigen, the lysine residues which have reacted with the cross-linker are left with a cross-linker molecule attached to the ε-amino group after the derivatization step. This leads to disappearance of one or several positive charges, which may be detrimental to the solubility and stability of the VLP. By replacing some of the lysine residues with arginines, as in the disclosed Qβ coat protein mutants described below, we prevent the excessive disappearance of positive charges since the arginine residues do not react with the cross-linker. Moreover, replacement of lysine residues by arginines may lead to more defined antigen arrays, as fewer sites are available for reaction to the antigen.

Accordingly, exposed lysine residues were replaced by arginines in the following Qβ coat protein mutants and mutant Qβ VLPs disclosed in this application: Qβ-240 (Lys13-Arg; SEQ ID NO:23), Qβ-250 (Lys 2-Arg, Lys13-Arg; SEQ ID NO:25) and Qβ-259 (Lys 2-Arg, Lys16-Arg; SEQ ID NO:27). The constructs were cloned, the proteins expressed, the VLPs purified and used for coupling to peptide and protein antigens. Qβ-251; (SEQ ID NO:26) was also constructed, and guidance on how to express, purify and couple the VLP of Qβ-251 coat protein can be found throughout the application.

In a further embodiment, we disclose a Qβ mutant coat protein with one additional lysine residue, suitable for obtaining even higher density arrays of antigens. This mutant Qβ coat protein, Qβ-243 (Asn 10-Lys; SEQ ID NO:24), was cloned, the protein expressed, and the capsid or VLP isolated and purified, showing that introduction of the additional lysine residue is compatible with self-assembly of the subunits to a capsid or VLP. Thus, protein or peptide of IL-5, IL-13 or eotaxin and conjugates, respectively, may be prepared using VLP of Qβ coat protein mutants. A particularly favored method of attachment of antigens to VLPs, and in particular to VLPs of RNA phage coat proteins is the linking of a lysine residue present on the surface of the VLP of RNA phage coat proteins with a cysteine residue naturally present or engineered on the antigen, i.e. the protein or peptide of IL-5, IL-13 or eotaxin. In order for a cysteine residue to be effective as second attachment site, a sulfhydryl group must be available for coupling. Thus, a cysteine residue has to be in its reduced state, that is, a free cysteine or a cysteine residue with a free sulfhydryl group has to be available. In the instant where the cysteine residue to function as second attachment site is in an oxidized form, for example if it is forming a disulfide bridge, reduction of this disulfide bridge with e.g. DTT, TCEP or β-mercaptoethanol is required. The concentration of reductant, and the molar excess of reductand over antigen has to be adjusted for each antigen. A titration range, starting from concentrations as low as 10 μM or lower, up to 10 to 20 mM or higher reductand if required is tested, and coupling of the antigen to the carrier assessed. Although low concentrations of reductand are compatible with the coupling reaction as described in pending U.S. application Ser. No. 10/050,902 filed by the present assignee on Jan. 18, 2002, higher concentrations inhibit the coupling reaction, as a skilled artisan would know, in which case the reductand has to be removed by dialysis or gel filtration. Advantageously, the pH of the dialysis or equilibration buffer is lower than 7, preferably 6. The compatibility of the low pH buffer with antigen activity or stability has to be tested.

Epitope density on the VLP of RNA phage coat proteins can be modulated by the choice of cross-linker and other reaction conditions. For example, the cross-linkers Sulfo- GMBS and SMPH typically allow reaching high epitope density. Derivatization is positively influenced by high concentration of reactands, and manipulation of the reaction conditions can be used to control the number of antigens coupled to VLPs of RNA phage coat proteins, and in particular to VLPs of Qβ coat protein.

Prior to the design of a non-natural second attachment site the position at which it should be fused, inserted or generally engineered has to be chosen. The selection of the position of the second attachment site may, by way of example, be based on a crystal structure of the antigen. Such a crystal structure of the antigen may provide information on the availability of the C- or N-termini of the molecule (determined for example from their accessibility to solvent), or on the exposure to solvent of residues suitable for use as second attachment sites, such as cysteine residues. Exposed disulfide bridges, as is the case for Fab fragments, may also be a source of a second attachment site, since they can be generally converted to single cysteine residues through mild reduction. Mild reduction conditions not affecting the immunogenicity of protein or peptide of IL-5, IL-13 or eotaxin will be choosen. In general, in the case where immunization with a self-antigen is aiming at inhibiting the interaction of this self-antigen with its natural ligands, the second attachment site will be added such that it allows generation of antibodies against the site of interaction with the natural ligands. Thus, the location of the second attachment site will be selected such that steric hindrance from the second attachment site or any amino acid linker containing the same is avoided. In further embodiments, an antibody response directed at a site distinct from the interaction site of the self-antigen with its natural ligand is desired. In such embodiments, the second attachment site may be selected such that it prevents generation of antibodies against the interaction site of the self-antigen with its natural ligands.

Other criteria in selecting the position of the second attachment site include the oligomerization state of the antigen, the site of oligomerization, the presence of a cofactor, and the availability of experimental evidence disclosing sites in the antigen structure and sequence where modification of the antigen is compatible with the function of the self-antigen, or with the generation of antibodies recognizing the self-antigen.

In the most preferred embodiments, the protein or peptide of IL-5, IL-13 or eotaxin comprises a single second attachment site or a single reactive attachment site capable of association with the first attachment sites on the core particle and the VLPs or VLP subunits, respectively. This ensures a defined and uniform binding and association, respectively, of the at least one, but typically more than one, preferably more than 10, 20, 40, 80, 120 antigens to the core particle and VLP, respectively. The provision of a single second attachment site or a single reactive attachment site on the antigen, thus, ensures a single and uniform type of binding and association, respectively leading to a very highly ordered and repetitive array. For example, if the binding and association, respectively, is effected by way of a lysine- (as the first attachment site) and cysteine- (as a second attachment site) interaction, it is ensured, in accordance with this preferred embodiment of the invention, that only one cysteine residue per antigen, independent whether this cysteine residue is naturally or non-naturally present on the antigen, is capable of binding and associating, respectively, with the VLP and the first attachment site of the core particle, respectively.

In some embodiments, engineering of a second attachment site onto the antigen require the fusion of an amino acid linker containing an amino acid suitable as second attachment site according to the disclosures of this invention. Therefore, in a preferred embodiment of the present invention, an amino acid linker is bound to the antigen or the antigenic determinant by way of at least one covalent bond. Preferably, the amino acid linker comprises, or alternatively consists of, the second attachment site. In a further preferred embodiment, the amino acid linker comprises a sulfhydryl group or a cysteine residue. In another preferred embodiment, the amino acid linker is cysteine. Some criteria of selection of the amino acid linker as well as further preferred embodiments of the amino acid linker according to the invention have already mentioned above.

In a further preferred embodiment of the invention, the at least one antigen or antigenic determinant, i.e. the protein or peptide of IL-5, IL-13 or eotaxin is fused to the core particle and the virus-like particle, respectively. As outlined above, a VLP is typically composed of at least one subunit assembling into a VLP. Thus, in again a further preferred embodiment of the invention, the antigen or antigenic determinant, preferably the at least one protein or peptide of IL-5, IL-13 or eotaxin, is fused to at least one subunit of the virus-like particle or of a protein capable of being incorporated into a VLP generating a chimeric VLP-subunit-protein or peptide of IL-5, IL-13 or eotaxin fusion.

Fusion of the protein or peptide of IL-5, IL-13 or eotaxin can be effected by insertion into the VLP subunit sequence, or by fusion to either the N- or C-terminus of the VLP-subunit or protein capable of being incorporated into a VLP. Hereinafter, when referring to fusion proteins of a peptide to a VLP subunit, the fusion to either ends of the subunit sequence or internal insertion of the peptide within the subunit sequence are encompassed.

Fusion may also be effected by inserting the protein or peptide of IL-5, IL-13 or eotaxin sequences into a variant of a VLP subunit where part of the subunit sequence has been deleted, that are further referred to as truncation mutants. Truncation mutants may have N- or C-terminal, or internal deletions of part of the sequence of the VLP subunit. For example, the specific VLP HBcAg with, for example, deletion of amino acid residues 79 to 81 is a truncation mutant with an internal deletion. Fusion of protein or peptide of IL-5, IL-13 or eotaxin to either the N- or C-terminus of the truncation mutants VLP-subunits also lead to embodiments of the invention. Likewise, fusion of an epitope into the sequence of the VLP subunit may also be effected by substitution, where for example for the specific VLP HBcAg, amino acids 79–81 are replaced with a foreign epitope. Thus, fusion, as referred to hereinafter, may be effected by insertion of the protein or peptide of IL-5, IL-13 or eotaxin sequence in the sequence of a VLP subunit, by substitution of part of the sequence of the VLP subunit with the protein or peptide of IL-5, IL-13 or eotaxin sequence, or by a combination of deletion, substitution or insertions.

The chimeric protein or peptide of IL-5, IL-13 or eotaxin subunit will be in general capable of self-assembly into a VLP. VLP displaying epitopes fused to their subunits are also herein referred to as chimeric VLPs. As indicated, the virus-like particle comprises or alternatively is composed of at least one VLP subunit. In a further embodiment of the invention, the virus-like particle comprises or alternatively is composed of a mixture of chimeric VLP subunits and non-chimeric VLP subunits, i.e. VLP subunits not having an antigen fused thereto, leading to so called mosaic particles. This may be advantageous to ensure formation of and assembly to a VLP. In those embodiments, the proportion of chimeric VLP-subunits may be 1, 2, 5, 10, 20, 30, 40, 50, 60, 70, 80, 90, 95% or higher.

Flanking amino acid residues may be added to either end of the sequence of the peptide or epitope to be fused to either end of the sequence of the subunit of a VLP, or for internal insertion of such peptidic sequence into the sequence of the subunit of a VLP. Glycine and serine residues are particularly favored amino acids to be used in the flanking sequences added to the protein or peptide of IL-5, IL-13 or eotaxin to be fused. Glycine residues confer additional flexibility, which may diminish the potentially destabilizing effect of fusing a foreign sequence into the the sequence of a VLP subunit.

In a specific embodiment of the invention, the VLP is a Hepatitis B core antigen VLP. Fusion proteins to either the N-terminus of a HBcAg (Neyrinck, S. et al., *Nature Med.* 5:1157–1163 (1999)) or insertions in the so called major immunodominant region (MIR) have been described (Pumpens, P. and Grens, E., *Intervirology* 44:98–114 (2001)), WO 01/98333), and are preferred embodiments of the invention. Naturally occurring variants of HBcAg with deletions in the MIR have also been described (Pumpens, P. and Grens, E., *Intervirology* 44:98–114 (2001), which is expressly incorporated by reference in their entirety), and fusions to the N- or C-terminus, as well as insertions at the position of the MIR corresponding to the site of deletion as compared to a wt HBcAg are further embodiments of the invention. Fusions to the C-terminus have also been described (Pumpens, P. and Grens, E., *Intervirology* 44:98–114 (2001)). One skilled in the art will easily find guidance on how to construct fusion proteins using classical molecular biology techniques (Sambrook, J. et al., eds., *Molecular Cloning, A Laboratory Manual,* 2nd. edition, Cold Spring Habor Laboratory Press, Cold Spring Harbor, N.Y. (1989), Ho et al., *Gene* 77:51 (1989)). Vectors and plasmids encoding HBcAg and HBcAg fusion proteins and useful for the expression of a HBcAg and HBcAg fusion proteins have been described (Pumpens, P. & Grens, E. Intervirology 44: 98–114 (2001), Neyrinck, S. et al., *Nature Med.* 5:1157–1163 (1999)) and can be used in the practice of the invention. We also describe by way of example (Example 6) the insertion of an epitope into the MIR of HBcAg, resulting in a chimeric self-assembling HBcAg. An important factor for the optimization of the efficiency of self-assembly and of the display of the epitope to be inserted in the MIR of HBcAg is the choice of the insertion site, as well as the number of amino acids to be deleted from the HBcAg sequence within the MIR (Pumpens, P. and Grens, E., *Intervirology* 44:98–114 (2001); EP 421,635; U.S. Pat. No. 6,231,864) upon insertion, or in other words, which amino acids form HBcAg are to be substituted with the new epitope. For example, substitution of HBcAg amino acids 76–80, 79–81, 79–80, 75–85 or 80–81 with foreign epitopes has been described (Pumpens, P. and Grens, E., *Intervirology* 44:98–114 (2001); EP0421635; U.S. Pat. No. 6,231,864). HBcAg contains a long arginine tail (Pumpens, P. and Grens, E., *Intervirology* 44:98–114 (2001)) which is dispensable for capsid assembly and capable of binding nucleic acids (Pumpens, P. and Grens, E., *Intervirology* 44:98–114 (2001)). HBcAg either comprising or lacking this arginine tail are both embodiments of the invention.

In a further preferred embodiment of the invention, the VLP is a VLP of a RNA phage. The major coat proteins of RNA phages spontaneously assemble into VLPs upon expression in bacteria, and in particular in *E. coli*. Specific examples of bacteriophage coat proteins which can be used to prepare compositions of the invention include the coat proteins of RNA bacteriophages such as bacteriophage Qβ (SEQ ID NO:10; PIR Database, Accession No. VCBPQβ referring to Qβ CP and SEQ ID NO: 11; Accession No. AAA16663 referring to Qβ A1 protein) and bacteriophage fr (SEQ ID NO:4; PIR Accession No. VCBPFR).

In a more preferred embodiment, the at least one protein or peptide of IL-5, IL-13 or eotaxin is fused to a Qβ coat protein. Fusion protein constructs wherein epitopes have been fused to the C-terminus of a truncated form of the A1 protein of Qβ, or inserted within the A1 protein have been described (Kozlovska, T. M., et al., *Intervirology,* 39:9–15 (1996)). The A1 protein is generated by suppression at the UGA stop codon and has a length of 329 aa, or 328 aa, if the cleavage of the N-terminal methionine is taken into account. Cleavage of the N-terminal methionine before an alanine (the second amino acid encoded by the Qβ CP gene) usually takes place in *E. coli*, and such is the case for N-termini of the Qβ coat proteins CP. The part of the A1 gene, 3' of the UGA amber codon encodes the CP extension, which has a length of 195 amino acids. Insertion of the at least one protein or peptide of IL-5, IL-13 or eotaxin between position 72 and 73 of the CP extension leads to further embodiments of the invention (Kozlovska, T. M., et al., *Intervirology* 39:9–15 (1996)). Fusion of a protein or peptide of IL-5, IL-13 or eotaxin at the C-terminus of a C-terminally truncated Qβ A1 protein leads to further preferred embodiments of the invention. For example, Kozlovska et al., (*Intervirology,* 39: 9–15 (1996)) describe Qβ A1 protein fusions where the epitope is fused at the C-terminus of the Qβ CP extension truncated at position 19.

As described by Kozlovska et al. (*Intervirology,* 39: 9–15 (1996)), assembly of the particles displaying the fused epitopes typically requires the presence of both the A1 protein-protein or peptide of IL-5, IL-13 or eotaxin fusion and the wt CP to form a mosaic particle. However, embodiments comprising virus-like particles, and hereby in particular the VLPs of the RNA phage Qβ coat protein, which are exclusively composed of VLP subunits having at least one protein or peptide of IL-5, IL-13 or eotaxin fused thereto, are also within the scope of the present invention.

The production of mosaic particles may be effected in a number of ways. Kozlovska et al., *Intervirology* 39:9–15 (1996), describe two methods, which both can be used in the practice of the invention. In the first approach, efficient display of the fused epitope on the VLPs is mediated by the expression of the plasmid encoding the Qβ A1 protein fusion having a UGA stop codon between CP and CP extension in a *E. coli* strain harboring a plasmid encoding a cloned UGA suppressor tRNA which leads to translation of the UGA codon into Trp (pISM3001 plasmid (Smiley B. K., et al., *Gene* 134:33–40 (1993))). In another approach, the CP gene stop codon is modified into UAA, and a second plasmid expressing the A1 protein-protein or peptide of IL-5, IL-13 or eotaxin fusion is cotransformed. The second plasmid encodes a different antibiotic resistance and the origin of replication is compatible with the first plasmid (Kozlovska, T. M., et al., *Intervirology* 39:9–15 (1996)). In a third approach, CP and the A1 protein-protein or peptide of IL-5, IL-13 or eotaxin fusion are encoded in a bicistronic manner, operatively linked to a promoter such as the Trp promoter, as described in FIG. 1 of Kozlovska et al., *Intervirology,* 39:9–15 (1996).

In a further embodiment, the protein or peptide of IL-5, IL-13 or eotaxin is inserted between amino acid 2 and 3 (numbering of the cleaved CP, that is wherein the N-terminal methionine is cleaved) of the fr CP, thus leading to a protein or peptide of IL-5, IL-13 or eotaxin -fr CP fusion protein. Vectors and expression systems for construction and expression of fr CP fusion proteins self-assembling to VLP and useful in the practice of the invention have been described (Pushko P. et al., *Prot. Eng.* 6:883–891 (1993)). In a specific embodiment, the protein or peptide of IL-5, IL-13 or eotaxin sequence is inserted into a deletion variant of the fr CP after amino acid 2, wherein residues 3 and 4 of the fr CP have been deleted (Pushko P. et al., *Prot. Eng.* 6:883–891 (1993)).

Fusion of epitopes in the N-terminal protuberant β-hairpin of the coat protein of RNA phage MS-2 and subsequent presentation of the fused epitope on the self-assembled VLP of RNA phage MS-2 has also been described (WO 92/13081), and fusion of protein or peptide of IL-5, IL-13 or eotaxin by insertion or substitution into the coat protein of MS-2 RNA phage is also falling under the scope of the invention.

In another embodiment of the invention, the protein or peptide of IL-5, IL-13 or eotaxin are fused to a capsid protein of papillomavirus. In a more specific embodiment, the protein or peptide of IL-5, IL-13 or eotaxin are fused to the major capsid protein L1 of bovine papillomavirus type 1 (BPV-1). Vectors and expression systems for construction and expression of BPV-1 fusion proteins in a baculovirus/insect cells systems have been described (Chackerian, B. et al., *Proc. Natl. Acad. Sci. USA* 96:2373–2378 (1999), WO 00/23955). Substitution of amino acids 130–136 of BPV-1 L1 with a protein or peptide of IL-5, IL-13 or eotaxin leads to a BPV-1 L1-protein or peptide of IL-5, IL-13 or eotaxin fusion protein, which is a preferred embodiment of the invention. Cloning in a baculovirus vector and expression in baculovirus infected Sf9 cells has been described, and can be used in the practice of the invention (Chackerian, B. et al., *Proc. Natl. Acad. Sci. USA* 96:2373–2378 (1999), WO 00/23955). Purification of the assembled particles displaying the fused protein or peptide of IL-5, IL-13 or eotaxin can be performed in a number of ways, such as for example gel filtration or sucrose gradient ultracentrifugation (Chackerian, B. et al., *Proc. Natl. Acad. Sci. USA* 96:2373–2378 (1999), WO 00/23955).

In a further embodiment of the invention, the protein or peptide of IL-5, IL-13 or eotaxin are fused to a Ty protein capable of being incorporated into a Ty VLP. In a more specific embodiment, the protein or peptide of IL-5, IL-13 or eotaxin are fused to the p1 or capsid protein encoded by the TYA gene (Roth, J. F., *Yeast* 16:785–795 (2000)). The yeast retrotransposons Ty1, 2, 3 and 4 have been isolated from *Saccharomyces Serevisiae*, while the retrotransposon Tf1 has been isolated from *Schizosaccharomyces Pombae* (Boeke, J. D. and Sandmeyer, S. B., "Yeast Transposable elements," in *The molecular and Cellular Biology of the Yeast Saccharomyces: Genome dynamics, Protein Synthesis, and Energetics*., p. 193, Cold Spring Harbor Laboratory Press (1991)). The retrotransposons Ty1 and 2 are related to the copia class of plant and animal elements, while Ty3 belongs to the gypsy family of retrotransposons, which is related to plants and animal retroviruses. In the Ty1 retrotransposon, the p1 protein, also referred to as Gag or capsid protein, has a length of 440 amino acids. P1 is cleaved during maturation of the VLP at position 408, leading to the p2 protein, the essential component of the VLP.

Fusion proteins to p1 and vectors for the expression of said fusion proteins in Yeast have been described (Adams, S. E., et al., *Nature* 329:68–70 (1987)). So, for example, a protein or peptide of IL-5, IL-13 or eotaxin peptide may be fused to p1 by inserting a sequence coding for the protein or peptide of IL-5, IL-13 or eotaxin into the BamH1 site of the pMA5620 plasmid (Adams, S. E., et al., *Nature* 329:68–70 (1987)). The cloning of sequences coding for foreign epitopes into the pMA5620 vector leads to expression of fusion proteins comprising amino acids 1–381 of p1 of Ty1–15, fused C-terminally to the N-terminus of the foreign epitope. Likewise, N-terminal fusion of protein or peptide of IL-5, IL-13 or eotaxin , or internal insertion into the p1 sequence, or substitution of part of the p1 sequence is also meant to fall within the scope of the invention. In particular, insertion of protein or peptide of IL-5, IL-13 or eotaxin into the Ty sequence between amino acids 30–31, 67–68, 113–114 and 132–133 of the Ty protein p1 (EP0677111) leads to preferred embodiments of the invention.

Further VLPs suitable for fusion of protein or peptide of IL-5, IL-13 or eotaxin are, for example, Retrovirus-like-particles (WO9630523), HIV2 Gag (Kang, Y. C., et al, *Biol. Chem.* 380:353–364 (1999)), Cowpea Mosaic Virus (Taylor, K. M. et al., *Biol. Chem.* 380:387–392 (1999)), parvovirus VP2 VLP (Rueda, P. et al., *Virology* 263:89–99 (1999)), HBsAg (U.S. Pat. No. 4,722,840, EP0020416B1).

Examples of chimeric VLPs suitable for the practice of the invention are also those described in *Intervirology* 39:1 (1996). Further examples of VLPs contemplated for use in the invention are: HPV-1, HPV-6, HPV-11, HPV-16, HPV-18, HPV-33, HPV-45, CRPV, COPV, HIV GAG, Tobacco Mosaic Virus. Virus-like particles of SV-40, Polyomavirus, Adenovirus, Herpes Simplex Virus, Rotavirus and Norwalk virus have also been made, and chimeric VLPs of those VLPs are also within the scope of the present invention.

In a further preferred embodiment of the present invention, the antigen or antigenic determinant is protein or peptide of IL-5, IL-13 or eotaxin In a further preferred embodiment of the invention, the antigen or antigenic determinant is a protein or peptide of IL-5, IL-13 or eotaxin variant, e.g. containing amino acid substitutions or peptide insertions or polymorphisms. As already indicated, compositions and vaccine compositions, respectively, comprising protein or peptide of IL-5, IL-13 or eotaxin variants are included within the scope of the present invention.

Protein or peptide of IL-5, IL-13 or eotaxin can be produced by expression of the IL-5, IL-13 or eotaxin cDNA in procaryotic or eucaryotic expression systems. Various examples hereto have been described in the literature and can be used, possibly after modifications, to express any protein or peptide of IL-5, IL-13 or eotaxin of any desired species. Disclosures how to produce protein or peptide of IL-5, is also given in WO 900/65058 and references provided within In a further preferred embodiment of the invention, the antigen or antigenic determinant is an IL-5, IL-13 or eotaxin peptide. Such IL-5, IL-13 or eotaxin peptides or fragments thereof can be produced using standard molecular biological technologies where the nucleotide sequence coding for the fragment of interest is amplified by PCR and is cloned as a fusion to a polypeptide tag, such as the GST tag, MBP tag, histdine tag, the Flag tag, myc tag or the constant region of an antibody (Fc region). By introducing a protease cleavage site between the IL-5, IL-13 or eotaxin fragment and the tag, the IL-5, IL-13 or eotaxin peptide can be separated from the tag after purification by digestion with corresponding protease. In another approach the protein or peptide of IL-5, IL-13 or eotaxin peptide can be synthesized in vitro using standard peptide synthesis reactions known to a person skilled in the art. In a further approach, peptides of IL-5, IL-13 or eotaxin can be produced by protease digestion or chemical cleavage of the full length protein of IL-5, IL-13 or eotaxin, both methods of which are well known to people trained in the art.

In a still further preferred embodiment of the present invention, the antigen or antigenic determinant further comprise at least one second attachment site being selected from the group consisting of: (i) an attachment site not naturally occurring with said antigen or antigenic determinant; and (ii) an attachment site naturally occurring with said antigen or antigenic determinant. Guidance on how to modify protein or peptide of IL-5, IL-13 or eotaxin for binding to the virus-like particle is given throughout the application. Preferred second attachment sites contain a cysteine residue for binding to the derivatized VLP and examples are given in the above description and in Example 12 and 13.

We have performed an analysis of the model for the 3-dimensional structure of IL-5 to determine accessiblity of the chosen second attachment ($NH_2$ terminus) to permit coupling to the first attachment site on the VLP in accordance with the present invention. The N-terminus is preferred for attaching a second attachment site comprising an amino acid linker with an additional cysteine residue. However, an amino-acid linker containing a cysteine residue as second attachment site and being fused at the C-terminus of the IL-5 construct leads to a further preferred embodiment of the invention. A human IL-5 construct with an N-terminal amino acid linker containing a cysteine residue fused L is a very preferred embodiment of the invention.

Similar procedures could be used by a person skilled in the art to model the accessibility of attachment sites on IL-13 and eotaxin to optimize coupling to the first attachment site of the VLP.

Mouse protein or peptide of IL-5, IL-13 or eotaxin constructs are disclosed, and preferred human protein or peptide of IL-5, IL-13 or eotaxin fragement constructs can also be generated. Further preferred constructs comprise the whole human protein of IL-5, IL-13 or eotaxin protein, a human peptide of IL-5, IL-13 or eotaxin. Immunization against protein or peptide of IL-5, IL-13 or eotaxin using the inventive compositions comprising, preferably a protein or peptide of IL-5, IL-13 or eotaxin bound to a VLP may provide a way of treatment or prevention of allergic diseases with an eosinophilic component.

In a further preferred embodiment of the present invention, the protein or peptide of IL-5, IL-13 or eotaxin comprises at least one antigenic site of a protein of IL-5, IL-13 or eotaxin. The skilled person in the art knows how to identify the corresponding peptides and amino acid sequences, respectively.

In a further preferred embodiment of the present invention non-contiguous or contiguous peptides of IL-5, IL-13 or eotaxin such as those defined by neutralizing monoclonal antibodies (Dickason, R. R. et al J. Immmunol. 156(3): 1030–7 1996) are included.

In a further preferred embodiment of the present invention non-contiguous or contiguous peptides of IL-5, IL-13 or eotaxin predicted to be involved in receptor interaction and crucial for interaction with the receptor such as those from the COO-terminal of IL-5, are included.

Further peptides of IL-5, IL-13 or eotaxin suitable for use in the present invention can be experimentally determined by their intrinsic property to induce a T cell or an antibody response. This is generally achieved by immunizing an experimental animal separately with selected peptides in an immunologically suitable formulation and by measuring T cell and B cell, i.e. antibody responses, using methods known to a person trained in the art. In the case where the antigen is a protein or a peptide, this region can be formed by a continuous amino acid sequence. Alternatively, the antibody epitope can be formed by a discontinuous amino acid sequence in which, after three dimensional folding of the protein, polypeptide or peptide, the aminoacids are arranged in such a manner that they spatially come close together and form the epitope. Continuous peptide fragments of interest can identified by immunization experiments as described above.

Further preferred peptides of IL-5, IL-13 or eotaxin suitable for use for the present invention can be identified by using existing or future monoclonal or polyclonal antibodies, the procedures hereto are know to those skilled in the art.

Further peptides of IL-5, IL-13 or eotaxin suitable for use for the present invention may be identified by screening phage display peptide libraries with antibodies specific for protein or peptide of IL-5, IL-13 or eotaxin, a method well known to a person trained in the art.

In a further preferred embodiment of the invention, the antigen or antigenic determinant is isolated protein IL-5, IL-13 or eotaxin of any animal as well as any antigenic peptides of IL-5, IL-13 or eotaxin of any animal. Those skilled in the art know how to produce peptides from those isolated proteins or peptides of IL-5, IL-13 or eotaxin.

In another preferred embodiment of the invention the antigenic determinant is Interleukin-13 (IL-13). IL-13 is a cytokine that is secreted by activated T lymphocytes and primarily impacts monocytes, macrophages, and B cells. The amino acid sequence of precursor human IL-13 is shown in SEQ ID No: 230 and the amino acid sequence of processed human IL-13 is shown in SEQ ID No: 231. The first 20 amino acids of the precursor protein correspond to the signal peptide, and are absent of the processed protein. The mouse sequence has also been described, and the processed amino acid sequence is shown in SEQ ID No: 232 (Brown K. D. et al., *J. Immunol.* 142:679–687 (1989)). Depending on the expression host, the IL-13 construct will comprise the sequence of the precursor protein, e.g. for expression and secretion in eukaryotic hosts, or consist of the mature protein, e.g. for cytoplasmic expression in *E. coli*. For expression in the periplasm of *E. coli*, the signal peptide of IL-13 is replaced by a bacterial signal peptide.

IL-13 is a T helper 2-derived cytokine (like IL-4, IL-5) that has recently been implicated in allergic airway responses (asthma). Upregulation of IL-13 and IL-13 receptor has been found in many tumour types (e.g. Hodgkin lymphoma). Interleukin 13 is secreted by and stimulates the growth of Hodgkin and Reed-Sternberg cells (Kapp U et al., *J Exp Med.* 189:1939–46 (1999)). Thus, immunization against IL-13 provides a way of treating among others the conditions described above, such as Asthma or Hodgkins Lymphoma.

Preferably, the composition comprises an amino acid linker containing a free cysteine residue and being fused to the N or C-terminus of the sequence of mature IL-13 to introduce a second attachment site within the protein. In further preferred embodiments, an amino acid linker containing a free cysteine is added to the N-terminus of the mature form of IL-13, since it is freely accessible according to the NMR structure of IL-13 (Eisenmesser, E. Z. et al., *J. Mol. Biol.* 310: 231 (2001)). In again further preferred embodiments, the amino acid linker containing a free cysteine is fused to the N-terminus of the sequence corresponding to the sequence of the processed protein, or inserted at the N-terminus of the sequence of the mature form of the protein, C-terminally of the signal peptide. In still further preferred embodiments, an amino acid linker containing a free cysteine residue is added to the C-terminus of the protein.

IL-13 may be expressed in *E. coli* (Eisenmesser E. Z. et al., *Protein Expr. Purif.* 20:186–95 (2000)), or in NS-0 cells (eukaryotic cell line) (Cannon-Carlson S. et al., *Protein Expr. Purif.* 12:239–48 (1998)). EXAMPLE 8 demonstrates cloning, and expression of constructs and purification of murine IL-13, fused to an amino acid linker containing a cysteine residue, in bacteria. It also describes production and testing of an Eoatxin-VLP vaccine. Human IL-13 constructs can be generated according to the teachings of EXAMPLE 8 and yielding the proteins human C-IL-13-F (SEQ ID NO:330) and human C-IL-13-S (SEQ ID NO:331) after expression of the fusion proteins and cleavage with Factor Xa, and enterokinase respectively. The so generated proteins can be coupled to VLPs and Pili, leading to preferred embodiments of the invention.

In yet another embodiment of the invention, the antigenic determinant is Interleukin-5 (IL-5). IL-5 is a lineage-specific cytokine for eosinophilopoiesis and plays an important part in diseases associated with increased number of eosinophils, such as asthma. The sequence of precursor and processed human IL-5 is provided in SEQ ID No: 233 and in SEQ ID No: 234, respectively, and the processed mouse amino acid sequence is shown in SEQ ID No: 235.

The biological function of IL-5 has been shown in several studies (Coffman R. L. et al., *Science* 245: 308–10 (1989); Kopf et al., *Immunity* 4:15–24 (1996)), which point to a beneficial effect of inhibiting IL-5 function in diseases mediated through eosinophils. Inhibition of the action of IL-5 provides thus a way of treatment against asthma and other diseases associated with eosinophils.

IL-5 forms a dimer, covalently linked by a disulfide bridge. A single chain (sc) construct has been reported wherein two monomers of IL-5 are linked by a peptide linker.

In preferred embodiments of the invention, a peptide linker containing a free cysteine is added at the N-terminus of the sequence of the processed form of IL-5. Addition of a linker containing a free cysteine is also, preferably, envisaged at the N-terminus of the sequence of the processed form of a scIL-5. In further preferred embodiments, the amino acid linker containing a free cysteine is fused to the N-terminus of the sequence corresponding to the sequence of the processed protein, or inserted at the N-terminus of the sequence of the mature form of the protein, C-terminally of the signal peptide.

In again further preferred embodiments, a linker containing a free cysteine is fused to the C-terminus of the sequence of IL-5, or to the C-terminus of a scIL-5 sequence.

A number of expression systems have been described for IL-5 and can be used in preparing the compositions of the invention. A bacterial expression system using *E. coli* has been described by Proudfoot et al., (*Biochem J.* 270:357–61 (1990)). In the case where IL-5 is expressed in the cytoplasm of *E. coli*, the IL-5 construct is devoid of a signal peptide. Insect cells may also be used for producing IL-5 constructs for making the compositions of the invention (Pierrot C. et al., *Biochem. Biophys. Res. Commun.* 253:756–60 (1998)). Likewise, Baculovirus expression systems (sf9 cells; Ingley E. et al., *Eur. J. Biochem.* 196:623–9 (1991) and Brown P. M. et al., *Protein Expr. Purif.* 6: 63–71 (1995)) can also be used. Finally, mammalian expression systems have also been reported (CHO cells) and can be used in preparing these compositions of the invention (Kodama S et al., J. Biochem. (Tokyo) 110:693–701 (1991)).

Baculovirus expression systems (Mitchell et al., *Biochem. Soc. Trans.* 21:332S (1993); Kunimoto D Y et al., *Cytokine* 3:224–30 (1991)) and a mammalian cell expression system using CHO cells (Kodama S et al., *Glycobiology* 2:419–27 (1992)) have also been described for mouse IL-5.

EXAMPLE 7 and 10 describes the expression, purification, coupling to VLP, immunisation and testing in a murine model of experimental asthma of a murine IL-5 construct wherein the IL-5 sequence is fused at its N-terminus to amino acid linkers containing a cysteine residue for coupling to VLPs and Pili. Human constructs can be generated according to the teaching of EXAMPLE 7 and 10 and yield the proteins human C-IL-5-E (SEQ ID NO:335), human C-IL-5-F (SEQ ID NO:336) and human C-IL-5-S: (SEQ ID NO:337) suitable for coupling to VLPs and Pili and leading to preferred embodiments of the invention.

In another specific embodiment, the antigenic determinant is Eotaxin. Eotaxin is a chemokine specific for Chemokine receptor 3, present on eosinophils, basophils and Th2 cells. Eotaxin seems however to be highly specific for Eosinophils (Zimmerman et al., *J. Immunol.* 165: 5839–46 (2000)). Eosinophil migration is reduced by 70% in the eotaxin-1 knock-out mouse, which however can still develop eosinophilia (Rothenberg et al., *J. Exp. Med.* 185: 785–90 (1997)). IL-5 seems to be responsible for the migration of eosinophils from bone-marrow to blood, and eotaxin for the local migration in the tissue (Humbles et al., *J. Exp. Med.* 186: 601–12 (1997).

Therefore, in a preferred embodiment, the inventive composition comprises an amino-acid linker containing a cysteine residue as second attachment site and being, preferably, fused to the C-terminus of the Eotaxin sequence. In other preferred embodiments, an amino acid linker containing a free cysteine is fused to the N-terminus of the sequence corresponding to the sequence of the processed protein, or inserted at the N-terminus of the sequence of the mature form of the protein, C-terminally of the signal peptide. The genes coding for these specific constructs are cloned in a suitable expression vector.

EXAMPLE 9 and 11 describes the cloning and expression of a murine eotaxin construct wherein the eotaxin sequence is fused at its C-terminus to amino acid linkers containing a cysteine residue for coupling to VLPs and Pili. Human constructs can be generated according to the teaching of EXAMPLE 9 and yield proteins suitable for coupling to VLPs and Pili and leading to preferred embodiments of the invention. Eotaxin can be chemically synthesized (Clark-Lewis et al., *Biochemistry* 30:3128–3135 (1991)). Expression in *E. coli* has also been described for Eotaxin-1, in the cytoplasm (Crump et al., *J. Biol. Chem.* 273: 22471–9 (1998)). Expression in *E. coli* as inclusion bodies with subsequent refolding (Mayer et al., Biochemistry 39: 8382–95 (2000)), and Insect cell expression (Forssmann et al., *J. Exp. Med.* 185: 2171–6 (1997)) have been described for Eotaxin-2, and may, moreover, be used to arrive at the specific embodiments of the invention.

It will be understood by one of ordinary skill in the relevant arts that other suitable modifications and adaptations to the methods and applications described herein are readily apparent and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Construction and Expression of Mutant Qβ Coat Proteins, and Purification of Mutant Qβ Coat Protein VLPs or Capsids

Plasmid Construction and Cloning of Mutant Coat Proteins

Construction of pQβ-240:

The plasmid pQβ10 (Kozlovska, T M, et al., *Gene* 137: 133–137) was used as an initial plasmid for the construction of pQβ-240. The mutation Lys13→Arg was created by inverse PCR. The inverse primers were designed in inverted tail-to-tail directions:

```
                                    (SEQ ID NO:356)
5'-GGTAACATCGGTCGAGATGGAAAACAAACTCTGGTCC-3'
and

                                    (SEQ ID NO:357)
5'-GGACCAGAGTTTGTTTTCCATCTCGACCGATGTTACC-3'.
```

The products of the first PCR were used as templates for the second PCR reaction, in which an upstream primer

```
                                    (SEQ ID NO:358)
5'-AGCTCGCCCGGGGATCCTCTAG-3'
and a downstream primer

                                    (SEQ ID NO:359)
5'-CGATGCATTTCATCCTTAGTTATCAATACGCTGGGTTCAG3'
```

were used. The product of the second PCR was digested with XbaI and Mph1103I and cloned into the pQβ10 expression vector, which was cleaved by the same restriction enzymes. The PCR reactions were performed with PCR kit reagents and according to producer protocol (MBI Fermentas, Vilnius, Lithuania).

Sequencing using the direct label incorporation method verified the desired mutations. *E. coli* cells harbouring pQβ-240 supported efficient synthesis of 14-kD protein co migrating upon SDS-PAGE with control Qβ coat protein isolated from Qβ phage particles.

```
Resulting amino acid sequence:   (SEQ ID NO: 23)
AKLETVTLGNIGRDGKQTLVLNPRGVNPTNGVASLSQAGAVP

ALEKRVTVSVSQPSRNRKNYKVQVKIQNPTACTANGSCDPSVTRQ

KYADVTFSFTQYSTDEERAFVRTELAALLASPLLIDAIDQLNPAY
```

Construction of pQβ-243:

The plasmid pQβ10 was used as an initial plasmid for the construction of pQβ-243.The mutation Asn10→Lys was created by inverse PCR. The inverse primers were designed in inverted tail-to-tail directions:

```
                                    (SEQ ID NO:360)
5'-GGCAAAATTAGAGACTGTTACTTTAGGTAAGATCGG-3'
and

                                    (SEQ ID NO:361)
5'-CCGATCTTACCTAAAGTAACAGTCTCTAATTTTGCC-3'.
```

The products of the first PCR were used as templates for the second PCR reaction, in which an upstream primer

```
                                    (SEQ ID NO:358)
5'-AGCTCGCCCGGGGATCCTCTAG-3'
and a downstream primer
                                    (SEQ ID NO:359)
5'-CGATGCATTTCATCCTTAGTTATCAATACGCTGGGTTCAG-3'
```

were used. The product of the second PCR was digested with XbaI and Mph1103I and cloned into the pQβ10 expression vector, which was cleaved by the same restriction enzymes. The PCR reactions were performed with PCR kit reagents and according to producer protocol (MBI Fermentas, Vilnius, Lithuania).

Sequencing using the direct label incorporation method verified the desired mutations. *E. coli* cells harbouring pQβ-243 supported efficient synthesis of 14-kD protein co migrating upon SDSD-PAGE with control Qβ coat protein isolated from Qβ phage particles.

```
Resulting amino acid sequence:   (SEQ ID NO: 24)
AKLETVTLGKIGKDGKQTLVLNPRGVNPTNGVASLSQAGAVP

ALEKRVTVSVSQPSRNRKNYKVQVKIQNPTACTANGSCDPSVTRQ

KYADVTFSFTQYSTDEERAFVRTELAALLASPLLIDAIDQLNPAY
```

Construction of pQβ-250:

The plasmid pQβ-240 was used as an initial plasmid for the construction of pQβ-250. The mutation Lys2→Arg was created by site-directed mutagenesis. An upstream primer

```
                                    (SEQ ID NO:362)
5'-GGCCATGGCACGACTCGAGACTGTTACTTTAGG-3'

and a downstream primer

                                    (SEQ ID NO:363)
5'-GATTTAGGTGACACTATAG-3'
```

were used for the synthesis of the mutant PCR-fragment, which was introduced into the pQβ-185 expression vector at the unique restriction sites NcoI and HindIII. The PCR reactions were performed with PCR kit reagents and according to producer protocol (MBI Fermentas, Vilnius, Lithuania).

Sequencing using the direct label incorporation method verified the desired mutations. *E. coli* cells harbouring pQβ-250 supported efficient synthesis of 14-kD protein co migrating upon PAGE with control Qβ coat protein isolated from Qβ phage particles.

```
Resulting amino acid sequence:   (SEQ ID NO: 25)
ARLETVTLGNIGRDGKQTLVLNPRGVNPTNGVASLSQAGAVP

ALEKRVTVSVSQPSRNRKNYKVQVKIQNPTACTANGSCDPSVTRQ

KYADVTFSFTQYSTDEERAFVRTELAALLASPLLIDAIDQLNPAY
```

Construction of pQβ-251:

The plasmid pQβ10 was used as an initial plasmid for the construction of pQβ-251. The mutation Lys16→Arg was created by inverse PCR. The inverse primers were designed in inverted tail-to-tail directions:

(SEQ ID NO:364)
5'-GATGGACGTCAAACTCTGGTCCTCAATCCGCGTGGGG-3'
and (SEQ ID NO:365)
5'-CCCCACGCGGATTGAGGACCAGAGTTTGACGTCCATC-3'.

The products of the first PCR were used as templates for the second PCR reaction, in which an upstream primer (SEQ ID NO:358)
5'-AGCTCGCCCGGGGATCCTCTAG-3' and a downstream primer (SEQ ID NO:359)
5'-CGATGCATTTCATCCTTAGTTATCAATACGCTGGGTTCAG-3' were used. The product of the second PCR was digested with XbaI and Mph1103I and cloned into the pQβ10 expression vector, which was cleaved by the same restriction enzymes. The PCR reactions were performed with PCR kit reagents and according to producer protocol (MBI Fermentas, Vilnius, Lithuania).

Sequencing using the direct label incorporation method verified the desired mutations. *E. coli* cells harbouring pQβ-251 supported efficient synthesis of 14-kD protein co migrating upon SDS-PAGE with control Qβ coat protein isolated from Qβ phage particles. The resulting amino acid sequence encoded by this construct is shown in SEQ. ID NO:26.

Construction of pQβ-259:

The plasmid pQβ-251 was used as an initial plasmid for the construction of pQβ-259. The mutation Lys2→Arg was created by site-directed mutagenesis. An upstream primer (SEQ ID NO:362)
5'-GGCCATGGCACGACTCGAGACTGTTACTTTAGG-3' and a downstream primer (SEQ ID NO:363)
5'-GATTTAGGTGACACTATAG-3' were used for the synthesis of the mutant PCR-fragment, which was introduced into the pQβ-185 expression vector at the unique restriction sites NcoI and HindIII. The PCR reactions were performed with PCR kit reagents and according to producer protocol (MBI Fermentas, Vilnius, Lithuania).

Sequencing using the direct label incorporation method verified the desired mutations. *E. coli* cells harbouring pQβ-259 supported efficient synthesis of 14-kD protein co migrating upon SDS-PAGE with control Qβ coat protein isolated from Qβ phage particles.

Resulting amino acid sequence: (SEQ ID NO: 27)
AKLETVTLGNIGKDGKQTLVLNPRGVNPTNGVASLSQAGAVP

ALEKRVTVSVSQPSRNRKNYKVQVKIQNPTACTANGSCDPSVTRQ

KYADVTFSFTQYSTDEERAFVRTELAALLASPLLIDAIDQLNPAY

General Procedures for Expression and Purification of Qβ and Qβ Mutants

Expression

*E. coli* JM109 was transformed with Qβ coat protein expression plasmids. 5 ml of LB liquid medium containing 20 μg/ml ampicillin were inoculated with clones transformed with with Qβ coat protein expression plasmids. The inoculated culture was incubated at 37° C. for 16–24 h without shaking. The prepared inoculum was subsequently diluted 1:100 in 100–300 ml of fresh LB medium, containing 20 μg/ml ampicillin. and incubated at 37° C. overnight without shaking. The resulting second inoculum was diluted 1:50 in M9 medium containing 1% Casamino acids and 0.2% glucose in flasks, and incubated at 37° C. overnight under shaking.

Purification

Solutions and buffers for the purification procedure:

1. Lysis buffer LB 50 mM Tris-HCl pH8.0 with 5 mM EDTA, 0.1% tritonX100 and freshly prepared PMSF at a concentration of 5 micrograms per ml. Without lysozyme and DNAse.

2. SAS

Saturated ammonium sulphate in water

3. Buffer NET.

20 mM Tris-HCl, pH 7.8 with 5 mM EDTA and 150 mM NaCl.

4. PEG

40% (w/v) polyethylenglycol 6000 in NET

Disruption and Lysis

Frozen cells were resuspended in LB at 2 ml/g cells. The mixture was sonicated with 22 kH five times for 15 seconds, with intervals of 1 min to cool the solution on ice. The lysate was then centrifuged at 14 000 rpm, for 1 h using a Janecki K 60 rotor. The centrifugation steps described below were all performed using the same rotor, except otherwise stated. The supernatant was stored at 4° C., while cell debris were washed twice with LB. After centrifugation, the supernatants of the lysate and wash fractions were pooled.

Fractionation

A saturated ammonium sulphate solution was added dropwise under stirring to the above pooled lysate. The volume of the SAS was adjusted to be one fifth of total volume, to obtain 20% of saturation. The solution was left standing overnight, and was centrifuged the next day at 14 000 rpm, for 20 min. The pellet was washed with a small amount of 20% ammonium sulphate, and centrifuged again . The obtained supernatants were pooled, and SAS was added dropwise to obtain 40% of saturation. The solution was left standing overnight, and was centrifuged the next day at 14 000 rpm, for 20 min. The obtained pellet was solubilised in NET buffer.

Chromatography

The capsid or VLP protein resolubilized in NET buffer was loaded on a Sepharose CL-4B column. Three peaks eluted during chromatography. The first one mainly contained membranes and membrane fragments, and was not collected. Capsids were contained in the second peak, while the third one contained other *E. coli* proteins.

The peak fractions were pooled, and the NaCl concentration was adjusted to a final concentration of 0.65 M. A volume of PEG solution corresponding to one half of the pooled peak fraction was added dropwise under stirring. The solution was left to stand overnight without stirring. The capsid protein was sedimented by centrifugation at 14 000 rpm for 20 min. It was then solubilized in a minimal volume of NET and loaded again on the Sepharose CL-4B column. The peak fractions were pooled, and precipitated with ammonium sulphate at 60% of saturation (w/v). After centrifugation and resolubilization in NET buffer, capsid protein was loaded on a Sepharose CL-6B column for rechromatography.

Dialysis and Drying

The peak fractions obtained above were pooled and extensively dialysed against sterile water, and lyophilized for storage.

Expression and Purification Qβ-240

Cells (*E. coli* JM 109, transformed with the plasmid pQβ-240) were resuspended in LB, sonicated five times for 15 seconds (water ice jacket) and centrifuged at 13000 rpm for one hour. The supernatant was stored at 4° C. until further processing, while the debris were washed 2 times with 9 ml of LB, and finally with 9 ml of 0.7 M urea in LB. All supernatants were pooled, and loaded on the Sepharose CL-4B column. The pooled peak fractions were precipitated with ammonium sulphate and centrifuged. The resolubilized protein was then purified further on a Sepharose 2B column and finally on a Sepharose 6B column. The capsid peak was finally extensively dialyzed against water and lyophilized as described above. The assembly of the coat protein into a capsid was confirmed by electron microscopy.

Expression and Purification Qβ-243

Cells (*E. coli* RR1) were resuspended in LB and processed as described in the general procedure. The protein was purified by two successive gel filtration steps on the sepharose CL-4B column and finally on a sepharose CL-2B column. Peak fractions were pooled and lyophilized as described above. The assembly of the coat protein into a capsid was confirmed by electron microscopy.

Expression and Purification of Qβ-250

Cells (*E. coli* JM 109, transformed with pQβ-250) were resuspended in LB and processed as described above. The protein was purified by gel filtration on a Sepharose CL-4B and finally on a Sepharose CL-2B column, and lyophilized as described above. The assembly of the coat protein into a capsid was confirmed by electron microscopy.

Expression and Purification of Qβ-259

Cells (*E. coli* JM 109, transformed with pQβ-259) were resuspended in LB and sonicated. The debris were washed once with 10 ml of LB and a second time with 10 ml of 0.7 M urea in LB. The protein was purified by two gel-filtration chromatogaphy steps, on a Sepharose CL-4 B column. The protein was dialyzed and lyophilized, as described above. The assembly of the coat protein into a capsid was confirmed by electron microscopy.

Example 2

Insertion of a Peptide Containing a Lysine Residue into the c/e1 Epitope of HBcAg(1–149)

The c/e1 epitope (residues 72 to 88) of HBcAg is located in the tip region on the surface of the Hepatitis B virus capsid (HBcAg). A part of this region (Proline 79 and Alanine 80) was genetically replaced by the peptide Gly-Gly-Lys-Gly-Gly (HBcAg-Lys construct). The introduced Lysine residue contains a reactive amino group in its side chain that can be used for intermolecular chemical crosslinking of HBcAg particles with any antigen containing a free cysteine group.

HBcAg-Lys DNA, having the amino acid sequence shown in SEQ ID NO:78, was generated by PCRs: The two fragments encoding HBcAg fragments (amino acid residues 1 to 78 and 81 to 149) were amplified separately by PCR. The primers used for these PCRs also introduced a DNA sequence encoding the Gly-Gly-Lys-Gly-Gly peptide. The HBcAg (1 to 78) fragment was amplified from pEco63 using primers EcoRIHBcAg(s) and Lys-HBcAg(as). The HBcAg (81 to 149) fragment was amplified from pEco63 using primers Lys-HBcAg(s) and HBcAg(1-149)Hind(as). Primers Lys-HBcAg(as) and Lys-HBcAg(s) introduced complementary DNA sequences at the ends of the two PCR products allowing fusion of the two PCR products in a subsequent assembly PCR. The assembled fragments were amplified by PCR using primers EcoRIHBcAg(s) and HbcAg(1–149)Hind(as).

For the PCRs, 100 pmol of each oligo and 50 ng of the template DNAs were used in the 50 ml reaction mixtures with 2 units of Pwo polymerase, 0.1 mM dNTPs and 2 mM MgSO4. For both reactions, temperature cycling was carried out as follows: 94° C. for 2 minutes; 30 cycles of 94° C. (1 minute), 50° C. (1 minute), 72° C. (2 minutes).

```
Primer sequences:
EcoRIHBcAg(s):
                                    (SEQ ID NO:366)
(5'-CCGGAATTCATGGACATTGACCCTTATAAAG-3');

Lys-HBcAg(as):
                                    (SEQ ID NO:367)
(5'-CCTAGAGCCACCTTTGCCACCATCTTCTAAATTA-
GTACCCACCCAGGTAGC-3');

Lys-HBcAg(s):
                                    (SEQ ID NO:368)
(5'-GAAGATGGTGGCAAAGGTGGCTCTAGGGACCTA-
GTAGTCAGTTATGTC-3');

HBcAg(1-149)Hind(as):
                                    (SEQ ID NO:369)
(5'-CGCGTCCCAAGCTTCTAAACAACAGTAGTCTCCGGAAG-3').
```

For fusion of the two PCR fragments by PCR 100 pmol of primers EcoRIHBcAg(s) and HBcAg(1–149)Hind(as) were used with 100 ng of the two purified PCR fragments in a 50 ml reaction mixture containing 2 units of Pwo polymerase, 0.1 mM dNTPs and 2 mM $MgSO_4$. PCR cycling conditions were: 94° C. for 2 minutes; 30 cycles of 94° C. (1 minute), 50° C. (1 minute), 72° C. (2 minutes). The assembled PCR product was analyzed by agarose gel electrophoresis, purified and digested for 19 hours in an appropriate buffer with EcoRI and HindIII restriction enzymes. The digested DNA fragment was ligated into EcoRI/HindIII-digested pKK vector to generate pKK-HBcAg-Lys expression vector. Insertion of the PCR product into the vector was analyzed by EcoRI/HindIII restriction analysis and DNA sequencing of the insert.

Example 3

Expression and Purification of HBcAg-Lys

*E. coli* strains K802 or JM109 were transformed with pKK-HBcAg-Lys. 1 ml of an overnight culture of bacteria was used to innoculate 100 ml of LB medium containing 100 μg/ml ampicillin. This culture was grown for 4 hours at 37° C. until an OD at 600 nm of approximately 0.8 was reached. Induction of the synthesis of HBcAg-Lys was performed by addition of IPTG to a final concentration of 1 mM. After induction, bacteria were further shaken at 37° C. for 4 hours.

Bacteria were harvested by centrifugation at 5000×g for 15 minutes. The pellet was frozen at −80° C. The pellet was thawed and resuspended in bacteria lysis buffer (10 mM $Na_2HPO_4$, pH 7.0, 30 mM NaCl, 0.25% Tween-20, 10 mM EDTA) supplemented with 200 μg/ml lysozyme and 10 μl of Benzonase (Merck). Cells were incubated for 30 minutes at room temperature and disrupted by sonication. *E. coli* cells harboring pKK-HBcAg-Lys expression plasmid or a control plasmid were used for induction of HBcAg-Lys expression with IPTG. Prior to the addition of IPTG, a sample was removed from the bacteria culture carrying the pKK-HBcAg-Lys plasmid and from a culture carrying the control plasmid. Four hours after addition of IPTG, samples were again removed from the culture containing pKK-HBcAg-Lys and from the control culture. Protein expression was monitored by SDS-PAGE followed by Coomassie staining.

The lysate was then centrifuged for 30 minutes at 12,000×g in order to remove insoluble cell debris. The supernatant and the pellet were analyzed by Western blotting using a monoclonal antibody against HBcAg (YVS1841, purchased from Accurate Chemical and Scientific Corp., Westbury, N.Y., U.S.A.), indicating that a significant amount of HBcAg-Lys protein was soluble. Briefly, lysates from *E. coli* cells expressing HBcAg-Lys and from control cells were centrifuged at 14,000×g for 30 minutes. Supernatant (=soluble fraction) and pellet (=insoluble fraction) were separated and diluted with SDS sample buffer to equal volumes. Samples were analyzed by SDS-PAGE followed by Western blotting with anti-HBcAg monoclonal antibody YVS 1841.

The cleared cell lysate was used for step-gradient centrifugation using a sucrose step gradient consisting of a 4 ml 65% sucrose solution overlaid with 3 ml 15% sucrose solution followed by 4 ml of bacterial lysate. The sample was centrifuged for 3 hrs with 100,000×g at 4° C. After centrifugation, 1 ml fractions from the top of the gradient were collected and analyzed by SDS-PAGE followed by Coomassie staining. The HBcAg-Lys protein was detected by Coomassie staining.

The HBcAg-Lys protein was enriched at the interface between 15 and 65% sucrose indicating that it had formed a capsid particle. Most of the bacterial proteins remained in the sucrose-free upper layer of the gradient, therefore step-gradient centrifugation of the HBcAg-Lys particles led both to enrichment and to a partial purification of the particles.

Expression and purification of HBcAg-Lys in large scale was performed as follows. An overnight culture was prepared by inoculating a single colony in 100 ml LB, 100 μg/ml Ampicillin and growing the culture overnight at 37° C. 25 ml of the preculture were diluted in 800 ml LB Ampicillin medium the next day, and the culture gorwn to an optical density $OD^{600}$ of 0.6–0.8. The culture was then induced with 1 mM IPTG, and left to grow for another 4 hours. The cells were harvested and lysed essentially as described above.

HBcAg-Lys was then purified by first precipitating the protein with ammonium sulphate (30% saturation) from the cleared cell lysate, then loading the resolubilized pellet on a gel filtration column (Sephacryl S-400, Pharmacia). The pooled fractions were precipitated again with ammonium sulphate, the pellet resolubilized and loaded a second time on the same gel filtration column. The fractions were finally pooled and concentrated, and the concentration assessed using a Bradford test (BioRad).

Example 4

Construction of a HBcAg Devoid of Free Cysteine Residues and Containing an Inserted Lysine Residue A Hepatitis core Antigen (HBcAg), referred to herein as HBcAg-lys-2cys-Mut, devoid of cysteine residues at positions corresponding to 48 and 107 in SEQ ID NO:77 and containing an inserted lysine residue was constructed using the following methods.

The two mutations were introduced by first separately amplifying three fragments of the HBcAg-Lys gene prepared as described above in Example 2 with the following PCR primer combinations. PCR methods and conventional cloning techniques were used to prepare the HBcAg-lys-2cys-Mut gene.

In brief, the following primers were used to prepare fragment 1:

```
Primer 1: EcoRIHBcAg(s)
                                        (SEQ ID NO:366)
CCGGAATTCATGGACATTGACCCTTATAAAG

Primer 2: 48as
                                        (SEQ ID NO:370)
GTGCAGTATGGTGAGGTGAGGAATGCTCAGGAGACTC
```

The following primers were used to prepare fragment 2:

```
Primer 3: 48s
                                        (SEQ ID NO:371)
GSGTCTCCTGAGCATTCCTCACCTCACCATACTGCAC

Primer 4: 107as
                                        (SEQ ID NO:372)
CTTCCAAAAGTGAGGGAAGAAATGTGAAACCAC
```

The following primers were used to prepare fragment 3:

```
Primer 5: HBcAg149hind-as
                                        (SEQ ID NO:369)
CGCGTCCCAAGCTTCTAAACAACAGTAGTCTCCGGA-
AGCGTTGATAG

Primer 6: 107s
                                        (SEQ ID NO:373)
GTGGTTTCACATTTCTTCCCTCACTTTTGGAAG
```

Fragments 1 and 2 were then combined with PCR primers EcoRIHBcAg(s) and 107as to give fragment 4. Fragment 4 and fragment 3 were then combined with primers EcoRIHBcAg(s) and HBcAg149hind—as to produce the full length gene. The full length gene was then digested with the EcoRI (GAATTC) and HindIII (AAGCTT) enzymes and cloned into the pKK vector (Pharmacia) cut at the same restriction sites. Expression and purification of HBcAg-lys-2cys-Mut were performed as set out in Example 3.

Example 5

Construction of HBcAg1–185-Lys

Hepatitis core Antigen (HBcAg) 1–185 was modified as described in Example 2. A part of the c/e1 epitope (residues 72 to 88) region (Proline 79 and Alanine 80) was genetically replaced by the peptide Gly-Gly-Lys-Gly-Gly (HBcAg1–185-Lys construct). The introduced Lysine residue contains a reactive amino group in its side chain that can be used for intermolecular chemical crosslinking of HBcAg particles with any antigen containing a free cysteine group. PCR methods and conventional cloning techniques were used to prepare the HBcAg1–185-Lys gene.

The Gly-Gly-Lys-Gly-Gly sequence was inserted by amplifying two separate fragments of the HBcAg gene from pEco63, as described above in Example 2 and subsequently fusing the two fragments by PCR to assemble the full length gene. The following PCR primer combinations were used:

```
fragment 1:
Primer 1: EcoRIHBcAg(s) (see Example 2)
Primer 2: Lys—HBcAg(as) (see Example 2)

fragment 2:
```

-continued

```
Primer 3: Lys—HBcAg(s) (see Example 2)
Primer 4: HBcAgwtHindIIII
                                    (SEQ ID NO:374)
CGCGTCCCAAGCTTCTAACATTGAGATTCCCGAGATTG

Assembly:
Primer 1: EcoRIHBcAg(s) (see example 2)
Primer 2: HBcAgwtHindIIII
```

The assembled full length gene was then digested with the EcoRI (GAATTC) (4–9 of SEQ ID NO: 366) and HindIII (AAGCTT) (9–14 of SEQ ID NO: 374) enzymes and cloned into the pKK vector (Pharmacia) cut at the same restriction sites.

Example 6

Fusion of a Peptide Epitope in the MIR Region of HbcAg

The residues 79 and 80 of HBcAg1–185 were substituted with the epitope CεH3 of sequence VNLTWSRASG. The CεH3 sequence stems from the sequence of the third constant domain of the heavy chain of human IgE. The epitope was inserted in the HBcAg1–185 sequence using an assembly PCR method. In the first PCR step, the HBcAg1–185 gene originating from ATCC clone pEco63 and amplified with primers HBcAg-wt EcoRI fwd and HBcAg-wt Hind III rev was used as template in two separate reactions to amplify two fragments containing sequence elements coding for the CεH3 sequence. These two fragments were then assembled in a second PCR step, in an assembly PCR reaction.

Primer combinations in the first PCR step: CεH3fwd with HBcAg-wt Hind III rev, and HBcAg-wt EcoRI fwd with CεH3rev. In the assembly PCR reaction, the two fragments isolated in the first PCR step were first assembled during 3 PCR cycles without outer primers, which were added afterwards to the reaction mixture for the next 25 cycles. Outer primers: HBcAg-wt EcoRI fwd and HBcAg-wt Hind III rev.

The PCR product was cloned in the pKK223.3 using the EcoRI and HindIII sites, for expression in *E. coli* (see Example 2). The chimeric VLP was expressed in *E. coli* and purified as described in Example 2. The elution volume at which the HBcAg1–185-CεH3 eluted from the gel filtration showed assembly of the fusion proteins to a chimeric VLP.

Primer sequences:

```
CεH3fwd:
                                                                (SEQ ID NO:375)
5' GTT AAC TTG ACC TGG TCT CGT GCT TCT GGT GCA TCC AGG GAT CTA GTA GTC 3'
    V   N   L   T   W   S   R   A   S   G  A80  S   R   D   L   V  V86

CεH3rev:
                                                                (SEQ ID NO:377)
5' ACC AGA AGC ACG AGA CCA GGT CAA GTT AAC ATC TTC CAA ATT ATT ACC CAC 3'

                                                                (SEQ ID NO:378)
                                          D78  E   L   N   N   G  V72

HBcAg-wt EcoRI fwd:
                                                                (SEQ ID NO:366)
5' CCGgaattcATGGACATTGACCCTTATAAAG

HBcAg-wt Hind III rev:
                                                                (SEQ ID NO:374)
5' CGCGTCCCaagcttCTAACATTGAGATTCCCGAGATTG
```

Example 7

Cloning, expression and purification of IL-5 with an N-terminal amino acid linker containing a cysteine residue. Coupling to VLP, immunization and demonstration of efficacy in an experimental model of allergic asthma with an eosinophilic component.

A. Cloning of Mouse His-C-IL-5 and Expression as Inclusion Bodies in *E. coli*

IL-5 was amplified from an ATCC clone (pmIL5-4G; ATCC number: 37562) by PCR using the following two primers: Spelinker3-F1 (SEQ ID NO:340) and Il5StopXho-R (SEQ ID NO:342). The product of this PCR was used as template for a second PCR with the primers SpeNlinker3-F2 (SEQ ID NO:341) and Il5StopXho-R. The insert was digested with SpeI and NotI. This insert was ligated into a pET vector derivative (pMODEC3-8 vector), previously digested with Nhe I and Not I, and transformed into *E. coli* TG1 cells. The construct generated by cloning IL5 into pMODEC3-8 comprises, from its N-terminus, a hexa-histidine tag (to facilitate purification), an Enterokinase cleavage site, a gamma 3 derived amino acid linker (flanked N-terminally by the amino acids ALV and C-terminally by AS) containing a cysteine residue and the DNA encoding the mature form of IL-5 protein. Fidelity of the cloning procedure was confirmed by DNA sequencing.

The construct containing IL-5 described above was termed pMODC6-IL5.2 (also referred to as pMODC6-IL5) and transformed into *E. coli* strain BL21-DE3. The recombinant protein expressed in *E. coli* is termed His-C-IL5.

Clonal BL21-DE3 cells harboring pMODC6-IL5 were grown over night in 5 ml of LB containing 1 mg/L Ampicillin. A 2.0 ml aliquot of this culture was diluted into 100 ml terrific broth (TB) containing 1 mg/L Ampicillin. The culture was grown to an optical density, $OD_{600\ nm}$, of 0.7–1.0 and expression induced for 4 hours by adding 0.1 ml of a 1.0 M stock of Ispropyl β-D-Thiogalactopyranoside (IPTG). Recombinant His-C-IL5 was expressed in an insoluble form and located in the inclusion body fraction of induced cells. Expression of His-C-IL5 was confirmed in the flowing manner. A 10 ml sample of culture was taken 4 hours after induction and centrifuged for 10 min at 4000×g. The pellet was suspended in 0.5 ml lysis buffer consisting of 50 mM Tris-HCl, 2 mM EDTA, 0.1% triton X-100 (pH 8.0). To the suspension was added 20 μl of Lysozyme (40 mg/ml) and after 30 min at 4° C. sonicated for 2 min. A 1.0 ml aliquot of benzonase and 100 μl aliquot of 50 mM $MgCl_2$ were added and incubated for 30 min at room temperature. After centrifugation for 15 min at 13000×g the supernatant was discarded and the pellet heated for 5 min at 98° C. in 100 μl of SDS loading buffer. Aliquots of 10 μl were then analyzed by SDS-PAGE under reducing conditions (FIG. 17A). SDS-PAGE analysis demonstrated a protein band of 17 kDa corresponding to the mass of IL-5. As control, BL21-DE2 cells containing pMODC6-IL5 were grown in the absence of IPTG and extracts prepared from the insoluble cell fraction as described above.

B. Purification and Refolding of Mouse His-C-IL5

A larger scale expression of IL-5 from clone pMODC6-IL5 in BL21-DE3 cells was performed in order to obtain sufficient quantities of pure IL-5 for vaccine production. Overnight cultures were grown and diluted into either 100 ml or 1 L volumes of TB medium containing 1.0 mg/L Ampicillin. A total of 3 liters of culture was thus prepared and grown at 37° C. until $OD_{600\ nm}$ reached 0.7 at which time IPTG was added to give a final concentration of 1.0 mM. After 4 h incubation cells were harvested by centrifugation for 30 min at 10 000×g. After harvesting the pellet was resuspended in PBS (5.0 ml/g wet weight) and centrifuged for 15 minutes at 10 000×g. The washed pellet was stored at −20° C. until further use.

The bacterial pellet was suspended in PBS (2.0 ml/g cell wet weight) using a Dounce homogenizer. Lysozyme (0.8 mg/ml) was added to the suspension and incubated for 30 minutes at room temperature. The suspension was sonicated for 1 minute, 3 times on ice then benzonase and $MgCl_2$ (10 mM final concentration) were added and incubated for 30 minutes at room temperature. Triton X-100 was added to a final concentration of 1% (w/v) the mixture gently stirred at room temperature for 30 minutes. The solution was centrifuged for 20 minutes at 20 000×g (SS34 tubes) and the supernatant discarded. The pellet harbouring the inclusion bodies was suspended (5.0 ml/g wet weight) in washing buffer (PBS containing 2M Urea and 1% (w/v) Triton X-100) using a Dounce homogenizer and agitated for 5 minutes. The solution was centrifuged for 20 minutes at 20 000×g and the supernatant discarded. The pellet was washed and centrifuged as above 2 more times. A final wash of the inclusion bodies was performed with washing buffer in the absence of Triton X-100.

The His-C-IL-5 present in inclusion bodies of the pellet was solubilized in (5.0 ml/g cell wet weight) denaturing buffer (100 mM $NaH_2PO_4$, 10 mM Tris-HCl, 6.0 M Guanidine-hydrochloride, pH 8.0) and gently stirred for 1 h at 25° C. The suspension was centrifuged for 20 min. at 20 000×g and the supernatant mixed with Ni-NTA resin (QIAgen, equilibrated with solubilization buffer). After 3 hours of gentle agitation at 4° C. the slurry was poured into a glass column (C10/10) and the resin washed with 100 ml of 100 mM $NaH_2PO_4$, 10 mM Tris, 6.0 M Guanidine-hydrochloride (pH 6.3). An additional washing step was performed with 15 ml of 100 mM $NaH_2PO_4$, 10 mM Tris, 6.0 M Guanidine-hydrochloride (pH 5.9). Mouse His-C-IL5 was eluted from the resin by applying 20 ml of 100 mM $NaH_2PO_4$, 10 mM Tris, 6.0 M Guanidine-hydrochloride (pH 4.5). Purification was anylysed by SDS-PAGE.

Fractions from the elution step containing His-C-IL-5 were pooled and dialysed against buffer comprising 8.0 M Urea 100 mM $NaH_2PO_4$, 10 mM Tris-HCl (pH 8.0) at 4° C. using a 10 kDa cut-off membrane. Following dialysis, the protein concentration was determined spectrophotometrically using the following formula; Protein (mg/ml)=$(1.55\times A_{280\ nm})-(0.76\times A_{260nm})$. The concentration of the protein was diluted with dialysis buffer to 0.2 mg/ml. The solution was then dialysed with a 3.5kDa membrane for 24 hours at 4° C. against refolding buffer 1 comprising 2.0 M urea, 50 mM $NaH_2PO_4$, 5 mM reduced Glutathione, 0.5 mM oxidized Glutathione, 0.5 M Arginine, 10% (v/v) glycerol (pH 8.5) and for a further 24 h against another refolding buffer 2 comprising 50 mM $NaH_2PO_4$, 5 mM reduced Glutathione, 0.5 mM oxidized Glutathione, 0.5 M Arginine, 10% (v/v) glycerol, (pH 8.5). At the end the protein was dialysed for 24 h at 4° C. against PBS pH 8.0 then centrifuged at 10 000×g for 30 min. The protein content of the supernatant was estimated by Bradford assay.

In order to further purifiy His-C-IL5, anion exchange with Hitrap Q resin (Amersham Pharmacia, Uppsala Sweeden) was performed. His-C-IL5 was concentrated to 1 mg/ml using Centrifugal Filters (Ultrafree-15 Millipore, 10 kDa cut-off) and dialyzed for 14 h against 50 mM Phosphate buffer pH 8.4. The solution was loaded onto a Hitrap Q column and washed with 50 mM Phosphate pH 8.4 buffer. His-C-IL-5 was eluted from the column by applying a NaCl gradient from 0–1 M. His-C-IL5 eluted from the column at 100 mM NaCl. Analysis of the purification was performed by SDS-PAGE and concentration measured by Bradford assay. Quartenary structure of the protein was assessed by SDS-PAGE performed under non-reducing conditions.

C. Vaccine Production: Coupling His-C-IL5 to Qβ

A variety of conditions were investigated to optimize the efficiency of the coupling reaction. These included the addition of reducing agent, (TCEP) to His-C-IL5 and varying the molar ratios of Qβ monomer and His-C-IL5 in the coupling reaction and are summarized in Table 1. The vaccine for the efficacy study was produced in the following way. Purified His-C-IL-5 (40 μM) was reduced for 1 h with an equimolar amount of TCEP in PBS pH 8.0. Reduced IL-5 (80 μM) was incubated for 4 hours at 22° C. with 40 μM Qβ derivatized with SMPH in a total volume of 700 μl. The reaction was dialysed 12 hours against PBS pH 8.0 using a 300 kDa cutt-off dialysis membrane. The coupling reaction was analysed by SDS-PAGE and Western-Blot with anti-His and anti-Qβ antibodies. Protein concentration was measured by Bradford. The coupling efficiency [i.e. mol Qβ-IL5/mol Qβ monomer (total)] was estimated, by densitometric analysis of the Coomassie blue stained SDS-PAGE.

TABLE 1

Different coupling conditions used to optimize the chemical cross-linking of His-C-IL5 to Qβ.

| Concentration of derivatized Qβ (μM) | Concentration of His-C-IL5 (μM) | TCEP/IL5 ratio (μM) |
|---|---|---|
| 70 | 40 | No TCEP |
| 70 | 40 | 1:2 |
| 70 | 40 | 1:1 |
| 70 | 40 | 1.5:1 |
| 70 | 40 | 2:1 |
| 70 | 40 | 16.6:1 |
| 20 | 30 | No TCEP |
| 20 | 30 | 1:2 |
| 20 | 30 | 1:1 |
| 20 | 30 | 1.5:1 |
| 20 | 30 | 2:1 |
| 20 | 30 | 16.6:1 |

D. ELISA to Assess Vaccine

Figure 4:
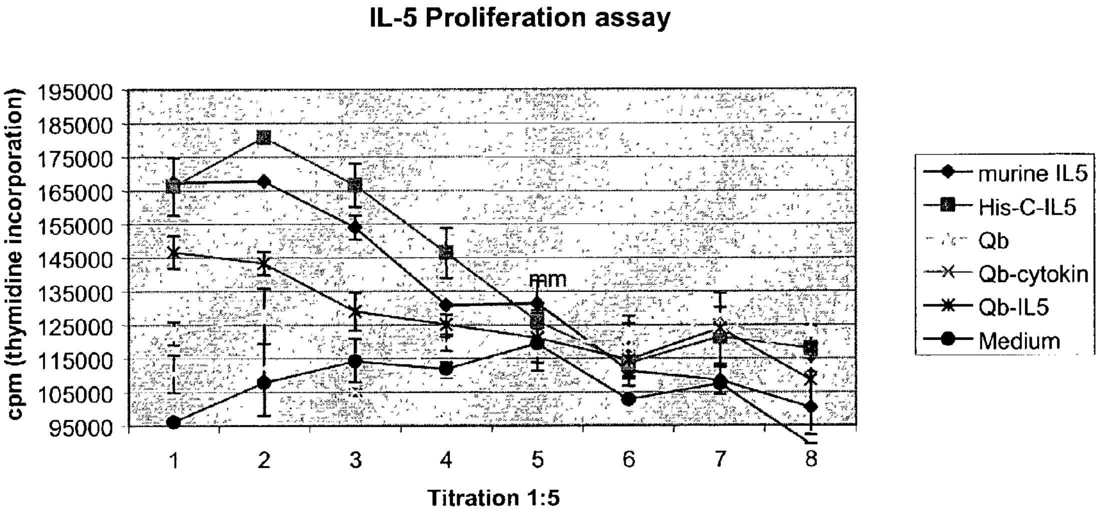
FIG. 4. Effect of His-C-IL-5 on the Proliferation of BCL1 cells. BCL1 cells were incubated with $^3$H-Thymidine in the presence of the following: Murine IL-5 (30 ng/ml) His-C-IL5, (30 ng/ml); Qβ (200 ng/ml); Qβ-chemically crosslinked with an unrelated cytokine (200 ng/ml) or Qβ-His-C-IL5 (105 ng/ml). Undiluted starting concentrations are indicated in parentheses and five-fold serial dilutions were made from the indicated starting concentrations. The incorporation of $^3$H-Thymidine was determined by liquid scintillation counting.

The coupling of mouse His-C-IL5 to Qβ, was assessed using a "quadruple" ELISA which is represented in FIG. 4. A 96 well ELISA plate was coated over-night with 100 ul of 1 mg/L goat anti-rabbit IgG per well. The plate was washed four times with PBS-Tween 0.1% (v/v) (PBST) then blocked for 2 h at 37° C. with 2% (w/v) Bovine serum albumin (BSA) in PBST. After washing with PBST polyclonal, anti-Qβ serum from rabbit (diluted 1:5000) was added and incubated for 1 h. The plate was washed twice with PBST and either varying amounts of Qβ-His-C-IL5 or control were added (FIG. 5) and incubated for 1 h at 25° C. Two different tertiary antibodies were used in the assay; rat anti-mouse IL5 (TRFK4) or rat anti-mouse IL5 (TRFK5), both are neutralizing monoclonal antibodies. All were used at concentrations of 1 μg/ml. The detecting antibodies were conjugated with Horse Radish Peroxidase (HRP) and specific for the particular Fc-fragment of the tertiary antibody. Binding in the sandwich assay was measured by a chemiluminescence (ECL) at 450 nm.

F. Assay of IL-5 Activity

The ability of the B cell lymphoma line BCL1 to proliferate in response to murine IL-5 was used to check the bioactivity of the re-folded recombinant His-C-IL-5 (Harriman G. R. (1991) Current Protocols in Immunology 6.5.1–6.5.5 John Wiley and Sons Inc). The proliferative activity of His-C-IL5 covalently coupled to Qβ was also assessed. Recombinant murine IL-5 (R&D systems, Minneapolis USA) was used as a control. The various forms of recombinat IL-5 were incubated in flat bottom 96 well plates with $2\times10^4$ BCL1 cells per well and incubated for 24 h at 37° C., 5% $CO_2$.1 μCi of $^3$H-Thymidine (Hartmann Analytic, Switzerland) was added to each well and the plates incubated for another 6 h at 37° C. 5% $CO_2$. The cells are harvested, washed and the incorporation of Thymidine determined by counting the β-emission with a liquid scintillation counter.

G. Immunization Protocol

In order to generate self reactive antibodies to mouse IL-5, four BalbC mice were injected subcutaneously a day 0 and day 14 with 25 μg of Qβ-His-C-IL5 vaccine in 200 μl of PBS. To serve as a negative control, five mice were immunized at day 0 and 14 with a simple mixture of 6.4 μg Qβ and 16 μg IL5 i.e. not covalently coupled (Qμ+His-C-IL-5) in PBS. Mice were bled prior to imunisation and at day 21 of the immunisation protocol. Sera were analysed by ELISA.

H. Sera Analysis

ELISA. Maxisorp ELISA plates (Nunc) were coated with 50 μl of purified His-C-IL-5 (3 μg/ml) for 14 h at 4° C. The plates were washed 3 times with PBS and blocked with 2% BSA in PBS for 2 h at 37° C. then washed twice with PBS. Five-fold dilutions of sera were added in 2% BSA, 0.1% FCS in PBS and incubated at room temperature for 1 hour. The plates were subsequently washed 3 times with PBS and incubated with anti-mouse IgG conjugated with HRP (dilution 1:1000) at room temperature for 1 h. The plates were again washed 3 times with PBS and 100 μl/well developing solution (0.066 M Na2HPO4, 0.035 M citric acid, 0.032% $H_2O_2$, 0.4% 1,2-Phenylenediamine dihydrochloride) were added. After 2 minutes of reaction at room temperature the ELISA was stopped with 50 μl per well 5% $H_2SO_4$. Absorbance was measured at 450 nm on a Spectramax spectrophotometer (Molecular Devices).

Western Blot Staining with Serum of Mice Immunized with Qβ-IL5. His-C-IL5, Qβ and controls were separted by SDS_PAGE and electroblotted onto a nitrocellulose membrane. The membrane was blocked for 1 h with 5% (w/v) milk powder in PBS, then incubated with 20 μl of day 21 serum from vaccinated mice in 10 ml 1% (w/v) milk powder in PBS. The membrane was washed with PBS for 15 minutes and then incubated for 1 h with 10 ml 1% (w/v) milk powder in PBS containing anti-mouse IgG antibody conjugated with horse raddish peroxidase (HRP) at a dilution of 1:1000. The membrane was washed for 15 minutes in PBS and developed with ECL (Amersham Pharmacia, Sweden) and exposed to Photographic film.

I. Eosinophilia Model

An experimental asthma model of allergic airway inflammation was used to assess the effects of vaccination on eosinophilia. Balb/c mice (4 per group) were immunised with either Qβ-His-C-IL-5 as described above. At day 23 of the vaccination program mice were injected intraperitonealy with 50 μg Ovalbumin (OVA) in Alumn (Alu-Gel-S) A third group of 4 mice which received no immunisation, were also injected. After 10 days (i.e. day 33) the the mice received 100 μg OVA in PBS administered intranasally each day for 4 days. 24 hours after the last challenge the mice were sacrified and the lungs washed with PBS. The cells contained in the broncho alveolar lavage (BAL) were stained with Maigrünwald-Giemsa and counted (Trifilieff A, et al. Clin Exp Allergy. 2001 June; 31(6):934–42.

Results and Discussion

Expression. Expression of the construct pMODC6-IL5 in BL21-DE2 cells was analysed by SDS-PAGE (FIG. 1). The Coomassie Blue stained gel demonstrated the IPTG-induced expression of a 17 kDa protein corresponding to the mass of IL-5. As control, BL21-DE2 cells containing pMODC6-IL5 were grown in the absence of IPTG and extracts prepared from the insoluble cell fraction as described above. As expected there was no induction of a 17 kDa under these conditions. His-C-IL5 was localized in the insoluble inclusion body fraction.

Figure 2:
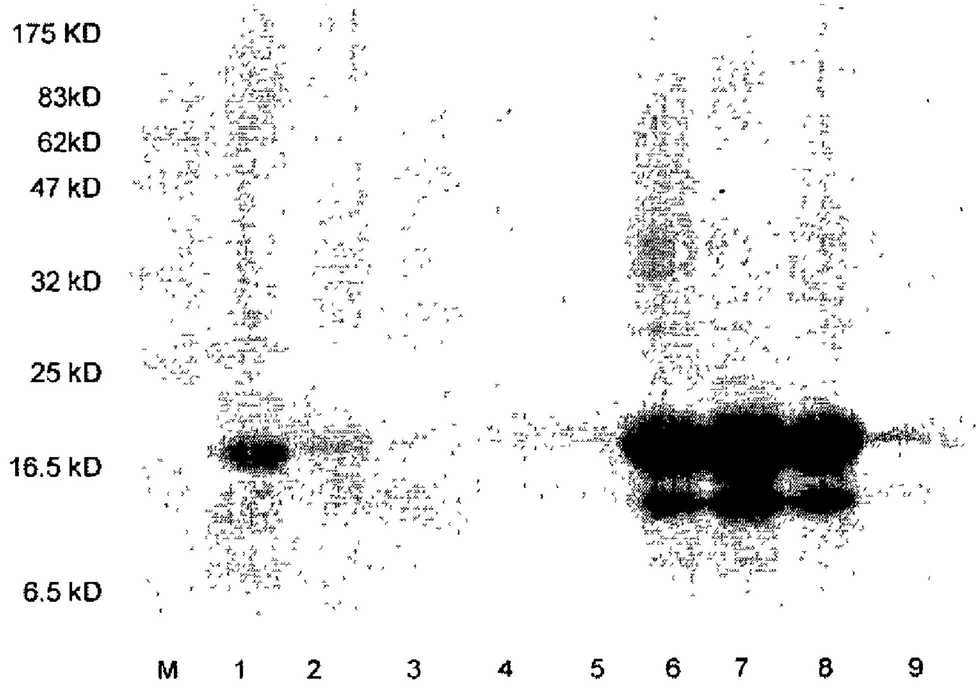
FIG. 2. SDS-PAGE analysis of the purification of His-C-IL-5 with Ni-NTA. Samples from various stages of the purification were applied to a 16% SDS-PAGE and run under reducing conditions. Proteins were stained with Coomassie blue. M, Marker; 1: Solubilised inclusion bodies; 2: Flow through (unbound material); 3: Wash 1 pH 6.5; 4: Wash 2 pH 6.5; 5: Wash 3 pH 5.9; 6–8: Eluate pH 4.5; 9: pure recombinant mouse IL-5.

Extraction Purification and Refolding. Insoluble His-C-IL5 was extracted from detergent washed inclusion bodies with 6M guanidine hydrochloride. The solubilised protein was purified by metal chelate affinity chromatography and analysed by SDS-PAGE (FIG. 2). Recombinant His-C-IL5 was found to be highly enriched by this procedure. The denatured protein was subjected to a refolding procedure in urea as described above and further purified by anion exchange chromatography. These steps yielded soluble, highly pure His-C-IL5 as judged by SDS-PAGE (FIG. 5, lane 1) with a recovery of 23% and yield of 6.9 mg.

Figure 3:
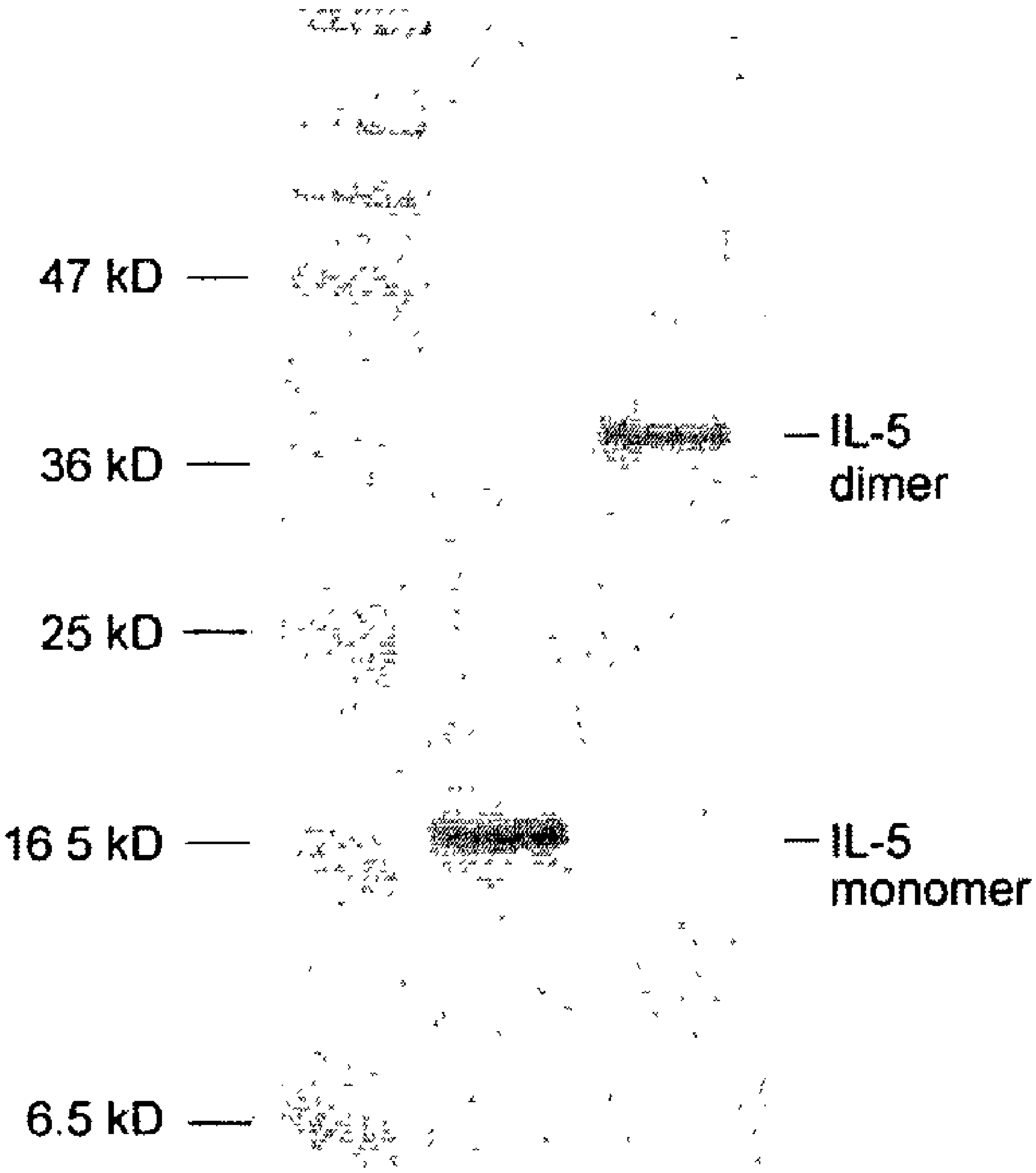
FIG. 3. SDS-PAGE showing purification of recombinant mouse-His-C-IL5. Five μg aliquots of purified mouse-His-C-IL5 were separated on a 16% SDS polyacrylamide gel either in the presence ($2^{nd}$ lane from left ) or absence ($3^{rd}$ Lane from left) of dithiothreitol. The gel was stained for protein with Coomassie Blue R-250. Lane M contains a size marker (NEB, Broad range, pre-stained marker).

Since biologically active native IL-5 is a disulfide-linked homodimer, the ability of purified recombinant His-C-IL5 to form dimmers was assessed by SDS-PAGE performed under non-reducing conditions (FIG. 3). As judged by the molecular mass of 37 kDa, His-C-IL5 was demonstrated be dimeric in nature indicating conservation of the native quarternary structure.

The biological activity of recombinant His-C-IL5 was assessed by determining its ability to stimulate proliferation of a murine B cell line (FIG. 4). BCL1 cells cultured in the presence of His-C-IL5 were shown to have enhanced proliferative rates when compared to culture medium alone or other proteins. Furthermore the enhanced proliferation was similar to that observed for a commercially obtained murine IL-5. The ability of His-C-IL5 to stimulate B cell proliferation, presumably by interacting with it's cognate receptor, and to adopt a dimeric structure both indicate the recombinant protein has adopted native conformation.

Figure 5:
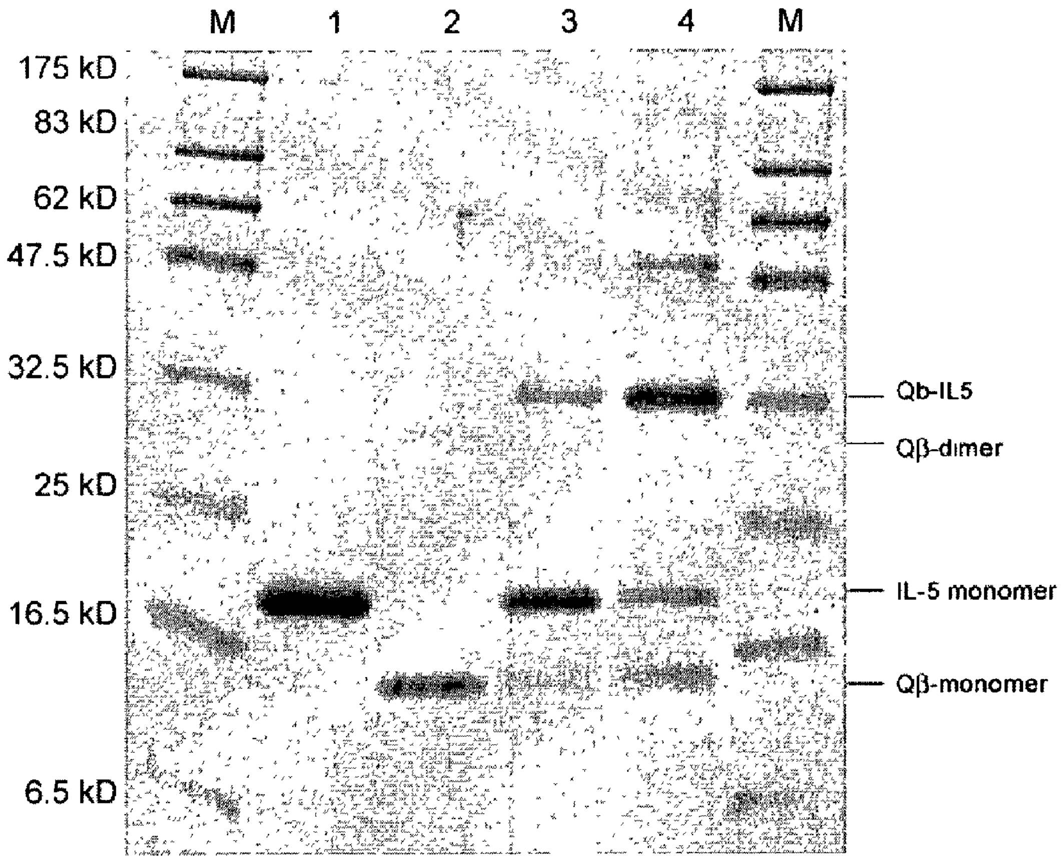
FIG. 5. Analysis of the coupling reaction by Coomassie blue stained SDS-PAGE. Lane M: pre-stained molecular weight marker Lane 1, Purified His-C-IL-5, Lane 2, Qβ after derivitisation with the chemical cross-linker SMPH. Lane 3, Coupling reaction, Lane 4, Coupling reaction after dialysis. The identity of the different molecular species in the coupling reaction is identified on the right of the figure.
Figure 6:
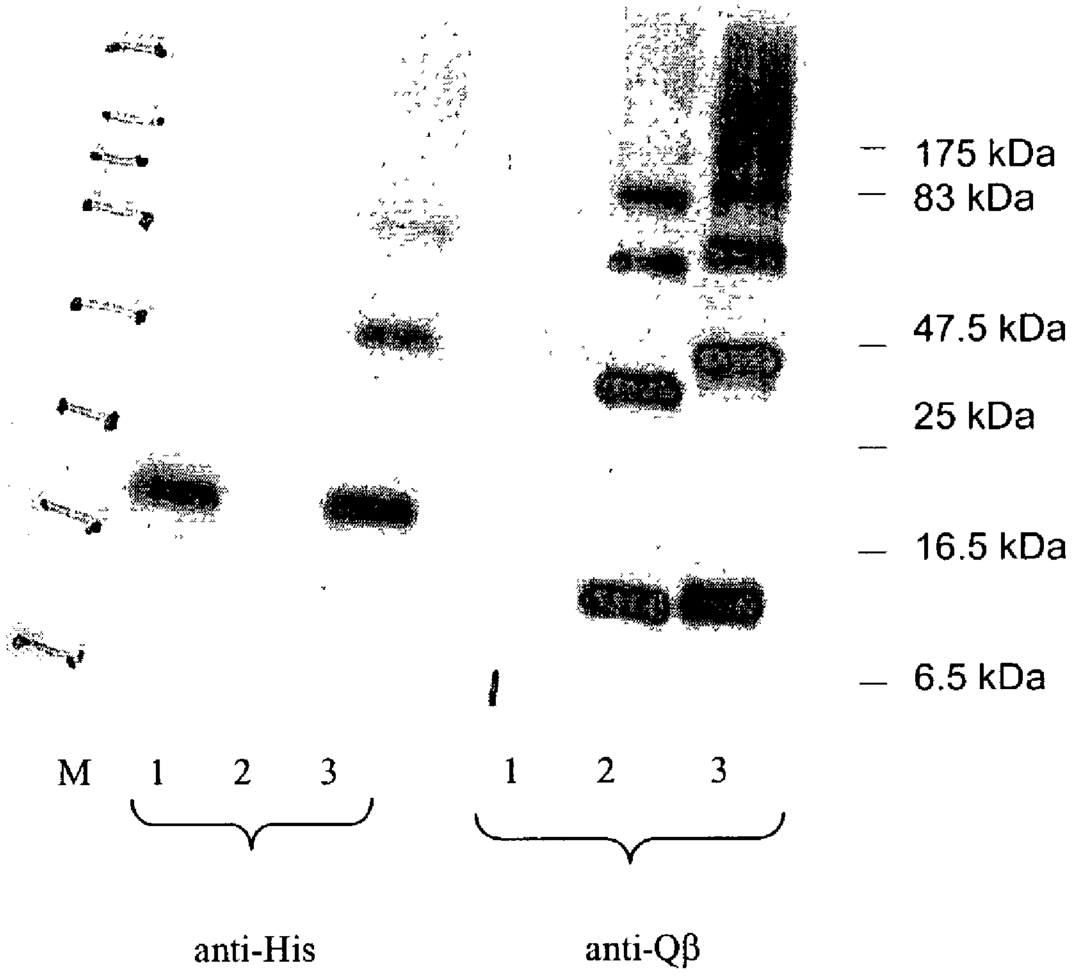
FIG. 6. Analysis of the coupling reaction by Western-blot. Lane M: Molecular weight marker; Lane 1, Purified His-C-IL-5; Lane 2, Qβ after derivitisation with the chemical cross-linker SMPH. Lane 3, Coupling reaction. The primary antibody for detecting His-C-IL5 was a rat anti-His antibody subsequently incubated with an anti-Rat antibody conjugated to HRP. Qβ was detected by staining with rabbit polyclonal antiserum against Qβ followed by an HRP-conjugated anti-rabbit antibody. Identical blots were stained as indicated.

Vaccine Production and Analytics. The covalent chemical coupling of His-C-IL5 to the virus-like particle Qβ was assessed by SDS-PAGE and Western blot analyses. Coomassie blue stained gels of the coupling reaction demonstrated the appearance of bands with molecular weights corresponding to those predicted for His-C-IL5 covalently linked to Qβ (FIG. 5). Moreover, Western analyses showed co-localisation of these bands when stained with either anti-His or anti-Qβ antibodies (FIG. 6). The coupling efficiency [i.e. mol Qβ-IL5/mol Qβ monomer (total)] was estimated, by densitometric analysis of the Coomassie blue stained SDS-PAGE, to be of 40.6%.

The ability of His-C-IL-5 covalently cross-linked to Qβ to stimulate B cell proliferation was assessed as described previously. FIG. 5 shows that Qβ-His-C-IL5 was able to cause enhanced proliferation compared to Qβ coupled to an unrelated cytokine.

Figure 7A:
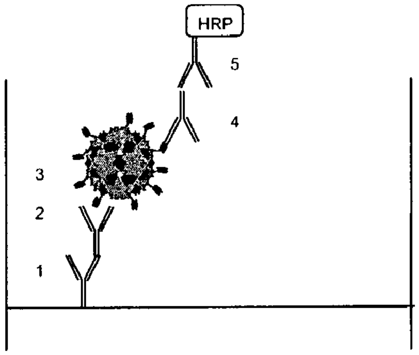
FIG. 7: Quadruple ELISA. A. Schematic representation of the capture ELISA. The various components of the assay are 1, goat anti-rabbit IgG; 2, rabbit anti-Qβ polyclonal antisera; 3, either Qβ-His-C-IL5, Qβ or PBS; 4, anti-IL5 monoclonal Ab, TRFK 4 or 5; 5, Anti mouse IgG-HRP. B. Results of the quadruple ELISA. The ability of neutralizing monoclonal antibodies to interact with His-C-IL5 covalently coupled to the ordered antigen array was determined by ELISA.
Figure 7B:
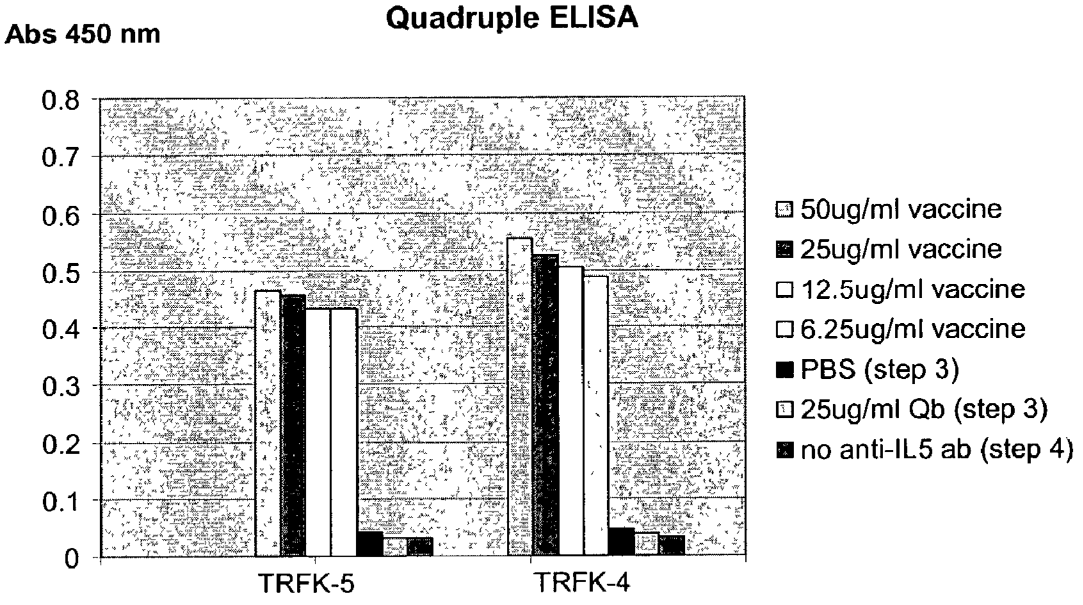

The conformation of His-C-IL5 coupled to Qβ was further analysed using a quadruple ELISA. (FIG. 7*a*). FIG. 7*b*, demonstrates that His-C-IL5 is recognised by the IL-5 neutralising monoclonal antibodies TRFK 4 and TRFK 5. When the reaction was performed with Qβ rather than Qβ-His-C-IL-5 no signal was detected. The monoclonal antibody TRFK4 recognises a neutralising epitope within IL-5. The ability of the IL-5 specific monoclonal antibodies to recognise covalently linked His-C-IL-5 indicates the neutralising epitopes are conserved within the vaccine preparation.

Figure 8:
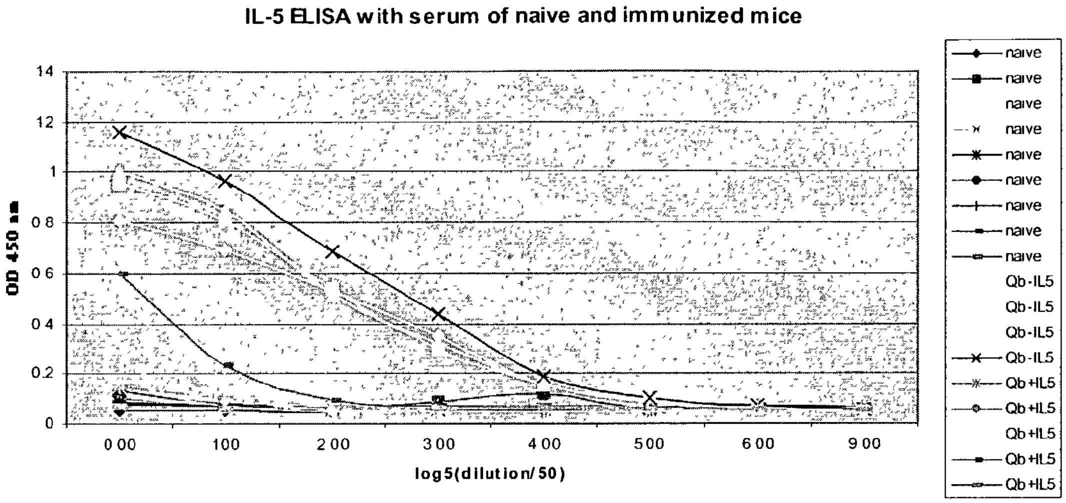
FIG. 8. ELISA of sera against IL-5. ELISA plates were coated with His-C-IL5 and incubated with either pre-immune or day 21 collected from mice vaccinated with Qβ-His-C-IL5 (4 mice) or Qβ mixed with His-C-IL-5 (5 mice). The starting dilution of the sera was 1:50 and five-fold dilutions were made. Binding of IL-5 specific antibodies was detected with anti-mouse IgG conjugated to HRP and the chromogenic substrate.
Figure 9:
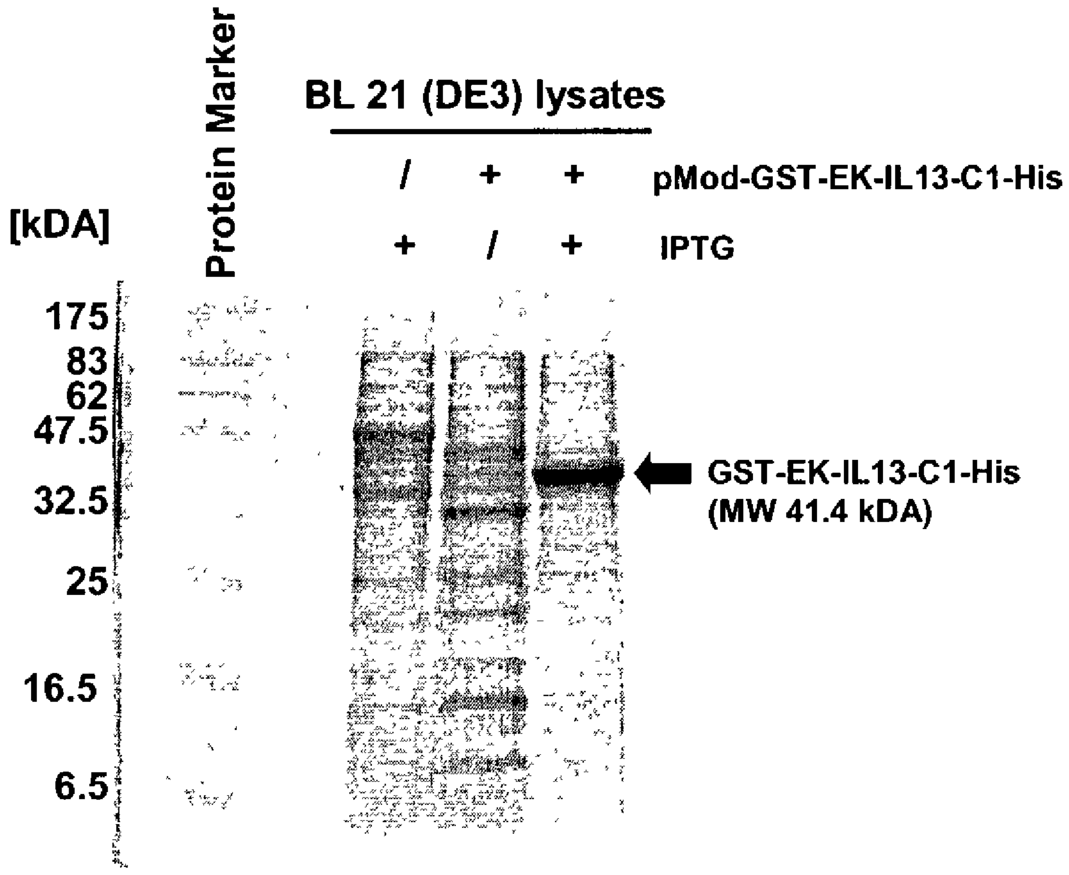
FIG. 9. Induction of recombinant GST-EK-IL13-C1-His expression. in BL21. Coomassie blue stain of a 16% SDS-PAGE. Load corresponds to 0.1 $OD_{600}$ of the indicated bacterial lysates. Expression of the IL-13-fusion protein was induced with 0.75 mM IPTG and samples were analysed after 4 hrs by SDS-PAGE. Note, there is strong expression of the IL-13-fusion protein in bacteria that had been transformed with the corresponding plasmid (pMod-GST-EK-IL13-C1-His) and induced with IPTG (see arrow).

Analysis of Sera. Preimmune sera and day 21 sera from mice vaccinated with Qβ-His-C-IL5 were collected and analysed by ELISA (FIG. 8). The result shows that immunological tolerance towards the self-antigen IL-5 was overcome in the absence of adjuvant and after only in 4/4 vaccinated mice. Half maximal titres were calculated to be in the range of 1:2000 to 1:6000. In the control group that received Qβ mixed with His-C-IL5 no significant anti-IL-5 titres were detected. However, 3 of the 5 mice produced a low antibody titre <1:50. Immune sera from mice vaccinated with Qβ-His-C-IL5 were further tested by Western blot analysis. In all cases the immune sera specifically recognized murine IL-5.

Vaccine Efficacy in an Animal Model of Experimental Asthma. The effect of vaccination with Qβ-His-C-IL-5 on eosinophilia was assessed in a murine model of allergic airway inflammation that mimics key pathologicical events in asthma. This experiment tested the ability of the anti-IL5 antibodies generated by vaccination with Qβ-His-C-IL-5 to down-regulate the in vivo action of endogenous IL-5. In the control experiment mice were vaccinated with PBS before OVA sensitisation and challenge. In this case high numbers of eosinophils were counted in the BAL. The mean number of eosinophils/200 cells counted was 96±14 S.D. In contrast mean value of the BAL eosinophils from the four mice vaccinated with Qβ-His-C-IL-5 was 27.5+11 S.D./200 cells counted. This is a reduction of 71.4% and is evidence the autoantibodies generated by immunisation with His-C-IL-5 presented as a highly ordered immune array recognise the endogenous target molecule and thereby down regulate eosinophilia in an experimental model of asthma.

Example 8

Molecular Cloning, Expression, Refolding and Purification of Mouse mIL-13 with a C-Terminal Amino Acid Linker Containing a Cysteine Residue for Coupling to VLPs and Pili. Coupling of Mouse Interleukin 13 to VLPs and Pili A. Cloning IL-13 for Prokaryotic Expression.

The DNA for cloning IL-13 was isolated by RT-PCR from in vitro activated splenocytes, wich were obtained as following: CD4+ T cells were isolated from mouse spleen cells and incubated 3 days in IMDM (+5% FCS+10 ng/ml IL4) in 6 well plates previously coated with anti-CD3 and anti-CD28 antibodies. RNA from these cells was used to amplify cDNA encoding IL13 by one-step RT-PCR (Qiagen one-step PCR kit). Primer XhoIL13-R was used for reverse transcription of the RNA and the primers NheIL13-F (SEQ ID NO:338) and XhoIL13-R (SEQ ID NO:339) were used for the PCR amplification of the IL13 cDNA. Amplified IL13 cDNA was ligated in a pMOD vector using the NheI/XhoI restriction sites (giving the vector pMODB1-IL13). The identity of the resulting cDNA sequence was determined by nucleotide sequencing.

Using the same primer, NheIL13-F (SEQ ID NO:338) and XhoIL13-R (SEQ ID NO:339), the IL-13 cDNA was amplified from the pModB1-IL13 plasmid and ligated into the pMODGST-EK-C1 vector resulting in the plasmid pModGST-EK-IL13-C1. The cDNA sequence of this plasmid was determined by nucleotide sequencing. A cDNA comprising the coding sequence for the glutathione S transferase fused to an enterokinase cleavage site followed by the IL-13 sequence with the C-terminal linker 1 was amplfied by PCR with the primer GST-BamHI ss and C1-BsmBI/XhoI using the plasmid pModGST-EK-IL13-C1 as template. This cDNA was digested with restriction enzymes BamHI and BsmBI and ligated into the pModB-N1 vector using the BamHI/XhoI restriction site. The resulting plasmid pModGST-EK-IL13-C1-His encodes a fusion protein consisting of glutathione S transferase, an enterokinase cleavage site, IL-13, a cysteine containing linker and a polyhistidin-tag (GST-EK-IL13-C1-His). The identity of the cDNA encoding this fusion protein was confirmed by nucleotide sequencing.

Sequence of Oligonucleotides:

```
Sequence of oligonucleotides:
GST-BamHI ss:
                                   (SEQ ID NO:379)
5'-CGCCGGATCCTATACTAGGTTATTGG-3'

C1-BsmBI/XhoI as:
                                   (SEQ ID NO:380)
5'-GGGCGCGTCTCCTCGAGACCGCAACCACCACCA-3'
```

Expression of IL-13 in *E. coli.*

The plasmid pMod-GST-EK-IL13-C1-His was transformed into the bacterial host strain BL 21 (DE3). After 90 minutes of recovery in LB-Media containing 2% Glucose (preculture), 250 ml MOPS-buffered SB-Media containing 0.2% Glucose and 100 μg Ampicillin/l was inoculated with 250 μl preculture and incubated on a shaking platform at 37° C. over night. The next morning the seed culture was diluted with 750 ml prewarmed MOPS-buffered SB-Media containing 100 μg Ampicillin/l and incubated on a shaking platform with 125 rpm at 37° C. for another 90 min until an $OD_{600}$ of 4.5 was reached. The 1000 ml culture was diluted with 500 ml MOPS-buffered SB-Media containing 100 μg Ampicillin/l and shifted to a 24° C. incubator where it was incubated with shaking platform for 30 min until an $OD_{600}$ of 3.75 was reached. Expression of the GST-EK-IL13-C1-His fusion protein was induced by adding 0.75 mM IPTG. After 4 hrs bacteria were harvested by centrifugation and disrupted by sonication.

Figure 10:
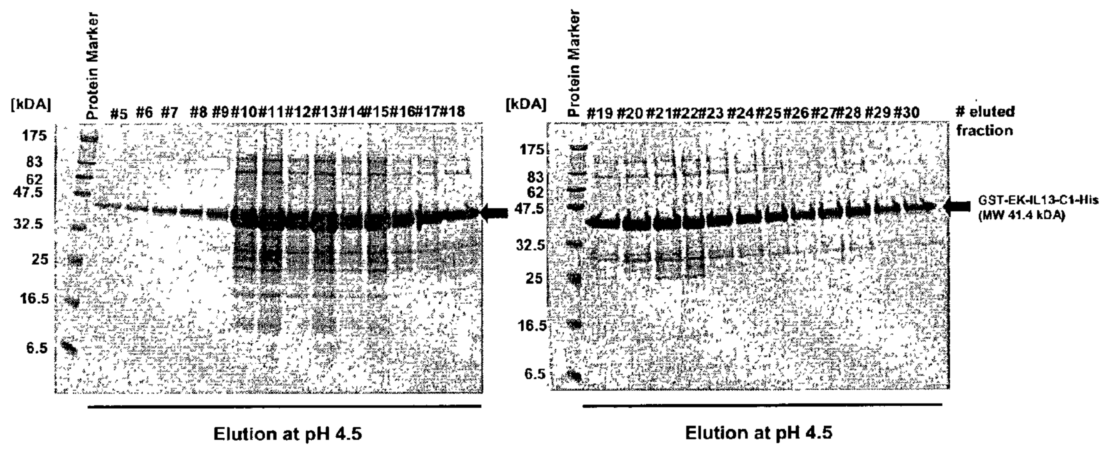
FIG. 10. Purification of GST-EK-IL13-C1-His under denaturating. Coomassie blue stain of two 16% SDS-PAGEs. Load corresponds to 5 μl of the indicated fraction. The IL-13-fusion protein was obtained from inclusion bodies, solubilized in a Guandine-HCl denaturing buffer and loaded onto a $Ni^{2+}$-agarose column, equilibrated with the same buffer. Bound proteins were eluted in two steps with different pH. The figure shows analysis of TCA-precipitated alliqouts of the indicated fractions (#5–#30) eluted with the second buffer at pH 4.5. Note, due to the C-terminal His-tag, the IL-13 fusion protein was efficiently bound to the $Ni^{2+}$-agarose column and eluted by lowering the pH.
Figure 11:
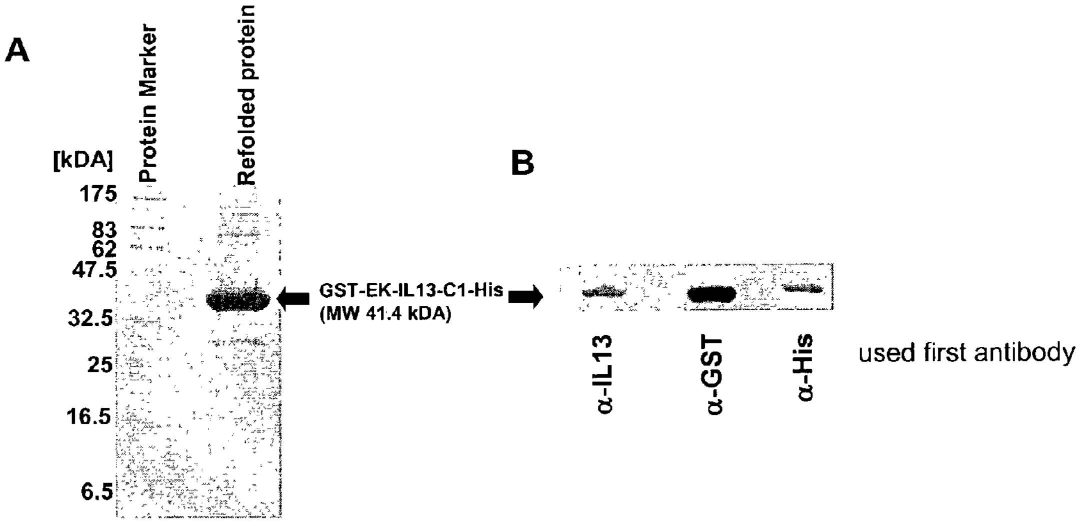
FIG. 11. Analysis of soluble IL-13 fusion protein after refolding. The GST-EK-IL13-C1-His fusion protein was refolded as described in section 18D. After the refolding reaction was finished an alliqout of the protein solution was analysed by SDS-PAGE followed by Coomassie-stain (A) or by Westernblot (B). The indicated primary antibodies were purchased from R&D Systems (α-IL13, AF-413-NA), by Qiagen (α-PentaHis, 34660) and Amersham Biosciences (α-GST, 24-4577), respectively. Antibodies were used in concentrations according to the manufacturer's manuals.

C. Purification of IL-13 from Inclusion Bodies under Denaturating Conditions:

After lysis the inclusion bodies were sedimented by low speed centrifugation (10 000 g, 60 min., at 4° C.). The supernatant was collected and centrifuged again under the same conditions. Pellets were kept as crude inclusion bodies fraction. The inclusion bodies were washed 4 times with the following wash-buffer: 50 mM TrisHCl, pH 7.6, 250 mM NaCl, 5 mM $MgCl_2$, 2 M Urea, 2% Triton X-100 and 10 U Benzonase/ml. Inclusion bodies were collected by centrifugation and resuspended in denaturating buffer containing 100 mM $NaH_2PO_4$, 10 mM TrisHCl and 6 M Guanidine-HC pH 8.0. Inclusion bodies were sonicated in the presence of 10 U Benzonase/ml and incubated for 2 hrs on a rotating wheel at room temperature. After centrifugation the supernatant were retained and the pellets resuspended again in denaturing buffer and treated as described above. Supernatants were pooled and loaded onto $Ni^{2+}$-agarose column equilibrated with the denaturing buffer. Bound protein was eluted in two steps with denaturing buffer pH 6.3 and pH 4.5. Aliqouts of the fractions were analysed by Amidoblack staining and after TCA-precipitation by SDS-PAGE (FIG. 10).

D. Refolding GST-EK-IL13-C1-His

β-Mercaptoethanol was added to the eluted protein to a final concentration of 10 mM and dialysed overnight against 2 liters of buffer containing 8.0 M Urea, 100 mM $NaH_2PO_4$, 10 mM TrisHCl, 10 mM β-Mercaptoethanol (pH 8.0) at 4° C. using a 10 kDa cut-off membrane. Following dialysis, the protein concentration was determined and the concentration of the protein diluted with dialysis buffer to 0.2 mg/ml. The solution was dialysed for 24 hrs at 4° C. against refolding-buffer 1 comprising 2.0 M Urea, 50 mM $NaH_2PO_4$, 5 mM reduced Glutathione, 0.5 mM oxidized Glutathione, 0.5 M Arginine, 10% (v/v) glycerol (pH 8.5). The next day the refolding buffer 1 was exchanged against refolding buffer 2 containing 50 mM $NaH_2PO_4$, 2.5 mM reduced Glutathione, 0.25 mM oxidized Glutathione, 0.25 M Arginine, 10% (v/v) glycerol (pH 8.5) and dialysed at 4° C. for another 24 hrs. Finally the solution was dialysed at 4° C. against refolding buffer 3 comprising 20 mM ethanolamine, 150 mM NaCl and 10% (v/v) glycerol (pH 9.0). Refolding buffer 3 was exchanged once after 2 hrs and dialysis proceeded for another 14 hrs. The dialysate was centrifuged at 4° C. and 20 000 g for 15 min. The supernatant was reatined and the protein concentrated by centrifugation in "biomax centrifugal filter devices" with a 5 kDa molecular weight cut-off (Millipore) to a final protein concentration of 2 mg/ml. Protein was analysed by SDS-PAGE and Western blot with monospecific antibodies against GST, mouse IL-13 and the His-tag, respectively.

E. Cleavage of GST-EK-IL13-C1-His Fusion Protein with Enterokinase:

The GST-EK-IL13-C1-His fusion protein is incubated with 1× enterokinase buffer (50 mM TrisHCl pH 8.0, 10 mM $CaCl_2$ and 1% Tween-20) and 1 U Enterokinase (Invitrogene) per 12.5 ug fusionprotein for 24 hrs at 4° C.

F. Purification of IL13-C1-His:

After the enterokinase treatment, cleaved GST is serparated by a combination of ion-exchange chromatography, gelfiltration and affinity chromatography. The IL-13-C1-His protein is concentrated to a final proteinconcentration of 2 mg/ml.

G. Preparing the IL-13-C1-His Protein for the Coupling Reaction:

In order to determine optimal conditions for coupling the IL-13-C1-His protein is treated under mild reducing conditions with various concentrations (0 μM to 500 μM) of a reducing reagent (DTT or TCEP). The reduced IL-13-C1-His protein is tested for efficient coupling to derivatized VLPs and Pilis.

H. Coupling of IL-13-C1-His to Qβ Capsids:

A solution of 120 μM Qβ capsid in 20 mM Hepes, 150 mM NaCi pH 7.2 is reacted for 30 minutes with a 25 fold molar excess of a heterobifunctional crosslinker like SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed, derivatized Qβ reaction mixture is then mixed with the prepared IL-13-C1-His protein. In the coupling reaction the IL-13-C1-His protein is in twofold molar excess over the derivatized Qβ capsid. The coupling reaction proceeds for four hours at 25° C. on a rocking shaker. Coupling products are analysed by SDS-PAGE and in addition by Westernblot.

Coupling of IL-13-C 1-His to fr Capsid Protein

A solution of 120 μM fr capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed fr capsid protein reaction mixture is then reacted with with the prepared IL-13-C1-His protein. In the coupling reaction the IL-13-C1-His protein is in twofold molar excess over the derivatized fr capsid. The coupling reaction proceeds for four hours at 25° C. on a rocking shaker. Coupling products are analysed by SDS-PAGE and in addition by Westernblot.

Coupling IL-13-C1-His to HBcAg-Lys-2cys-Mut

A solution of 120 μM HBcAg-Lys-2cys-Mut capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed HBcAg-Lys-2cys-Mut reaction mixture is then reacted with the prepared IL-13-C1-His protein. In the coupling reaction the IL-13-C1-His protein is in twofold molar excess over the derivatized HBcAg-Lys-2cys-Mut capsid. The coupling reaction proceeds for four hours at 25°

C. on a rocking shaker. Coupling products are analysed by SDS-PAGE and in addition by Westernblot.

Coupling of IL-13-C1-His Protein to Pili

A solution of 125 μM Type-1 pili of *E. coli* in 20 mM Hepes, pH 7.4, is reacted for 60 minutes with a 50-fold molar excess of cross-linker SMPH, diluted from a stock solution in DMSO, at RT on a rocking shaker. The reaction mixture is desalted on a PD-10 column (Amersham-Pharmacia Biotech). The protein-containing fractions eluating from the column are pooled, and the desalted derivatized pili protein is reacted with the prepared IL-13-C1-His protein. In the coupling reaction the IL-13-C1-His protein is in twofold molar excess over the derivatized Type-1 pili of *E. coli*. The coupling reaction proceeds for four hours at 25° C. on a rocking shaker. Coupling products are analysed by SDS-PAGE and in addition by Westernblot.

Immunization of Mice with IL-13-C1-His Coupled to Qβ Capsid Protein

Female Balb/c mice are vaccinated with IL-13-C1-His coupled to a VLP without the addition of adjuvants. 25 μg of total protein of each sample is diluted in PBS to 200 ul and injected subcutaneously (100 μl on two ventral sides) on day 0 and day 14. Mice are bleed retroorbitally on day 31 and their serum is analyzed using a IL-13-specific ELISA.

Example 9

Cloning, Expression, Purification and Coupling of Eotaxin with a cys-Containing Amino Acide Linker Sequence Mouse eotaxin was recombinantly expressed with an amino acid linker C1 fused at its C-terminus. This linker contained one cysteine for coupling to VLP.

Construction of pmEo-C1 and pmHisEo-C1

The MCS of pET22b(+) (Novagen, Inc.) was changed to GTTTAACTTTAAGAAGGAGATATA-CATATGGATCCGGCTAGCGCTC-GAGGGTTTAAACGGCGGCCGCATGCACC (SEQ ID NO: 381) by replacing the original sequence from the NdeI site to XhoI site with annealed oligos primerMCS-1F and primerMCS-1R (annealing in 15 mM TrisHCl pH 8 buffer). The resulting plasmid was termed pMod00, which had NdeI, BamHI, NheI, XhoI, PmeI and NotI restriction sites in its MCS. The annealed pair of oligos Bamhis6-EK-Nhe-F and Bamhis6-EKNhe-R and the annealed pair of oligo1F-C-glycine-linker and oligo1R-C-glycine-linker were together ligated into BamHI-NotI digested pMod00 plasmid to get pModEC1, which had an N terminal hexahistidine tag, an enterokinase cleavage site and a C-terminal amino acid glycine linker containing one cysteine residue. Mouse eotaxin was amplified from an ATCC clone (ATCC number 3148394) by PCR using the following primers: mEotaxin-F, Nhe-mEotaxin-F, and mEotaxin-Xho-R. mEotaxin-F had an internal NdeI site, Nhe-mEotaxin-F had an internal NheI site and mEotaxin-Xho-R had an internal XhoI site. The PCR product from primer pair mEotaxin-F and mEotaxin-Xho-R was digested with NdeI and XhoI and ligated into pModEC1 digested with the same enzymes. The resulting plasmid was named pmEo-C1, which encodes a fusing protein consisting of eotaxin and a cysteine containing linker at its C-terminus. The PCR product from primer pair Nhe-mEotaxin-F and mEotaxin-Xho-R was digested with NheI and XhoI and ligated into pModEC1 digested with the same enzymes. The resulting plasmid was named pHismEo-C1, which encodes a fusing protein consisting of an N-terminal His-tag followed by an enterokinase cleavage site, eotaxin and a cysteine linker.

For the PCR reaction, 15 pmol of each oligo and 1 ng of the template DNA was used in the 50 μl reaction mixture (2 units of PFX polymerase, 0.3 mM dNTPs and 2 mM $MgSO_4$). The temperature cycles were as following: 94° C. for 2 minutes, followed by 30 cycles of 94° C. (30 seconds), 60° C. (30 seconds), 68° C. (30 seconds) and followed by 68° C. for 2 minutes. All other steps were performed by standard molecular biology protocols.

Sequence of the oligonucleotides:

```
mEotaxin-F:
                                        (SEq ID NO:382)
5'GGAATTCCATATGCACCCAGGCTCCATCCCAAC3'

Nhe-mEotaxin-F:
                                        (SEQ ID NO:383)
5'CCTAGCTAGCGCACCCAGGCTCCATCCCAAC3'

mEotaxin-Xho-R:
                                        (SEQ ID NO:384)
5'CCCGCTCGAGTGGTTTTGGAGTTTGGAGTT3'
```

Expression of pmEo-C1

Figure 12:
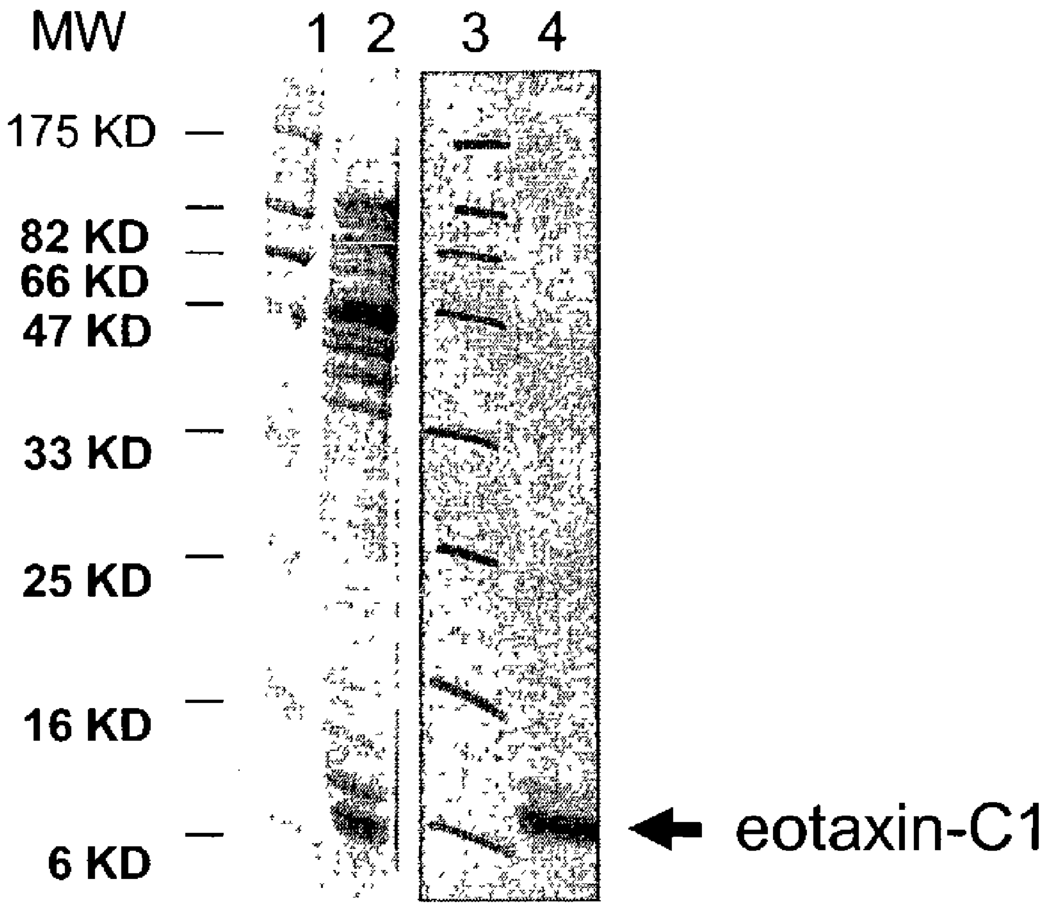
FIG. 12. Expression of mouse eotaxin-C1. The supernatants from cell lysates of BL21/DE3 cells transformed with pmEo-C1, after 9 hours of induction with 1 mM of IPTG were run on 16% PAGE gel, blotted to nitrocellulose membrane and reacted with gaot anti-mouse eotaxin antiboy (R & D system). Lane 1: Pre-stained protein marker (New England Biolabs). Lane 2: the supernatant of the cell lysates of BL21/DE3 cells transformed with pmEo-C1, after 9 hours of induction with 1 mM of IPTG. Lane 3: Pre-stained protein marker (New England Biolabs). Lane 4. Western blot of the same lysates as lane 2 probed with anti-mouse eotaxin antibody.

Competent *E. coli* BL21 (DE3) cells were transformed with plasmid pmEo-C 1. Single colonies from ampicillin (Amp)-containing agar plates were expanded in liquid culture (SB with 150 mM MOPS, pH 7.0, 100 ug/ml Amp, 0.5% glucose) and incubated at 30° C. with 220 rpm shaking overnight. 1 l of SB (150 mM MOPS, pH 7.0, 100 ug/ml Amp) was then inoculated 1:50 v/v with the overnight culture and grown to OD600=1.7 at 30° C. with 150 rpm shaking. Expression was induced with 1 mM IPTG. Cells were harvested after 9 hours' induction by centrifuging at 6000 rpm for 5 minutes. Cell pellet was suspended in lysis buffer (10 mM $Na_2HPO_4$, 30 mM NaCl, 10 mM EDTA and 0.25% Tween-20) with 0.8 mg/ml lysozyme, sonicated and treated with benzonase. After centrifugation with 48000 RCF for 20 minutes, the supernatant was resolved on 16% PAGE gel and the mouse eotaxin expression was confirmed by anti-mouse eotaxin antibody (R & D system) on Western blot (FIG. 12). This clearly demonstrated the expression of eotaxin-C1 which ran at the expected molecular weight of 8.8 KD.

The protein sequences of the mouse eotaxin-C1 and mouse His-eotaxin-C1 were translated from the cDNA sequences.

```
Mouse eotaxin-C1:
MHPGSIPTSCCFIMTSKKIPNTLLKSYKRITNNRCTLKAIVFKTRLGKEI
CADPKKKWVQDATKHLDQKLQTPKPLRGGGGGCG

Mouse His-eotaxin-C1:
MDPHHHHHHGSGDDDDKALAHPGSIPTSCCFIMTSKKIPNTLLKSYKR
ITNNRCTLKAIVFKTRLGKEICADPKKKWVQDATKHLDQKLQTPKPLR
GGGGGCG
```

Coupling of Mouse Eotaxin-C1 to Qβ Capsid Protein

A solution of 1.48 ml of 6 mg/ml Qβ capsid protein in 20 mM Hepes, 150 mM NaCl pH 7.2 is reacted for 60 minutes with 14.8 μl of a SMPH (Pierce) (from a 100 mM stock solution dissolved in DMSO) at 25° C. The reaction solution is subsequently dialyzed twice for 3 hours against 2 l of 20 mM Hepes, 150 mM NaCl, pH 7.0 at 4° C. A solution of 1.3 ml of 3.6 mg/ml mouse eotaxin-C1 protein in 20 mM Hepes, 150 mM NaCl pH 7.2 is reacted for 1 hour with 9.6 μl of a TCEP (Pierce) (from a 36 mM stock solution dissolved in $H_2O$) at 25° C. 130 μl of the derivatized and dialyzed Qβ is then react with 129 μl of reduced eotaxin-C1 in 241 μl of 20 mM Hepes, 150 mM NaCl, pH 7.0 over night at 25° C. Western blot analyses with an anti-Qβ, and an anti eotaxin antibody demonstrate covalent coupling of eotaxin to Qβ.

B. Immunization of Mice with Mouse Eotaxin-C1 Coupled to Qβ Capsid Protein

Female Balb/c mice are vaccinated with mouse eotaxin-C1 coupled to Qβ capsid protein without the addition of adjuvants. 25 μg of total protein of each sample is diluted in PBS to 200 ul and injected subcutaneously (100 μl on two ventral sides) on day 0 and day 14. Mice are bled retroorbitally on day 31 and their serum is analyzed using an eotaxin-specific ELISA.

C. ELISA

ELISA plates are coated with mouse eotaxin-C1 at a concentration of 5 μg/ml. The plates are blocked and then incubated with serially diluted mouse sera. Bound antibodies are detected with enzymatically labeled anti-mouse IgG antibody. As a control, preimmune serum from the same mice are also tested.

Example 10

Cloning and Expression of Interleukin 5 (IL-5) with an N-Terminal Amino Acid Linker Containing a Cysteine Residue for Coupling to VLPs and Pili A. Cloning of IL-5 for Expression as Inclusion Bodies in *E. coli*

IL-5 was amplified from an ATCC clone (pmIL5-4G; ATCC number: 37562) by PCR using the following two primers: Spelinker3-F1 (SEQ ID NO:340) and Il5StopXho-R (SEQ ID NO:342). The product of this PCR was used as template for a second PCR with the primers SpeNlinker3-F2 (SEQ ID NO:341) and Il5StopXho-R. The insert was digested with SpeI and NotI. This insert was ligated into a pET vector derivative (pMODEC3-8 vector), previously digested with NheI and NotI (not dephosphorylated), and transformed into *E. coli* TG1 cells. The IL5 construct generated by cloning into pMODEC3-8 vector contains at its N-terminus a hexa-histidine tag, followed by an enterokinase site, an N-terminal gamma 3 amino acid linker containing a cysteine residue, flanked C-terminally by the sequence AS and N-terminally by the sequence ALV, and the mature form of the IL 5 gene. The protein released by cleavage with enterokinase is called "mouse C-IL-5-E" (SEQ ID NO:332). Plasmid DNA of resulting clone pMODC6-IL5.2 (also called pMODC6-IL5), whose sequence had been confirmed by DNA sequencing, was transformed into *E. coli* strain BL21.

Clone pMODC6-IL5/BL21 was grown over night in 5 ml LB containing 1 mg/L Ampicillin. 2 ml of this culture were diluted in 100 ml terrific broth (TB) containing 1 mg/L Ampicillin. The culture was induced by adding 0.1 ml of a 1M solution of Ispropyl β-D-Thiogalactopyranoside (IPTG) when the culture reached an optical density OD600=0.7. 10 ml samples were taken every 2 h. The samples were centrifugated 10 min at 4000×g. The pellet was resuspended in 0.5 ml Lysis buffer containing 50 mM Tris-HCl, 2 mM EDTA, 0.1% triton X-100 (pH8). After having added 20 μl of Lysozyme (40 mg/ml) and having incubated the tube 30 min at 4° C., the cells were sonicated for 2 min. 100 μl of a 50 mM $MgCl_2$ solution and 1 ml of benzonase were added. The cells were then incubated 30 min at room temperature and centrifugated 15 min at 13000×g.

The supernatant was discarded and the pellet was boiled 5 min at 98° C. in 100 μl of SDS loading buffer. 10 μl of the samples in loading buffer were analyzed by SDS-PAGE under reducing conditions (FIG. 17A). The gel of FIG. 17A clearly demonstrates expression of the IL-5 construct. The samples loaded on the gel of FIG. 17A were the following:

Lane M: Marker (NEB, Broad range prestained marker). Lane 1: cell exctract of 1 ml culture before induction. Lane 2: cell extract of 1 ml culture 4 h after induction.

B. Cloning of IL-5 for Expression in Mammalian Cells (HEK-293T)

a) IL-5 Fused at its N-Terminus to an Amino Acid Linker Containing a Cysteine Residue and Fused at its C-Terminus to the Fc Fragment The template described under (A) (ATCC clone 37562) was used for the cloning of the following construct. The plasmid pMODB1-IL5 (a pET derivative) was digested with BamHI/XhoI to yield a small fragement encoding IL5 fused to an N terminal amino acid linker containing a cysteine. This fragment was ligated in the vector pCEP-SP-XA-Fc* (ΔXho) which had previously been digested with BamHI and XhoI. The ligation was electroporated into *E. coli* strain TG1 and plasmid DNA of resulting clone pCEP-SP-IL5-Fc.2, whose sequence had been confirmed by DNA sequencing, was used to transfect HEK-293T cells. The resulting IL-5 construct encoded by this plasmid had the amino acid sequence ADPGCGGGGGLA (1–12 of SEQ ID NO: 333) fused at the N-terminus of the IL-5 mature sequence. This sequence comprises the amino acid linker sequence GCGGGGG (4–10 of SEQ ID NO: 333) containing a cysteine and flanked by additional amino acids introduced during the cloning procedure. The IL-5 protein released by cleavage of the fusion protein with Factor-Xa is named hereinafter "mouse C-IL-5-F" (SEQ ID NO:333).

After transfection and selection on Puromycin the culture supernatant was analyzed by Western-Blot (FIG. 17 B) using an anti-His (mouse) and an anti-mouse IgG antibody conjugated to Horse raddish peroxidase. The anti-mouse IgG antibody conjugated to Horse raddish peroxidase also detects Fc-fusion proteins. Purification of the protein was performed by affinity chromatography on Protein-A resin. The result of FIG. 17B clearly demonstrates expression of the IL-5 construct.

The samples loaded on the Western-Blot of FIG. 17B were the following:

Lane 1: supernatant of HEK culture expressing IL5-Fc (20 μl). SDS-PAGE was performed under reducing conditions. Lane 2: supernatant of HEK culture expressing IL13-Fc (20 μl). SDS-PAGE was performed under non reducing conditions. Lane 3: supernatant of HEK culture expressing IL5-Fc (20 μl). SDS-PAGE was performed under non reducing conditions.

b) IL-5 Cloned with GST (Glutathion-S-Transferase) and an Amino Acid Linker Containing a Cysteine Residue Fused at its N-Terminus IL-5 (ATCC 37562) was amplified with the primers Nhe-link1-IL13-F and IL5StopXho-R. After digestion with NheI and XhoI the insert was ligated into pCEP-SP-GST-EK which had been previously digested with NheI and XhoI. The resulting plasmid pCEP-SP-GST-IL5 was sequenced and used for transfection of HEK-293T cells. The resulting IL-5 construct encoded by this plasmid had the amino acid sequence LACGGGGG (1–8 of SEQ ID NO: 334) fused at the N-terminus of the IL-5 mature sequence. This sequence comprises the amino acid linker sequence ACGGGGG (2–8 of SEQ ID NO: 334) containing a cysteine residue and flanked by additional amino acids introduced during the cloning procedure. The protein released by cleavage with enterokinase was named hereinafter "mouse C-IL-5-S" (SEQ ID NO:334). The purification of the resulting protein was performed by affinity chromatography on Glutathione affinity resin.

C. Coupling of Mouse C-IL-5-F or Mouse C-IL-5-S to Qβ Capsid Protein

A solution of 120 μM Qβ capsid protein in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed Qβ reaction mixture is then reacted with the mouse C-IL-5-F or mouse C-IL-5-S solution (end concentrations: 60 μM Qβ capsid protein, 60 μM mouse C-IL-5-F or mouse C-IL-5-S) for four hours at 25° C. on a rocking shaker. Coupling products are analysed by SDS-PAGE.

D. Coupling of Mouse Mouse C-IL-5-F or Mouse C-IL-5-S to fr Capsid Protein

A solution of 120 μM fr capsid protein in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed fr reaction mixture is then reacted with the the mouse C-IL-5-F or mouse C-IL-5-S solution (end concentrations: 60 μM fr capsid protein, 60 μM mouse C-IL-5-F or mouse C-IL-5-S) for four hours at 25° C. on a rocking shaker. Coupling products are analysed by SDS-PAGE.

E. Coupling of Mouse C-IL-5-F or Mouse C-IL-5-S Solution to HBcAg-Lys-2cys-Mut

A solution of 120 μM HBcAg-Lys-2cys-Mut capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed HBcAg-Lys-2cys-Mut reaction mixture is then reacted with the mouse mouse C-IL-5-F or mouse C-IL-5-S solution (end concentrations: 60 μM HBcAg-Lys-2cys-Mut, 60 μM mouse C-IL-5-F or mouse C-IL-5-S) for four hours at 25° C. on a rocking shaker. Coupling products are analysed by SDS-PAGE.

F. Coupling of Mouse C-IL-5-F or Mouse C-IL-5-S Solution to Pili

A solution of 125 μM Type-1 pili of *E. coli* in 20 mM Hepes, pH 7.4, is reacted for 60 minutes with a 50-fold molar excess of cross-linker SMPH, diluted from a stock solution in DMSO, at RT on a rocking shaker. The reaction mixture is desalted on a PD-10 column (Amersham-Pharmacia Biotech). The protein-containing fractions eluating from the column are pooled, and the desalted derivatized pili protein is reacted with the mouse mouse C-IL-5-F or mouse C-IL-5-S solution (end concentrations: 60 μM pili, 60 μM mouse C-IL-5-F or mouse C-IL-5-S) for four hours at 25° C. on a rocking shaker. Coupling products are analysed by SDS-PAGE.

Example 11

Cloning, Expression and Purification of IL-13 to VLPs and Pili

A. Cloning and Expression of Interleukin 13 (IL-13) with an N-Terminal Amino Acid Linker Containing a Cysteine Residue for Coupling to VLPs and Pili a) Cloning of Mouse IL-13 (HEK-293T) for Expression in Mammalian Cells as Fc Fusion Protein The DNA for the cloning of IL-13 was isolated by RT-PCR from in vitro activated splenocytes, wich were obtained as following: CD4+ T cells were isolated from mouse spleen cells and incubated 3 days in IMDM (+5% FCS+10 ng/ml IL4) in 6 well plates which have been previously coated with anti-CD3 and anti-CD28 antibodies. The RNA from these cells was used to amplify IL13 by one-step RT-PCR (Qiagen one-step PCR kit). Primer XhoIL13-R was used for the reverse transccription of the RNA and the primers NheIL13-F (SEQ ID NO:338) and XhoIL13-R (SEQ ID NO:339) were used for the PCR amplification of the IL13 cDNA. Amplified IL13 cDNA was ligated in a pMOD vector using the NheI/XhoI restriction sites (giving the vector pMODB1-IL13). pMODB1-Il13 was digested BamHI/XhoI and the fragment containing IL13 was ligated in the pCEP-SP-XA-Fc*(Δxho) vector, an analogue of pCEP-SP-XA-Fc* where a XhoI site at the end of the Fc sequence has been removed, which had been previously digested with BamHI/XhoI. The plasmid resulting from this ligation (pCEP-SP-IL13-Fc) was sequenced and used to transfect HEK-293T cells. The resulting IL 13 construct encoded by this plasmid had the amino acid sequence ADPGCGGGGGLA (1–12 of SEQ ID NO: 328) fused at the N-terminus of the IL-13 mature sequence. This sequence comprises the amino acid linker sequence GCGGGGG (4–10 of SEQ ID NO: 328) flanked by additional amino acids introduced during the cloning procedure. IL13-Fc could be purified with Protein-A resin from the supernatant of the cells transfected with pCEP-SP-IL13-Fc. The result of the expression is shown on FIG. 17B (see EXAMPLE 10 for description of the samples). Mature IL-13 fused at its N-terminus with the aforementioned amino acid sequence is released upon cleavage of the fusion protein with Factor-Xa, leading to a protein called hereinafter "mouse C-IL-13-F" and having a sequence of SEQ ID NO:328. The result of FIG. 17B clearly demonstrates expression of the IL-13 construct.

b) Cloning of Mouse IL-13 (HEK-293T) for Expression in Mammalian Cells with GST (Glutathion-S-Transferase) Fused at its N-Terminus The cDNA used for cloning IL-13 with an N-terminal GST originated from the cDNA of TH2 actiated T-cells as described above (a.). IL-13 was amplified from this cDNA using the primers Nhelink1IL13-F and IL13StopXhoNot-R. The PCR product was digested with NheI and XhoI and ligated in the pCEP-SP-GST-EK vector previously digested with NheI/XhoI. The plasmid which could be isolated from the ligation (pCEP-SP-GST-IL13) was used to transfect HEK-293T cells. The resulting IL 13 construct encoded by this plasmid had the amino acid sequence LACGGGGG (1–8 of SEQ ID NO: 329) fused at the N-terminus of the IL-13 mature sequence. This sequence comprises the amino acid linker sequence ACGGGGG (2–8 of SEQ ID NO: 329) flanked by an additional amino acid introduced during the cloning procedure. The culture supernatant of the cells transfected with pCEP-SP-GST-IL13 contained the fusion protein GST-IL13 which could be purified by Glutathione affinity chromatography according to standard protocols. Mature IL-13 fused at its N-terminus with aforementioned amino acid sequence is released upon cleavage of the fusion protein with enterokinase, leading to a protein called hereinafter "mouse C-IL-13-S" and having a sequence of SEQ ID NO:329.

B. Coupling of Mouse C-IL-13-F, Mouse C-IL-13-S to Qβ Capsid Protein

A solution of 120 μM Qβ capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed Qβ reaction mixture is then reacted with the mouse C-IL-13-F or mouse C-IL-13-S solution (end concentrations: 60 μM Qβ capsid protein, 60 μM mouse C-IL-13-F or mouse C-IL-13-S) for four hours at 25° C. on a rocking shaker. Coupling products are analysed by SDS-PAGE.

C. Coupling of Mouse C-IL-13-F, Mouse C-IL-13-S to fr Capsid Protein

A solution of 120 μM fr capsid protein in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed fr reaction mixture is then reacted with the the mouse C-IL-13-F or mouse C-IL-13-S solution (end concentrations: 60 μM fr capsid protein, 60 μM mouse C-IL-13-F or mouse C-IL-13-S) for four hours at 25° C. on a rocking shaker. Coupling products are analysed by SDS-PAGE.

D. Coupling of Mouse C-IL-13-F or Mouse C-IL-13-S Solution to HBcAg-Lys-2cys-Mut A solution of 120 μM HBcAg-Lys-2cys-Mut capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed HBcAg-Lys-2cys-Mut reaction mixture is then reacted with the mouse C-IL-13-F or mouse C-IL-13-S solution (end concentrations: 60 μM HBcAg-Lys-2cys-Mut, 60 μM mouse C-IL-13-F or mouse C-IL-13-S) for four hours at 25° C. on a rocking shaker. Coupling products are analysed by SDS-PAGE.

E. Coupling of Mouse C-IL-13-F or Mouse C-IL-13-S Solution to Pili

A solution of 125 μM Type-1 pili of *E. coli* in 20 mM Hepes, pH 7.4, is reacted for 60 minutes with a 50-fold molar excess of cross-linker SMPH, diluted from a stock solution in DMSO, at RT on a rocking shaker. The reaction mixture is desalted on a PD-10 column (Amersham-Pharmacia Biotech). The protein-containing fractions eluating from the column are pooled, and the desalted derivatized pili protein is reacted with the mouse C-IL-13-F or mouse C-IL-13-S solution (end concentrations: 60 μM pili, 60 μM mouse C-IL-13-F or mouse C-IL-13-S) for four hours at 25° C. on a rocking shaker. Coupling products are analysed by SDS-PAGE.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A composition comprising:

(a) a virus-like particle of an RNA-bacteriophage; and (b) at least one antigen or antigenic determinant, wherein said antigen or said antigenic determinant is a protein or peptide of IL-5, IL-13 or eotaxin, and wherein said at least one antigen or antigenic determinant is bound to said virus-like particle by at least one non-peptide bond.

2. The composition of claim 1, wherein said virus-like particle is a recombinant virus-like particle.

3. The composition of claim 1, wherein said virus-like particle comprises recombinant proteins, or fragments thereof, of a RNA-phage.

4. The composition of claim 3, wherein said RNA-phage is selected from the group consisting of:

(a) bacteriophage Qβ;
(b) bacteriophage R17;
(c) bacteriophage fr;
(d) bacteriophage GA;
(e) bacteriophage SP;
(f) bacteriophage MS2;
(g) bacteriophage M11;
(h) bacteriophage MX1;
(i) bacteriophage NL95;
(j) bacteriophage f2;
(k) bacteriophage PP7; and
(l) bacteriophage AP205.

5. The composition of claim 1, wherein said virus-like particle comprises recombinant proteins, or fragments thereof, of RNA-phage Qβ.

6. The composition of claim 1, wherein said virus-like particle comprises recombinant proteins, or fragments thereof, of RNA-phage fr or RNA-phage AP205.

7. The composition of claim 1, wherein said antigen or antigenic determinant is a protein or peptide of IL-5.

8. The composition of claim 7, wherein said protein or peptide of IL-5 comprises an amino acid sequence selected from the group consisting of:

(a) the amino acid sequence of SEQ ID NO:233;
(b) the amino acid sequence of SEQ ID NO:234; and
(c) the amino acid sequence of a fragment of any of SEQ ID NO:233 or 234.

9. The composition of claim 1, wherein said antigen or antigenic determinant is a protein or peptide of IL-13.

10. The composition of claim 9, wherein said protein or peptide of IL-13 comprises an amino acid sequence selected from the group consisting of:

(a) the amino acid sequence of SEQ ID NO:230;
(b) the amino acid sequence of SEQ ID NO:231; and
(c) the amino acid sequence of a fragment of any of SEQ ID NO:230 or 231.

11. The composition of claim 1, wherein said antigen or antigenic determinant is a protein or peptide of eotaxin.

12. The composition of claim 11, wherein said protein or peptide of eotaxin comprises an amino acid sequence selected from the group consisting of:

(a) the amino acid sequence of SEQ ID NO:242;
(b) the amino acid sequence of SEQ ID NO:243;
(c) the amino acid sequence of SEQ ID NO:244; and
(d) the amino acid sequence of a fragment of any of SEQ ID NO:242, 243 or 244.

13. The composition of claim 1, wherein said RNA-bacteriophage comprises at least one first attachment site, and wherein said antigen or antigenic determinant comprises at least one second attachment site selected from the group consisting of:

(i) an attachment site not naturally occurring with said antigen or antigenic determinant; and (ii) an attachment site naturally occurring with said antigen or antigenic determinant.

14. The composition of claim 13, wherein said antigen or antigenic determinant is a protein or peptide of IL-5, and wherein said antigen or antigenic determinant with said second attachment site comprises an amino acid sequence selected from the group consisting of:

(a) the amino acid sequence of SEQ ID NO:335;

(b) the amino acid sequence of SEQ ID NO:336;

(c) the amino acid sequence of SEQ ID NO:337; and (d) the amino acid sequence of a fragment of any of SEQ ID NO:335–337.

15. The composition of claim 13, wherein said antigen or antigenic determinant is a protein or peptide of IL-13, and wherein said antigen or antigenic determinant with said at least second attachment site comprises an amino acid sequence selected from the group consisting of:

(a) the amino acid sequence of SEQ ID NO:330;

(b) the amino acid sequence of SEQ ID NO:331; and (c) the amino acid sequence of a fragment of SEQ ID NO:330 or 331.

16. A composition comprising:

(a) a core particle with at least one first attachment site, wherein said core particle is a virus-like particle or a recombinant form thereof; and (b) at least one antigen or antigenic determinant with one or more second attachment sites;

wherein said antigen or antigenic determinant is a protein or peptide of IL-5, IL-13 or eotaxin, and wherein said one or more second attachment sites are selected from the group consisting of:

(i) an attachment site not naturally occurring with said antigen or antigenic determinant; and (ii) an attachment site naturally occurring with said antigen or antigenic determinant, wherein only one of said second attachment sites associates with said first attachment site through at least one non-peptide covalent bond leading to a single and uniform type of binding of said antigen to said core particle, wherein said only one second attachment site that associates with said first attachment site is a sulfhydryl group, and wherein said antigen or antigenic determinant and said core particle interact through said association to form an ordered and repetitive antigen array.

17. The composition of claim 16, wherein said core particle is a virus-like particle of an RNA-phage.

18. The composition of claim 16, wherein said core particle is a recombinant virus-like particle.

19. The composition of claim 18, wherein said virus-like particle comprises recombinant proteins, or fragments thereof, selected from the group consisting of:

(a) recombinant proteins of Hepatitis B virus;

(b) recombinant proteins of measles virus;

(c) recombinant proteins of Sindbis virus;

(d) recombinant proteins of Rotavirus;

(e) recombinant proteins of Foot-and-Mouth-Disease virus;

(f) recombinant proteins of Retrovirus;

(g) recombinant proteins of Norwalk virus;

(h) recombinant proteins of Alphavirus;

(i) recombinant proteins of human Papilloma virus;

(j) recombinant proteins of Polyoma virus;

(k) recombinant proteins of bacteriophages;

(l) recombinant proteins of RNA-phages;

(m) recombinant proteins of Ty;

(n) recombinant proteins of Qβ-phage;

(o) recombinant proteins of GA-phage; and (p) recombinant proteins of fr-phage.

20. The composition of claim 16, wherein said virus-like particle comprises Hepatitis B virus core antigen.

21. The composition of claim 16, wherein said virus-like particle comprises recombinant proteins, or fragments thereof, of a RNA-phage.

22. The composition of claim 21, wherein said RNA-phage is selected from the group consisting of:

(a) bacteriophage Qβ;

(b) bacteriophage R17;

(c) bacteriophage fr;

(d) bacteriophage GA;

(e) bacteriophage SP;

(f) bacteriophage MS2;

(g) bacteriophage M11;

(h) bacteriophage MX1;

(i) bacteriophage NL95;

(j) bacteriophage f2;

(k) bacteriophage PP7; and (l) bacteriophage AP205.

23. The composition of claim 22, wherein said virus-like particle comprises recombinant proteins, or fragments thereof, of RNA-phage Qβ.

24. The composition of claim 22, wherein said virus-like particle comprises recombinant proteins, or fragments thereof, of RNA-phage fr or RNA-phage AP205.

25. The composition of claim 16, wherein said antigen or antigenic determinant is a protein or peptide of IL-5.

26. The composition of claim 25, wherein said protein or peptide of IL-5 comprises an amino acid sequence selected from the group consisting of:

(a) the amino acid sequence of SEQ ID NO:233;

(b) the amino acid sequence of SEQ ID NO:234; and (c) the amino acid sequence of a fragment of any of SEQ ID NO:233 or 234.

27. The composition of claim 16, wherein said antigen or antigenic determinant is a protein or peptide of IL-13.

28. The composition of claim 27, wherein said protein or peptide of IL-13 comprises an amino acid sequence selected from the group consisting of:

(a) the amino acid sequence of SEQ ID NO:230;

(b) the amino acid sequence of SEQ ID NO:231; and (c) the amino acid sequence of a fragment of any of SEQ ID NO:230 or 231.

29. The composition of claim 16, wherein said antigen or antigenic determinant is a protein or peptide of eotaxin.

30. The composition of claim 29, wherein said protein or peptide of eotaxin comprises an amino acid sequence selected from the group consisting of:

(a) the amino acid sequence of SEQ ID NO:242;

(b) the amino acid sequence of SEQ ID NO:243;

(c) the amino acid sequence of SEQ ID NO:244; and (d) the amino acid sequence of a fragment of any of SEQ ID NO:242, 243 or 244.

31. The composition of claim 16, wherein said antigen or antigenic determinant is a protein or peptide of IL-5, and wherein said antigen or antigenic determinant with said second attachment site comprises an amino acid sequence selected from the group consisting of:

(a) the amino acid sequence of SEQ ID NO:335;

(b) the amino acid sequence of SEQ ID NO:336;

(c) the amino acid sequence of SEQ ID NO:337; and (d) the amino acid sequence of a fragment of any of SEQ ID NOs:335–337.

32. The composition of claim 16, wherein said antigen or antigenic determinant is a protein or peptide of IL-13, and wherein said antigen or antigenic determinant with said second attachment site comprises an amino acid sequence selected from the group consisting of:

(a) the amino acid sequence of SEQ ID NO:330;

(b) the amino acid sequence of SEQ ID NO:331; and (c) the amino acid sequence of a fragment of SEQ ID NO:330 or 331.

33. A pharmaceutical composition comprising:

(a) the composition of claim 1; and (b) a pharmaceutically acceptable carrier.

34. A pharmaceutical composition comprising:

(a) the composition of claim 16; and (b) a pharmaceutically acceptable carrier.

35. A process for producing a composition of claim 1 comprising:

(a) providing a virus-like particle of an RNA-bacteriophage;

(b) providing at least one antigen or antigenic determinant, wherein said antigen or antigenic determinant is a protein or peptide of IL-5, IL-13 or eotaxin; and (c) combining said virus-like particle and said antigen or antigenic determinant so that said at least one antigen or antigenic determinant is bound to said virus-like particle by at least one non-peptide bond.

36. A process for producing the composition of claim 16 comprising:

(a) providing a core particle with at least one first attachment site, wherein said core particle is a virus like particle or a recombinant form thereof;

(b) providing at least one antigen or antigenic determinant with one or more second attachment sites, wherein said antigen or antigenic determinant is a protein or peptide of IL-5, IL-13 or eotaxin, and wherein said one or more second attachment sites are selected from the group consisting of:

(i) an attachment site not naturally occurring with said antigen or antigenic determinant; and (ii) an attachment site naturally occurring with said antigen or antigenic determinant; and (c) combining said core particle and said antigen or antigenic determinant, such that only one of said second attachment sites associates with said first attachment site through at least one non-peptide covalent bond leading to a single and uniform type of binding of said antigen to said core particle, wherein said only one second attachment site that associates with said first attachment site is a sulfhydryl group, and wherein said antigen or antigenic determinant and said core particle interact through said association to form an ordered and repetitive antigen array.

37. A method of immunizing an animal comprising administering the composition of claim 1 to an animal whereby an immune response against said antigen or antigenic determinant is attained.

38. The method of claim 37, wherein said animal is a human.

39. A composition comprising:

(a) at least one first core particle and at least one second core particle with each core particle comprising at least one first attachment site; and (b) at least one first antigen or antigenic determinant and at least one second antigen or antigenic determinant with each antigen or antigenic determinant comprising at least one second attachment site;

wherein said first antigen or antigenic determinant and said second antigen or antigenic determinant is selected from a protein or peptide of IL-5, IL-13 or eotaxin, and wherein said first antigen or antigenic determinant is different from said second antigen or antigenic determinant, and wherein said second attachment site is selected from the group consisting of:

(i) an attachment site not naturally occurring with said antigen or antigenic determinant; and (ii) an attachment site naturally occurring with said antigen or antigenic determinant, and wherein, through said first and said second attachment sites, said first core particle interacts with said first antigen or antigen determinant to form an ordered and repetitive antigen array, and said second core particle interacts with said second antigen or antigen determinant to form an ordered and repetitive antigen array.

40. The composition of claim 39, wherein said first antigen or antigenic determinant is a protein or peptide of IL-5, and said second antigen or antigenic determinant is a protein or peptide of IL-13.

41. The composition of claim 39, wherein said first core particle and said second core particle is selected from the group consisting of:

(a) a virus;

(b) a virus-like particle;

(c) a bacteriophage;

(d) a bacterial pilus;

(e) a viral capsid particle; and (f) a recombinant form of any one of (a), (b), (c), (d) or (e).

42. The composition of claim 39, wherein said first core particle and said second core particle are selected from the group consisting of:

(a) a virus-like particle;

(b) a bacterial pilus; and (c) a virus-like particle of a RNA-phage.

43. The composition of claim 39, wherein said first core particle and said second core particle are recombinant virus-like particles.

44. The composition of claim 43, wherein said virus-like particles comprise recombinant proteins, or fragments thereof, selected from the group consisting of:

(a) recombinant proteins of Hepatitis B virus;

(b) recombinant proteins of measles virus;

(c) recombinant proteins of Sindbis virus;

(d) recombinant proteins of Rotavirus;

(e) recombinant proteins of Foot-and-Mouth-Disease virus;

(f) recombinant proteins of Retrovirus;

(g) recombinant proteins of Norwalk virus;

(h) recombinant proteins of Alphavirus;

(i) recombinant proteins of human Papilloma virus;

(j) recombinant proteins of Polyoma virus;

(k) recombinant proteins of bacteriophages;

(l) recombinant proteins of RNA-phages;

(m) recombinant proteins of Ty;

(n) recombinant proteins of Qβ-phage;

(o) recombinant proteins of GA-phage; and (p) recombinant proteins of fr-phage.

45. The composition of claim 43, wherein said first core particle and said second core particle are the same recombinant virus-like particle.

46. The composition of claim 45, wherein said virus-like particle comprises Hepatitis B virus core antigen.

47. The composition of claim 45, wherein said virus-like particle comprises recombinant proteins, or fragments thereof, of a RNA-phage.

48. The composition of claim 47, wherein said RNA-phage is selected from the group consisting of:

(a) bacteriophage Qβ;
(b) bacteriophage R17;
(c) bacteriophage fr;
(d) bacteriophage GA;
(e) bacteriophage SP;
(f) bacteriophage MS2;
(g) bacteriophage M11;
(h) bacteriophage MX1;
(i) bacteriophage NL95;
(j) bacteriophage f2;
(k) bacteriophage PP7; and
(l) bacteriophage AP205.

49. The composition of claim 45, wherein said virus-like particle comprises recombinant proteins, or fragments thereof, of RNA-phage Qβ.

50. The composition of claim 45, wherein said virus-like particle comprises recombinant proteins, or fragments thereof, of RNA-phage fr or RNA-phage AP205.

51. The composition of claim 45, wherein said first antigen or antigenic determinant is a protein or peptide of IL-5, and said second antigen or antigenic determinant is a protein or peptide of IL-13.

52. A method of immunization comprising administering the composition of claim 39 to an animal whereby an immune response against said antigen or antigenic determinant is produced in said animal.

53. The method of claim 52, wherein said antigen or antigenic determinant is a protein or peptide of human IL-5, human IL-13 or human eotaxin.

54. A method for treatment of an allergic eosinophilic disease comprising administering the composition of claim 1 to an animal suffering from allergic eosinophilic disease, whereby an immune response against said antigen or antigenic determinant is produced in said animal.

55. A method for treatment of an allergic eosinophilic disease comprising administering the composition of claim 16 to an animal suffering from allergic eosinophilic disease, whereby an immune response against said antigen or antigenic determinant is produced in said animal.

56. A method for treatment of an allergic eosinophilic disease comprising administering the composition of claim 39 to an animal suffering from allergic eosinophilic disease, whereby an immune response against said antigen or antigenic determinant is produced in said animal.

57. The method of any one of claims 54–56, wherein said animal is a human.

58. The composition of claim 1, wherein said antigen or antigenic determinant is bound to said virus-like particle of an RNA-bacteriophage by at least one non-peptide covalent bond.

59. The composition of claim 13, wherein said first attachment site associates with said second attachment site to form an ordered and repetitive antigen array.

60. The composition of claim 13, wherein said first attachment site comprises an amino group.

61. The composition of claim 13, wherein said second attachment site comprises a sulfhydryl group.

62. The composition of claim 13, wherein said first attachment site comprises an amino group and wherein said second attachment site comprises a sulffiydryl group.

63. The composition of claim 13 or claim 16, wherein said first attachment site is not a sulfhydryl group of a cysteine.

64. The composition of claim 16, wherein said first attachment site comprises an amino group.

65. The composition of claim 39, wherein said first antigen or antigenic deteminant is a protein or peptide of IL-5, and said second antigen or antigenic determinant is a protein or peptide of eotaxin.

66. A composition comprising a virus-like particle to which is bound a protein or peptide of eotaxin.

67. A pharmaceutical composition comprising the composition of claim 39 and a pharmaceutically acceptable carrier.

68. A pharmaceutical composition comprising the composition of claim 66 and pharmaceutically acceptable carrier.

69. A vaccine composition comprising the composition of claim 1 and an adjuvant.

70. A vaccine composition comprising the composition of claim 16 and an adjuvant.

71. A vaccine composition comprising the composition of claim 39 and an adjuvant.

72. A vaccine composition comprising the composition of claim 66 and an adjuvant.

73. A process for producing the composition of claim 39 comprising:

(a) providing a first core particle and a second core particle, each of which comprises at least one first attachment site;

(b) providing a first antigen or antigenic determinant and a second antigen or antigenic determinant, each of which comprises a second attachment site, wherein each antigen or antigenic determinant is a protein or peptide of IL-5, IL-13 or eotaxin, and wherein said first antigen or antigenic determinant is different from said second antigen or antigenic determinant; and (c) combining said first core particle with said first antigen or antigenic determinant, whereby said first core particle with said first antigen or antigenic determinant associates via said first and said second attachment sites to form an ordered an repetitive antigen array, and combining said second core particle with said second antigen or antigenic determinant, whereby said second core particle with said second antigen or antigenic determinant associates via said first and said second attachment sites to form an ordered an repetitive antigen array.

74. A process for producing the composition of claim 66 comprising:

(a) providing a virus-like particle;

(b) providing an antigen or antigenic determinant, wherein said antigen or antigenic determinant is a protein or peptide of eotaxin; and (c) combining said virus-like particle and said antigen or antigenic determinant whereby said protein or peptide of eotaxin is bound to said virus-like particle.

75. A method of immunizing an animal comprising administering the composition of claim 16 to an animal, whereby an immune response against said antigen or antigenic determinant is produced in said animal.

76. A method of immunizing an animal comprising administering the composition of claim 66 to an animal, whereby an immune response against said antigen or antigenic determinant is produced in said animal.

77. A method for treatment of allergic eosinophilic diseases in an animal, comprising administering the composition of claim 66 to an animal, whereby an immune response against said antigen or antigenic determinant is produced in said animal.

78. The method of claim 75, wherein said animal is human.

79. The method of claim 76, wherein said animal is human.

* * * * *